US011185543B2

(12) United States Patent
Alexander et al.

(10) Patent No.: US 11,185,543 B2
(45) Date of Patent: *Nov. 30, 2021

(54) ANTIPROLIFERATIVE COMPOUNDS AND METHODS OF USE THEREOF

(71) Applicant: Celgene Corporation, Summit, NJ (US)

(72) Inventors: Matthew D. Alexander, San Diego, CA (US); Gerald D. Artman, III, Asbury, NJ (US); James Carmichael, Nottingham (GB); Brian E. Cathers, San Diego, CA (US); Matthew D. Correa, San Diego, CA (US); Joshua Hansen, La Jolla, CA (US); Courtney G. Havens, San Diego, CA (US); Timothy S. Kercher, Longmont, CO (US); Antonia Lopez-Girona, San Diego, CA (US); Xiaoling Lu, Whippany, NJ (US); Hon-Wah Man, Princeton, NJ (US); Mark A. Nagy, Encinitas, CA (US); Joseph R. Piccotti, Encinitas, CA (US); Daniel W. Pierce, Belmont, CA (US); Paula A. Tavares-Greco, Parsippany, NJ (US); Brandon W. Whitefield, San Diego, CA (US); Lilly L. Wong, Solana Beach, CA (US); Nanfei Zou, Fanwood, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/859,357

(22) Filed: Apr. 27, 2020

(65) Prior Publication Data

US 2020/0253964 A1    Aug. 13, 2020

Related U.S. Application Data

(60) Division of application No. 16/430,189, filed on Jun. 3, 2019, now Pat. No. 10,675,281, which is a continuation of application No. 16/030,695, filed on Jul. 9, 2018, now Pat. No. 10,357,489.

(60) Provisional application No. 62/675,581, filed on May 23, 2018, provisional application No. 62/593,185, filed on Nov. 30, 2017, provisional application No. 62/530,778, filed on Jul. 10, 2017.

(51) Int. Cl.
| *A61K 31/496* | (2006.01) |
| *C07D 401/04* | (2006.01) |
| *A61K 31/573* | (2006.01) |
| *A61P 35/02* | (2006.01) |
| *A61K 38/05* | (2006.01) |
| *A61P 35/00* | (2006.01) |
| *A61K 31/69* | (2006.01) |

(52) U.S. Cl.
CPC .......... *A61K 31/496* (2013.01); *A61K 31/573* (2013.01); *A61K 38/05* (2013.01); *A61P 35/00* (2018.01); *A61P 35/02* (2018.01); *C07D 401/04* (2013.01); *A61K 31/69* (2013.01); *A61K 2300/00* (2013.01)

(58) Field of Classification Search
CPC ... A61K 31/496; A61K 31/573; C07D 401/04
USPC .................................... 514/253.09; 544/358
See application file for complete search history.

(56) References Cited

U.S. PATENT DOCUMENTS

| 6,284,755 | B1 | 9/2001 | deSolms et al. |
| 7,834,035 | B2 | 11/2010 | Bessis et al. |
| 8,022,214 | B2 | 9/2011 | Facchetti et al. |
| 8,039,490 | B2 | 10/2011 | Gobbi et al. |
| 8,518,972 | B2 | 8/2013 | Man et al. |
| 8,912,330 | B2 | 12/2014 | Qi et al. |
| 9,090,585 | B2 | 7/2015 | DeWitt |
| 9,115,101 | B2 | 8/2015 | Bodil van Niel et al. |
| 9,221,839 | B2 | 12/2015 | Cumming et al. |
| 9,346,807 | B2 | 5/2016 | Kearneyl |
| 9,422,279 | B2 | 8/2016 | Metcalf et al. |
| 10,357,489 | B2 * | 7/2019 | Alexander .............. A61P 35/02 |
| 2006/0074103 | A1 | 4/2006 | Corte et al. |
| 2010/0204224 | A1 | 8/2010 | Hamlyn et al. |
| 2011/0312996 | A1 | 12/2011 | Buckman et al. |
| 2014/0031547 | A1 | 1/2014 | Sheridan et al. |
| 2016/0199324 | A1 | 7/2016 | Polymeropoulos et al. |
| 2017/0210731 | A1 | 7/2017 | Kumar et al. |

(Continued)

FOREIGN PATENT DOCUMENTS

| CN | 108690020 A | 10/2018 |
| CN | 108794453 A | 11/2018 |

(Continued)

OTHER PUBLICATIONS

Matyskiela et al., "A Cereblon Modulator (CC-220) with Improved Degradation of Ikaros and Aiolos", Journal of Medicinal Chemistry, 2018, 61(2):535-542, online Apr. 20, 2017.

(Continued)

*Primary Examiner* — Niloofar Rahmani
(74) *Attorney, Agent, or Firm* — Jones Day

(57) ABSTRACT

Provided herein is 4-(4-(4-(((2-(2,6-dioxopiperidin-3-yl)-1-oxoisoindolin-4-yl)oxy)methyl)benzyl)piperazin-1-yl)-3-fluorobenzonitrile, or an enantiomer, a mixture of enantiomers, a tautomer, or a pharmaceutically acceptable salt thereof, and methods for treating, preventing or managing multiple myeloma using such compounds. Also provided are pharmaceutical compositions comprising the compounds, and methods of use of the compositions.

20 Claims, 31 Drawing Sheets

(56) References Cited

U.S. PATENT DOCUMENTS

| | | | |
|---|---|---|---|
| 2018/0099940 A1 | 4/2018 | Crew et al. |
| 2018/0177795 A1 | 6/2018 | Junutula et al. |
| 2018/0215731 A1 | 8/2018 | Crew et al. |
| 2019/0054097 A1 | 2/2019 | Zhou et al. |
| 2019/0062320 A1 | 2/2019 | Chan et al. |

FOREIGN PATENT DOCUMENTS

| | | |
|---|---|---|
| JP | 5728921 B2 | 6/2015 |
| WO | 2010057087 A1 | 5/2010 |
| WO | 2014/025960 A1 | 2/2014 |
| WO | 201619386 A1 | 12/2016 |
| WO | 2017005900 A1 | 1/2017 |
| WO | 2017161028 A1 | 9/2017 |
| WO | 2017176957 A1 | 10/2017 |
| WO | 2017184995 A1 | 10/2017 |
| WO | 2018039896 A1 | 3/2018 |
| WO | 2018075820 A2 | 4/2018 |
| WO | 2018106870 A1 | 6/2018 |
| WO | 2019114770 A1 | 6/2019 |

OTHER PUBLICATIONS

Rajkumar et al., "Multiple Myeloma: Diagnosis and Treatment", Mayo Clinic Proceedings, 2016, 91(1):101-119.

* cited by examiner

Figure 18:
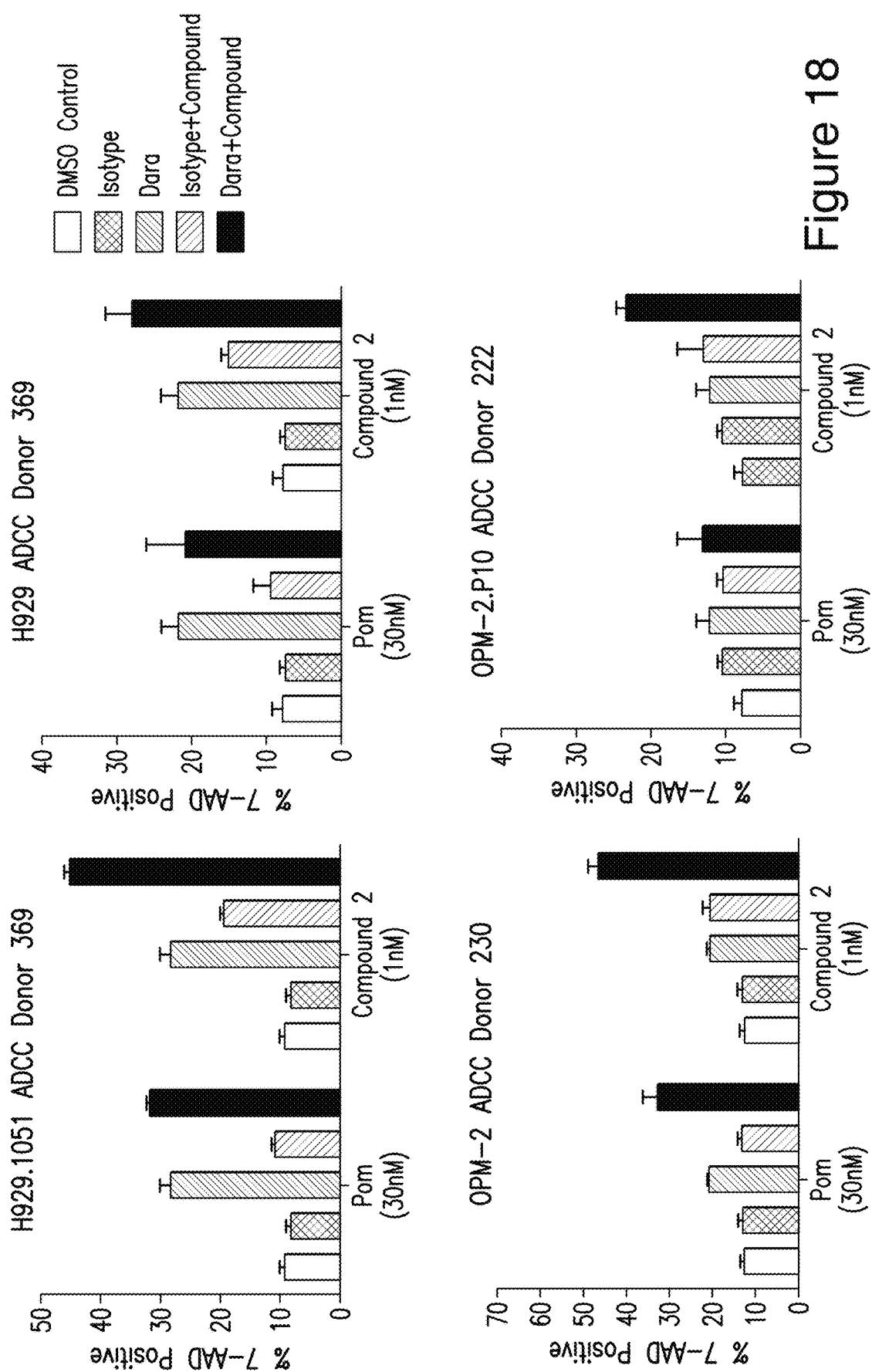

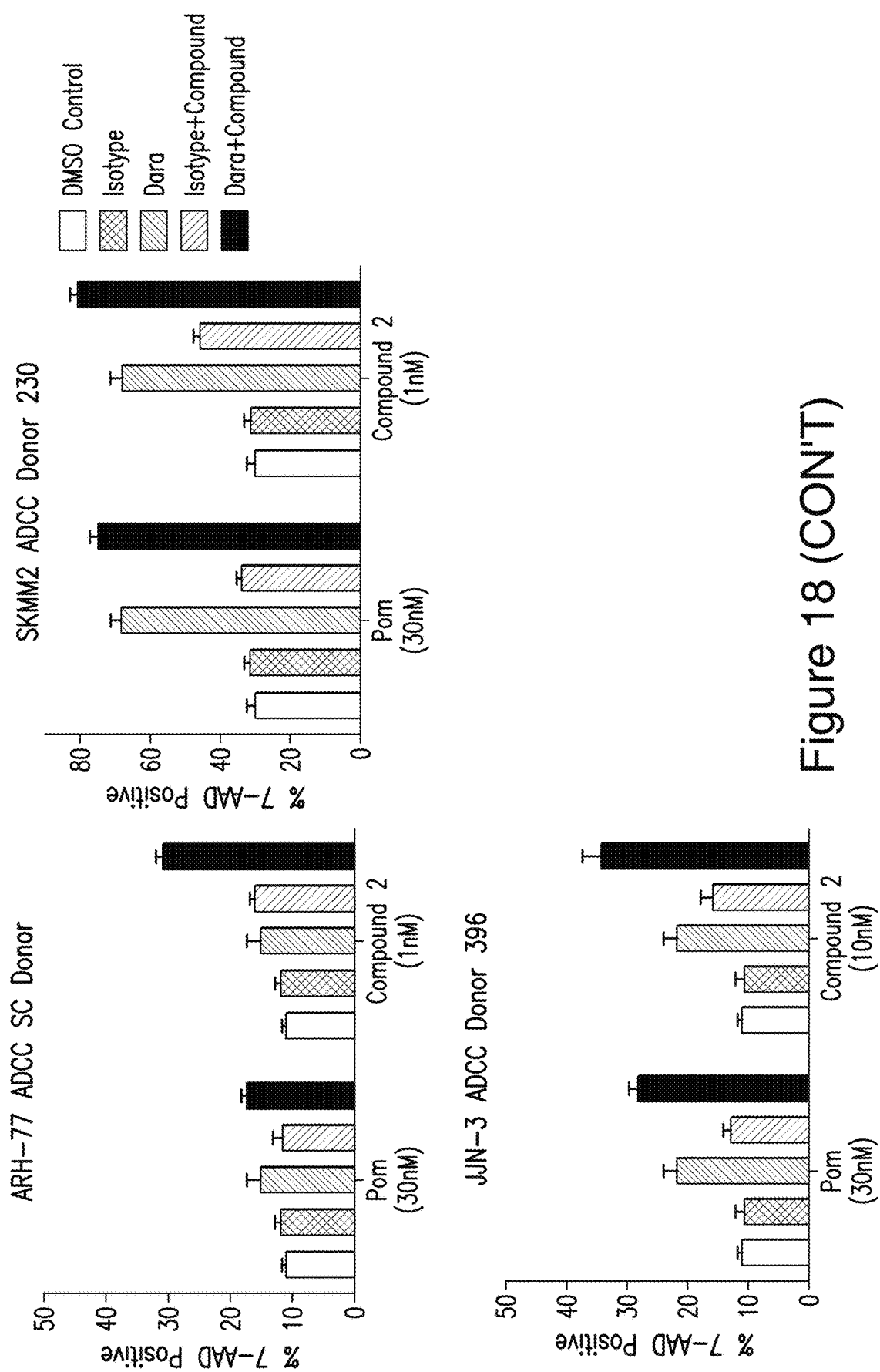
Figure 18 (CON'T)

Figure 19A:
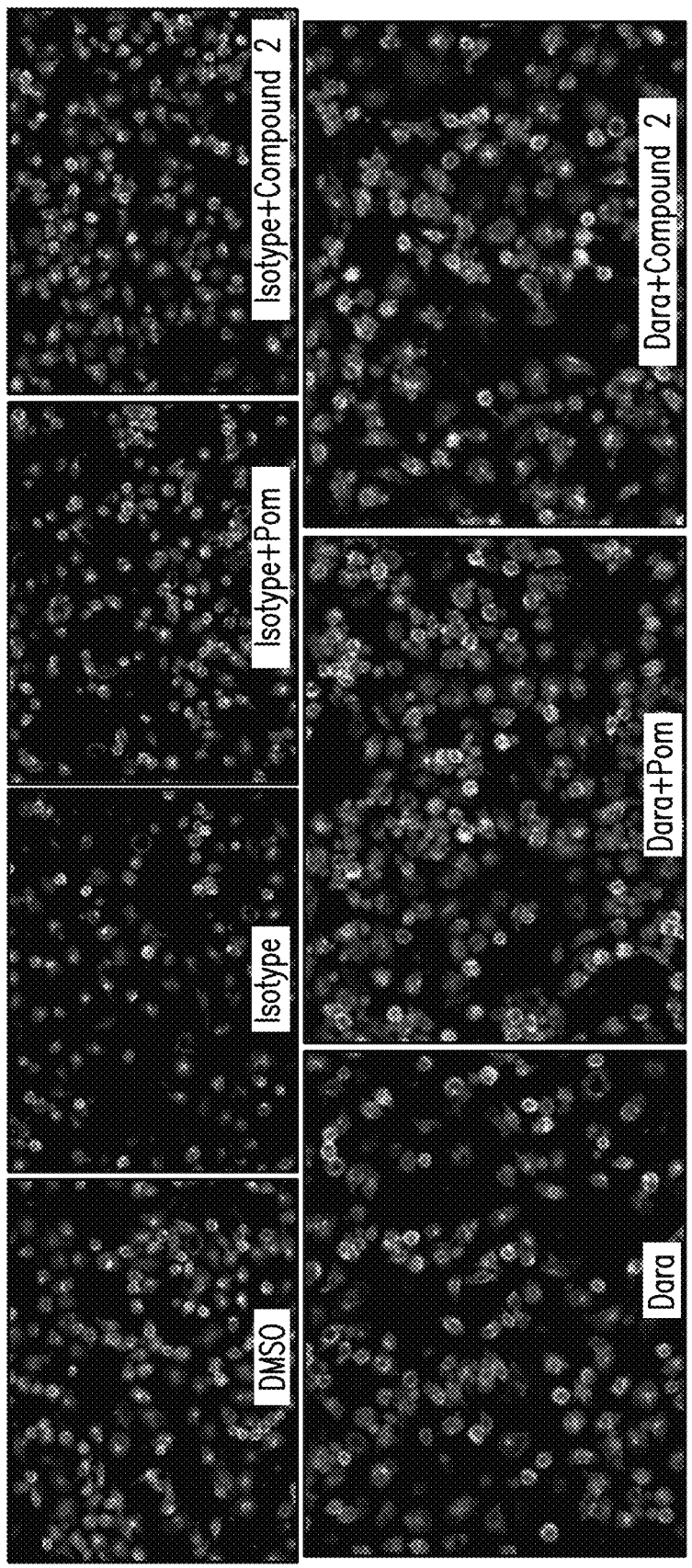
Figure 19B:
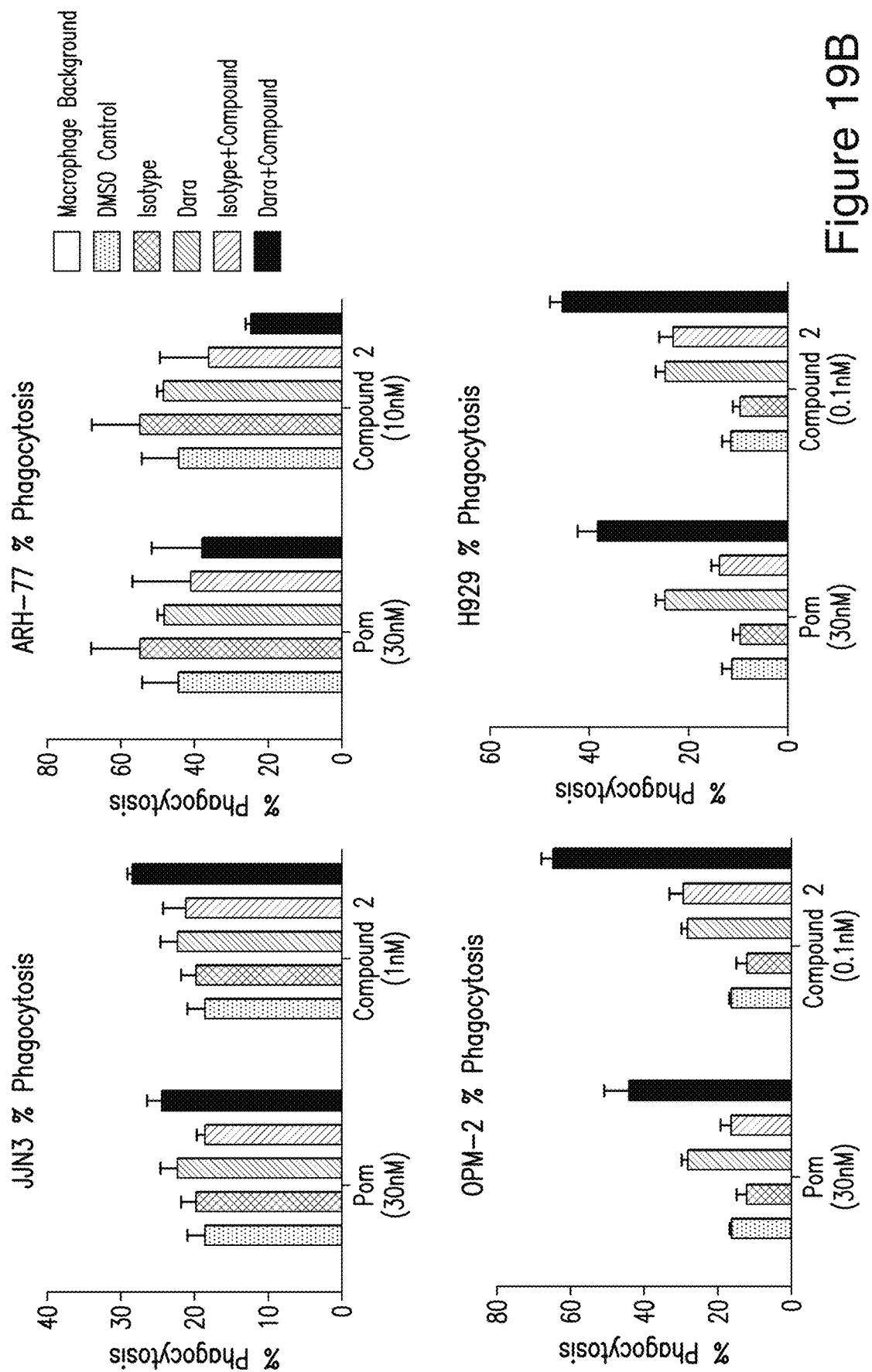

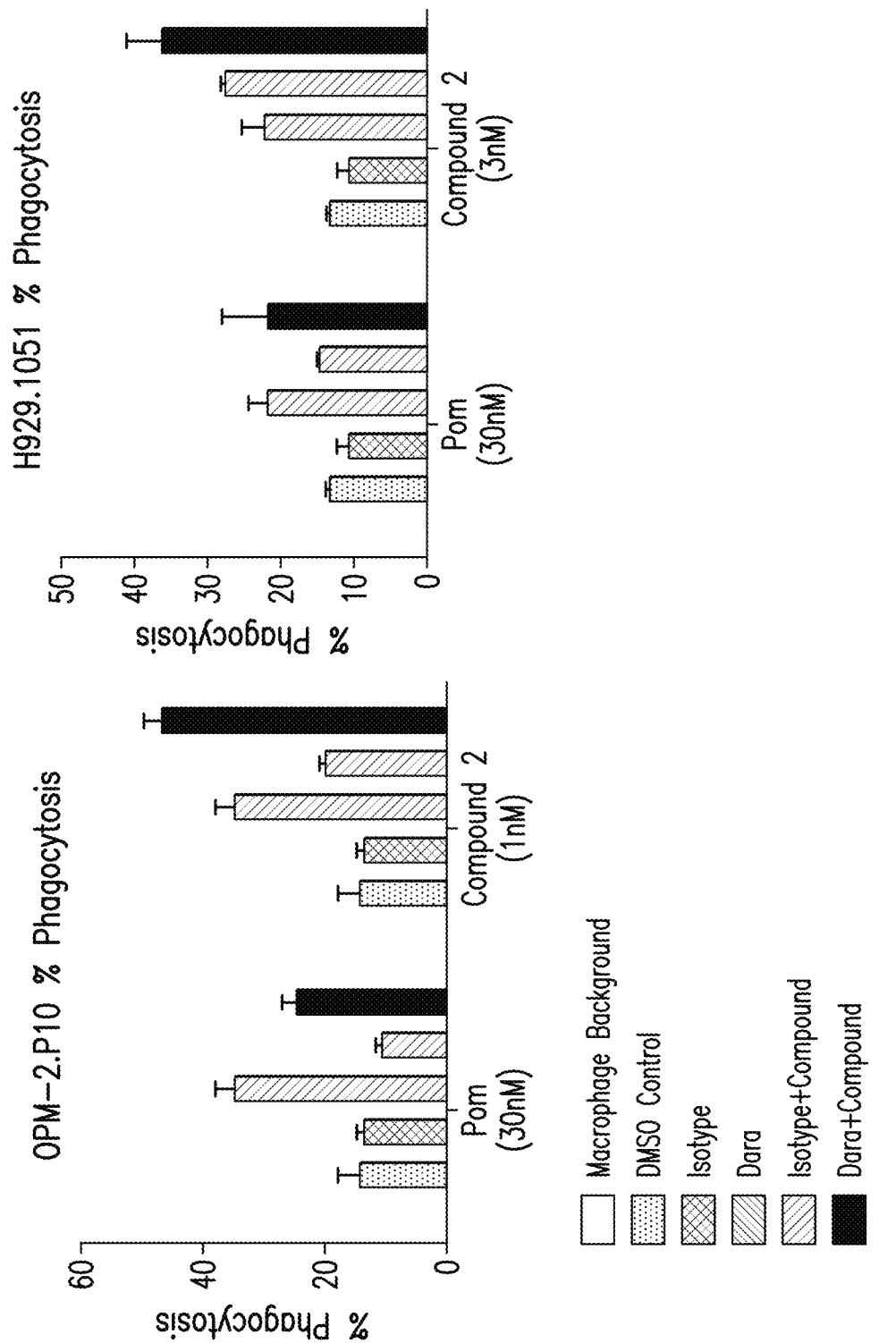
Figure 19B (CON'T)

- Binary call: surface response differs from null model (* p-value <0.05)

- Quantification: % synergistic wells (maxR)

Abbreviations for cell lines:
1051=NCI-H929.1051
P10=OPM-2.P10
KMS12=KMS-12-PE
RPMI=RPMI-8226

ANTIPROLIFERATIVE COMPOUNDS AND METHODS OF USE THEREOF

This application is a divisional application of U.S. application Ser. No. 16/430,189, filed on Jun. 3, 2019, which is a continuation application of U.S. application Ser. No. 16/030,695, filed on Jul. 9, 2018, now U.S. Pat. No. 10,357,489, which claims the benefit of U.S. Provisional Application Ser. No. 62/530,778, filed on Jul. 10, 2017, U.S. Provisional Application Ser. No. 62/593,185, filed on Nov. 30, 2017, and U.S. Provisional Application Ser. No. 62/675,581, filed on May 23, 2018, all of which are incorporated herein by reference in their entirety.

1. FIELD

Provided herein is 4-(4-(4-(((2-(2,6-dioxopiperidin-3-yl)-1-oxoisoindolin-4-yl)oxy)methyl)benzyl)piperazin-1-yl)-3-fluorobenzonitrile, or an enantiomer, a mixture of enantiomers, a tautomer, or a pharmaceutically acceptable salt thereof, and methods for treating, preventing or managing multiple myeloma using such compounds. Also provided are pharmaceutical compositions comprising the compounds, and methods of use of the compositions, including combination treatments.

2. BACKGROUND

Multiple myeloma (MM) is a cancer of plasma cells in the bone marrow. Normally, plasma cells produce antibodies and play a key role in immune function. However, uncontrolled growth of these cells leads to bone pain and fractures, anemia, infections, and other complications. Multiple myeloma is the second most common hematological malignancy, although the exact causes of multiple myeloma remain unknown. Multiple myeloma causes high levels of proteins in the blood, urine, and organs, including but not limited to M-protein and other immunoglobulins (antibodies), albumin, and beta-2-microglobulin, except in some patients (estimated at 1% to 5%) whose myeloma cells do not secrete these proteins (termed non-secretory myeloma). M-protein, short for monoclonal protein, also known as paraprotein, is a particularly abnormal protein produced by the myeloma plasma cells and can be found in the blood or urine of almost all patients with multiple myeloma, except for patients who have non-secretory myeloma or whose myeloma cells produce immunoglobulin light chains with heavy chain.

Skeletal symptoms, including bone pain, are among the most clinically significant symptoms of multiple myeloma. Malignant plasma cells release osteoclast stimulating factors (including IL-1, IL-6 and TNF) which cause calcium to be leached from bones causing lytic lesions; hypercalcemia is another symptom. The osteoclast stimulating factors, also referred to as cytokines, may prevent apoptosis, or death of myeloma cells. Fifty percent of patients have radiologically detectable myeloma-related skeletal lesions at diagnosis. Other common clinical symptoms for multiple myeloma include polyneuropathy, anemia, hyperviscosity, infections, and renal insufficiency.

Current multiple myeloma therapy may involve one or more of surgery, stem cell transplantation, chemotherapy, immune therapy, and/or radiation treatment to eradicate multiple myeloma cells in a patient. All of the current therapy approaches pose significant drawbacks for the patient.

In the last decade, novel therapeutic agents, in particular immunomodulatory drugs such as lenalidomide and pomalidomide, significantly increased the response rates and prolonged progression free survival (PFS) and overall survival (OS) in multiple myeloma patients. However, persistent levels of residual disease that are below the sensitivity of bone marrow (BM) morphology, protein electrophoresis with immunofixation, and light chain quantitation exists in many patients with multiple myeloma, even after these patients have achieved complete response (CR), and will eventually cause relapse of the disease. Minimal residual disease (MRD) in myeloma is an independent predictor of progression-free survival (PFS) and is under consideration as a surrogate trial endpoint to improve the identification of effective treatments, particularly for frontline trials, which now require 5 to 10 years of follow-up to identify survival differences. Monitoring minimal residual disease (MRD) in patients with multiple myeloma thus provides prognostic value in predicting PFS and OS and making treatment decisions. The detection of minimal residual disease (MRD) in myeloma can use a 0.01% threshold ($10^{-4}$) after treatment, i.e., having $10^{-4}$ cells or fewer multiple myeloma cells as a proportion of total bone marrow mononuclear cells is considered MRD-negative, and having $10^{-4}$ cells or higher MRD-positive. The $10^{-4}$ MRD threshold was originally based on technical capability, but quantitative MRD detection is now possible at $10^{-5}$ by flow cytometry and $10^{-6}$ by high-throughput sequencing. (Rawstron et al., *Blood* 2015; 125(12):1932-1935). Methods for measuring MRD include DNA sequencing of VDJ, polymerase chain reaction (PCR) (including allele specific PCR, ASO PCR) and multiparameter flow cytometry (MPF). Assays for MRD, e.g., based on clonotype profile measurement are also described in U.S. Pat. No. 8,628,927, to Faham et al., which is incorporated herein by reference.

There exists a significant need for safe and effective compounds and methods for treating, preventing and managing multiple myeloma, including for patients whose multiple myeloma is newly diagnosed or refractory to standard treatments, while reducing or avoiding the toxicities and/or side effects associated with the conventional therapies.

Citation or identification of any reference in Section 2 of this application is not to be construed as an admission that the reference is prior art to the present application.

3. SUMMARY

Provided herein are compounds, pharmaceutical compositions containing the compounds and methods of use thereof in treating multiple myeloma. In one embodiment, the compound for use in the compositions and methods provided herein is 4-(4-(4-(((2-(2,6-dioxopiperidin-3-yl)-1-oxoisoindolin-4-yl)oxy)methyl)benzyl)piperazin-1-yl)-3-fluorobenzonitrile (Compound 1):

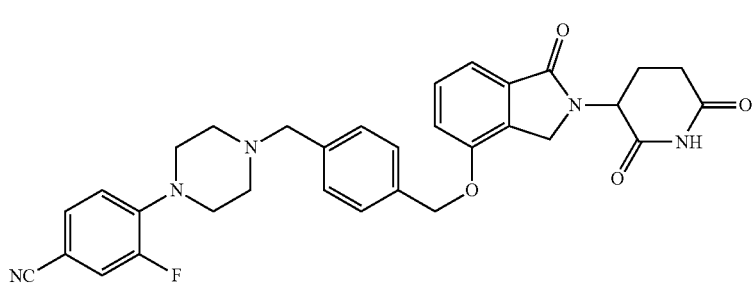

or an enantiomer, mixture of enantiomers, tautomer, isotopolog, or pharmaceutically acceptable salt thereof.

In one embodiment, the compound for use in the compositions and methods provided herein is (S)-4-(4-(4-(((2-(2,6-dioxopiperidin-3-yl)-1-oxoisoindolin-4-yl)oxy)methyl)benzyl)piperazin-1-yl)-3-fluorobenzonitrile (Compound 2):

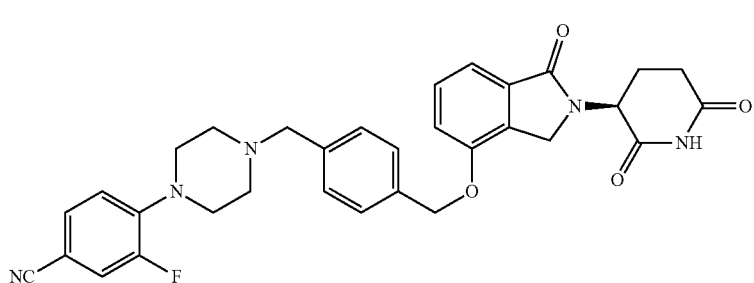

or a tautomer, isotopolog, or pharmaceutically acceptable salt thereof.

In another embodiment, the compound for use in the compositions and methods provided herein is (R)-4-(4-(4-(((2-(2,6-dioxopiperidin-3-yl)-1-oxoisoindolin-4-yl)oxy)methyl)benzyl)piperazin-1-yl)-3-fluorobenzonitrile (Compound 3):

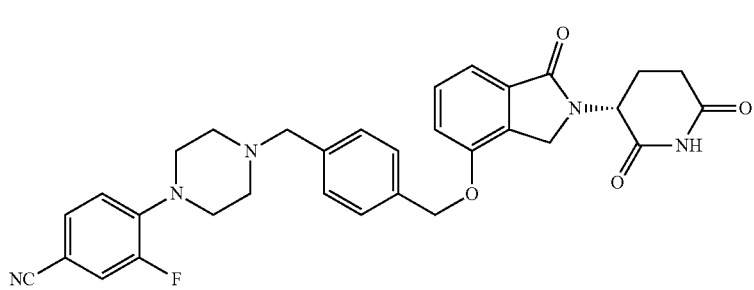

or a tautomer, isotopolog, or pharmaceutically acceptable salt thereof.

Also provided are pharmaceutical compositions formulated for administration by an appropriate route and means containing effective concentrations of the compounds provided herein, for example Compound 1, Compound 2 or Compound 3, or an enantiomer, mixture of enantiomers, tautomer, isotopolog, or pharmaceutically acceptable salt thereof, and optionally comprising at least one pharmaceutical carrier.

In one embodiment, the pharmaceutical compositions deliver amounts effective for the treatment of multiple myeloma. In one embodiment, the pharmaceutical compositions deliver amounts effective for the prevention of multiple myeloma. In one embodiment, the pharmaceutical compositions deliver amounts effective for the amelioration of multiple myeloma.

Also provided herein are combination therapies using the compounds or compositions provided herein, or an enantiomer, mixture of enantiomers, tautomer, isotopolog, or pharmaceutically acceptable salt thereof, in combination with a therapy e.g., another pharmaceutical agent with activity against multiple myeloma or its symptoms. Examples of therapies within the scope of the methods include, but are not limited to, surgery, chemotherapy, radiation therapy, biological therapy, stem cell transplantation, cell therapy, and combinations thereof.

The compounds or compositions provided herein, or pharmaceutically acceptable derivatives thereof, may be administered simultaneously with, prior to, or after administration of one or more of the above therapies. Pharmaceutical compositions containing a compound provided herein and one or more of the above therapies are also provided.

In one embodiment, effective amounts of the compounds or compositions containing therapeutically effective concentrations of the compounds are administered to an individual exhibiting the symptoms of multiple myeloma to be treated. The amounts are effective to ameliorate or eliminate one or more symptoms of multiple myeloma. In practicing the methods of treatment, effective amounts of the compounds or compositions containing therapeutically effective concentrations of the compounds are administered to a multiple myeloma patient in need thereof.

Further provided is a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like.

These and other aspects of the subject matter described herein will become evident upon reference to the following detailed description.

4. DETAILED DESCRIPTION OF THE INVENTION

A. Definitions

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

"$IC_{50}$" refers to an amount, concentration or dosage of a particular test compound that achieves a 50% inhibition of a maximal response, such as receptor binding, receptor activity, cell growth or proliferation, as measured via any of the in vitro or cell based assays described herein.

Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, fumarates and organic sulfonates.

Unless specifically stated otherwise, where a compound may assume alternative tautomeric, regioisomeric and/or stereoisomeric forms, all alternative isomers are intended to be encompassed within the scope of the claimed subject matter. For example, where a compound can have one of two tautomeric forms, it is intended that both tautomers be encompassed herein.

Thus, the compounds provided herein may be enantiomerically pure, or be stereoisomeric or diastereomeric mixtures. As used herein and unless otherwise indicated, the term "stereoisomerically pure" means a composition that comprises one stereoisomer of a compound and is substantially free of other stereoisomers of that compound. For example, a stereoisomerically pure composition of a compound having one chiral center will be substantially free of the opposite enantiomer of the compound. A stereoisomerically pure composition of a compound having two chiral centers will be substantially free of other diastereomers of the compound. A typical stereoisomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. A stereoisomerically pure compound as used herein comprises greater than about 80% by weight of one stereoisomer of the compound, more preferably greater than about 90% by weight of one stereoisomer of the compound, even more preferably greater than about 95% by weight of one stereoisomer of the compound, and most preferably greater than about 97% by weight of one stereoisomer of the compound. As used herein and unless otherwise indicated, the term "stereoisomerically enriched" means a composition that comprises greater than about 60% by weight of one stereoisomer of a compound, preferably greater than about 70% by weight, more preferably greater than about 80% by weight of one stereoisomer of a compound. As used herein and unless otherwise indicated, the term "enantiomerically pure" means a stereoisomerically pure composition of a compound having one chiral center. Similarly, the term "stereoisomerically enriched" means a stereoisomerically enriched composition of a compound having one chiral center. As used herein, stereoisomeric or diastereomeric mixtures means a composition that comprises more than one stereoisomer of a compound. A typical stereoisomeric mixture of a compound comprises about 50% by weight of one stereoisomer of the compound and about 50% by weight of other stereoisomers of the compound, or comprises greater than about 50% by weight of one stereoisomer of the compound and less than about 50% by weight of other stereoisomers of the compound, or comprises greater than about 45% by weight of one stereoisomer of the compound and less than about 55% by weight of the other stereoisomers of the compound, or comprises greater than about 40% by weight of one stereoisomer of the compound and less than about 60% by weight of the other stereoisomers of the compound, or comprises greater than about 35% by weight of one stereoisomer of the compound and less than about 65% by weight of the other stereoisomers of the compound.

It is to be understood that the compounds provided herein may contain chiral centers. Such chiral centers may be of either the (R) or (S) configuration, or may be a mixture thereof. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Optically active (+) and (−), (R)- and (S)-, or (D)- and (L)-isomers may be prepared using chiral synthons or chiral reagents, or resolved using conventional techniques, such as chromatography on a chiral stationary phase.

As used herein, an "isotopolog" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., multiple myeloma therapeutic agents, research reagents, e.g., binding assay reagents, and diagnostic agents, e.g., in vivo imaging agents. All isotopic variations of the compounds as described herein, whether radioactive or not, are intended to be encompassed within the scope of the embodiments provided herein. In some embodiments, there are provided isotopologues of the compounds, for example, the isotopologues of Compound 1, Compound 2 or Compound 3 are deuterium, carbon-13, or nitrogen-15 enriched compounds. In some embodiments, isotopologues provided herein are deuterium enriched compounds. In some embodiments, isotopologues provided herein are deuterium enriched compounds, where the deuterium enrichment occurs on the chiral center.

In the description herein, if there is any discrepancy between a chemical name and chemical structure, the structure controls.

As used herein "multiple myeloma" refers to hematological conditions characterized by malignant plasma cells and includes the following disorders: monoclonal gammopathy of undetermined significance (MGUS); low risk, intermediate risk, and high risk multiple myeloma; newly diagnosed multiple myeloma (including low risk, intermediate risk, and high risk newly diagnosed multiple myeloma); transplant eligible and transplant ineligible multiple myeloma; smoldering (indolent) multiple myeloma (including low risk, intermediate risk, and high risk smouldering multiple myeloma); active multiple myeloma; solitary plasmacytoma; extramedullary plasmacytoma; plasma cell leukemia; central nervous system multiple myeloma; light chain myeloma; non-secretory myeloma; Immunoglobulin D myeloma; and Immunoglobulin E myeloma; and multiple myeloma characterized by genetic abnormalities, such as Cyclin D translocations (for example, t(11;14)(q13;q32); t(6; 14)(p21;32); t(12; 14)(p13;q32); or t(6;20);); MMSET translocations (for example, t(4; 14)(p16;q32)); MAF translocations (for example, t(14;16)(q32;q32); t(20;22); t(16; 22)(q11;q13); or t(14;20)(q32;q11)); or other chromosome factors (for example, deletion of 17p13, or chromosome 13; del(17/17p), nonhyperdiploidy, and gain(1q)).

As used herein and unless otherwise indicated, the terms "treat," "treating" and "treatment" refer to alleviating or reducing the severity of a symptom associated with the disease or condition being treated, for example, multiple myeloma.

The term "prevention" includes the inhibition of a symptom of the particular disease or disorder, for example multiple myeloma. In some embodiments, patients with familial history of multiple myeloma are candidates for preventive regimens. Generally, the term "preventing" refers to administration of the drug prior to the onset of symptoms, particularly to patients at risk of multiple myeloma.

As used herein and unless otherwise indicated, the term "managing" encompasses preventing the recurrence of the particular disease or disorder, such as multiple myeloma, in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

As used herein, "subject" or "patient" is an animal, typically a mammal, including a human, such as a human patient.

The term "relapsed" refers to a situation where patients, who have had a remission of multiple myeloma after therapy, have a return of myeloma cells and/or reduced normal cells in the marrow.

The term "refractory or resistant" refers to a circumstance where patients, even after intensive treatment, have residual myeloma cells and/or reduced normal cells in the marrow.

As used herein, "induction therapy" refers to the first treatment given for a disease, or the first treatment given with the intent of inducing complete remission in a disease, such as cancer. When used by itself, induction therapy is the one accepted as the best available treatment. If residual cancer is detected, patients are treated with another therapy, termed reinduction. If the patient is in complete remission after induction therapy, then additional consolidation and/or maintenance therapy is given to prolong remission or to potentially cure the patient.

As used herein, "consolidation therapy" refers to the treatment given for a disease after remission is first achieved. For example, consolidation therapy for cancer is the treatment given after the cancer has disappeared after initial therapy. Consolidation therapy may include radiation therapy, stem cell transplant, or treatment with cancer drug therapy. Consolidation therapy is also referred to as intensification therapy and post-remission therapy.

As used herein, "maintenance therapy" refers to the treatment given for a disease after remission or best response is achieved, in order to prevent or delay relapse. Maintenance therapy can include chemotherapy, hormone therapy or targeted therapy.

"Remission" as used herein, is a decrease in or disappearance of signs and symptoms of a cancer, for example, multiple myeloma. In partial remission, some, but not all, signs and symptoms of the cancer have disappeared. In complete remission, all signs and symptoms of the cancer have disappeared, although the cancer still may be in the body.

As used herein "transplant" refers to high-dose therapy with stem cell rescue. Hematopoietic (blood) or bone marrow stem cells are used not as treatment but to rescue the patient after the high-dose therapy, for example high dose chemotherapy and/or radiation. Transplant includes "autologous" stem cell transplant (ASCT), which refers to use of the patients' own stem cells being harvested and used as the replacement cells. In some embodiments, transplant also includes tandem transplant or multiple transplants.

As used herein, and unless otherwise specified, the terms "therapeutically effective amount" and "effective amount" of a compound refer to an amount sufficient to provide a therapeutic benefit in the treatment, prevention and/or management of a disease, for example multiple myeloma, or to delay or minimize one or more symptoms associated with the disease or disorder to be treated. The terms "therapeutically effective amount" and "effective amount" can encompass an amount that improves overall therapy, reduces or avoids symptoms or causes of disease or disorder, or enhances the therapeutic efficacy of another therapeutic agent.

The terms "co-administration" and "in combination with" include the administration of one or more therapeutic agents (for example, a compound provided herein and another anti-multiple myeloma agent, cancer agent or supportive care agent) either simultaneously, concurrently or sequentially with no specific time limits. In one embodiment, the agents are present in the cell or in the patient's body at the same time or exert their biological or therapeutic effect at the same time. In one embodiment, the therapeutic agents are in the same composition or unit dosage form. In another embodiment, the therapeutic agents are in separate compositions or unit dosage forms.

The term "supportive care agent" refers to any substance that treats, prevents or manages an adverse effect from treatment with Compound 1, Compound 2 or Compound 3, or an enantiomer or a mixture of enantiomers, tautomers, isotopolog or a pharmaceutically acceptable salt thereof.

The term "biological therapy" refers to administration of biological therapeutics such as cord blood, stem cells, growth factors and the like.

In the context of a cancer, such as multiple myeloma, inhibition may be assessed by inhibition of disease progression, inhibition of tumor growth, reduction of primary tumor, relief of tumor-related symptoms, inhibition of tumor secreted factors, delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from treatment onset until death from any cause. TTP, as used herein, means the time from treatment onset until tumor progression; TTP does not include deaths. In one embodiment, PFS means the time from treatment onset until tumor progression or death. In one embodiment, PFS means the time from the first dose of compound to the first occurrence of disease progression or death from any cause. In one embodiment, PFS rates will be computed using the Kaplan-Meier estimates. Event-free survival (EFS) means the time from treatment onset until any treatment failure, including disease progression, treatment discontinuation for any reason, or death. In one embodiment, overall response rate (ORR) means the percentage of patients who achieve a response. In one embodiment, ORR means the sum of the percentage of patients who achieve complete and partial responses. In one embodiment, ORR means the percentage of patients whose best response≥partial response (PR), according to the IMWG Uniform Response Criteria. In one embodiment, duration of response (DoR) is the time from achieving a response until relapse or disease progression. In one embodiment, DoR is the time from achieving a response≥partial response (PR) until relapse or disease progression. In one embodiment, DoR is the time from the first documentation of a response until to the first documentation of progressive disease or death. In one embodiment, DoR is the time from the first documentation of a response≥partial response (PR) until to the first documentation of progressive disease or death. In one embodiment, time to response (TTR) means the time from the first dose of compound to the first documentation of a response. In one embodiment, TTR means the time from the first dose of compound to the first documentation of a response≥partial response (PR). In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

In certain embodiments, the treatment of multiple myeloma may be assessed by the International Uniform Response Criteria for Multiple Myeloma (IURC) (see Durie B G M, Harousseau J-L, Miguel J S, et al. International uniform response criteria for multiple myeloma. *Leukemia*, 2006; (10) 10: 1-7), using the response and endpoint definitions shown below:

| Response Subcategory | Response Criteria[a] |
|---|---|
| sCR | CR as defined below plus |
| | Normal FLC ratio and |
| | Absence of clonal cells in bone marrow[b] by |
| | immunohistochemistry or immunofluorescence[c] |
| CR | Negative immunofixation on the serum and urine and |
| | Disappearance of any soft tissue plasmacytomas and < |
| | 5% plasma cells in bone marrow[b] |
| VGPR | Serum and urine M-protein detectable by immunofixation but |
| | not on electrophoresis or 90% or greater reduction in serum |
| | M-protein plus urine M-protein level < 100 mg per 24 h |
| PR | ≥50% reduction of serum M-protein and reduction in 24-h |
| | urinary M-protein by ≥ 90% or to < 200 mg per 24 h |
| | If the serum and urine M-protein are unmeasurable,[d] a ≥ 50% |
| | decrease in the difference between involved and uninvolved |
| | FLC levels is required in place of the M-protein criteria |
| | If serum and urine M-protein are unmeasurable, and serum free |
| | light assay is also unmeasurable, ≥50% reduction in plasma |
| | cells is required in place of M-protein, provided baseline bone |
| | marrow plasma cell percentage was ≥ 30% |

| Response Subcategory | Response Criteria[a] |
|---|---|
| | In addition to the above listed criteria, if present at baseline, a ≥ 50% reduction in the size of soft tissue plasmacytomas is also required |
| SD (not recommended for use as an indicator of response; stability of disease is best described by providing the time to progression estimates) | Not meeting criteria for CR, VGPR, PR or progressive disease |

Abbreviations:
CR, complete response;
FLC, free light chain;
PR, partial response;
SD, stable disease;
sCR, stringent complete response;
VGPR, very good partial response.
[a]All response categories require two consecutive assessments made at any time before the institution of any new therapy; all categories also require no known evidence of progressive or new bone lesions if radiographic studies were performed. Radiographic studies are not required to satisfy these response requirements.
[b]Confirmation with repeat bone marrow biopsy not needed.
[c]Presence/absence of clonal cells is based upon the κ/λ ratio. An abnormal κ/λ ratio by immunohistochemistry and/or immunofluorescence requires a minimum of 100 plasma cells for analysis. An abnormal ratio reflecting presence of an abnormal clone is κ/λ of > 4:1 or < 1:2.
[d]Measurable disease defined by at least one of the following measurements: Bone marrow plasma cells ≥ 30%; Serum M-protein ≥ 1 g/dl (≥10 gm/l)[10 g/l]; Urine M-protein ≥ 200 mg/24 h; Serum FLC assay: Involved FLC level ≥ 10 mg/dl (≥100 mg/l); provided serum FLC ratio is abnormal.

As used herein, ECOG status refers to Eastern Cooperative Oncology Group (ECOG) Performance Status (Oken M, et al Toxicity and response criteria of the Eastern Cooperative Oncology Group. *Am J Clin Oncol* 1982; 5(6):649-655), as shown below:

| Score | Description |
|---|---|
| 0 | Fully active, able to carry on all pre-disease performance without restriction |
| 1 | Restricted in physically strenuous activity but ambulatory and able to carry out work of a light or sedentary nature, eg, light housework, office work. |
| 2 | Ambulatory and capable of all self-care but unable to carry out any work activities. Up and about more than 50% of waking hours. |
| 3 | Capable of only limited self-care, confined to bed or chair more than 50% of waking hours. |
| 4 | Completely disabled. Cannot carry on any self-care. Totally confined to bed or chair |
| 5 | Dead |

The term "about," as used herein, unless otherwise indicated, refers to a value that is no more than 10% above or below the value being modified by the term. For example, the term "about 10 mg/m$^2$" means a range of from 9 mg/m$^2$ to 11 mg/m$^2$.

B. Brief Description of the Figures

Figure 1A:
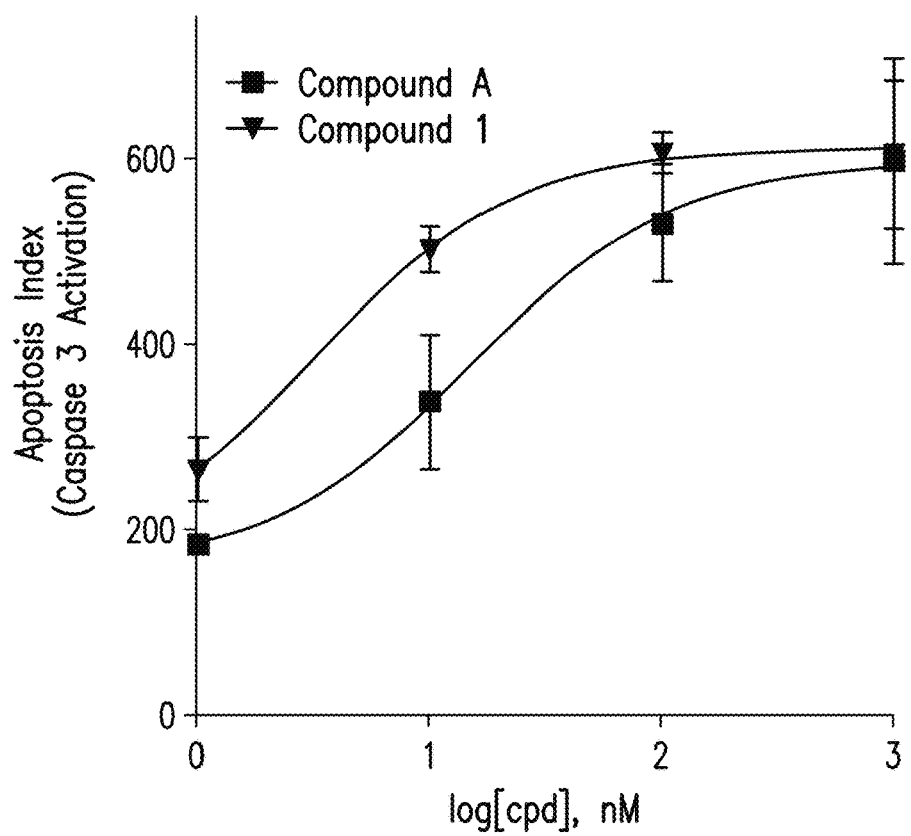

FIG. 1. (A) Change in apoptosis induction, as measured by area under the curve of Caspase 3 fold induction (aka apoptosis index) over time in lenalidomide resistant H929-1051 cells. Abscissa: log nM (compound), ordinate: apoptosis index. The lines of best fit are a 3-parameter logistic equation calculated in GraphPad Prism. (B) The area under the curve of the concentration-response curves for Compound 1 and Compound A in H929-1051 cells were used to compare the compounds' ability to induce apoptosis after a 6 h exposure and then dilution resulting in about a 20-fold reduction of compound concentration.

Figure 2A:
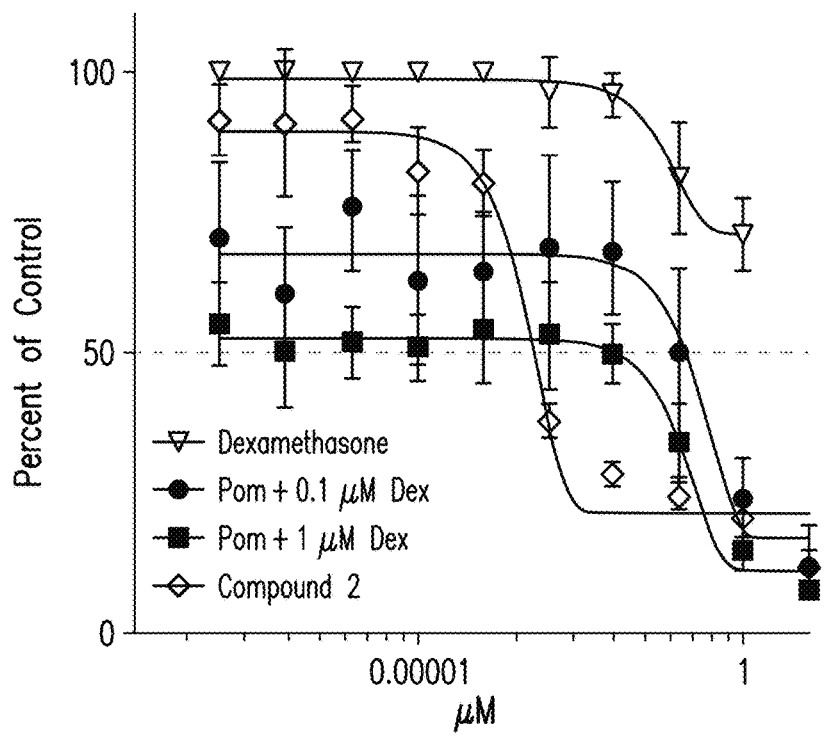
Figure 2B:
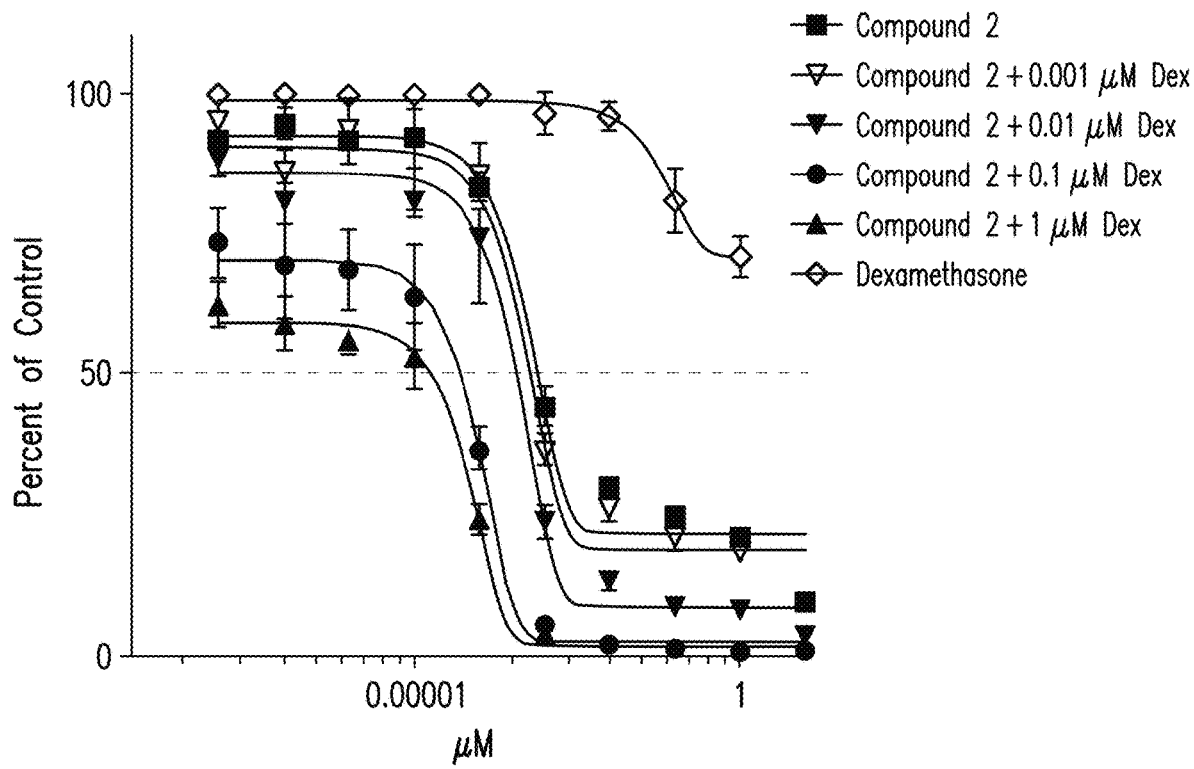

FIG. 2. Comparison of the anti-proliferative activity of pomalidomide-dexamethasone combination treatment and single agent Compound 2 (A), and with combination treatment with Compound 2-dexamethasone (B) in lenalidomide-resistant MM cells H929-1051. Proliferation was assessed using an ATP determination assay (CellTiter-Glo) after 120 h treatment. The percent control was calculated by subtracting the background and normalizing to the DMSO control (100% of control). Each data point represents the mean of at least three independent experiments in duplicate.

Figure 3A:
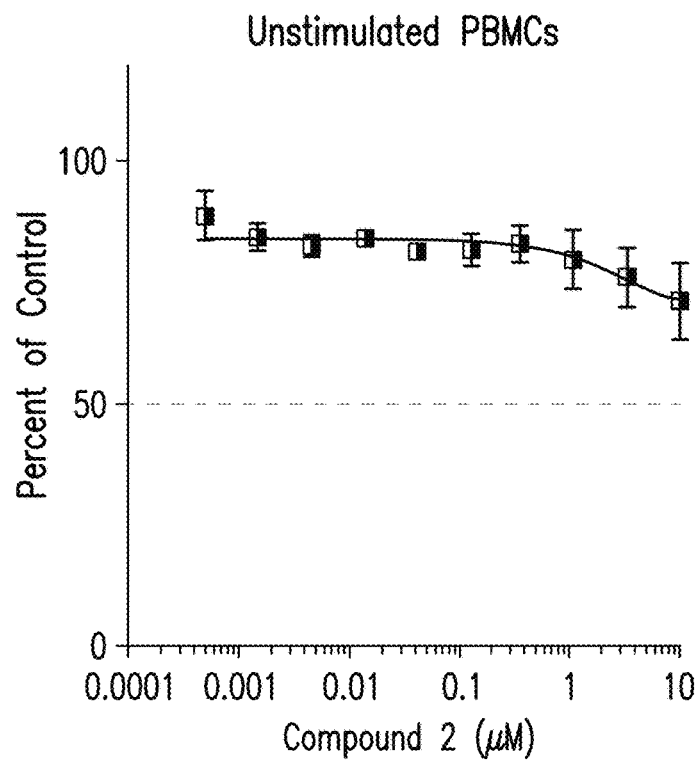
Figure 3B:
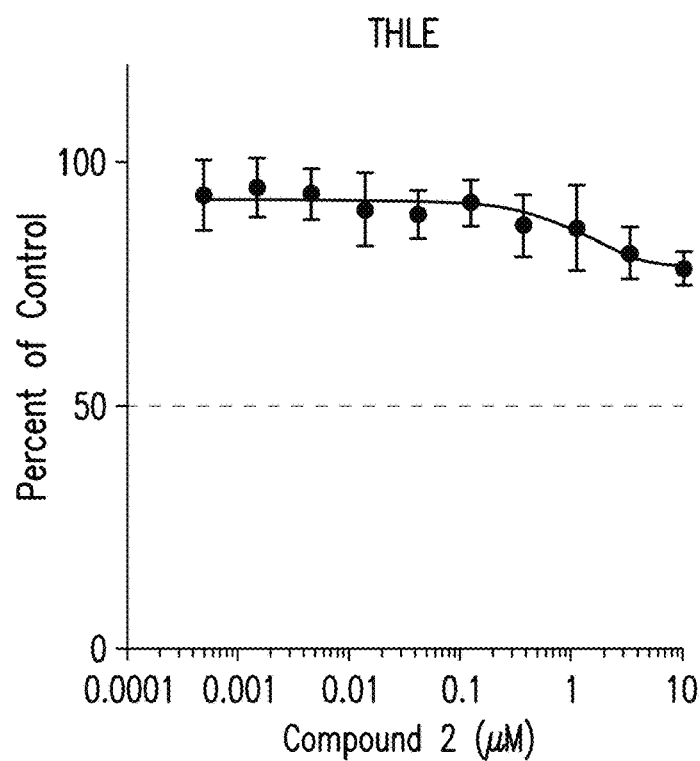

FIG. 3. (A) Anti-proliferative effects on unstimulated PBMCs and (B) THLE-2, treated with Compound 2 for 72 h were assessed using an ATP determination assay (CellTiter-Glo). The percent control was calculated by subtracting the background and normalizing to the DMSO control (100% of control).

Figure 4:
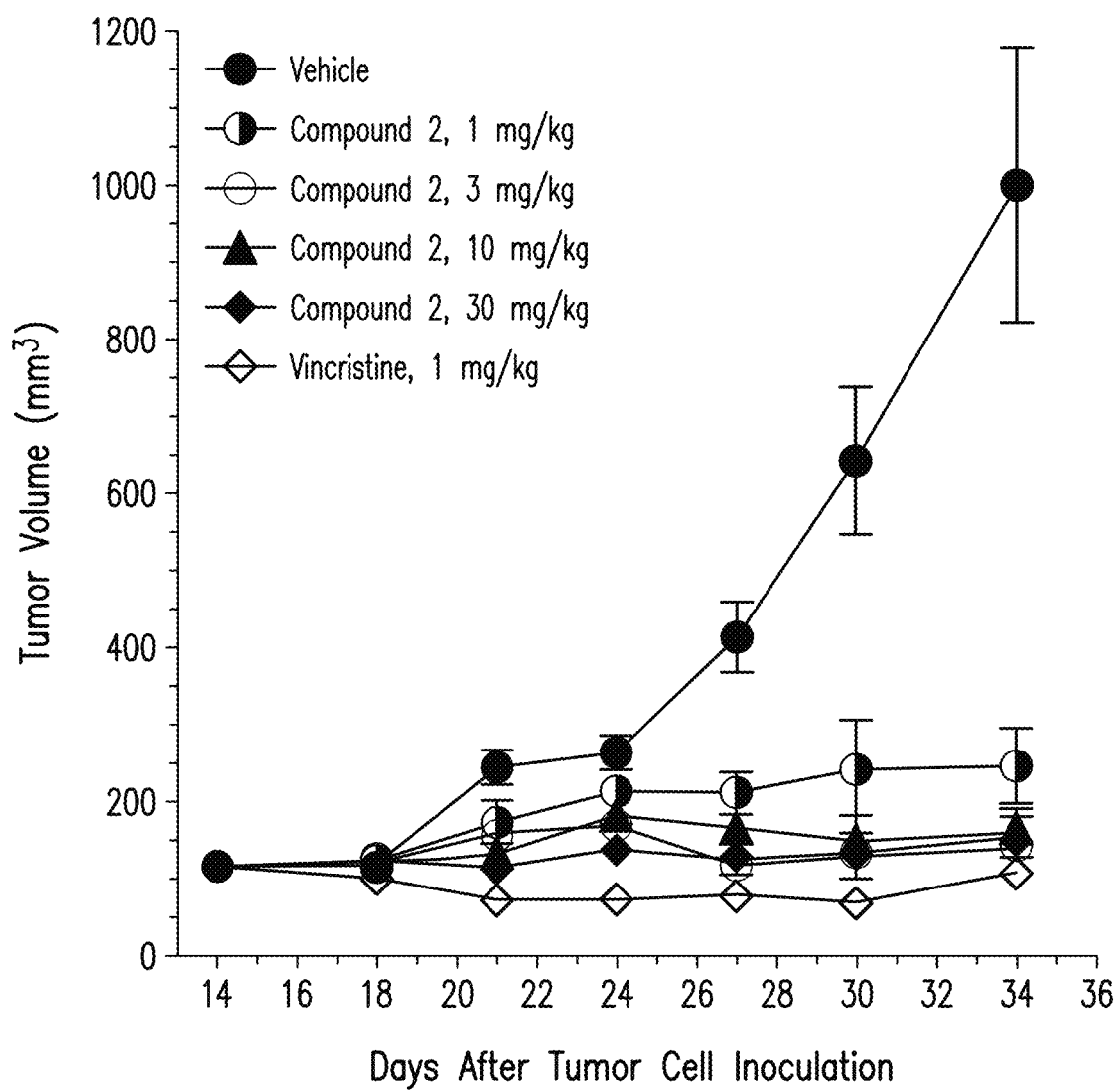

FIG. 4. Antitumor activity of Compound 2 with continuous dosing in lenalidomide-resistant H929-1051 xenograft model. Female SCID mice were inoculated with 10×10$^6$ H929-1051 tumor cells into the right flank. Mice were randomized into treatment groups (n=10/group) at the time of treatment initiation. Test article treatment started on Day 14 when the tumors were approximately 120 mm$^3$.

Figure 5:
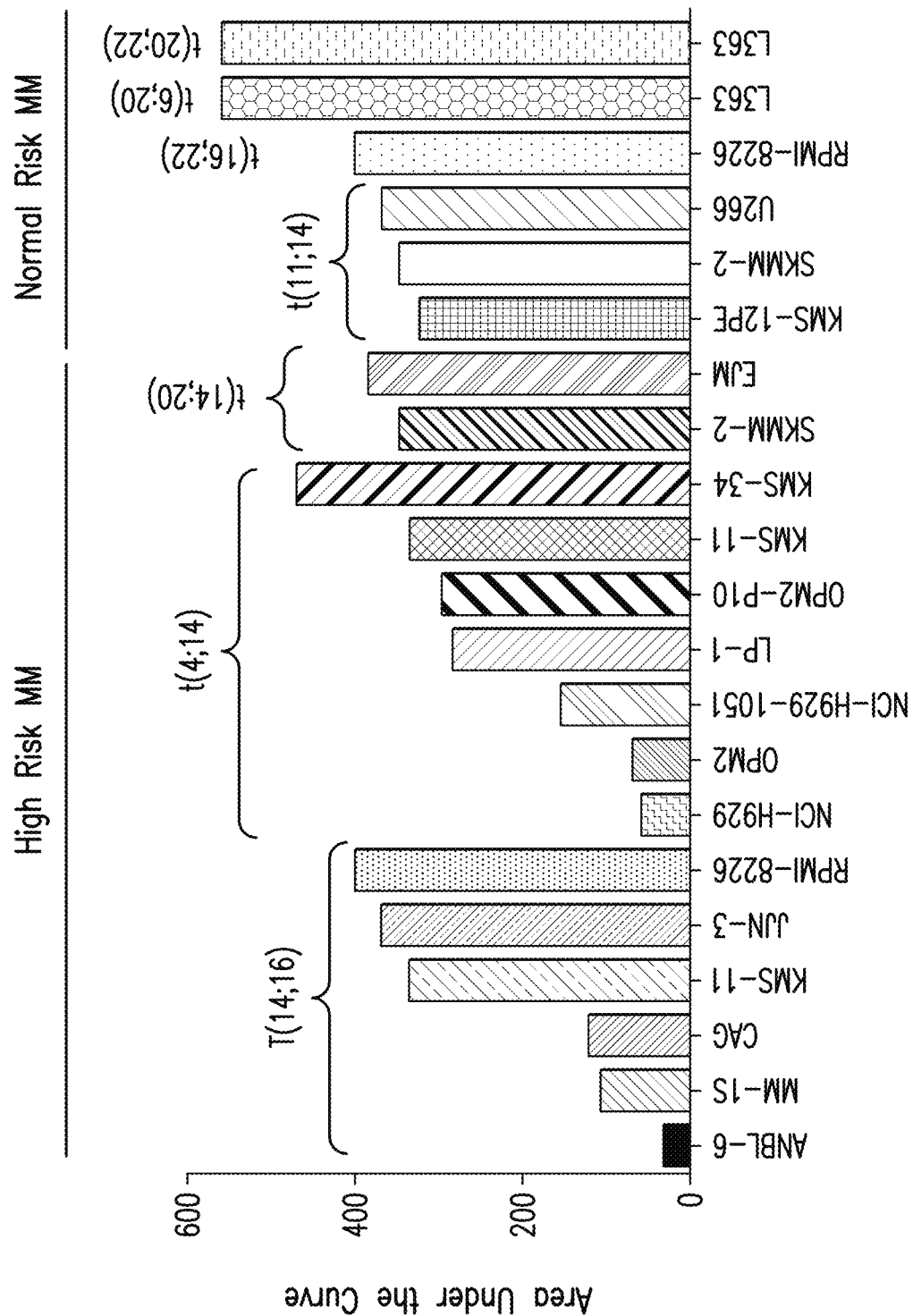

FIG. 5: Compound 2 antiproliferative activity in multiple myeloma cell lines grouped by chromosomal translocations. Graph represents the area under the curve (AUC) of concentration-response growth curves measuring live cell numbers by flow cytometry for 15 MM cell lines containing common translocations found in MM. The AUC value reported corresponds to the area under the dose response curve in which values of 0 correspond to complete reduction in proliferation/viability at all doses and values of 10000 correspond to no reduction of proliferation/viability. Cell lines are grouped first by chromosomal translocation found and, second, by whether the translocation is known to be high risk or not.

Figure 6:
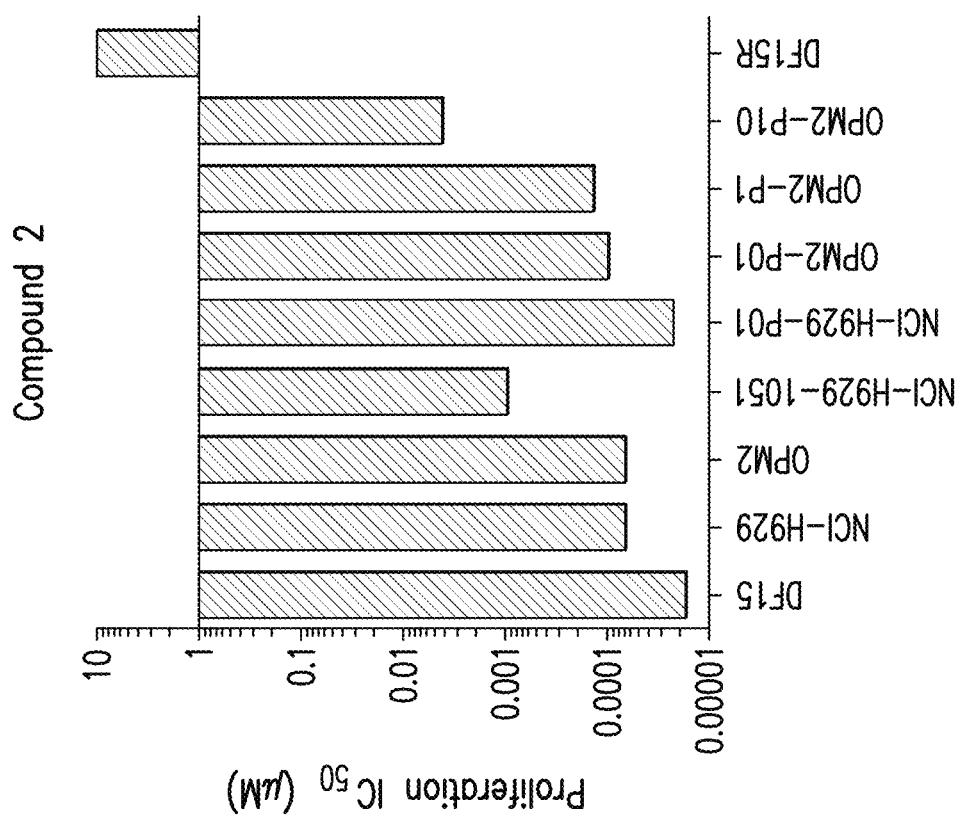
Figure 6:
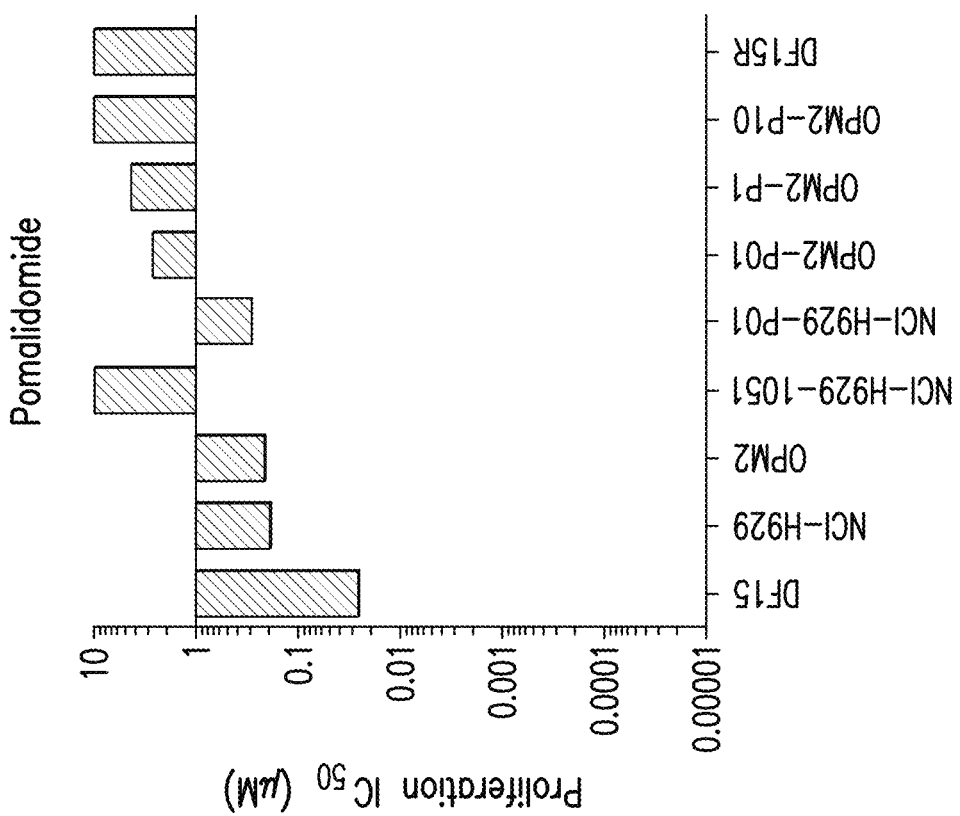

FIG. 6: Antiproliferative activity of Compound 2 and pomalidomide in lenalidomide- and pomalidomide-resistant multiple myeloma cell lines. $IC_{50}$=concentration of Compound 2 and pomalidomide resulting in 50% inhibition of cell growth compared to control. Graph showing the comparison of Compound 2 and pomalidomide antiproliferative $IC_{50}$ values (bars) was determined using CellTitre-Glo assay in parental (DF15, NCI-H929 and OPM2), lenalidomide-resistant (NCI-H929-1051), or pomalidomide-resistant (NCI-H929-P01, OPM2-P01, OPM2-P1, OPM2-P10 and DF15R) MM cell lines presented in Table 11.

Figure 7:
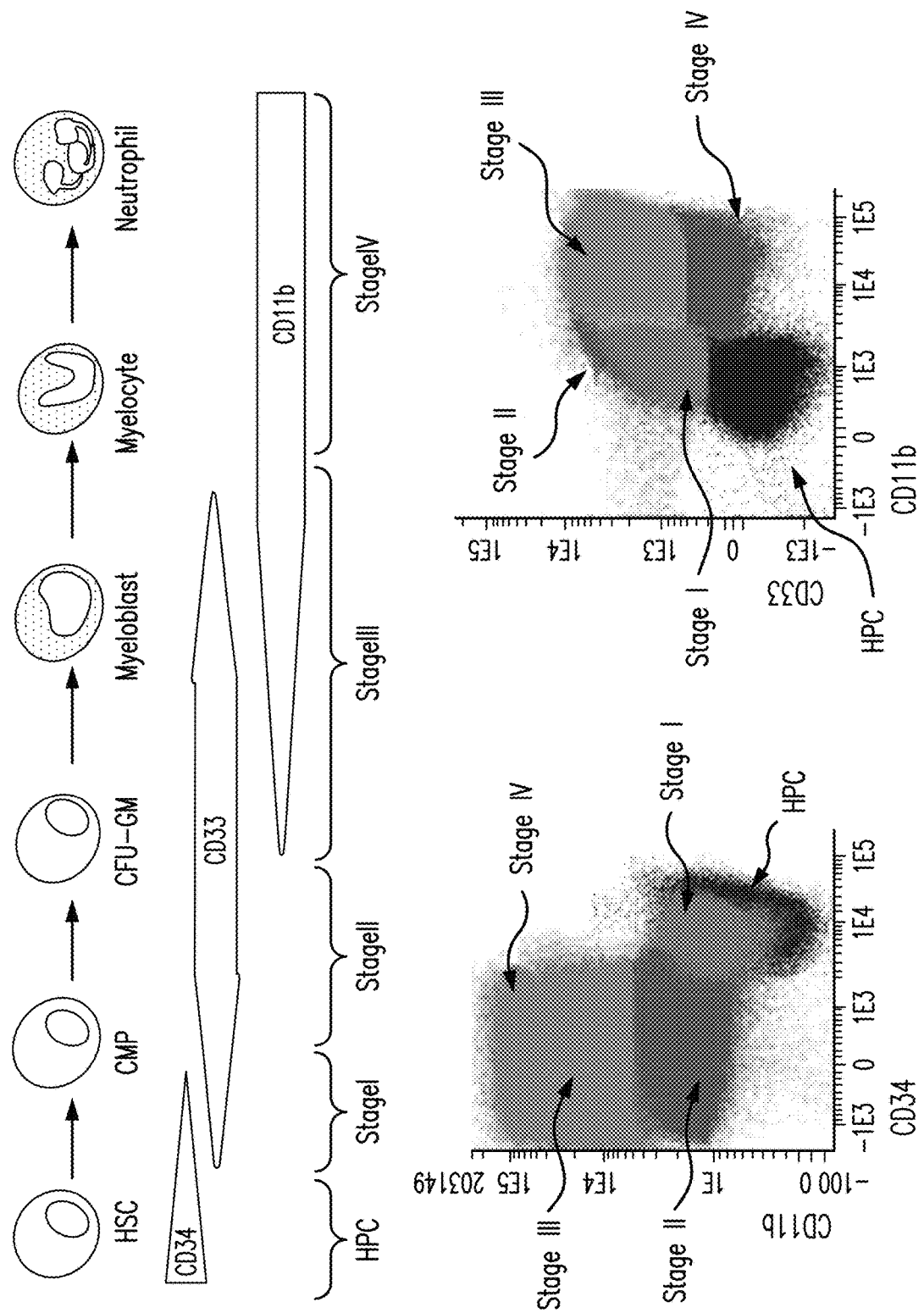

FIG. 7: Gating strategy for myeloid subpopulations.

Figure 8:
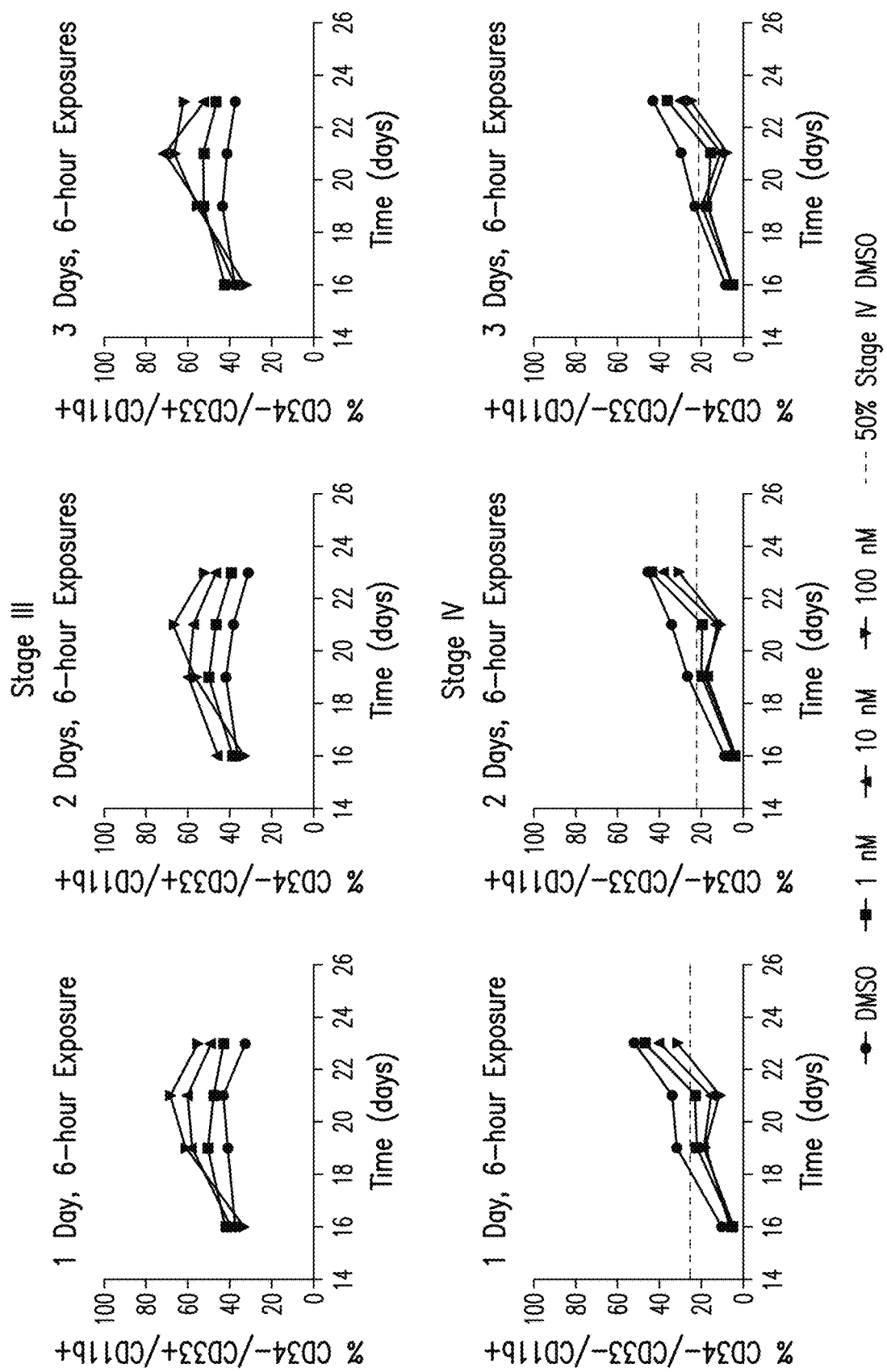

FIG. 8: Last stages of in vitro neutrophil progenitor differentiation-effects of short daily Compound 2 exposures for up to three days. $CD34^+$ cells derived from healthy donor bone marrow were exposed to Compound 2 at concentrations of 1, 10, and 100 nM on each of 1, 2, or 3 consecutive days. Only live cells were included in the analysis. Data are the mean of results for Donors 1 and 2 and represent an example of percentage of Stage III and Stage IV cells defined as $CD34^-/CD33^+/CD11b^+$ and $CD34^-/CD33^-/CD11b^+$, respectively, after 6 h of exposure.

Figure 9:
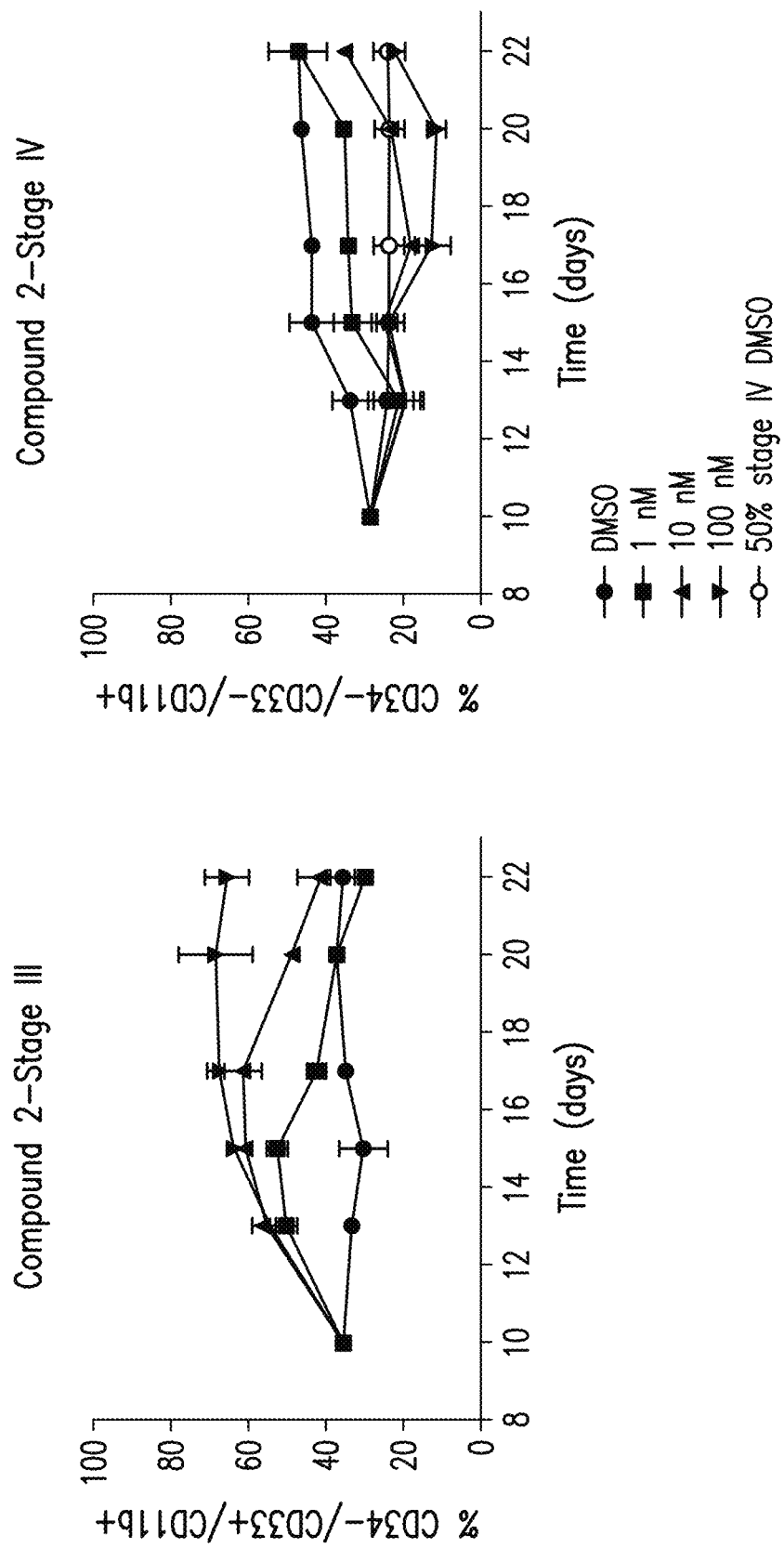

FIG. 9: Late stage maturation of neutrophil progenitors following 6-hour exposures to Compound 2 on 3 consecutive days. $CD34^+$ cells derived from healthy donor bone marrow were exposed to Compound 2 at concentrations of 1, 10, or 100 nM for 6 h on each of 3 consecutive days starting on Day 10. Data represent the mean percentage of Stage III cells defined as $CD34^-/CD33^+/CD11b^+$ and the percentage of Stage IV cells defined as $CD34^-/CD33^-/CD11b^+$ from Donors No. 1 and No. 2. Error bars represent standard deviation.

Figure 10:
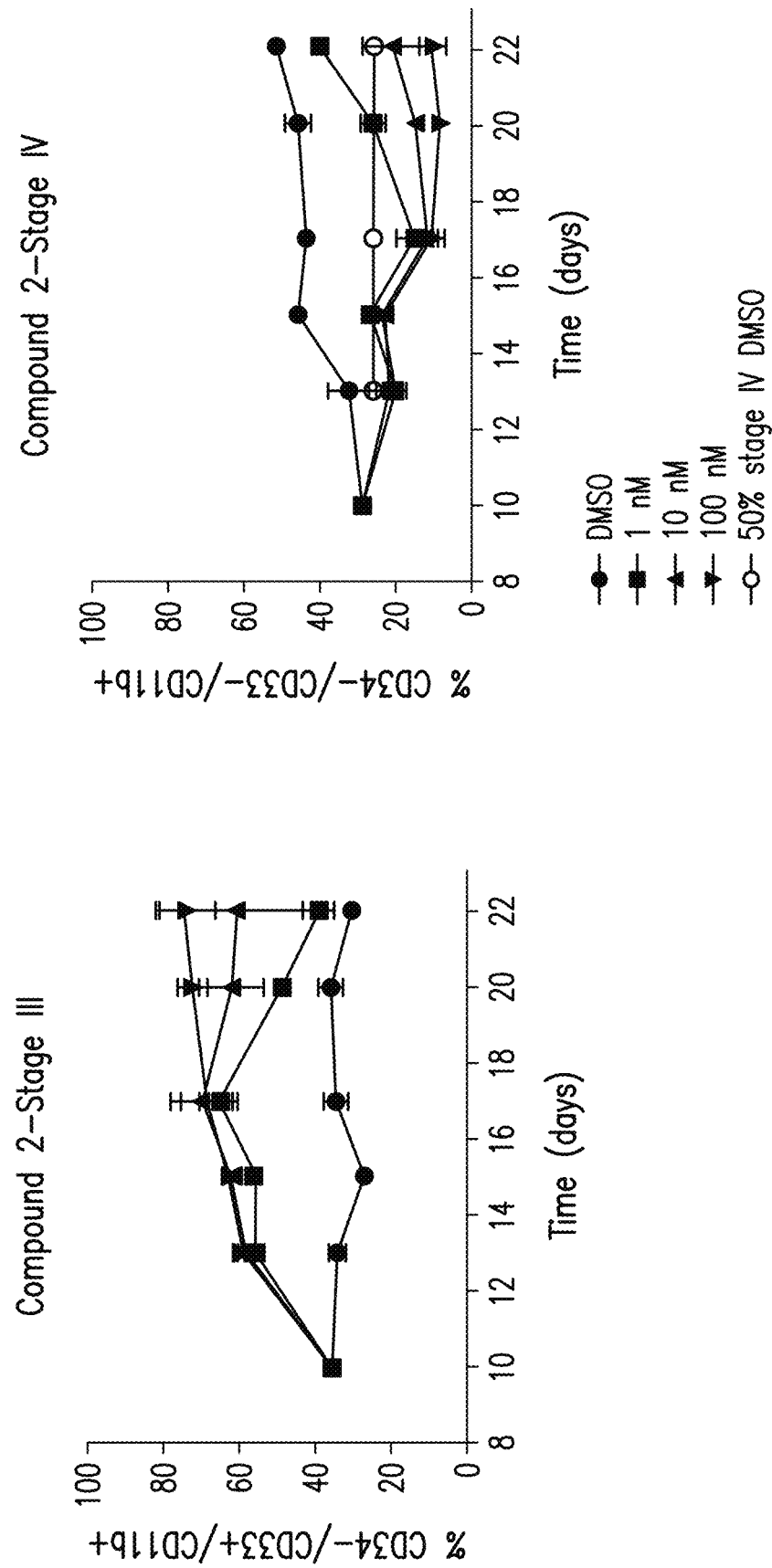

FIG. 10: Late stage maturation of neutrophil progenitors following 6-hour exposures to Compound 2 on 5 consecutive days. $CD34^+$ cells derived from healthy donor bone marrow were exposed to Compound 2 at concentrations of 1, 10, or 100 nM for 6 h on each of 5 consecutive days starting on Day 10. Data represent the mean percentage of Stage III cells defined as $CD34^-/CD33^+/CD11b^+$ and the percentage of Stage IV cells defined as $CD34^-/CD33^-/CD11b^+$ from Donors No. 1 and No. 2. Error bars represent standard deviation.

Figure 11:
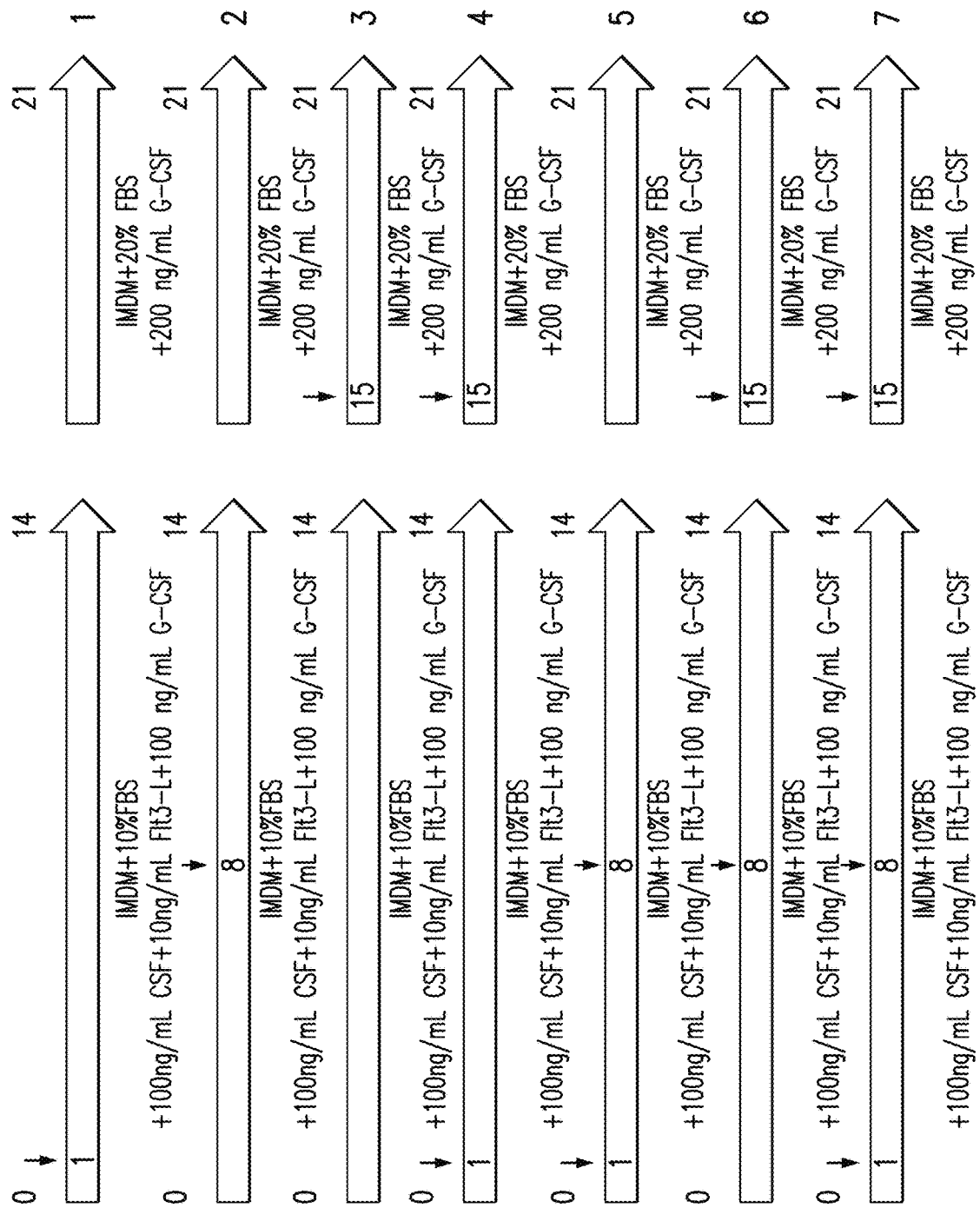

FIG. 11: Treatment schedule diagrams for single agent dexamethasone.

Figure 12:
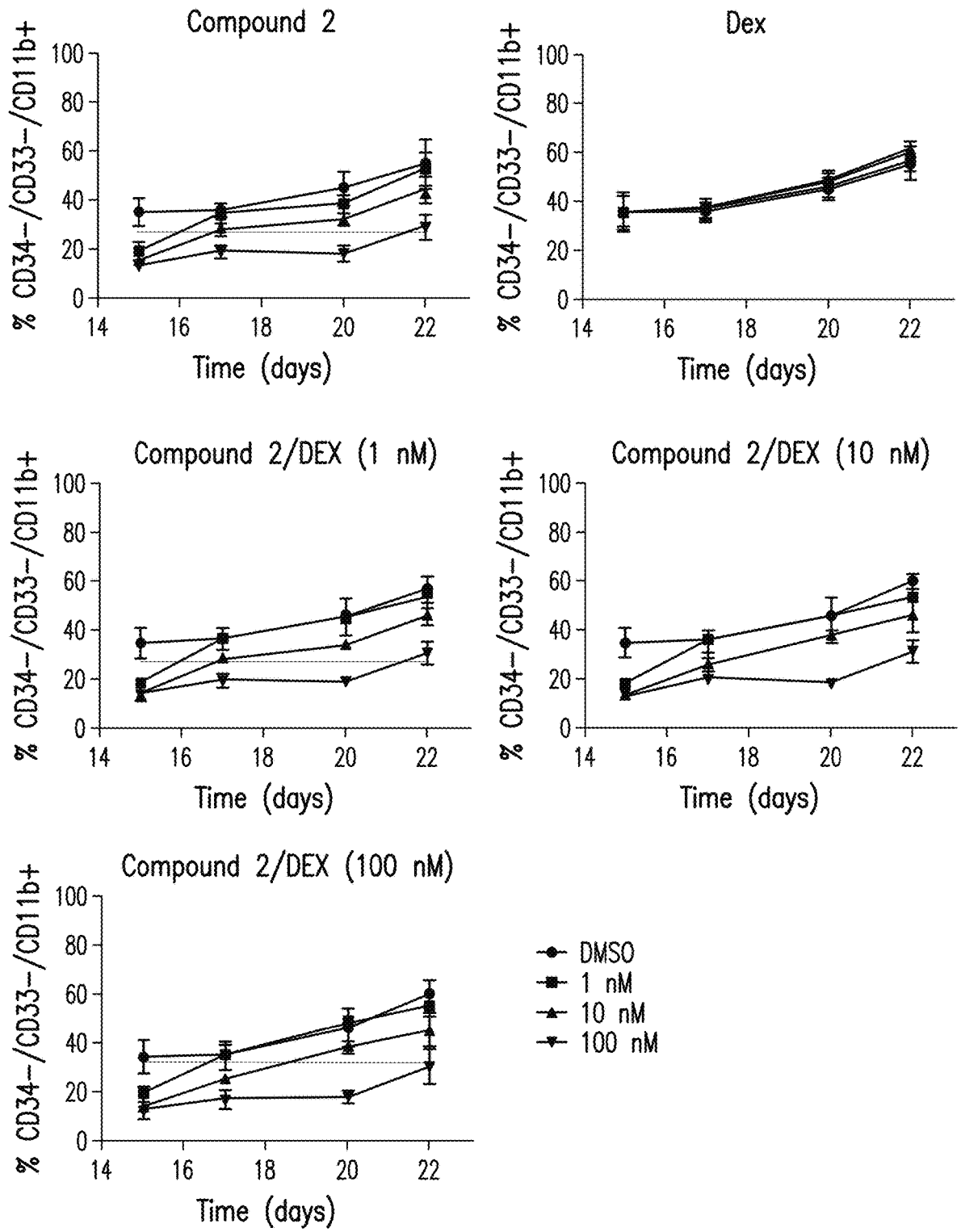

FIG. 12: Percentage of mature neutrophils during myeloid differentiation after one exposure to dexamethasone or Compound 2 alone or in combination at different concentrations. $CD34^+$ cells derived from healthy donor bone marrow were exposed to Compound 2 (for 6 h) and dexamethasone (for 30 h) alone (top row), or in combination (bottom row), at concentrations of 1, 10, or 100 nM at Day 13. In each of the bottom panels, the concentration of Compound 2 was varied and the concentration of dexamethasone was held constant at 1 nM (left), 10 nM (middle), or 100 nM (right). For the combinations, cultures were exposed to both agents simultaneously for 6 h. Cells were then washed and reincubated with dexamethasone for the next 24 h. Then cells were washed and reincubated without Compound 2 or dexamethasone for the remainder of the study. Data represent the percentage of Stage IV cells defined as $CD34^-/CD33^+/CD11b^+$ from Donors 3, 4, and 5. The red line represents 50% of the level of Stage IV cells in the DMSO control.

Figure 13:
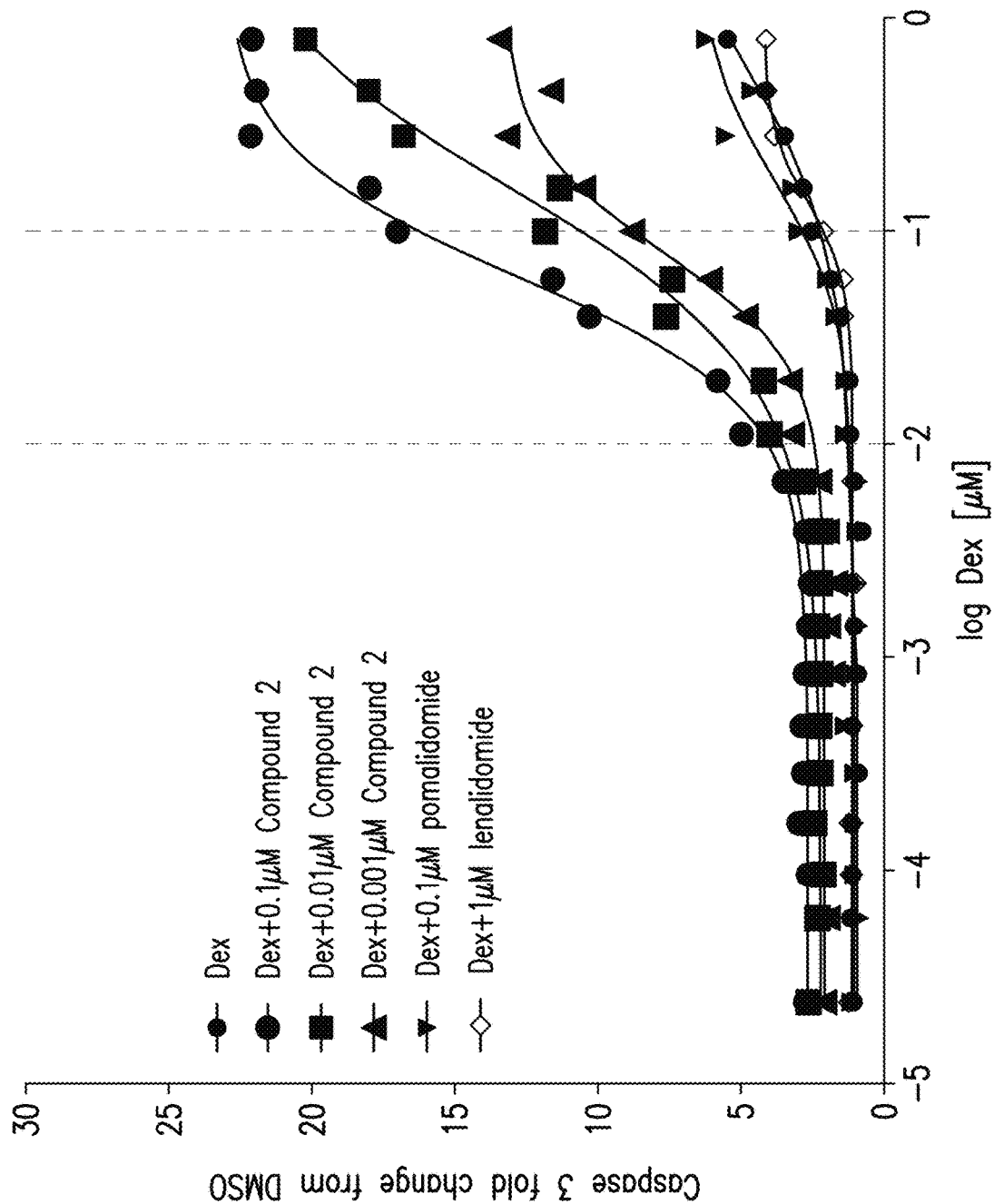

FIG. 13: The effect of treatment with dexamethasone alone or in combination with Compound 2, lenalidomide and pomalidomide, on apoptosis in a lenalidomide-resistant multiple myeloma cell line. The y-axis shows the fold change for caspase-3 from DMSO and the x-axis is the log concentration of dexamethasone.

Figure 14:
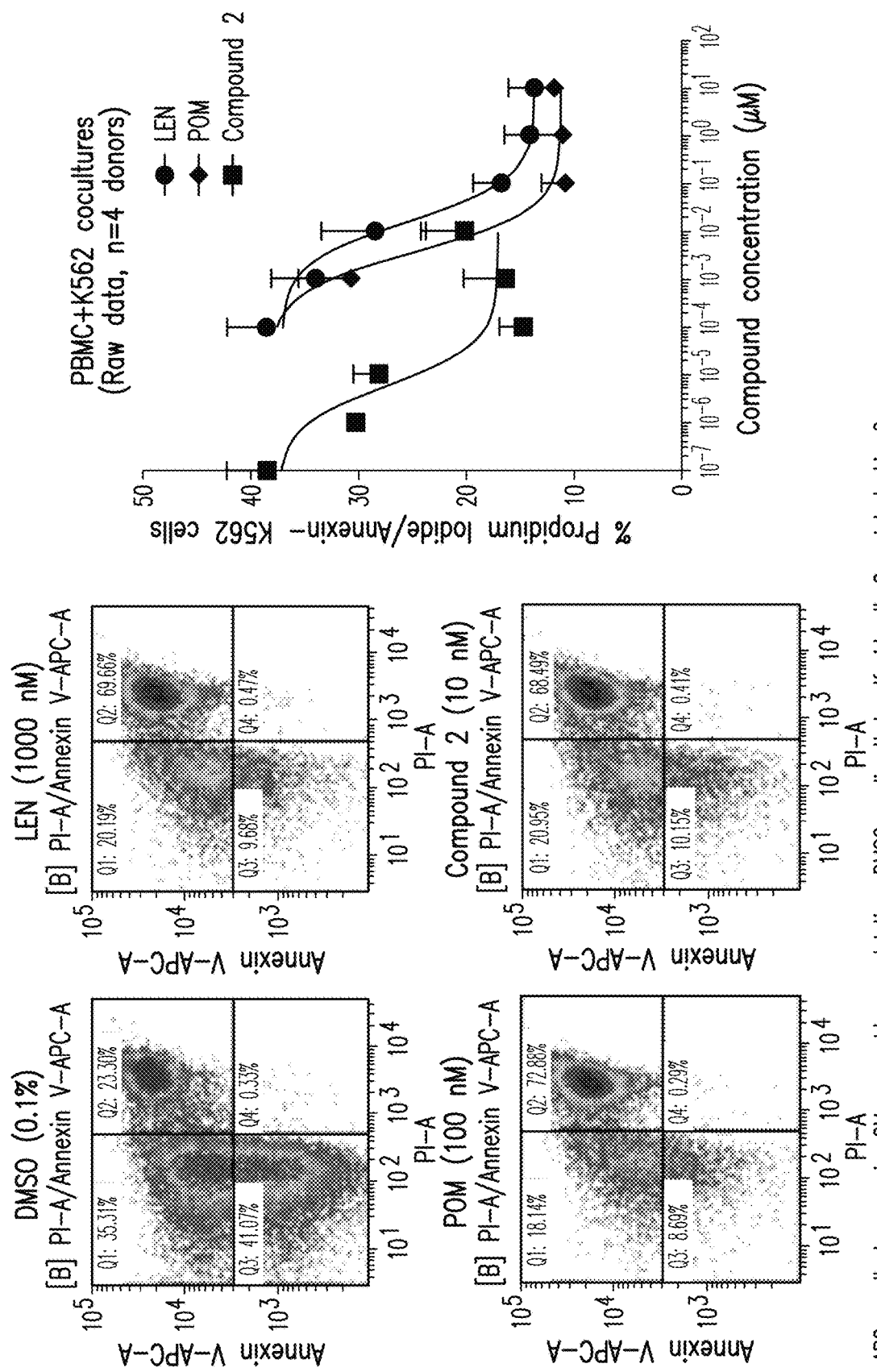

FIG. 14: Compound 2 directly activates human peripheral blood mononuclear cells (PBMCs) to lyse K562 erythromyelocytic leukemia cells in a concentration-dependent manner. (Left) Representative fluorescence-activated cell sorting plots of K562 cells co-cultured with human PBMCs that had been preincubated with Compound 2, lenalidomide, pomalidomide, or DMSO. (Right) Raw data of the percentage of PI-Annexin V-K562 cells showing a concentration-dependent decrease in viable K562 cells in co-culture. Data are presented as mean with error bars representing standard error of the mean.

Figure 15:
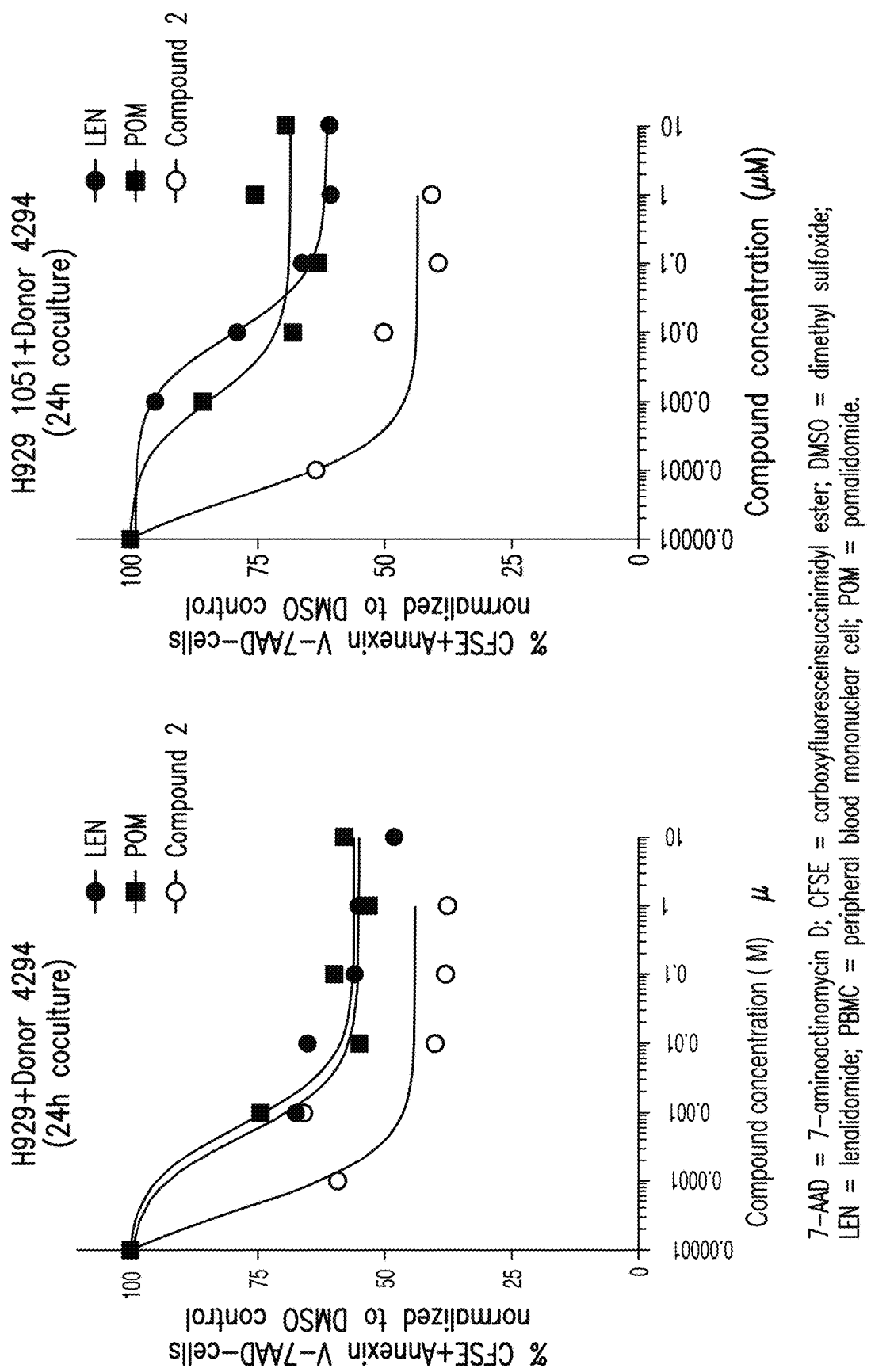
Figure 16A:
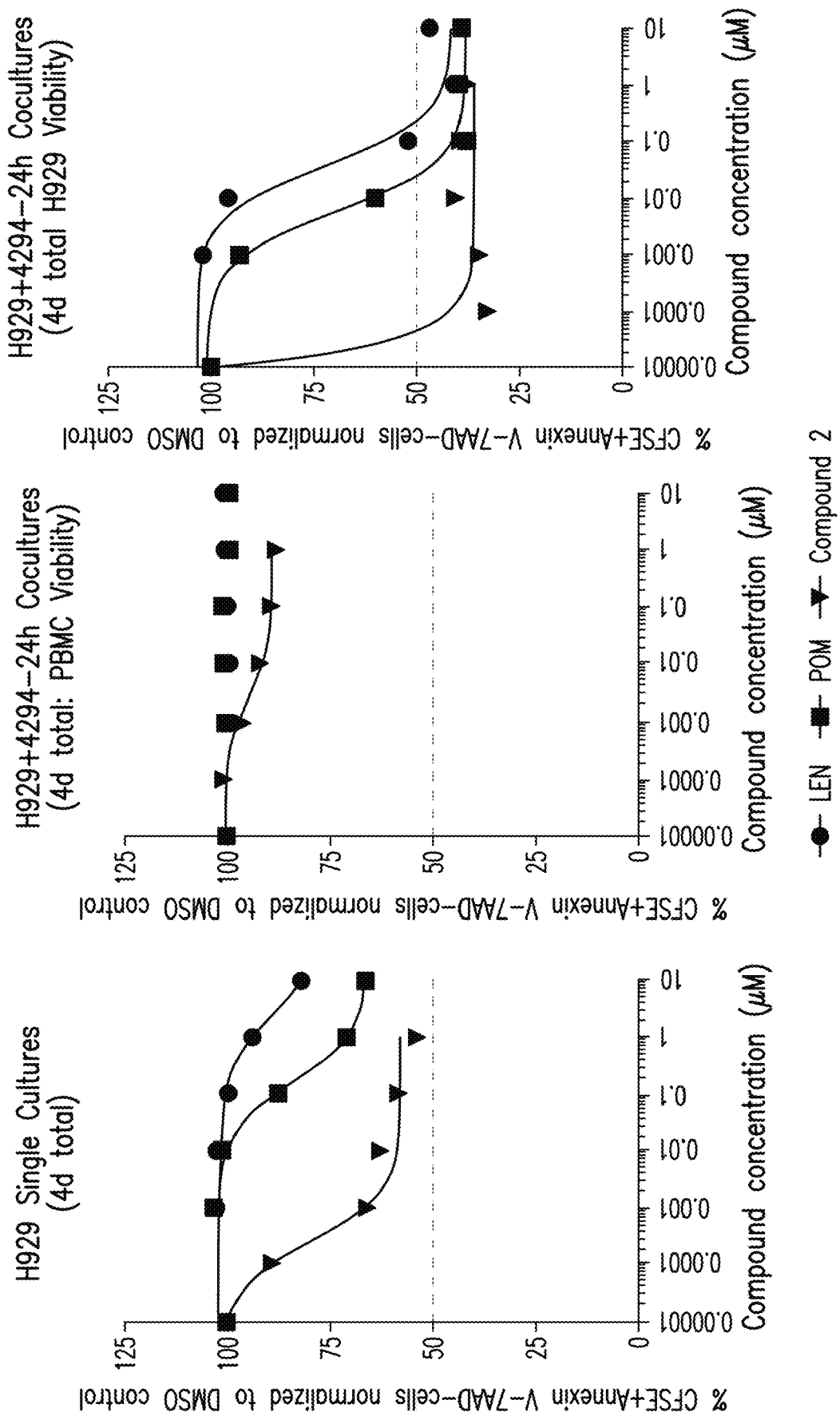
Figure 16B:
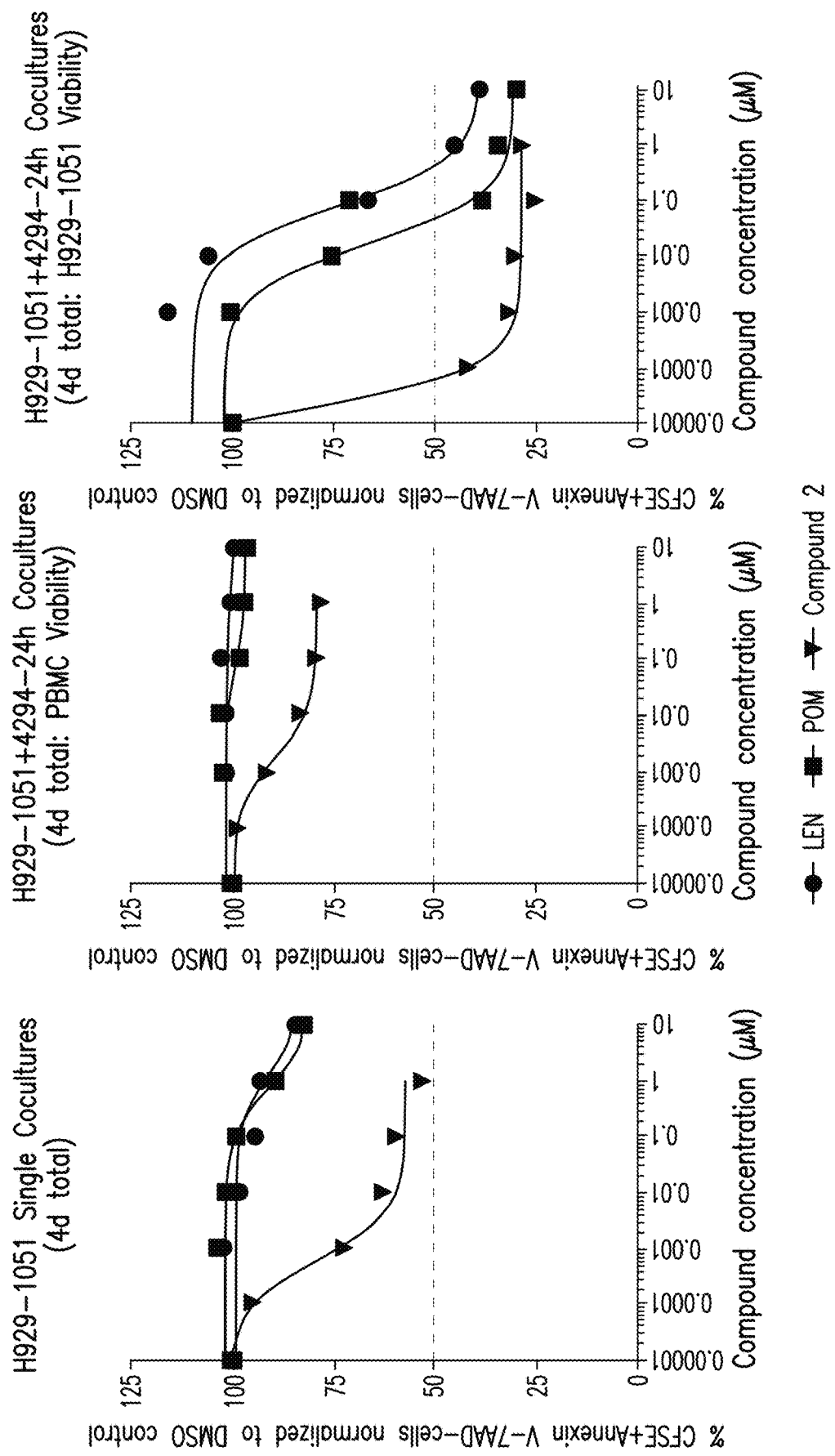
Figure 16C:
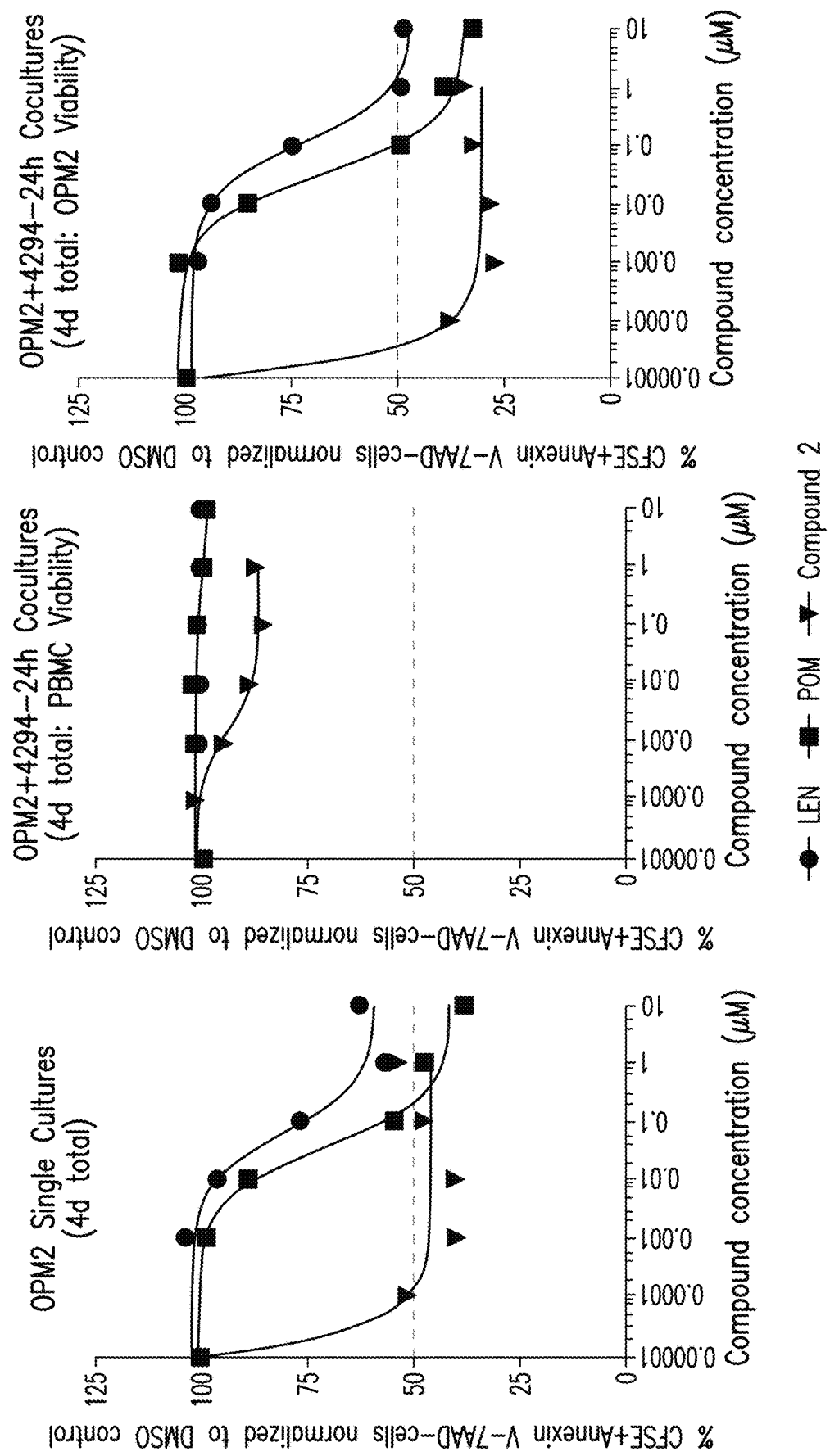
Figure 16D:
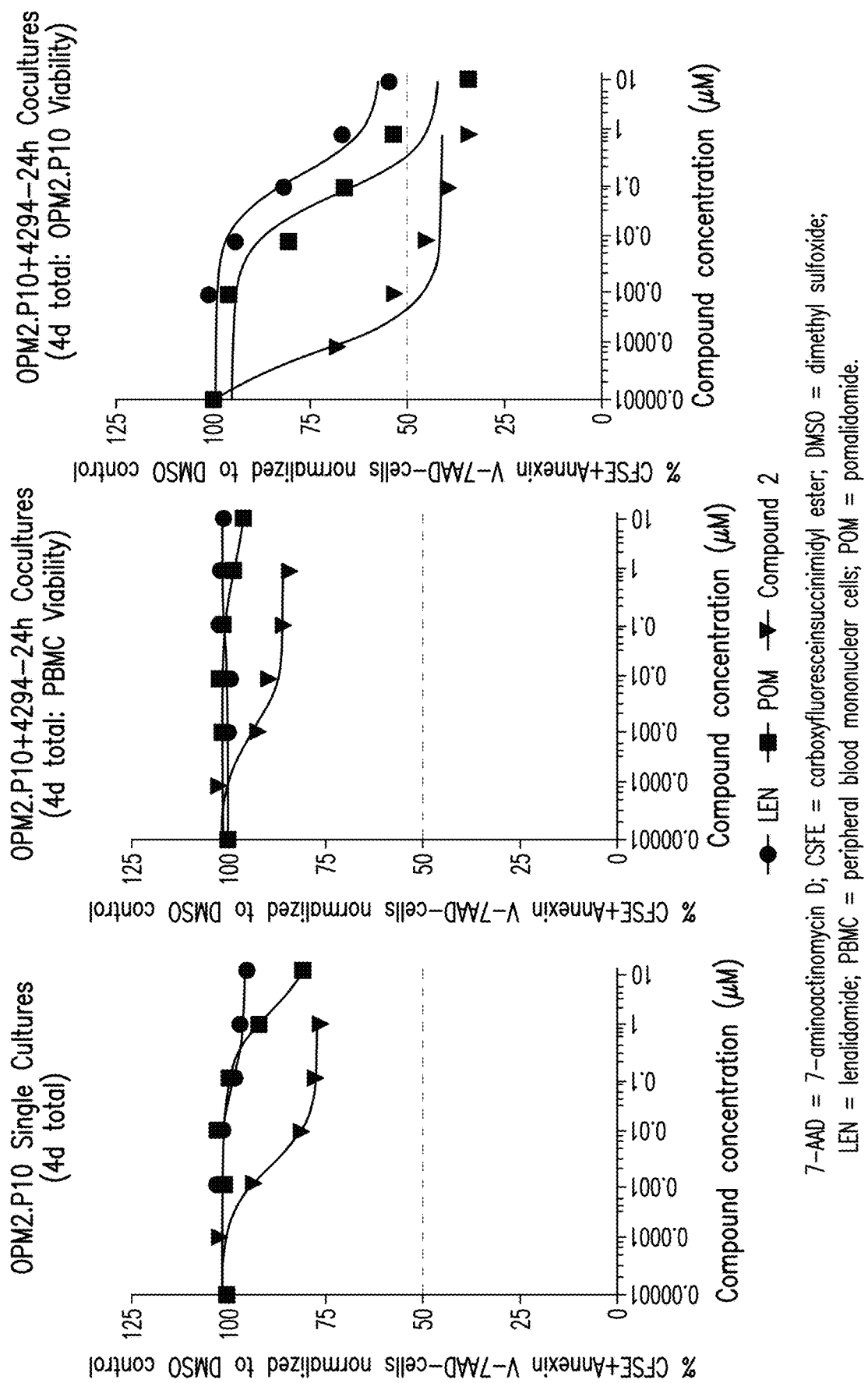

FIG. 15: Immune cells are directly activated by Compound 2 to lyse lenalidomide-sensitive and lenalidomide-resistant multiple myeloma cell lines. Peripheral blood mononuclear donor cells (PBMCs) (effector cells) were pretreated with the indicated test articles or Compound 2 for 2 h before being cultured on anti-CD3 antibody-coated plates for 72 h. Prior to co-culture with untreated CFSE labeled multiple myeloma cell lines, the PBMCs were washed and placed in media with no compound present and then co-cultured with the multiple myeloma cell lines (target cells) for 24 h. An increase in immune cell-mediated multiple myeloma cell killing was evident in Compound 2-treated PBMCs co-cultured (Target:Effector ratio of 1:5) with either (A) NCI-H929 cells or (B) H929-1051 cells.

FIG. 16: Compound-primed immune cells show enhanced tumor cell killing when multiple myeloma cells are pretreated with lenalidomide, pomalidomide, or Compound 2 prior to co-culture. Peripheral blood mononuclear cells were preincubated with lenalidomide, pomalidomide, or Compound 2 for 2 h before being cultured on anti-CD3 antibody-coated plates for 72 h. At the same time, 4 multiple myeloma (MM) cells lines were cultured in medium containing test articles. After 72 h, cells were co-cultured together for 24 h (Target:Effector [T:E] ratio of 1:5). An increase in immune cell mediated MM killing was evident in the co-cultures (graphs on the right in each row) compared with the MM single cultures (graphs on left in each row) in all cell types tested (A) NCI-H929, (B) H929-1051, (C) OPM2, and (D) OPM2 P10 cell lines. The compounds had little effect on PBMC viability (shown in middle graphs in each row).

Figure 17:
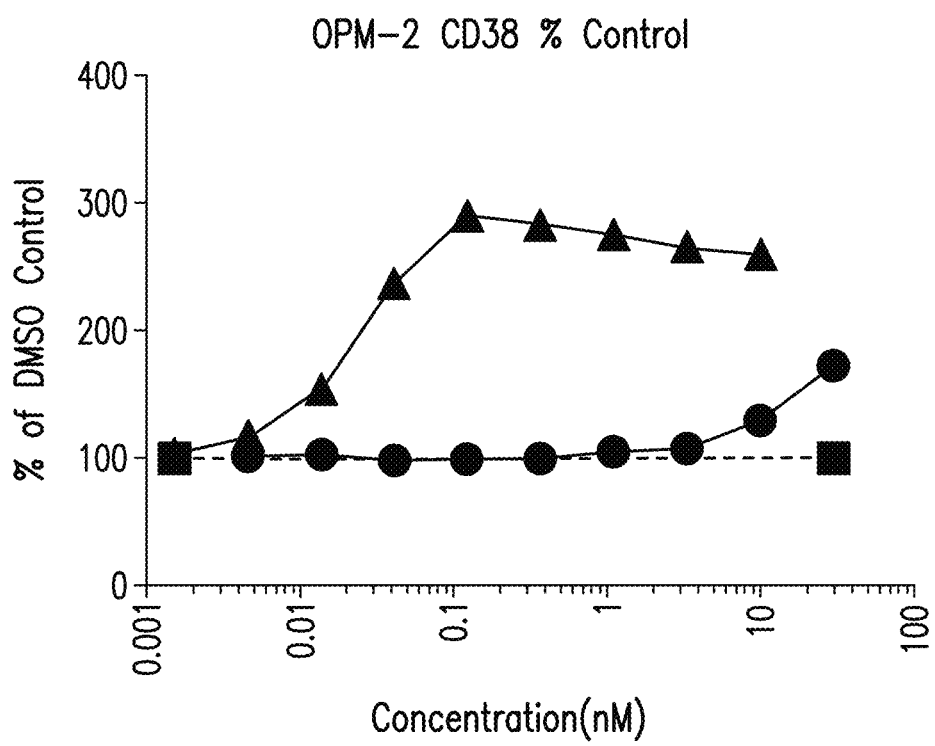
Figure 17:
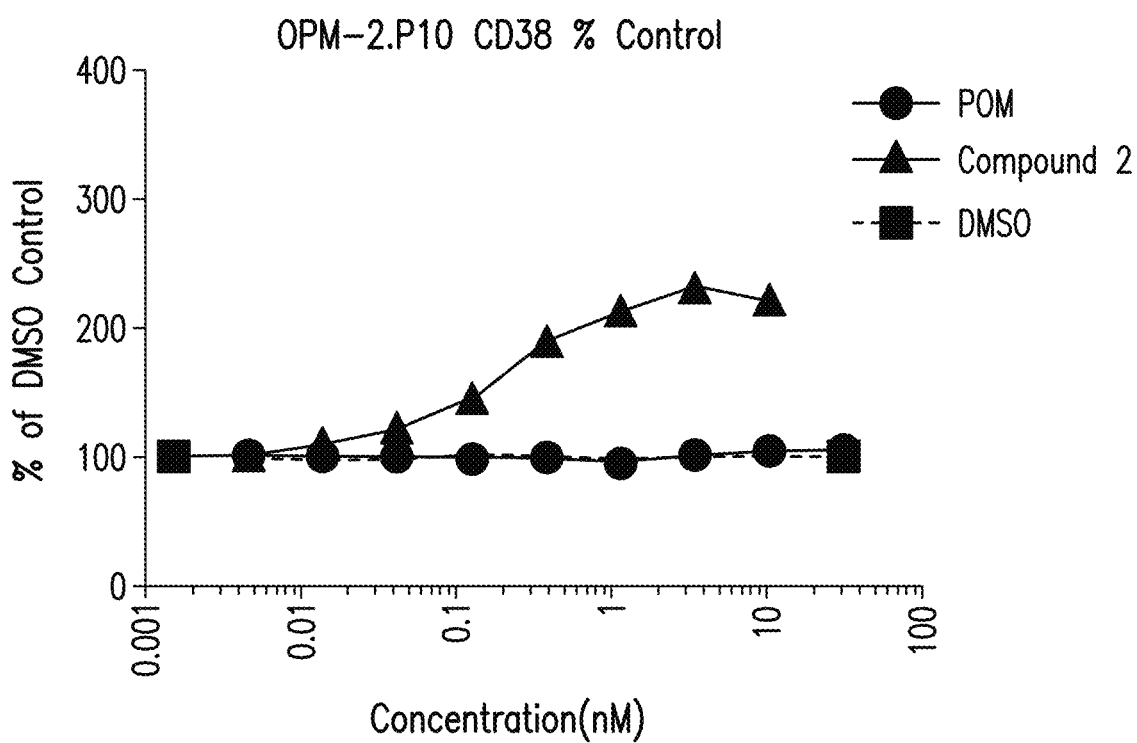

FIG. 17: Compound 2 upregulates CD38 expression in MM cell lines. The cell surface expression of CD38 was evaluated in MM cells pretreated with Compound 2 or pomalidomide for 72 h. The dose response effects are shown for OPM-2 and OPM-2.P10 cell lines.

FIG. 18: Compound 2 increases daratumamab-mediated ADCC of MM cells. Seven MM cell lines were treated with sub-lethal concentrations of Compound 2 or pomalidomide for 72 h prior to co-culturing with NK cells at an effector to target [E:T] ratio of 10:1 for the ADCC assay. Graphs illustrate representative data obtained for the 7 MM cell lines. The assays were performed twice with NK cells from two different donors. DMSO control is the baseline NK cell activity with untreated tumor cells; the Isotype and Dara are the NK cell activity in the presence of isotype control and daratumamab, respectively, with untreated tumor cells; the Isotype+Compound and Dara+Compound are the NK cell activity in the presence of isotype control and daratumamab, respectively, with treated tumor cells.

FIG. 19: Compound 2 enhances the daratumamab-mediated ADCP of MM cells. Phagocytosis assays were performed with an effector to target ratio [E:T] of 2:1. Six MM cell lines+/−Compound 2 or pomalidomide pretreatment were subjected to daratumamab-mediated ADCP. A) Representative images of ADCP with the OPM2 cell line. Macrophages are in red and OPM2 cells are in green. B) Quantitation of phagocytosis by flow cytometry. DMSO control is the baseline NK cell activity with untreated tumor cells; the Isotype and Dara are the NK cell activity in the presence of isotype control and daratumamab, respectively, with untreated tumor cells; the Isotype+Compound and Dara+Compound are the NK cell activity in the presence of isotype control and daratumamab, respectively, with treated tumor cells.

Figure 20A:
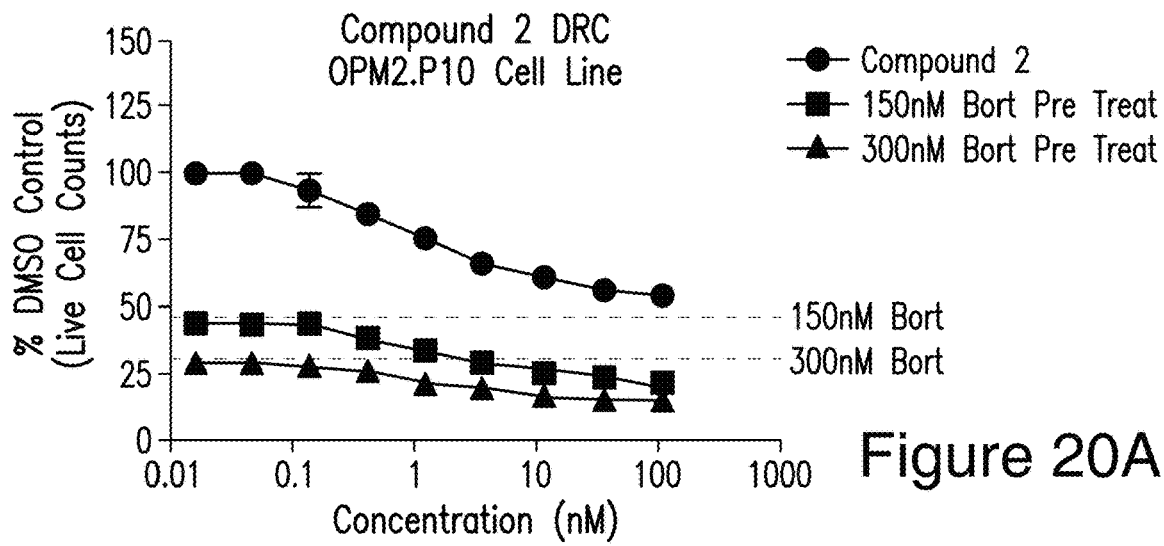
Figure 20B:
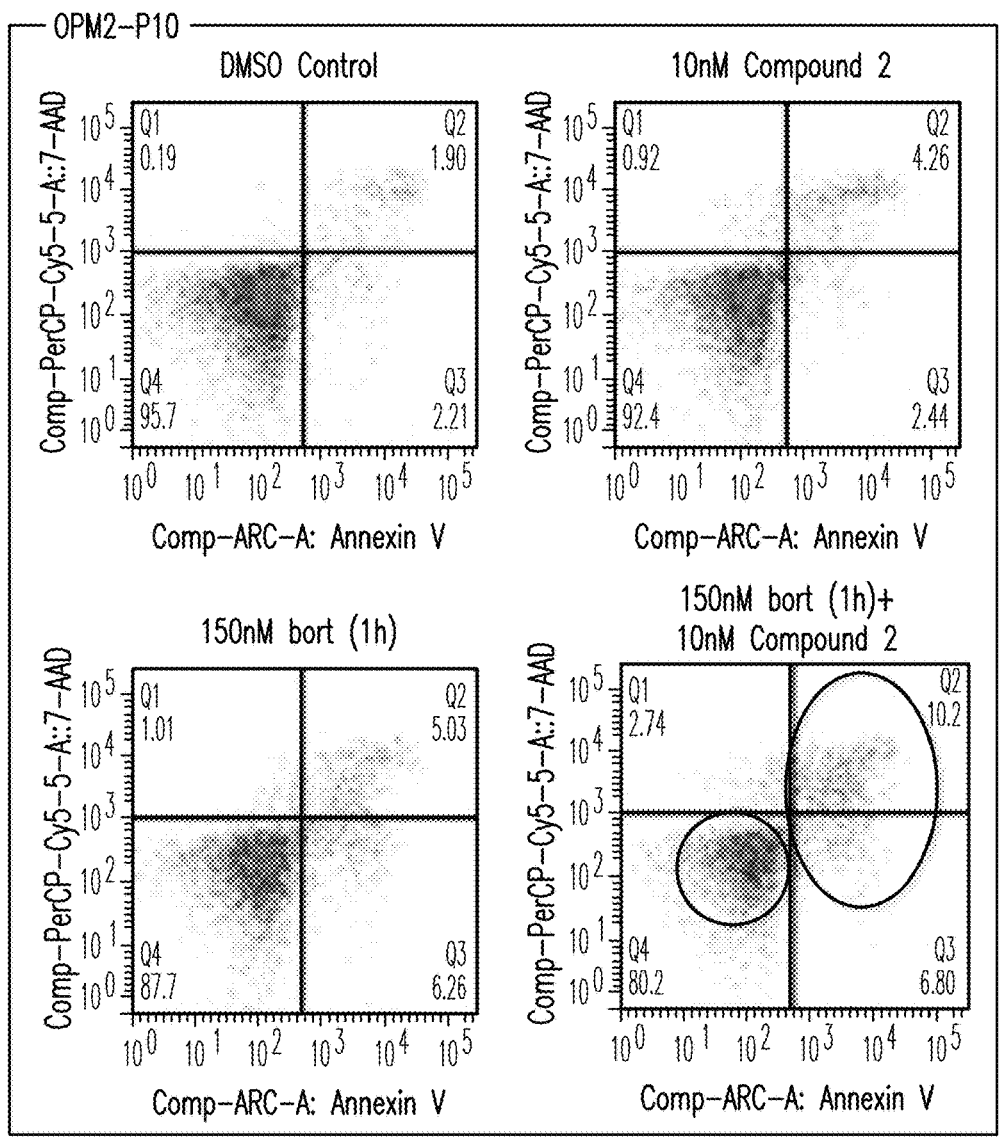

FIG. 20: Combination of Compound 2 with proteasome inhibitor results in increased apoptosis in MM cell models. MM cell lines were treated with a pulse of bortezomib or DMSO for 1 h followed by a washout. The pretreated cells were incubated with different concentrations of Compound 2 for 72 h followed by staining of samples with 7-AAD and Annexin-V solution and analysis by flow cytometry. A) Percent of live cells of Compound 2 alone or with bortezomib pretreatment. B) Scatter plots of OPM2-P10 cells at the various treatment conditions.

FIG. 21: Combination of Compound 2 with bortezomib or carfilzomib in MM cells. Four MM cell lines were treated with a pulse of bortezomib or DMSO for 1 h followed by a washout. The pretreated cells were incubated with different concentrations of Compound 2 for 72 hours followed by staining of samples with 7-AAD and Annexin-V solution and analysis by flow cytometry. A) Antiproliferative effect of Compound 2 alone or with bortezomib pretreatment. B) Antiproliferative effect of Compound 2 alone or with carfilzomib pretreatment. DRC=dose-response curve FIG. 22. Treatment of MM cells with Compound 2 in combination with histone deacetylase inhibitors, chemotherapy agents, Bcl-2 inhibitors, Mcl-1 inhibitors, BET inhibitors, or LSD-1 inhibitors is shown. Synergy calculations were performed for treatment with Compound 2 in combination with 13 small molecule inhibitors across a panel of MM cell lines. The blue color boxes illustrate the percentage of wells that are synergistic when combined with Compound 2. The * represents the significance of the surface response difference from the null model.

Figure 23:
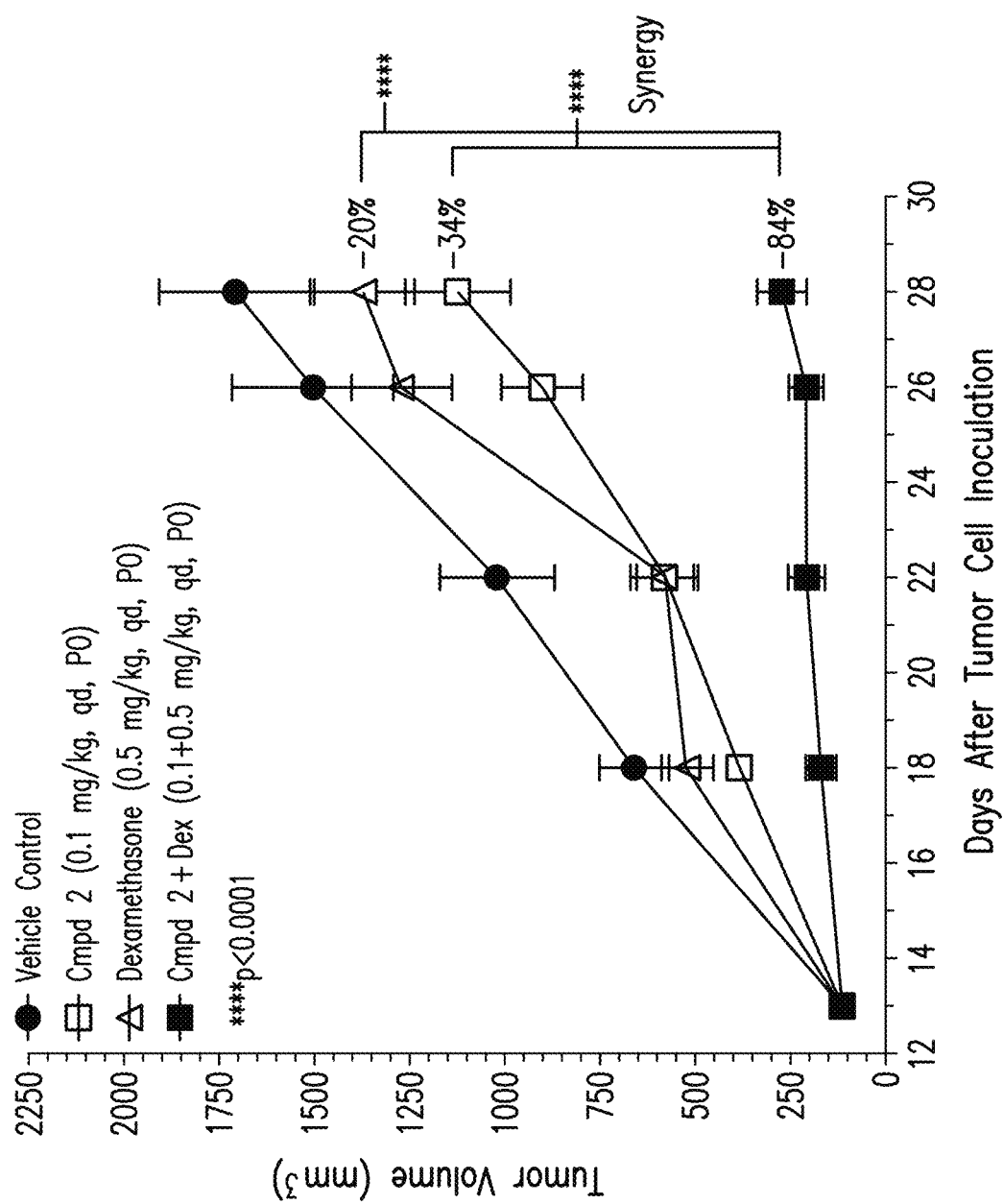

FIG. 23: The effect of treatment with Compound 2 (0.1 mg/kg, qd) and dexamethasone (0.5 mg/kg, qd) as single agents and in combination in the lenalidomide resistant H929-1051 xenograft model.

Figure 24:
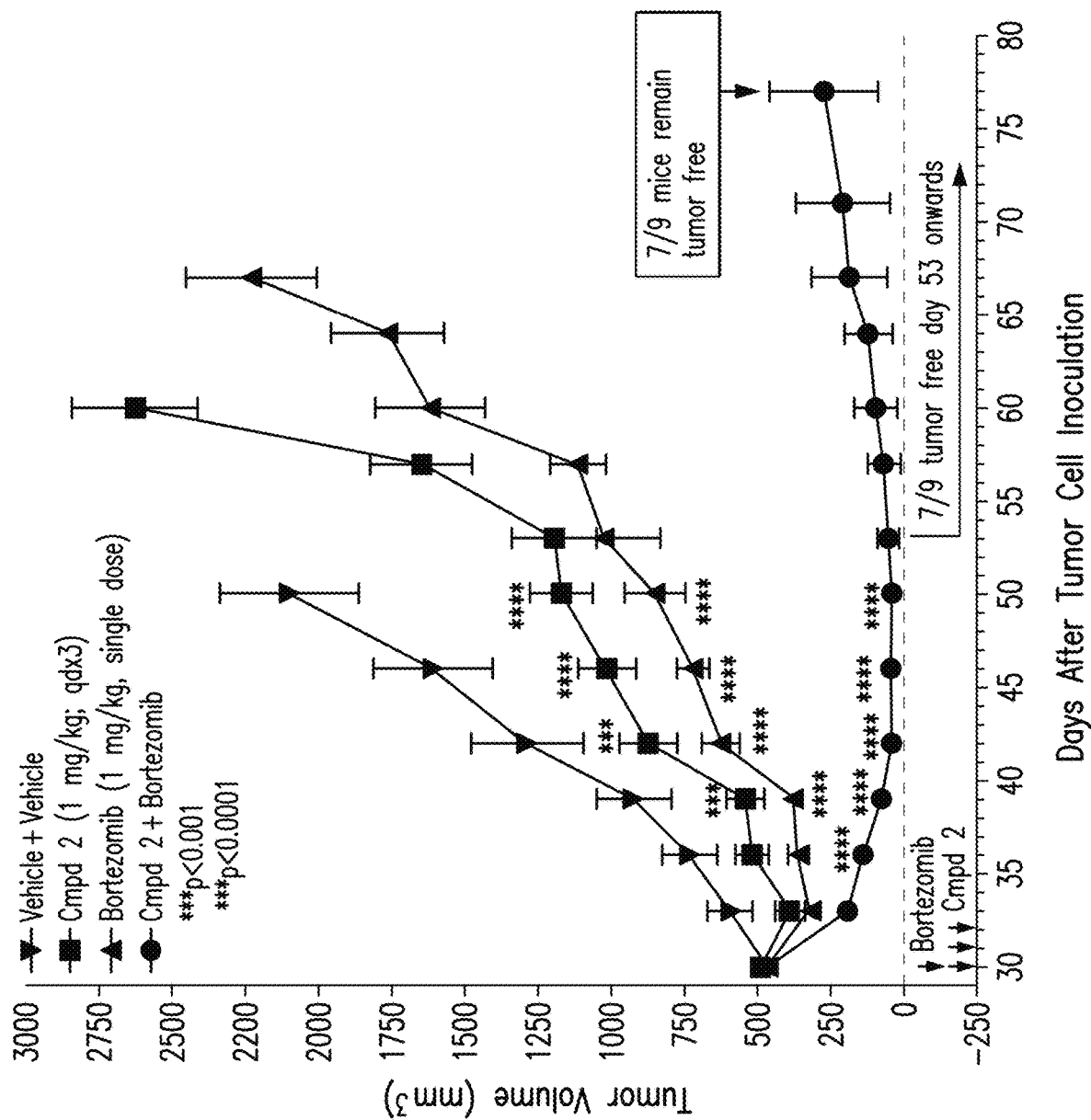

FIG. 24: The anti-tumor activity of Compound 2 alone and in combination with bortezomib in a lenalidomide-resistant NCI-H929 (H929-1051) multiple myeloma/plasmacytoma xenograft model. Dosing days are indicated with arrows on the X axis.

C. Compounds

Provided herein is the compound 4-(4-(4-(((2-(2,6-dioxopiperidin-3-yl)-1-oxoisoindolin-4-yl)oxy)methyl)benzyl)piperazin-1-yl)-3-fluorobenzonitrile, referred to as "Compound 1":

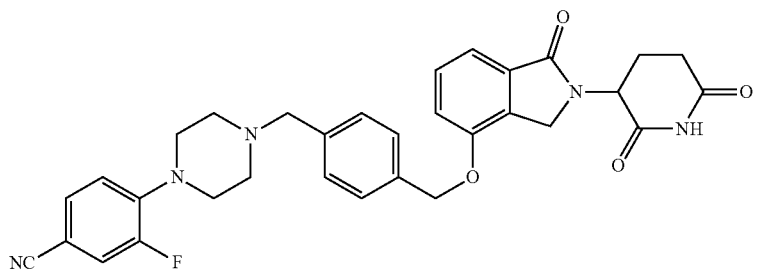

or an enantiomer or a mixture of enantiomers, tautomer, isotopolog or a pharmaceutically acceptable salt thereof.

In certain embodiments, the compound for use in the compositions and methods provided herein is Compound 1, or an enantiomer or a mixture of enantiomers, tautomer, isotopolog or a pharmaceutically acceptable salt thereof.

Also provided herein is the compound (S)-4-(4-(4-(((2-(2,6-dioxopiperidin-3-yl)-1-oxoisoindolin-4-yl)oxy)methyl)benzyl)piperazin-1-yl)-3-fluorobenzonitrile, referred to as "Compound 2":

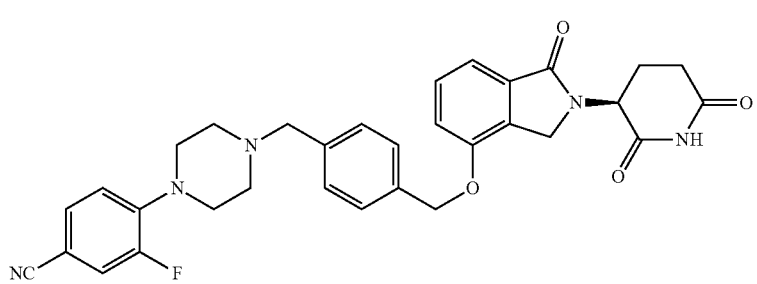

or a tautomer, isotopolog, or pharmaceutically acceptable salt thereof.

In certain embodiments, the compound for use in the compositions and methods provided herein is Compound 2, or a tautomer, isotopolog, or pharmaceutically acceptable salt thereof.

Also provided herein is the compound (R)-4-(4-(4-(((2-(2,6-dioxopiperidin-3-yl)-1-oxoisoindolin-4-yl)oxy)methyl)benzyl)piperazin-1-yl)-3-fluorobenzonitrile, referred to as "Compound 3":

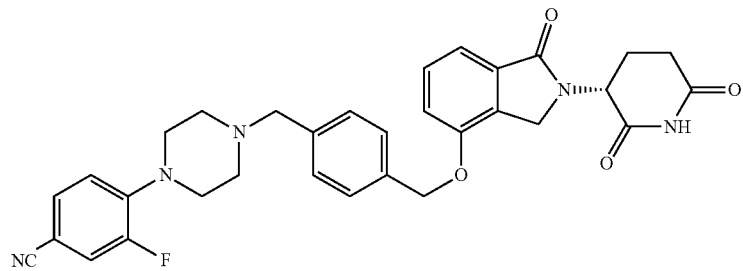

3 or a tautomer, isotopolog, or pharmaceutically acceptable salt thereof.

In certain embodiments, the compound for use in the compositions and methods provided herein is Compound 3, or a tautomer, isotopolog, or pharmaceutically acceptable salt thereof.

Provided herein is Compound 1. Provided herein is a tautomer of Compound 1. Provided herein is an enantiomer of Compound 1. Provided herein is a mixture of enantiomers of Compound 1. Provided herein is a pharmaceutically acceptable salt of Compound 1.

Provided herein is Compound 2. Provided herein is a tautomer of a Compound 2. Provided herein is a pharmaceutically acceptable salt of Compound 2.

Provided herein is Compound 3. Provided herein is a tautomer of a Compound 3. Provided herein is a pharmaceutically acceptable salt of Compound 3.

Also provided herein are isotopically enriched analogs of the compounds provided herein. Isotopic enrichment (for example, deuteration or deuterium enrichment) of pharmaceuticals to improve pharmacokinetics ("PK"), pharmacodynamics ("PD"), and toxicity profiles, has been demonstrated previously with some classes of drugs. See, for example, Lijinsky et. al., *Food Cosmet. Toxicol.*, 20: 393 (1982); Lijinsky et. al., *J. Nat. Cancer Inst.*, 69: 1127 (1982); Mangold et. al., *Mutation Res.* 308: 33 (1994); Gordon et. al., *Drug Metab. Dispos.*, 15: 589 (1987); Zello et. al., *Metabolism*, 43: 487 (1994); Gately et. al., *J. Nucl. Med.*, 27: 388 (1986); Wade D, *Chem. Biol. Interact.* 117: 191 (1999). Without being limited by any particular theory, isotopic enrichment of a compound can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not. Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g, Foster et al., *Adv. Drug Res.*, vol. 14, pp. 1-36 (1985); Kushner et al., *Can. J Physiol. Pharmacol.*, vol. 77, pp. 79-88 (1999)). The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. Without being limited by a particular theory, high DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects.

Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, will provide a similar kinetic isotope effects.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. As a result, these drugs often require the administration of multiple or high daily doses.

Isotopic enrichment at certain positions of a compound provided herein may produce a detectable KIE that affects the pharmacokinetic, pharmacologic, and/or toxicological profiles of a compound provided herein in comparison with a similar compound having a natural isotopic composition. In one embodiment, the deuterium enrichment is performed on the site of C—H bond cleavage during metabolism.

In one embodiment, provided herein is an isotopolog of Compound 1, or an enantiomer or a mixture of enantiomers, tautomer, or a pharmaceutically acceptable salt thereof. In some embodiments, the isotopolog of Compound 1 is a deuterium enriched Compound 1, or an enantiomer or a mixture of enantiomers, tautomer, or a pharmaceutically acceptable salt thereof. In some embodiments, the isotopolog of Compound 1 is a deuterium enriched Compound 1, or an enantiomer or a mixture of enantiomers, tautomer, or a pharmaceutically acceptable salt thereof, where the deuterium enrichment occurs on the chiral center. In another embodiment, provided herein is an isotopolog of Compound 2, or a tautomer, or a pharmaceutically acceptable salt thereof. In some embodiments, the isotopolog of Compound 2 is a deuterium enriched Compound 2, or a tautomer, or a pharmaceutically acceptable salt thereof. In some embodiments, the isotopolog of Compound 2 is a deuterium enriched Compound 2, or a tautomer, or a pharmaceutically acceptable salt thereof, where the deuterium enrichment occurs on the chiral center.

In certain embodiments, provided herein are isotopologues of 4-(4-(4-(((2-(2,6-dioxopiperidin-3-yl)-1-oxoisoindolin-4-yl)oxy)methyl)benzyl)piperazin-1-yl)-3-fluorobenzonitrile, or an enantiomer or a mixture of enantiomers, tautomer, or a pharmaceutically acceptable salt thereof, in which one or more atomic positions of the 4-(4-(4-(((2-(2,6-dioxopiperidin-3-yl)-1-oxoisoindolin-4-yl)oxy)methyl)benzyl)piperazin-1-yl)-3-fluorobenzonitrile molecule is/are isotopically enriched, for example with deuterium. Certain embodiments herein provide compounds of the following formula:

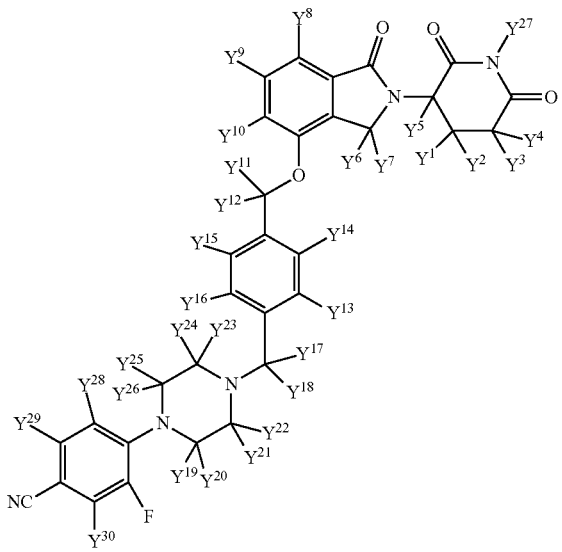

in which one or more Y atoms (i.e., $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, $Y^{22}$, $Y^{23}$, $Y^{24}$, $Y^{25}$, $Y^{26}$, $Y^{27}$, $Y^{28}$, $Y^{29}$, and $Y^{30}$) is/are hydrogen(s) isotopically enriched with deuterium, and any remaining Y atom(s) is/are non-enriched hydrogen atom(s).

In one embodiment, the compound is of the following formula:

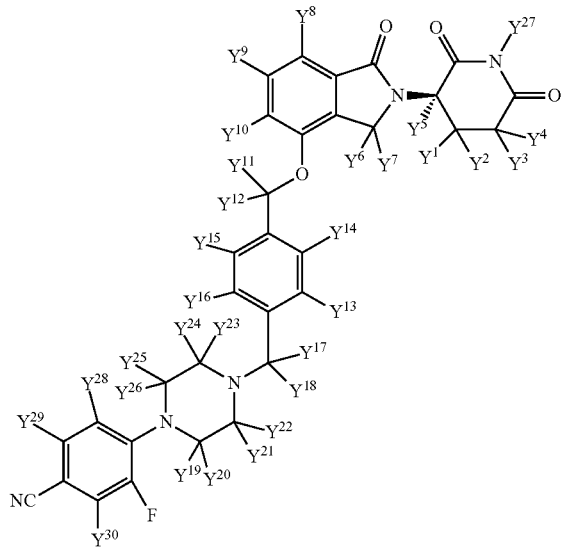

In one embodiment, the compound is of the following formula:

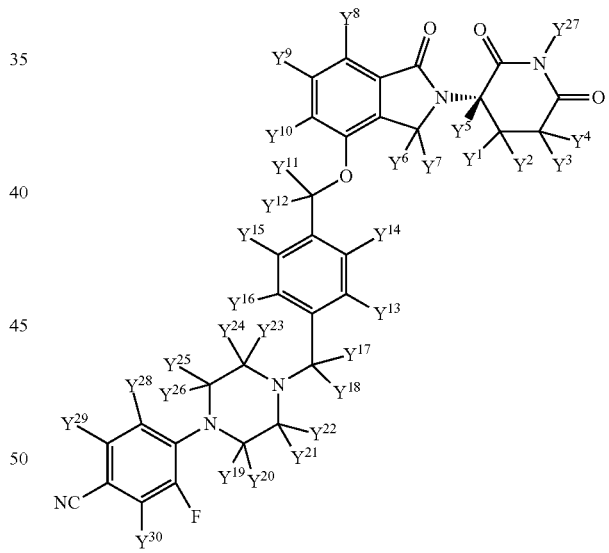

In certain embodiments, one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine or all of the indicated Y atoms is/are isotopically enriched with deuterium, and any remaining Y atom(s) is/are non-enriched hydrogen(s). In one embodiment, one of the indicated Y atoms is isotopically enriched with deuterium, and any remaining Y atoms are non-enriched hydrogens. In one embodiment, $Y^5$ is enriched with deuterium.

In certain embodiments, one or more Y atoms on the glutarimide portion of the compounds ($Y^1$, $Y^2$, $Y^3$, $Y^4$, $Y^5$, and $Y^{27}$) are deuterium-enriched. In certain embodiments, one or more Y atoms on the isoindolinone portion of the compounds ($Y^6$, $Y^7$, $Y^8$, $Y^9$, and $Y^{10}$) are deuterium-enriched. In certain embodiments, one or more Y atoms on the phenyl alkyl portion of the compounds ($Y^{11}$, $Y^{12}$, $Y^{13}$, $Y^{14}$, $Y^{15}$, $Y^{16}$, $Y^{17}$, and $Y^{18}$) are deuterium-enriched. In certain embodiments, one or more Y atoms on the piperazine portion of the compounds ($Y^{19}$, $Y^{20}$, $Y^{21}$, $Y^{22}$, $Y^{23}$, $Y^{24}$, $Y^{25}$, and $Y^{26}$) are deuterium-enriched. In certain embodiments, one or more Y atoms on the distant phenyl ring portion of the compounds ($Y^{28}$, $Y^{29}$, and $Y^{30}$) are deuterium-enriched. A compound provided herein may be any combination of deuterium enrichments as disclosed herein. In other words, any combination of the deuterium-enriched glutarimide portion, deuterium-enriched isoindoline portion, deuterium-enriched phenyl alkyl portion, deuterium-enriched piperazine portion, and deuterium-enriched distant phenyl ring portion is encompassed herein.

In one embodiment, $Y^1$ and $Y^2$ are deuterium enriched, and any remaining Y atoms are non-enriched hydrogens. In one embodiment, $Y^3$ and $Y^4$ are deuterium enriched, and any remaining Y atoms are non-enriched hydrogens. In one embodiment, $Y^5$ is deuterium enriched, and any remaining Y atoms are non-enriched hydrogens. In one embodiment, $Y^1$ to $Y^5$ are deuterium enriched, and any remaining Y atoms are non-enriched hydrogens. In one embodiment, $Y^3$ to $Y^5$ are deuterium enriched, and any remaining Y atoms are non-enriched hydrogens. In one embodiment, $Y^6$ and $Y^7$ are deuterium enriched, and any remaining Y atoms are non-enriched hydrogens. In one embodiment, $Y^8$ to $Y^{10}$ are deuterium enriched, and any remaining Y atoms are non-enriched hydrogens. In one embodiment, $Y^{11}$ and $Y^{12}$ are deuterium enriched, and any remaining Y atoms are non-enriched hydrogens. In one embodiment, $Y^{13}$ to $Y^{16}$ are deuterium enriched, and any remaining Y atoms are non-enriched hydrogens. In one embodiment, $Y^{17}$ and $Y^{18}$ are deuterium enriched, and any remaining Y atoms are non-enriched hydrogens. In one embodiment, $Y^{11}$ to $Y^{18}$ are deuterium enriched, and any remaining Y atoms are non-enriched hydrogens. In one embodiment, $Y^{19}$ to $Y^{26}$ are deuterium enriched, and any remaining Y atoms are non-enriched hydrogens. In one embodiment, $Y^{27}$ is deuterium enriched, and any remaining Y atoms are non-enriched hydrogens. In one embodiment, $Y^{28}$ to $Y^{30}$ are deuterium enriched, and any remaining Y atoms are non-enriched hydrogens.

In one embodiment, the isotopolog of Compound 1 is Compound 1-D:

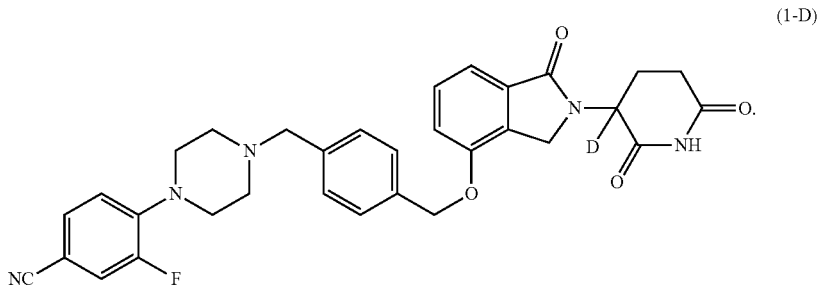 [SMILES: [2H]C1(N2Cc3c(OCc4ccc(CN5CCN(c6ccc(C#N)cc6F)CC5)cc4)cccc3C2=O)CCC(=O)NC1=O]

(1-D)

In another embodiment, the isotopolog of Compound 1 is a mixture of

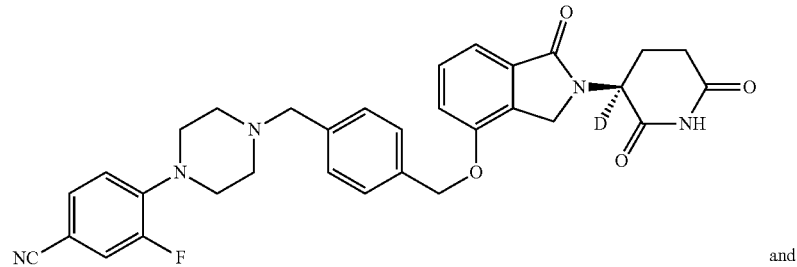

and

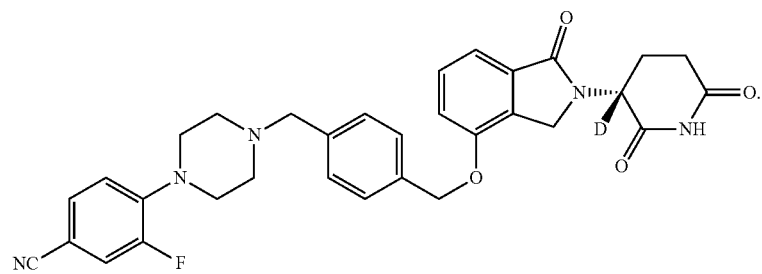

In still another embodiment, the isotopolog of Compound 2 is Compound 2-D

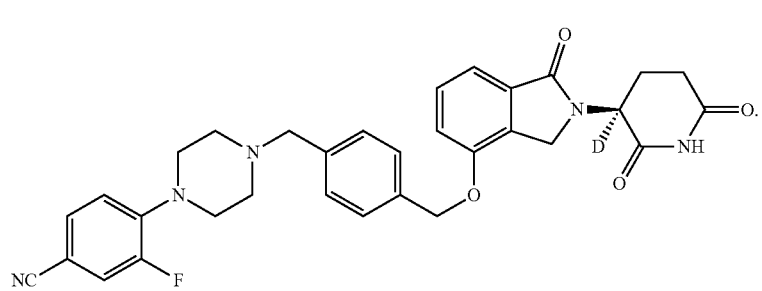

(2-D)

In still another embodiment, the isotopolog of Compound 3 is Compound 3-D

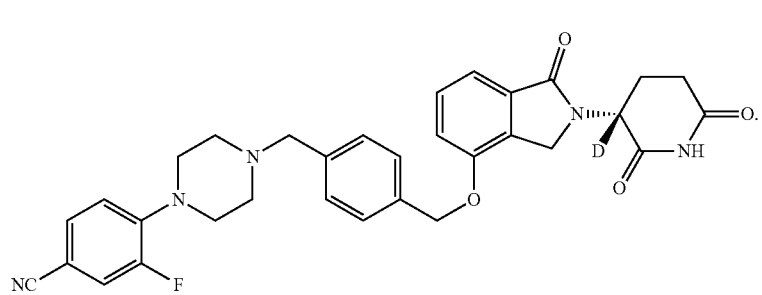

(3-D)

In certain embodiments, any of the deuterium enriched positions independently has an abundance of deuterium of at least 30%, at least 40%, at least 50%, at least 60%, at least 70%, at least 80%, at least 90%, at least 95%, at least 97%, or about 100%. In one embodiment, $Y^5$ is deuterium enriched and has an abundance of deuterium of at least 30%, at least 40%, at least 50%, at least 60%, at least 70%, at least 80%, at least 90%, at least 95%, at least 97%, or about 100%.

In one embodiment, the D (at the chiral center) in Compound 1-D has an abundance of deuterium of at least 30%, at least 40%, at least 50%, at least 60%, at least 70%, at least 80%, at least 90%, at least 95%, at least 97%, or about 100%. In one embodiment, the D has an abundance of deuterium of at least 90%.

In one embodiment, the D (at the chiral center) in Compound 2-D has an abundance of deuterium of at least 30%, at least 40%, at least 50%, at least 60%, at least 70%, at least 80%, at least 90%, at least 95%, at least 97%, or about 100%. In one embodiment, the D has an abundance of deuterium of at least 90%.

In one embodiment, the D (at the chiral center) in Compound 3-D has an abundance of deuterium of at least 30%, at least 40%, at least 50%, at least 60%, at least 70%, at least 80%, at least 90%, at least 95%, at least 97%, or about 100%. In one embodiment, the D has an abundance of deuterium of at least 90%.

In certain embodiments, a deuterium enriched compound provided herein has enantiomeric excess of at least 5%, at least 10%, at least 20%, at least 30%, at least 40%, at least 50%, at least 60%, at least 70%, at least 80%, at least 90%, at least 95%, at least 97%, at least 98%, or at least 99%. Additional examples of the stereoisomeric purity include an enantiomeric excess of at least 10, 11, 12, 13, 14, 15, 16, 17 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%.

In one embodiment, Compound 2-D has enantiomeric excess of at least 5%, at least 10%, at least 20%, at least 30%, at least 40%, at least 50%, at least 60%, at least 70%, at least 80%, at least 90%, at least 95%, at least 97%, at least 98%, or at least 99%. In one embodiment, Compound 2-D has enantiomeric excess of at least 90%.

In one embodiment, Compound 3-D has enantiomeric excess of at least 5%, at least 10%, at least 20%, at least 30%, at least 40%, at least 50%, at least 60%, at least 70%, at least 80%, at least 90%, at least 95%, at least 97%, at least 98%, or at least 99%. In one embodiment, Compound 3-D has enantiomeric excess of at least 90%.

The deuterium enriched compounds provided herein can be prepared according to the synthetic scheme and examples provided herein, but using corresponding deuterium enriched starting material(s). The deuterium enriched compounds provided herein can also be prepared according to the general chemistry known to those skilled in the art to prepare deuterium-enriched isoindolinone and glutarimide compounds, including but not limited to those described in WO 2014/039421 and WO 2014/116573, the entirety of each of which is incorporated herein by reference.

D. Preparation of Compound 1, Compound 2 and Compound 3

The compounds provided herein can be prepared by methods known to one of skill in the art and following procedures similar to those described in the Examples section herein and routine modifications thereof. An exemplary reaction scheme for the preparation of the compounds is illustrated below in Scheme 1 for Compound 1, Compound 2 and Compound 3, and Scheme 2 for Compound 2.

As shown in Scheme 1, protection of 3-hydroxy-2-methylbenzoic acid (by, for example, methyl ester and tert-butyl (dimethyl)silylether formation) was followed by bromination, for example using N-bromosuccinimide and azobisisobutyronitrile. Reaction with methyl-4,5-diamino-5-oxo-pentanoate (also referred to as H-D,L-Glu(OMe)-$NH_2$), in the presence of a base (such as DIEA), resulted in derivatized isoindoline formation, which was followed by TBS deprotection using a base, such as potassium carbonate. Reaction of the derivatized isoindoline with 1,4-bis(bromomethyl)benzene in the presence of a base (such as potassium carbonate), was followed by glutarimide formation in the presence of potassium tert-butoxide. Finally, reaction with 3-fluoro-4-(piperazin-1-yl)benzonitrile afforded the target Compound 1. Chiral separation affords Compound 2 and Compound 3.

Scheme 1

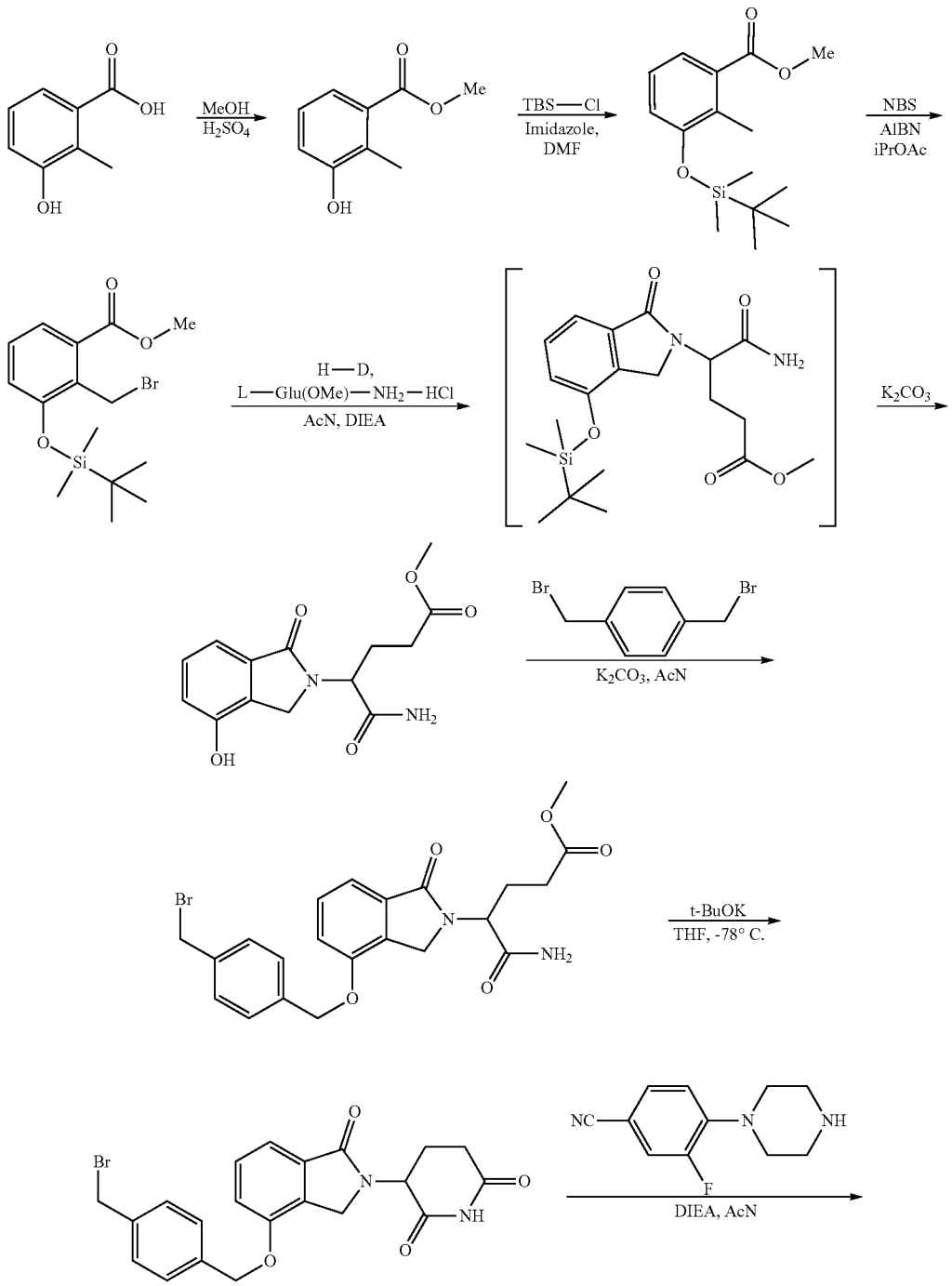

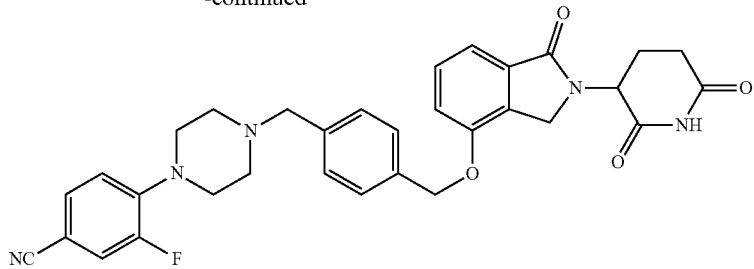

Alternatively as exemplified in Scheme 2, reaction of the methyl 2-(bromomethyl)-3-[tert-butyl(dimethyl)silyl]oxy-benzoate intermediate with the chiral tert-butyl (4S)-4,5-diamino-5-oxo-pentanoate (also referred to as H-L-Glu(OtBu)-NH$_2$; reaction with H-D-Glu(OtBu)-NH$_2$ provides the opposite enantiomer), in the presence of a base (such as DIEA), resulted in derivatized isoindoline formation, which was followed by TBS deprotection using tetrabutylammonium fluoride. Reaction of the derivatized isoindoline with 4-(4-(4-(chloromethyl)benzyl)piperazin-1-yl)-3-fluorobenzonitrile, or a salt thereof, in the presence of a base (such as potassium carbonate), followed by deprotection and glutarimide formation afforded the target Compound 2.

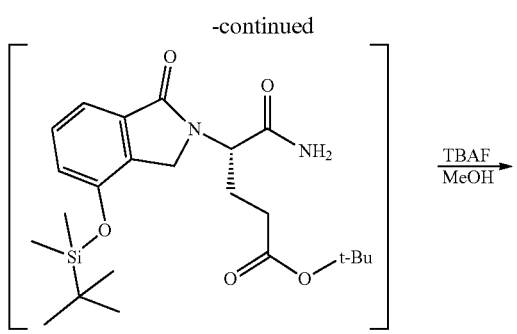

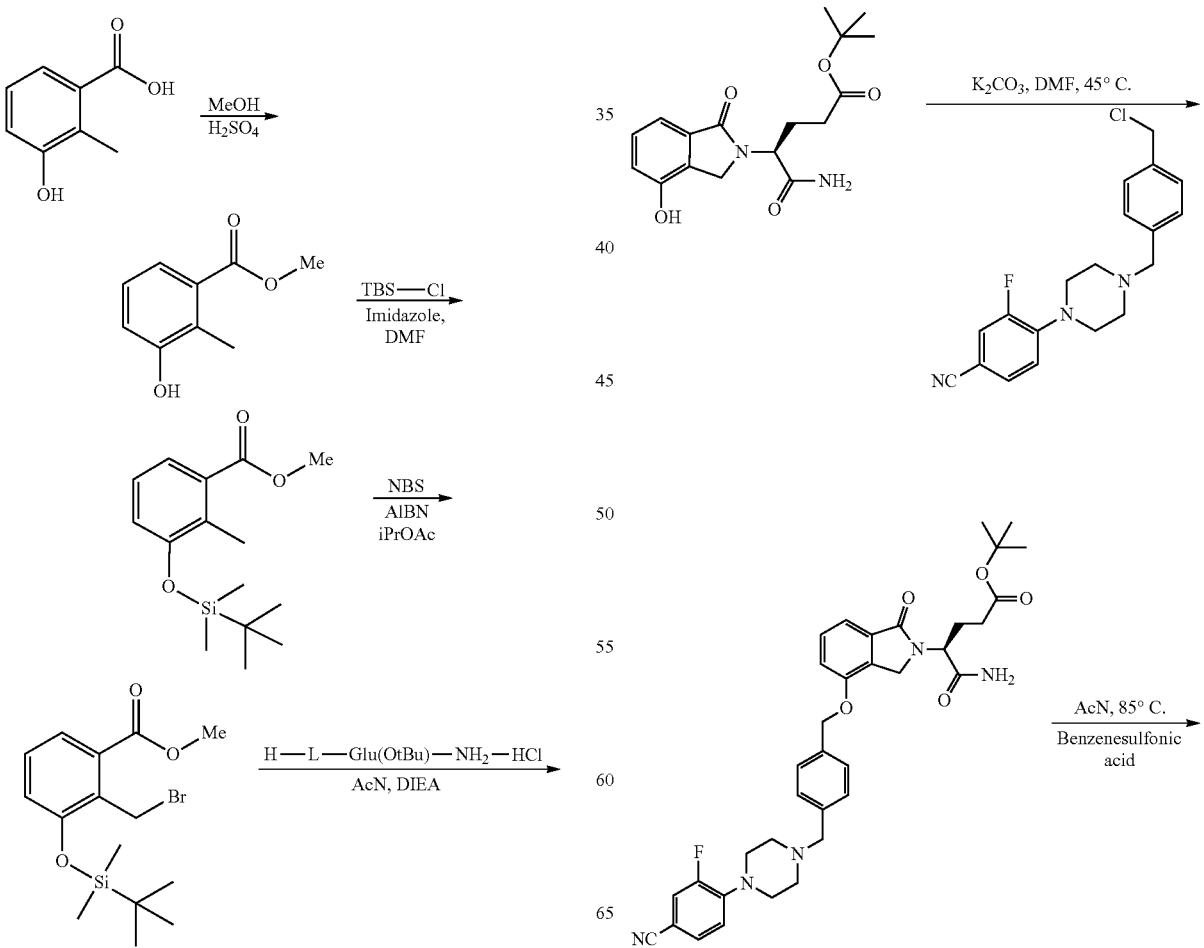

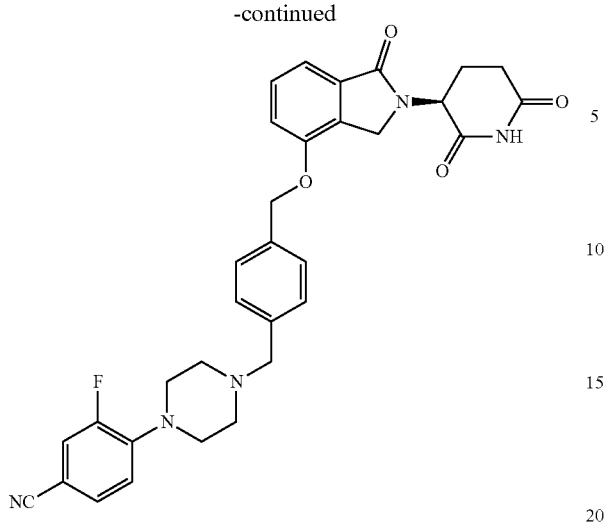

One skilled in the art would know how to modify the procedures set forth in the illustrative schemes and examples to arrive at the desired products.

In one aspect, provided herein are methods for preparing Compound 1,

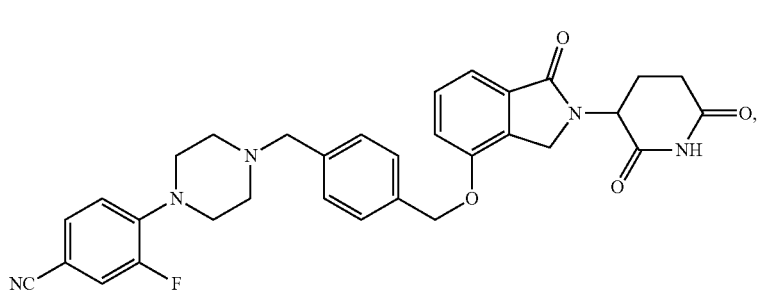

or an enantiomer or a mixture of enantiomers, tautomer, or isotopolog thereof, the methods comprising contacting Compound 1a

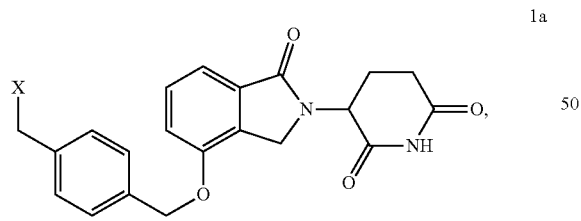

or an enantiomer or a mixture of enantiomers, tautomer, or isotopolog thereof, with 3-fluoro-4-(piperazin-1-yl)benzonitrile, in an organic solvent in the presence of a base, under conditions suitable to provide Compound 1; wherein X is a leaving group.

In one embodiment, the method is a method for preparing an enantiomer of Compound 1, for example, Compound 2,

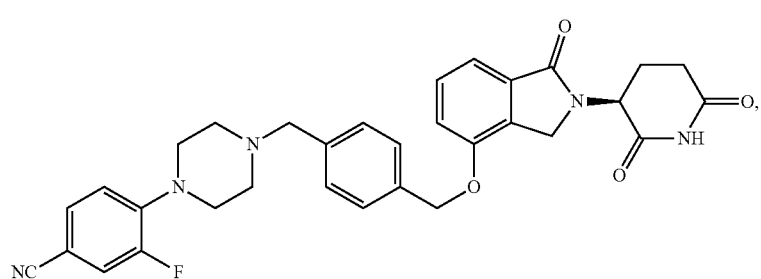

2 the method comprising contacting an enantiomer of Compound 1a, for example Compound 2a

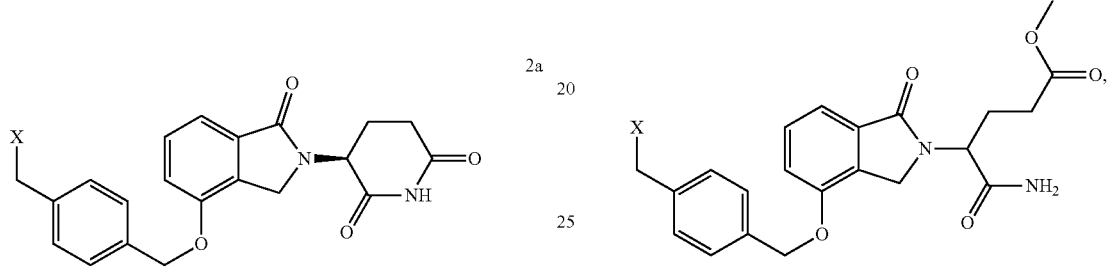

with 3-fluoro-4-(piperazin-1-yl)benzonitrile, in an organic solvent in the presence of a base, under conditions suitable to provide Compound 2; wherein X is a leaving group.

In one embodiment, X is halogen, for example Br or Cl. In another embodiment, X is methanesulfonate (also referred to as —OMs). In one embodiment, the solvent is acetonitrile, THF, or DMSO. In another, the base is DIEA or TEA. In some embodiments, the contacting is performed at elevated temperature, for example, at about 35° C. to about 50° C.

In some embodiments, the methods further comprise preparing Compound 1a,

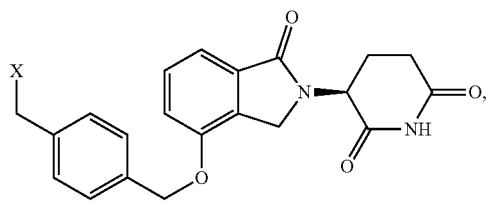

or an enantiomer or a mixture of enantiomers, tautomer, or isotopolog thereof, the methods comprising contacting a compound 1b

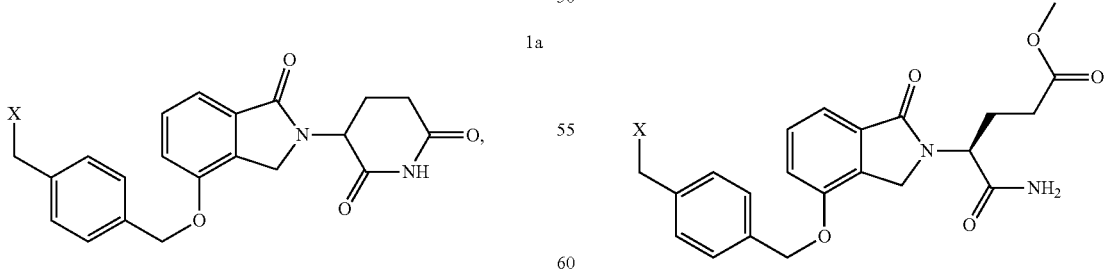

or an enantiomer or a mixture of enantiomers, tautomer, or isotopolog thereof, with potassium tert-butoxide, in an organic solvent, under conditions suitable to provide Compound 1a.

In one embodiment, the method is a method for preparing an enantiomer of Compound 1a, for example, Compound 2a, 2a the method comprising contacting an enantiomer of Compound 1b, for example Compound 2b 2b with potassium tert-butoxide, in an organic solvent, under conditions suitable to provide Compound 2a.

In one embodiment, X is Br. In one embodiment, the solvent is THF. In some embodiments, the contacting is performed at reduced temperature, for example, at about −70° C. to about −80° C.

In some embodiments, the methods further comprise preparing Compound 1b,

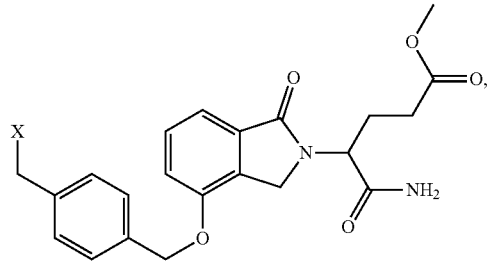

1b or an enantiomer or a mixture of enantiomers, tautomer, or isotopolog thereof, the methods comprising contacting a compound 1c

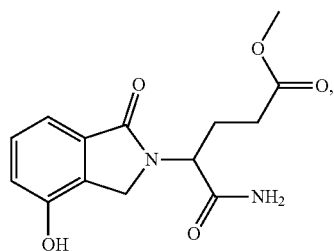

1c or an enantiomer or a mixture of enantiomers, tautomer, or isotopolog thereof, with

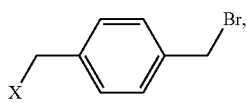

in an organic solvent, in the presence of a base, under conditions suitable to provide Compound 1b.

In one embodiment, the method is a method for preparing an enantiomer of Compound 1b, for example, Compound 2b,

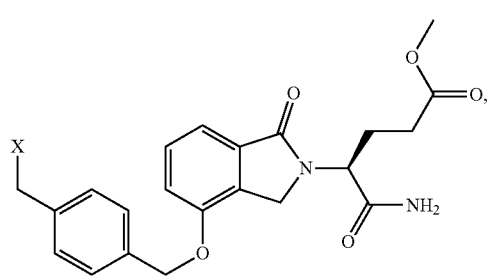

2b the method comprising contacting an enantiomer of Compound 1c, for example Compound 2c

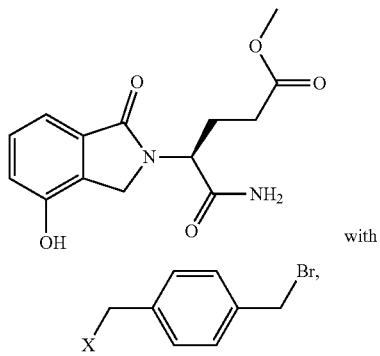

2c with in an organic solvent, in the presence of a base, under conditions suitable to provide Compound 1b.

In one embodiment, X is Br. In one embodiment, the solvent is acetonitrile. In some embodiments, the base is potassium carbonate. In some embodiments, the contacting is performed at elevated temperature, for example, at about 50° C. to about 70° C.

In some embodiments, the methods further comprise preparing Compound 1c,

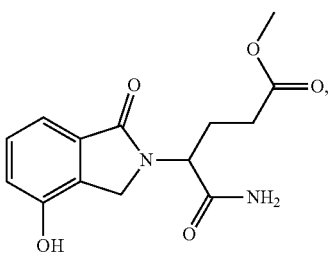

1c or an enantiomer or a mixture of enantiomers, tautomer, or isotopolog thereof, the methods comprising contacting a compound 1d

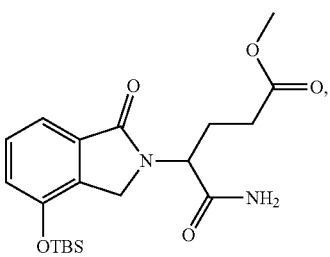

1d or an enantiomer or a mixture of enantiomers, tautomer, or isotopolog thereof, with a base in a solvent, under conditions suitable to provide Compound 1c.

In one embodiment, the method is a method for preparing an enantiomer of Compound 1c, for example, Compound 2c,

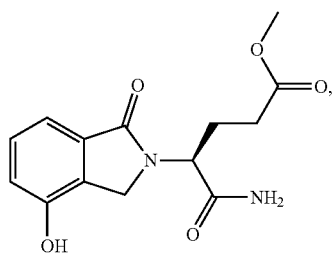

2c the method comprising contacting an enantiomer of Compound 1d, for example Compound 2d

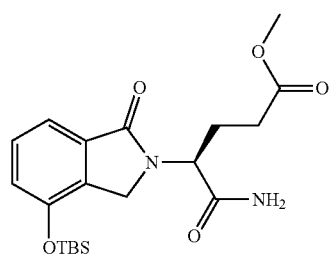

2d with a base in a solvent, under conditions suitable to provide Compound 2c. In one embodiment, the solvent is water. In some embodiments, the base is potassium carbonate.

In some embodiments, the methods further comprise preparing Compound 1d,

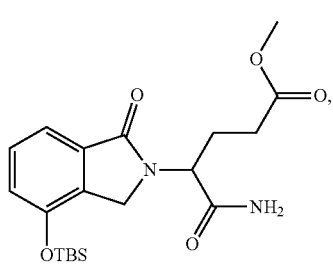

1d or an enantiomer or a mixture of enantiomers, tautomer, or isotopolog thereof, the methods comprising contacting a compound 1e COOMe $H_2N$ — — $NH_2$

O

1e or an enantiomer or a mixture of enantiomers, tautomer, or isotopolog thereof, with methyl 2-(bromomethyl)-3-[tert-butyl(dimethyl)silyl] oxy-benzoate in a solvent, in the presence of a base, under conditions suitable to provide Compound 1d.

In one embodiment, the method is a method for preparing an enantiomer of Compound 1d, for example, Compound 2d,

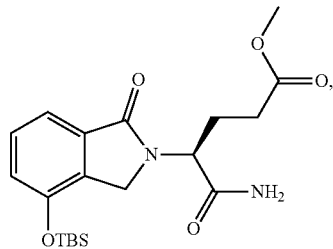

2d the method comprising contacting an enantiomer of Compound 1e, for example Compound 2e COOMe $H_2N$ — — $NH_2$

O

2e with methyl 2-(bromomethyl)-3-[tert-butyl(dimethyl)silyl] oxy-benzoate in a solvent, in the presence of a base, under conditions suitable to provide Compound 2d.

In one embodiment, the solvent is acetonitrile. In some embodiments, the base is DIEA. In some other embodiments, the contacting is performed at elevated temperature, for example, at about 50° C. to about 70° C.

In another aspect, provided herein are methods for preparing Compound 1,

1

(structure of Compound 1)

or an enantiomer or a mixture of enantiomers, tautomer, or isotopolog thereof, the methods comprising contacting Compound 1f

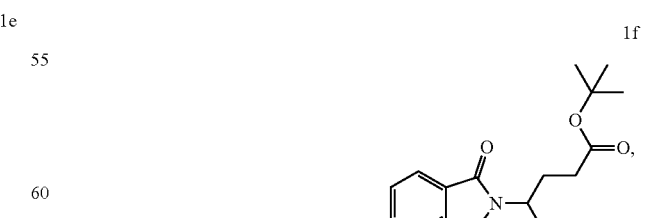

1f or an enantiomer or a mixture of enantiomers, tautomer, or isotopolog thereof, with an acid, in an organic solvent, under conditions suitable to provide Compound 1.

In one embodiment, the method is a method for preparing an enantiomer of Compound 1, for example, Compound 2,

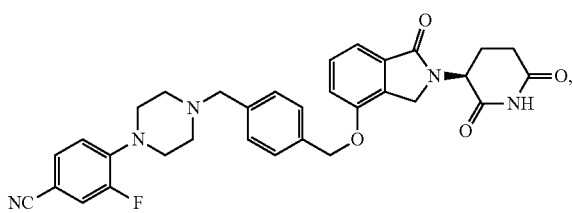

2 the method comprising contacting an enantiomer of Compound 1f, for example Compound 2f

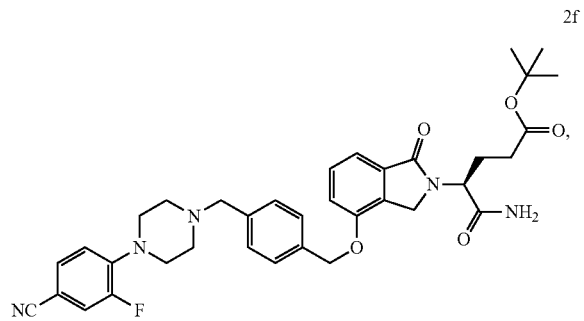 [SMILES: CC(C)(C)OC(=O)CC[C@@H](C(N)=O)N1Cc2c(OCc3ccc(CN4CCN(c5ccc(C#N)cc5F)CC4)cc3)cccc2C1=O]

2f with an acid, in an organic solvent, under conditions suitable to provide Compound 2.

In one embodiment, the solvent is acetonitrile. In another, the acid is benzene sulfonic acid. In some embodiments, the contacting is performed at elevated temperature, for example, at about 75° C. to about 95° C.

In some embodiments, the methods further comprise preparing Compound 1f,

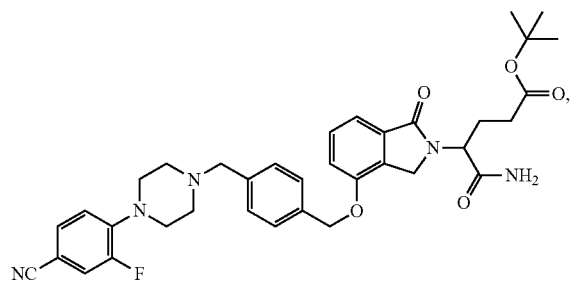

1f or an enantiomer or a mixture of enantiomers, tautomer, or isotopolog thereof, the methods comprising contacting Compound 1g

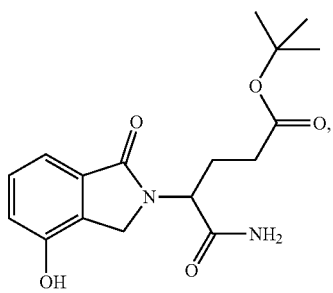

1g or an enantiomer or a mixture of enantiomers, tautomer, or isotopolog thereof, with 4-(4-(4-(chloromethyl)benzyl)piperazin-1-yl)-3-fluorobenzonitrile, or a salt thereof, in a solvent, in the presence of a base, under conditions suitable to provide Compound 1f.

In one embodiment, the method is a method for preparing an enantiomer of Compound 1f, for example, Compound 2f,

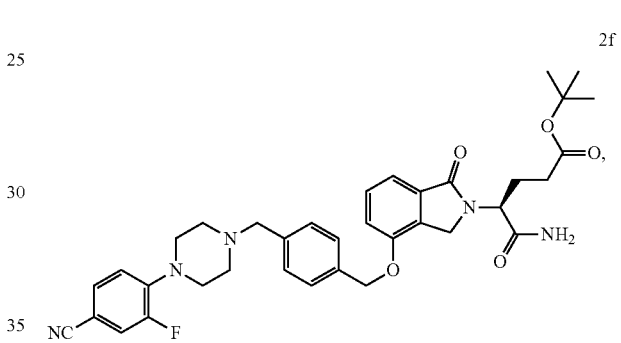

2f the method comprising contacting an enantiomer of Compound 1g, for example Compound 2g

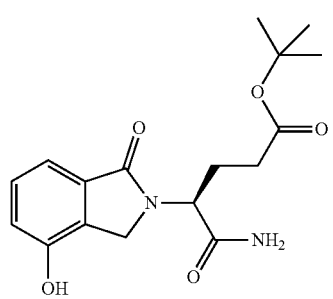

2g with 4-(4-(4-(chloromethyl)benzyl)piperazin-1-yl)-3-fluorobenzonitrile a salt thereof, in a solvent, in the presence of a base, under conditions suitable to provide Compound 2f.

In one embodiment, the solvent is DMF. In one embodiment, the solvent is DMSO. In another, the base is potassium carbonate. In some embodiments, the contacting is performed at elevated temperature, for example, at about 35° C. to about 55° C.

In some embodiments, the methods for preparing Compound 1f further comprises a purification method, the purification method comprising (i) contacting Compound 1f (free base) with an acid in a first solvent; (ii) filtering to provide the acid salt of Compound 1f; and (iii) washing the acid salt of Compound 1f in a second solvent with a base to provide Compound 1f (free base). In one embodiment, the acid is tartaric acid (e.g., L-tartaric acid). In one embodiment, the first solvent is methanol. In one embodiment, the acid salt of Compound 1f is a tartrate salt (e.g., L-tartaric acid salt) of Compound 1f. In one embodiment, the second solvent is 2-methyltetrahydrofuran. In one embodiment, the base is potassium carbonate.

In some embodiments, the methods for preparing an enantiomer of Compound 1f, for example, Compound 2f, further comprises a purification method, the purification method comprising (i) contacting Compound 2f (free base) with an acid in a first solvent; (ii) filtering to provide the acid salt of Compound 2f; and (iii) washing the acid salt of Compound 2f in a second solvent with a base to provide Compound 2f (free base). In one embodiment, the acid is tartaric acid (e.g., L-tartaric acid). In one embodiment, the first solvent is methanol. In one embodiment, the acid salt of Compound 2f is a tartrate salt (e.g., L-tartaric acid salt) of Compound 2f. In one embodiment, the second solvent is 2-methyltetrahydrofuran. In one embodiment, the base is potassium carbonate.

In some embodiments, the methods further comprise preparing 4-(4-(4-(chloromethyl)benzyl)piperazin-1-yl)-3-fluorobenzonitrile, or a salt thereof, the methods comprising contacting 4-(chloromethyl)benzaldehyde with 3-fluoro-4-(piperazin-1-yl)benzonitrile, in a solvent, in the presence of a reducing agent, under conditions suitable to provide 4-(4-(4-(chloromethyl)benzyl)piperazin-1-yl)-3-fluorobenzonitrile.

In one embodiment, the reducing agent is sodium triacetoxyborohydride (NaBH(OAc)$_4$). In one embodiment, the solvent is toluene. In one embodiment, the contacting is performed in the presence of an acid. In one embodiment, the acid is acetic acid.

In one embodiment, the 4-(4-(4-(chloromethyl)benzyl)piperazin-1-yl)-3-fluorobenzonitrile, or a salt thereof, prepared and used in the methods provided herein is an HCl salt of 4-(4-(4-(chloromethyl)benzyl)piperazin-1-yl)-3-fluorobenzonitrile. In one embodiment, the HCl salt is prepared by contacting 4-(4-(4-(chloromethyl)benzyl)piperazin-1-yl)-3-fluorobenzonitrile free base with hydrochloric acid in isopropanol.

E. Methods of Treatment and Prevention

Surprisingly it has been found that Compound 1, Compound 2 and Compound 3 are very potent anti-myeloma compounds that have distinguishing characteristics, such as an improved safety profile, including selective cell killing of multiple myeloma cells compared to normal cells, reduced activity at off-target receptors, and reduced CYP enzyme inhibition, reducing the potential for adverse drug interactions.

In one embodiment, provided herein is a method of treating multiple myeloma, which comprises administering to a patient Compound 1, or an enantiomer, mixture of enantiomers, tautomer, isotopolog, or pharmaceutically acceptable salt thereof. In one embodiment, provided herein is Compound 1, or an enantiomer, mixture of enantiomers, tautomer, isotopolog, or pharmaceutically acceptable salt thereof, for use in a method of treating multiple myeloma, wherein the method comprises administering said compound to a patient.

In one embodiment, provided herein is a method of treating multiple myeloma, which comprises administering to a patient Compound 2, or a tautomer, isotopolog, or pharmaceutically acceptable salt thereof. In one embodiment, provided herein is Compound 2, or a tautomer, isotopolog, or pharmaceutically acceptable salt thereof, for use in a method of treating multiple myeloma, wherein the method comprises administering said compound to a patient.

In one embodiment, provided herein is a method of treating multiple myeloma, which comprises administering to a patient Compound 3, or a tautomer, isotopolog, or pharmaceutically acceptable salt thereof. In one embodiment, provided herein is Compound 3, or a tautomer, isotopolog, or pharmaceutically acceptable salt thereof, for use in a method of treating multiple myeloma, wherein the method comprises administering said compound to a patient.

In one embodiment, provided herein is a method of preventing multiple myeloma, which comprises administering to a patient a compound provided herein, e.g., Compound 1, Compound 2 or Compound 3, or an enantiomer, mixture of enantiomers, tautomer, isotopolog, or pharmaceutically acceptable salt thereof. In one embodiment, provided herein is a compound provided herein, e.g., Compound 1, Compound 2 or Compound 3, or an enantiomer, mixture of enantiomers, tautomer, isotopolog, or pharmaceutically acceptable salt thereof, for use in a method of preventing multiple myeloma, wherein the method comprises said compound to a patient.

In another embodiment, provided herein is a method of managing multiple myeloma, which comprises administering to a patient a compound provided herein, e.g., Compound 1, Compound 2 or Compound 3, or an enantiomer, mixture of enantiomers, tautomer, isotopolog, or pharmaceutically acceptable salt thereof. In one embodiment, provided herein is a compound provided herein, e.g., Compound 1, Compound 2 or Compound 3, or an enantiomer, mixture of enantiomers, tautomer, isotopolog, or pharmaceutically acceptable salt thereof, for use in a method of managing multiple myeloma, wherein the method comprises administering said compound to a patient.

In one embodiment, also provided herein are methods for inducing a therapeutic response assessed with the International Uniform Response Criteria for Multiple Myeloma (IURC) (see Durie BGM, Harousseau J-L, Miguel J S, et al. International uniform response criteria for multiple myeloma. *Leukemia*, 2006; (10) 10: 1-7) of a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, to a patient having multiple myeloma. In another embodiment, provided herein are methods for achieving a stringent complete response, complete response, or very good partial response, as determined by the International Uniform Response Criteria for Multiple Myeloma (IURC) in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, to patient having multiple myeloma. In another embodiment, provided herein are methods for achieving an increase in overall survival, progression-free survival, event-free survival, time to progression, or disease-free survival in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, to patient having multiple myeloma. In another embodiment, provided herein are methods for achieving an increase in overall survival in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, to patient having multiple myeloma. In another embodiment, provided herein are methods for achieving an increase in progression-free survival in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, to patient having multiple myeloma. In another embodiment, provided herein are methods for achieving an increase in event-free survival in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, to patient having multiple myeloma. In another embodiment, provided herein are methods for achieving an increase in time to progression in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, to patient having multiple myeloma. In another embodiment, provided herein are methods for achieving an increase in disease-free survival in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, to patient having multiple myeloma.

Also provided herein are methods of treating patients who have been previously treated for multiple myeloma but are non-responsive to standard therapies, as well as those who have not previously been treated. Further encompassed are methods of treating patients who have undergone surgery in an attempt to treat multiple myeloma, as well as those who have not. Also provided herein are methods of treating patients who have been previously undergone transplant therapy, as well as those who have not.

The methods provided herein include treatment of multiple myeloma that is relapsed, refractory or resistant. The methods provided herein include prevention of multiple myeloma that is relapsed, refractory or resistant. The methods provided herein include management of multiple myeloma that is relapsed, refractory or resistant. In some such embodiments, the myeloma is primary, secondary, tertiary, quadruply or quintuply relapsed multiple myeloma. In one embodiment, the methods provided herein reduce, maintain or eliminate minimal residual disease (MRD). In one embodiment, methods provided herein encompass treating, preventing or managing various types of multiple myeloma, such as monoclonal gammopathy of undetermined significance (MGUS), low risk, intermediate risk, and high risk multiple myeloma, newly diagnosed multiple myeloma (including low risk, intermediate risk, and high risk newly diagnosed multiple myeloma), transplant eligible and transplant ineligible multiple myeloma, smoldering (indolent) multiple myeloma (including low risk, intermediate risk, and high risk smouldering multiple myeloma), active multiple myeloma, solitary plasmacytoma, extramedullary plasmacytoma, plasma cell leukemia, central nervous system multiple myeloma, light chain myeloma, non-secretory myeloma, Immunoglobulin D myeloma, and Immunoglobulin E myeloma, by administering a therapeutically effective amount of a compound described herein. In another embodiment, methods provided herein encompass treating, preventing or managing multiple myeloma characterized by genetic abnormalities, such as Cyclin D translocations (for example, t(11;14)(q13;q32); t(6;14)(p21;32); t(12; 14)(p13;q32); or t(6;20);); MMSET translocations (for example, t(4;14)(p16; q32)); MAF translocations (for example, t(14;16)(q32;q32); t(20;22); t(16; 22)(q11;q13); or t(14;20)(q32;q11)); or other chromosome factors (for example, deletion of 17p13, or chromosome 13; del(17/17p), nonhyperdiploidy, and gain (1q)), by administering a therapeutically effective amount of a compound described herein.

In one embodiment, the methods comprise administering a therapeutically effective amount of Compound 1, or an enantiomer, mixture of enantiomers, tautomer, isotopolog, or pharmaceutically acceptable salt thereof. In another embodiment, the methods comprise administering a therapeutically effective amount of Compound 2, or a tautomer, isotopolog, or pharmaceutically acceptable salt thereof. In another embodiment, the methods comprise administering a therapeutically effective amount of Compound 3, or a tautomer, isotopolog, or pharmaceutically acceptable salt thereof.

In some embodiments, the methods comprise administering a therapeutically effective amount of Compound 1, or an enantiomer, mixture of enantiomers, tautomer, isotopolog, or pharmaceutically acceptable salt thereof, as induction therapy. In another embodiment, the methods comprise administering a therapeutically effective amount of Compound 2, or a tautomer, isotopolog, or pharmaceutically acceptable salt thereof, as induction therapy. In another embodiment, the methods comprise administering a therapeutically effective amount of Compound 3, or a tautomer, isotopolog, or pharmaceutically acceptable salt thereof, as induction therapy. In some embodiments, the methods comprise administering a therapeutically effective amount of Compound 1, or an enantiomer, mixture of enantiomers, tautomer, isotopolog, or pharmaceutically acceptable salt thereof, as consolidation therapy. In another embodiment, the methods comprise administering a therapeutically effective amount of Compound 2, or a tautomer, isotopolog, or pharmaceutically acceptable salt thereof, as consolidation therapy. In another embodiment, the methods comprise administering a therapeutically effective amount of Compound 3, or a tautomer, isotopolog, or pharmaceutically acceptable salt thereof, as consolidation therapy. In some embodiments, the methods comprise administering a therapeutically effective amount of Compound 1, or an enantiomer, mixture of enantiomers, tautomer, isotopolog, or pharmaceutically acceptable salt thereof, as maintenance therapy. In another embodiment, the methods comprise administering a therapeutically effective amount of Compound 2, or a tautomer, isotopolog, or pharmaceutically acceptable salt thereof, as maintenance therapy. In another embodiment, the methods comprise administering a therapeutically effective amount of Compound 3, or a tautomer, isotopolog, or pharmaceutically acceptable salt thereof, as maintenance therapy.

In one particular embodiment of the methods described herein, the multiple myeloma is plasma cell leukemia.

In one embodiment of the methods described herein, the multiple myeloma is high risk multiple myeloma. In some such embodiments, the high risk multiple myeloma is relapsed or refractory. In one embodiment, the high risk multiple myeloma is multiple myeloma that is relapsed within 12 months of first treatment. In yet another embodiment, the high risk multiple myeloma is multiple myeloma that is characterized by genetic abnormalities, for example, one or more of del(17/17p) and t(14; 16)(q32;q32). In some such embodiments, the high risk multiple myeloma is relapsed or refractory to one, two or three previous treatments.

In one embodiment, the multiple myeloma is characterized by a p53 mutation. In one embodiment, the p53 mutation is a Q331 mutation. In one embodiment, the p53 mutation is a R273H mutation. In one embodiment, the p53 mutation is a K132 mutation. In one embodiment, the p53 mutation is a K132N mutation. In one embodiment, the p53 mutation is a R337 mutation. In one embodiment, the p53 mutation is a R337L mutation. In one embodiment, the p53 mutation is a W146 mutation. In one embodiment, the p53 mutation is a S261 mutation. In one embodiment, the p53 mutation is a S261T mutation. In one embodiment, the p53 mutation is a E286 mutation. In one embodiment, the p53 mutation is a E286K mutation. In one embodiment, the p53 mutation is a R175 mutation. In one embodiment, the p53 mutation is a R175H mutation. In one embodiment, the p53 mutation is a E258 mutation. In one embodiment, the p53 mutation is a E258K mutation. In one embodiment, the p53 mutation is a A161 mutation. In one embodiment, the p53 mutation is a A161T mutation.

In one embodiment, the multiple myeloma is characterized by homozygous deletion of p53. In one embodiment, the multiple myeloma is characterized by homozygous deletion of wild type p53.

In one embodiment, the multiple myeloma is characterized by wild type p53.

In one embodiment, the multiple myeloma is characterized by activation of one or more oncogenic drivers. In one embodiment, the one or more oncogenic drivers are selected from the group consisting of C-MAF, MAFB, FGFR3, MMset, Cyclin D1, and Cyclin D. In one embodiment, the multiple myeloma is characterized by activation of C-MAF. In one embodiment, the multiple myeloma is characterized by activation of MAFB. In one embodiment, the multiple myeloma is characterized by activation of FGFR3 and MMset. In one embodiment, the multiple myeloma is characterized by activation of C-MAF, FGFR3, and MMset. In one embodiment, the multiple myeloma is characterized by activation of Cyclin D1. In one embodiment, the multiple myeloma is characterized by activation of MAFB and Cyclin D1. In one embodiment, the multiple myeloma is characterized by activation of Cyclin D.

In one embodiment, the multiple myeloma is characterized by one or more chromosomal translocations. In one embodiment, the chromosomal translocation is t(14;16). In one embodiment, the chromosomal translocation is t(14;20). In one embodiment, the chromosomal translocation is t(4; 14). In one embodiment, the chromosomal translocations are t(4; 14) and t(14; 16). In one embodiment, the chromosomal translocation is t(11;14). In one embodiment, the chromosomal translocation is t(6;20). In one embodiment, the chromosomal translocation is t(20;22). In one embodiment, the chromosomal translocations are t(6;20) and t(20;22). In one embodiment, the chromosomal translocation is t(16;22). In one embodiment, the chromosomal translocations are t(14;16) and t(16;22). In one embodiment, the chromosomal translocations are t(14;20) and t(11;14).

In one embodiment, the multiple myeloma is characterized by a Q331 p53 mutation, by activation of C-MAF, and by a chromosomal translocation at t(14; 16). In one embodiment, the multiple myeloma is characterized by homozygous deletion of p53, by activation of C-MAF, and by a chromosomal translocation at t(14; 16). In one embodiment, the multiple myeloma is characterized by a K132N p53 mutation, by activation of MAFB, and by a chromosomal translocation at t(14;20). In one embodiment, the multiple myeloma is characterized by wild type p53, by activation of FGFR3 and MMset, and by a chromosomal translocation at t(4; 14). In one embodiment, the multiple myeloma is characterized by wild type p53, by activation of C-MAF, and by a chromosomal translocation at t(14;16). In one embodiment, the multiple myeloma is characterized by homozygous deletion of p53, by activation of FGFR3, MMset, and C-MAF, and by chromosomal translocations at t(4;14) and t(14;16). In one embodiment, the multiple myeloma is characterized by homozygous deletion of p53, by activation of Cyclin D1, and by a chromosomal translocation at t(11; 14). In one embodiment, the multiple myeloma is characterized by a R337L p53 mutation, by activation of Cyclin D1, and by a chromosomal translocation at t(11;14). In one embodiment, the multiple myeloma is characterized by a W146 p53 mutation, by activation of FGFR3 and MMset, and by a chromosomal translocation at t(4; 14). In one embodiment, the multiple myeloma is characterized by a S261T p53 mutation, by activation of MAFB, and by chromosomal translocations at t(6;20) and t(20;22). In one embodiment, the multiple myeloma is characterized by a E286K p53 mutation, by activation of FGFR3 and MMset, and by a chromosomal translocation at t(4; 14). In one embodiment, the multiple myeloma is characterized by a R175H p53 mutation, by activation of FGFR3 and MMset, and by a chromosomal translocation at t(4; 14). In one embodiment, the multiple myeloma is characterized by a E258K p53 mutation, by activation of C-MAF, and by chromosomal translocations at t(14;16) and t(16;22). In one embodiment, the multiple myeloma is characterized by wild type p53, by activation of MAFB and Cyclin D1, and by chromosomal translocations at t(14;20) and t(11;14). In one embodiment, the multiple myeloma is characterized by a A161T p53 mutation, by activation of Cyclin D, and by a chromosomal translocation at t(11;14).

In some embodiments of the methods described herein, the multiple myeloma is transplant eligible newly diagnosed multiple myeloma. In another embodiment, the multiple myeloma is transplant ineligible newly diagnosed multiple myeloma.

In yet other embodiments, the multiple myeloma is characterized by early progression (for example less than 12 months) following initial treatment. In still other embodiments, the multiple myeloma is characterized by early progression (for example less than 12 months) following autologous stem cell transplant. In another embodiment, the multiple myeloma is refractory to lenalidomide. In another embodiment, the multiple myeloma is refractory to pomalidomide. In some such embodiments, the multiple myeloma is predicted to be refractory to pomalidomide (for example, by molecular characterization). In another embodiment, the multiple myeloma is relapsed or refractory to 3 or more treatments and was exposed to a proteasome inhibitor (for example, bortezomib, carfilzomib, ixazomib, oprozomib, or marizomib) and an immunomodulatory compound (for example thalidomide, lenalidomide, pomalidomide, iberdomide, or avadomide), or double refractory to a proteasome inhibitor and an immunomodulatory compound. In still other embodiments, the multiple myeloma is relapsed or refractory to 3 or more prior therapies, including for example, a CD38 monoclonal antibody (CD38 mAb, for example, daratumumab or isatuximab), a proteasome inhibitor (for example, bortezomib, carfilzomib, ixazomib, or marizomib), and an immunomodulatory compound (for example thalidomide, lenalidomide, pomalidomide, iberdomide, or avadomide) or double refractory to a proteasome inhibitor or immunomodulatory compound and a CD38 mAb. In still other embodiments, the multiple myeloma is triple refractory, for example, the multiple myeloma is refractory to a proteasome inhibitor (for example, bortezomib, carfilzomib, ixazomib, oprozomib or marizomib), an immunomodulatory compound (for example thalidomide, lenalidomide, pomalidomide, iberdomide, or avadomide), and one other active agent, as described herein.

In some such embodiments, the methods comprise administering a therapeutically effective amount of Compound 1, or an enantiomer, mixture of enantiomers, tautomer, isotopolog, or pharmaceutically acceptable salt thereof, as induction therapy. In another embodiment, the methods comprise administering a therapeutically effective amount of Compound 2, or a tautomer, isotopolog, or pharmaceutically acceptable salt thereof, as induction therapy. In another embodiment, the methods comprise administering a therapeutically effective amount of Compound 3, or a tautomer, isotopolog, or pharmaceutically acceptable salt thereof, as induction therapy.

In certain embodiments, provided herein are methods of treating, preventing, and/or managing multiple myeloma, including relapsed/refractory multiple myeloma in patients with impaired renal function or a symptom thereof, comprising administering a therapeutically effective amount of Compound 1, Compound 2 or Compound 3, or an enantiomer, mixture of enantiomers, tautomer, isotopolog, or pharmaceutically acceptable salt thereof to a patient having relapsed/refractory multiple myeloma with impaired renal function.

In certain embodiments, provided herein are methods of treating, preventing, and/or managing multiple myeloma, including relapsed or refractory multiple myeloma in frail patients or a symptom thereof, comprising administering a therapeutically effective amount of Compound 1, Compound 2 or Compound 3, or an enantiomer, mixture of enantiomers, tautomer, isotopolog, or pharmaceutically acceptable salt thereof to a frail patient having multiple myeloma. In some such embodiments, the frail patient is characterized by ineligibility for induction therapy, or intolerance to dexamethasone treatment. In some such embodiment the frail patient is elderly, for example, older than 65 years old.

In certain embodiments, provided herein are methods of treating, preventing or managing multiple myeloma, comprising administering to a patient a therapeutically effective amount of Compound 1, or a tautomer, isotopolog, or pharmaceutically acceptable salt thereof, wherein the multiple myeloma is fourth line relapsed/refractory multiple myeloma. In certain embodiments, provided herein are methods of treating, preventing or managing multiple myeloma, comprising administering to a patient a therapeutically effective amount of Compound 2, or a tautomer, isotopolog, or pharmaceutically acceptable salt thereof, wherein the multiple myeloma is fourth line relapsed/refractory multiple myeloma. In certain embodiments, provided herein are methods of treating, preventing or managing multiple myeloma, comprising administering to a patient a therapeutically effective amount of Compound 3, or a tautomer, isotopolog, or pharmaceutically acceptable salt thereof, wherein the multiple myeloma is fourth line relapsed/refractory multiple myeloma.

In certain embodiments, provided herein are methods of treating, preventing or managing multiple myeloma, comprising administering to a patient a therapeutically effective amount of Compound 1, or a tautomer, isotopolog, or pharmaceutically acceptable salt thereof as induction therapy, wherein the multiple myeloma is newly diagnosed, transplant-eligible multiple myeloma. In certain embodiments, provided herein are methods of treating, preventing or managing multiple myeloma, comprising administering to a patient a therapeutically effective amount of Compound 2, or a tautomer, isotopolog, or pharmaceutically acceptable salt thereof as induction therapy, wherein the multiple myeloma is newly diagnosed, transplant-eligible multiple myeloma. In certain embodiments, provided herein are methods of treating, preventing or managing multiple myeloma, comprising administering to a patient a therapeutically effective amount of Compound 3, or a tautomer, isotopolog, or pharmaceutically acceptable salt thereof as induction therapy, wherein the multiple myeloma is newly diagnosed, transplant-eligible multiple myeloma.

In certain embodiments, provided herein are methods of treating, preventing or managing multiple myeloma, comprising administering to a patient a therapeutically effective amount of Compound 1, or a tautomer, isotopolog, or pharmaceutically acceptable salt thereof as maintenance therapy after other therapy or transplant, wherein the multiple myeloma is newly diagnosed, transplant-eligible multiple myeloma prior to the other therapy or transplant. In certain embodiments, provided herein are methods of treating, preventing or managing multiple myeloma, comprising administering to a patient a therapeutically effective amount of Compound 2, or a tautomer, isotopolog, or pharmaceutically acceptable salt thereof as maintenance therapy after other therapy or transplant, wherein the multiple myeloma is newly diagnosed, transplant-eligible multiple myeloma prior to the other therapy or transplant. In certain embodiments, provided herein are methods of treating, preventing or managing multiple myeloma, comprising administering to a patient a therapeutically effective amount of Compound 3, or a tautomer, isotopolog, or pharmaceutically acceptable salt thereof as maintenance therapy after other therapy or transplant, wherein the multiple myeloma is newly diagnosed, transplant-eligible multiple myeloma prior to the other therapy or transplant.

In certain embodiments, provided herein are methods of treating, preventing or managing multiple myeloma, comprising administering to a patient a therapeutically effective amount of Compound 1, or a tautomer, isotopolog, or pharmaceutically acceptable salt thereof as maintenance therapy after other therapy or transplant. In some embodiments, the multiple myeloma is newly diagnosed, transplant-eligible multiple myeloma prior to the other therapy and/or transplant. In some embodiments, the other therapy prior to transplant is treatment with chemotherapy or Compound 1, Compound 2 or Compound 3. In certain embodiments, provided herein are methods of treating, preventing or managing multiple myeloma, comprising administering to a patient a therapeutically effective amount of Compound 2, or a tautomer, isotopolog, or pharmaceutically acceptable salt thereof as maintenance therapy after other therapy or transplant. In some embodiments, the multiple myeloma is newly diagnosed, transplant-eligible multiple myeloma prior to the other therapy and/or transplant. In some embodiments, the other therapy prior to transplant is treatment with chemotherapy or Compound 1, Compound 2 or Compound 3. In certain embodiments, provided herein are methods of treating, preventing or managing multiple myeloma, comprising administering to a patient a therapeutically effective amount of Compound 3, or a tautomer, isotopolog, or pharmaceutically acceptable salt thereof as maintenance therapy after other therapy or transplant. In some embodiments, the multiple myeloma is newly diagnosed, transplant-eligible multiple myeloma prior to the other therapy and/or transplant. In some embodiments, the other therapy prior to transplant is treatment with chemotherapy or Compound 1, Compound 2 or Compound 3.

In certain embodiments, provided herein are methods of treating, preventing or managing multiple myeloma, comprising administering to a patient a therapeutically effective amount of Compound 1, or a tautomer, isotopolog, or pharmaceutically acceptable salt thereof, wherein the multiple myeloma is high risk multiple myeloma, that is relapsed or refractory to one, two or three previous treatments. In certain embodiments, provided herein are methods of treating, preventing or managing multiple myeloma, comprising administering to a patient a therapeutically effective amount of Compound 2, or a tautomer, isotopolog, or pharmaceutically acceptable salt thereof, wherein the multiple myeloma is high risk multiple myeloma, that is relapsed or refractory to one, two or three previous treatments. In certain embodiments, provided herein are methods of treating, preventing or managing multiple myeloma, comprising administering to a patient a therapeutically effective amount of Compound 3, or a tautomer, isotopolog, or pharmaceutically acceptable salt thereof, wherein the multiple myeloma is high risk multiple myeloma, that is relapsed or refractory to one, two or three previous treatments.

In certain embodiments, provided herein are methods of treating, preventing or managing multiple myeloma, comprising administering to a patient a therapeutically effective amount of Compound 1, or a tautomer, isotopolog, or pharmaceutically acceptable salt thereof, wherein the multiple myeloma is newly diagnosed, transplant-ineligible multiple myeloma. In certain embodiments, provided herein are methods of treating, preventing or managing multiple myeloma, comprising administering to a patient a therapeutically effective amount of Compound 2, or a tautomer, isotopolog, or pharmaceutically acceptable salt thereof, wherein the multiple myeloma is newly diagnosed, transplant-ineligible multiple myeloma. In certain embodiments, provided herein are methods of treating, preventing or managing multiple myeloma, comprising administering to a patient a therapeutically effective amount of Compound 3, or a tautomer, isotopolog, or pharmaceutically acceptable salt thereof, wherein the multiple myeloma is newly diagnosed, transplant-ineligible multiple myeloma.

In certain embodiments, a therapeutically or prophylactically effective amount of the compound is from about from about 0.01 to about 25 mg per day, from about 0.01 to about 10 mg per day, from about 0.01 to about 5 mg per day, from about 0.01 to about 2 mg per day, from about 0.01 to about 1 mg per day, from about 0.01 to about 0.5 mg per day, from about 0.01 to about 0.25 mg per day, from about 0.1 to about 25 mg per day, from about 0.1 to about 10 mg per day, from about 0.1 to about 5 mg per day, from about 0.1 to about 2 mg per day, from about 0.1 to about 1 mg per day, from about 0.1 to about 0.5 mg per day, from about 0.1 to about 0.25 mg per day, from about 0.5 to about 25 mg per day, from about 0.5 to about 10 mg per day, from about 0.5 to about 5 mg per day, from about 0.5 to about 2 mg per day, from about 0.5 to about 1 mg per day, from about 1 to about 25 mg per day, from about 1 to about 10 mg per day, from about 1 to about 5 mg per day, from about 1 to about 2.5 mg per day, or from about 1 to about 2 mg per day. In one embodiment, a therapeutically or prophylactically effective amount of Compound 1, Compound 2 or Compound 3 is from about 0.1 mg per day to about 0.4 mg per day.

In certain embodiments, the therapeutically or prophylactically effective amount is about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 15, about 20, or about 25 mg per day. In some such embodiments, the therapeutically or prophylactically effective amount is about 0.1, about 0.2, about 0.3, about 0.4, about 0.5, about 0.6 or about 0.7 mg per day.

In one embodiment, the recommended daily dose range of Compound 1, Compound 2 or Compound 3, or an enantiomer, mixture of enantiomers, tautomer, isotopolog, or pharmaceutically acceptable salt thereof, for the conditions described herein lie within the range of from about 0.1 mg to about 25 mg per day, preferably given as a single once-a-day dose, or in divided doses throughout a day. In other embodiments, the dosage ranges from about 0.1 to about 10 mg per day. Specific doses per day include 0.1, 0.2, 0.3, 0.4, 0.5, 1, 2, 3, 4, 5, 6, 7, 8, 9, 10, 11, 12, 13, 14, 15, 16, 17, 18, 19, 20, 21, 22, 23, 24, or 25 mg per day. More specific doses per day include 0.1, 0.2, 0.3, 0.4, or 0.5 mg per day.

In a specific embodiment, the recommended starting dosage may be 0.1, 0.2, 0.3, 0.4, 0.5, 1, 2, 3, 4, 5, 10, 15, 20, or 25 mg per day. In another embodiment, the recommended starting dosage may be 0.1, 0.2, 0.3, 0.4, or 0.5, mg per day. The dose may be escalated to 1, 2, 3, 4, or 5 mg per day.

In certain embodiments, the therapeutically or prophylactically effective amount is from about 0.001 to about 5 mg/kg/day, from about 0.001 to about 4 mg/kg/day, from about 0.001 to about 3 mg/kg/day, from about 0.001 to about 2 mg/kg/day, from about 0.001 to about 1 mg/kg/day, from about 0.001 to about 0.05 mg/kg/day, from about 0.001 to about 0.04 mg/kg/day, from about 0.001 to about 0.03 mg/kg/day, from about 0.001 to about 0.02 mg/kg/day, from about 0.001 to about 0.01 mg/kg/day, or from about 0.001 to about 0.005 mg/kg/day.

The administered dose can also be expressed in units other than mg/kg/day. For example, doses for parenteral administration can be expressed as $mg/m^2/day$. One of ordinary skill in the art would readily know how to convert doses from mg/kg/day to $mg/m^2/day$ given either the height or weight of a subject or both (see, www.fda.gov/cder/cancer/animalframe.htm). For example, a dose of 1 mg/kg/day for a 65 kg human is approximately equal to 38 $mg/m^2/day$.

In certain embodiments, the patient to be treated with one of the methods provided herein has not been treated with multiple myeloma therapy prior to the administration of Compound 1, Compound 2 or Compound 3 provided herein, or an enantiomer, mixture of enantiomers, tautomer, isotopolog, or pharmaceutically acceptable salt thereof. In certain embodiments, the patient to be treated with one of the methods provided herein has been treated with multiple myeloma therapy prior to the administration of Compound 1, Compound 2 or Compound 3 provided herein or an enantiomer, mixture of enantiomers, tautomer, isotopolog, or pharmaceutically acceptable salt thereof. In certain embodiments, the patient to be treated with one of the methods provided herein has developed drug resistance to the anti-multiple myeloma therapy. In some such embodiments, the patient has developed resistance to one, two, or three anti-multiple myeloma therapies, wherein the therapies are selected from a CD38 monoclonal antibody (CD38 mAb, for example, daratumumab or isatuximab), a proteasome inhibitor (for example, bortezomib, carfilzomib, ixazomib, or marizomib), and an immunomodulatory compound (for example thalidomide, lenalidomide, pomalidomide, iberdomide, or avadomide).

The methods provided herein encompass treating a patient regardless of patient's age. In some embodiments, the subject is 18 years or older. In other embodiments, the subject is more than 18, 25, 35, 40, 45, 50, 55, 60, 65, or 70 years old. In other embodiments, the subject is less than 65 years old. In other embodiments, the subject is more than 65 years old. In one embodiment, the subject is an elderly multiple myeloma subject, such as a subject older than 65 years old. In one embodiment, the subject is an elderly multiple myeloma subject, such as a subject older than 75 years old.

Depending on the state of the disease to be treated and the subject's condition, Compound 1, Compound 2, or Compound 3 provided herein, or an enantiomer, mixture of enantiomers, tautomer, isotopolog, or pharmaceutically acceptable salt thereof, may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. Compound 1, Compound 2 or Compound 3 provided herein, or an enantiomer, mixture of enantiomers, tautomer, isotopolog, or pharmaceutically acceptable salt thereof, may be formulated, alone or together, in suitable dosage unit with pharmaceutically acceptable excipients, carriers, adjuvants and vehicles, appropriate for each route of administration.

In one embodiment, Compound 1, Compound 2 or Compound 3 provided herein, or an enantiomer, mixture of enantiomers, tautomer, isotopolog, or pharmaceutically acceptable salt thereof, is administered orally. In another embodiment, the compound of Compound 1, Compound 2 or Compound 3 provided herein, or an enantiomer, mixture of enantiomers, tautomer, isotopolog, or pharmaceutically acceptable salt thereof, is administered parenterally. In yet another embodiment, the compound of Compound 1, Compound 2 or Compound 3 provided herein, or an enantiomer, mixture of enantiomers, tautomer, isotopolog, or pharmaceutically acceptable salt thereof, is administered intravenously.

Compound 1, Compound 2 or Compound 3 provided herein, or an enantiomer, mixture of enantiomers, tautomer, isotopolog, or pharmaceutically acceptable salt thereof, can be delivered as a single dose such as, e.g., a single bolus injection, or oral tablets or pills; or over time, such as, e.g., continuous infusion over time or divided bolus doses over time. The compounds as described herein can be administered repeatedly if necessary, for example, until the patient experiences stable disease or regression, or until the patient experiences disease progression or unacceptable toxicity. Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

Compound 1, Compound 2 or Compound 3 provided herein, or an enantiomer, mixture of enantiomers, tautomer, isotopolog, or pharmaceutically acceptable salt thereof, can be administered once daily (QD or qd), or divided into multiple daily doses such as twice daily (BID or bid), three times daily (TID or tid), and four times daily (QID or qid). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as Compound 1, Compound 2 or Compound 3 provided herein, or an enantiomer, mixture of enantiomers, tautomer, isotopolog, or pharmaceutically acceptable salt thereof, is administered once or more than once each day, for example, for a period of time. The term "continuous" is intended to mean that a therapeutic compound, such as Compound 1, Compound 2 or Compound 3 provided herein, or an enantiomer, mixture of enantiomers, tautomer, isotopolog, or pharmaceutically acceptable salt thereof, is administered daily for an uninterrupted period of at least 7 days to 52 weeks. The term "intermittent" or "intermittently" as used herein is intended to mean stopping and starting at either regular or irregular intervals. For example, intermittent administration of Compound 1, Compound 2 or Compound 3 provided herein, or an enantiomer, mixture of enantiomers, tautomer, isotopolog, or pharmaceutically acceptable salt thereof, is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as Compound 1, Compound 2 or Compound 3 provided herein, or an enantiomer, mixture of enantiomers, tautomer, isotopolog, or pharmaceutically acceptable salt thereof, is administered daily or continuously but with a rest period. In some such embodiments, administration is once a day for two to six days, then a rest period with no administration for five to seven days.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, Compound 1, Compound 2 or Compound 3 provided herein, or an enantiomer, mixture of enantiomers, tautomer, isotopolog, or pharmaceutically acceptable salt thereof, is administered once a day. In another embodiment, Compound 1, Compound 2 or Compound 3 provided herein, or an enantiomer, mixture of enantiomers, tautomer, isotopolog, or pharmaceutically acceptable salt thereof, is administered twice a day. In yet another embodiment, Compound 1, Compound 2 or Compound 3 provided herein, or an enantiomer, mixture of enantiomers, tautomer, isotopolog, or pharmaceutically acceptable salt thereof, is administered three times a day. In still another embodiment, Compound 1, Compound 2 or Compound 3 provided herein, or an enantiomer, mixture of enantiomers, tautomer, isotopolog, or pharmaceutically acceptable salt thereof, is administered four times a day.

In one embodiment, a therapeutically effective amount of Compound 1, Compound 2 or Compound 3 is administered in a treatment cycle which includes an administration period of up to 20 days followed by a rest period. In one embodiment, a therapeutically effective amount of Compound 1, Compound 2 or Compound 3 is administered in a treatment cycle which includes an administration period of up to 15 days followed by a rest period. In one embodiment, a therapeutically effective amount of Compound 1, Compound 2 or Compound 3 is administered in a treatment cycle which includes an administration period of up to 10 days followed by a rest period. In one embodiment, a therapeutically effective amount of Compound 1, Compound 2 or Compound 3 is administered in a treatment cycle which includes an administration period of up to 7 days followed by a rest period. In one embodiment, a therapeutically effective amount of Compound 1, Compound 2 or Compound 3 is administered in a treatment cycle which includes an administration period of up to 5 days followed by a rest period. In one embodiment, a therapeutically effective amount of Compound 1, Compound 2 or Compound 3 is administered in a treatment cycle which includes an administration period of up to 4 days followed by a rest period. In one embodiment, a therapeutically effective amount of Compound 1, Compound 2 or Compound 3 is administered in a treatment cycle which includes an administration period of up to 3 days followed by a rest period.

In one embodiment, the treatment cycle includes an administration period of up to 14 days followed by a rest period. In one embodiment, the treatment cycle includes an administration period of up to 10 days followed by a rest period. In one embodiment, the treatment cycle includes an administration period of up to 7 days followed by a rest period. In one embodiment, the treatment cycle includes an administration period of up to 5 days followed by a rest period. In one embodiment, the treatment cycle includes an administration period of up to 4 days followed by a rest period. In one embodiment, the treatment cycle includes an administration period of up to 3 days followed by a rest period.

In one embodiment, the rest period is from about 2 days up to about 11 days. In one embodiment, the rest period is from about 2 days up to about 10 days. In one embodiment, the rest period is about 2 days. In one embodiment, the rest period is about 3 days. In one embodiment, the rest period is about 4 days. In one embodiment, the rest period is about 5 days. In one embodiment, the rest period is about 6 days. In another embodiment, the rest period is about 7 days. In another embodiment, the rest period is about 8 days. In another embodiment, the rest period is about 9 days. In another embodiment, the rest period is about 10 days. In another embodiment, the rest period is about 11 days.

In one embodiment, the treatment cycle includes an administration period of up to 15 days followed by a rest period from about 2 days up to about 10 days. In one embodiment, the treatment cycle includes an administration period of up to 10 days followed by a rest period from about 2 days up to about 10 days. In one embodiment, the treatment cycle includes an administration period of up to 7 days followed by a rest period from about 2 days up to about 10 days. In one embodiment, the treatment cycle includes an administration period of up to 5 days followed by a rest period from about 2 days up to about 10 days. In one embodiment, the treatment cycle includes an administration period of up to 3 days followed by a rest period from about 10 days up to about 15 days. In one embodiment, the treatment cycle includes an administration period of up to 3 days followed by a rest period from about 3 days up to about 15 days.

In one embodiment, the treatment cycle includes an administration period of up to 15 days followed by a rest period of 7 days. In one embodiment, the treatment cycle includes an administration period of up to 10 days followed by a rest period of 5 days. In one embodiment, the treatment cycle includes an administration period of up to 10 days followed by a rest period of 4 days. In one embodiment, the treatment cycle includes an administration period of up to 10 days followed by a rest period of 3 days. In one embodiment, the treatment cycle includes an administration period of up to 10 days followed by a rest period of 2 days. In one embodiment, the treatment cycle includes an administration period of up to 7 days followed by a rest period of 7 days. In one embodiment, the treatment cycle includes an administration period of up to 5 days followed by a rest period of 5 days. In one embodiment, the treatment cycle includes an administration period of up to 3 days followed by a rest period of 11 days. In another embodiment, the treatment cycle includes an administration period of up to 5 days followed by a rest period of 9 days. In another embodiment, the treatment cycle includes an administration period of up to 5 days followed by a rest period of 2 days. In another embodiment, the treatment cycle includes an administration period of up to 3 days followed by a rest period of 4 days.

In one embodiment, the treatment cycle includes an administration of a therapeutically effective amount of Compound 1, Compound 2 or Compound 3 on days 1 to 5 of a 28 day cycle. In another embodiment, the treatment cycle includes an administration of Compound 1, Compound 2 or Compound 3 on days 1 to 10 of a 28 day cycle. In one embodiment, the treatment cycle includes an administration of a therapeutically effective amount of Compound 1, Compound 2 or Compound 3 on days 1 to 21 of a 28 day cycle. In another embodiment, the treatment cycle includes an administration of a therapeutically effective amount of Compound 1, Compound 2 or Compound 3 on days 1 to 5 of a 7 day cycle. In another embodiment, the treatment cycle includes an administration of a therapeutically effective amount of Compound 1, Compound 2 or Compound 3 on days 1 to 7 of a 7 day cycle. In one embodiment, the treatment cycle includes an administration of a therapeutically effective amount of Compound 1, Compound 2 or Compound 3 on days 1 to 10 and days 15 to 24 of a 28 day cycle (herein referred to as 20/28 dosing cycle). In one embodiment, the treatment cycle includes an administration of a therapeutically effective amount of Compound 1, Compound 2 or Compound 3 on days 1 to 3 and days 15 to 18 of a 28 day cycle. In one embodiment, the treatment cycle includes an administration of a therapeutically effective amount of Compound 1, Compound 2 or Compound 3 on days 1 to 7 and days 15 to 21 of a 28 day cycle (herein referred to as 14/28 dosing cycle). In one embodiment, the treatment cycle includes an administration of a therapeutically effective amount of Compound 1, Compound 2 or Compound 3 on days 1 to 5 and days 15 to 19 of a 28 day cycle (herein referred to as 10/28 dosing cycle). In one embodiment, the treatment cycle includes an administration of a therapeutically effective amount of Compound 1, Compound 2 or Compound 3 on days 1 to 3 and days 15 to 17 of a 28 day cycle (herein referred to as 6/28 dosing cycle).

In one embodiment, the treatment cycle includes an administration of a therapeutically effective amount of Compound 1, Compound 2 or Compound 3 on days 1 to 14 of a 21 day cycle. In another embodiment, the treatment cycle includes an administration of Compound 1, Compound 2 or Compound 3 on days 1 to 4 and 8 to 11 of a 21 day cycle. In one embodiment, the treatment cycle includes an administration of a therapeutically effective amount of Compound 1, Compound 2 or Compound 3 on days 1 to 5 and 8 to 12 of a 21 day cycle. In another embodiment, the treatment cycle includes an administration of a therapeutically effective amount of Compound 1, Compound 2 or Compound 3 on days 1 to 5 and 11 to 15 of a 21 day cycle. In another embodiment, the treatment cycle includes an administration of a therapeutically effective amount of Compound 1, Compound 2 or Compound 3 on days 1 to 5, 8 to 12 and 15 to 19 of a 21 day cycle. In another embodiment, the treatment cycle includes an administration of a therapeutically effective amount of Compound 1, Compound 2 or Compound 3 on days 1 to 4, 8 to 11 and 15 to 18 of a 21 day cycle. In another embodiment, the treatment cycle includes an administration of a therapeutically effective amount of Compound 1, Compound 2 or Compound 3 on days 1 to 4, 8 to 10 and 15 to 17 of a 21 day cycle. In another embodiment, the treatment cycle includes an administration of a therapeutically effective amount of Compound 1, Compound 2 or Compound 3 on days 1 to 3, and 8 to 11 of a 21 day cycle. In another embodiment, the treatment cycle includes an administration of a therapeutically effective amount of Compound 1, Compound 2 or Compound 3 on days 1 to 3 and 11 to 13 of a 21 day cycle.

Any treatment cycle described herein can be repeated for at least 2, 3, 4, 5, 6, 7, 8, or more cycles. In certain instances, the treatment cycle as described herein includes from 1 to about 24 cycles, from about 2 to about 16 cycles, or from about 2 to about 4 cycles. In certain instances a treatment cycle as described herein includes from 1 to about 4 cycles. In certain embodiments, cycle 1 to 4 are all 28 day cycles. In some embodiments, a therapeutically effective amount of Compound 1, Compound 2 or Compound 3 is administered for 1 to 13 cycles of 28 days (e.g. about 1 year). In certain instances, the cycling therapy is not limited to the number of cycles, and the therapy is continued until disease progression. Cycles can in certain instances include varying the duration of administration periods and/or rest periods described herein.

In one embodiment the treatment cycle includes administering Compound 1, Compound 2 or Compound 3 at a dosage amount of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 5.0 mg/day, or 10 mg/day, administered once per day. In one embodiment the treatment cycle includes administering Compound 1, Compound 2 or Compound 3 at a dosage amount of about 0.1 mg/day, 0.2 mg/day, 0.3 mg/day, 0.4 mg/day, 0.5 mg/day, 0.6 mg/day, 0.7 mg/day, or 0.8 mg/day, administered once per day. In some such embodiments, the treatment cycle includes administering Compound 1, Compound 2 or Compound 3 once a day at a dosage amount of about 0.1 mg, 0.2 mg, 0.3 mg, 0.4 mg, or 0.5 mg on days 1 to 10 of a 28 day cycle. In some such embodiments, the treatment cycle includes administering Compound 1, Compound 2 or Compound 3 once a day at a dosage amount of about 0.1 mg, 0.2 mg, 0.3 mg, 0.4 mg, or 0.5 mg on days 1 to 10 and 15 to 24 of a 28 day cycle. In some such embodiments, the treatment cycle includes administering Compound 1, Compound 2 or Compound 3 once a day at a dosage amount of about 0.1 mg on days 1 to 10 and 15 to 24 of a 28 day cycle. In other embodiments, the treatment cycle includes administering Compound 1, Compound 2 or Compound 3 twice a day at a dosage amount of about 0.1 mg, 0.2 mg, 0.3 mg, 0.4 mg, or 0.5 mg on days 1 to 3 of a 28 day cycle. In other embodiments, the treatment cycle includes administering Compound 1, Compound 2 or Compound 3 twice a day at a dosage amount of about 0.1 mg, 0.2 mg, 0.3 mg, 0.4 mg, or 0.5 mg on days 1 to 3 and 15 to 19 of a 28 day cycle. In other embodiments, the treatment cycle includes administering Compound 1, Compound 2 or Compound 3 twice a day at a dosage amount of about 0.1 mg, 0.2 mg, 0.3 mg, 0.4 mg, or 0.5 mg on days 1 to 3 and 15 to 17 of a 28 day cycle. In other embodiments, the treatment cycle includes administering Compound 1, Compound 2 or Compound 3 twice a day at a dosage amount of about 0.2 mg on days 1 to 3 and 15 to 17 of a 28 day cycle. In one such embodiment, the compound is administered on days 1 to 3 (morning and evening), day 14 (evening only), days 15 and 16 (morning and evening), and day 17 (morning only) of a 28 day cycle, for example in Cycle 1.

F. Combination Therapy with a Second Active Agent

Compound 1, Compound 2 or Compound 3 provided herein, or an enantiomer, mixture of enantiomers, tautomer, isotopolog, or pharmaceutically acceptable salt thereof, can also be combined or used in conjunction with (e.g. before, during, or after) conventional therapy including, but not limited to, surgery, biological therapy (including immunotherapy, for example with checkpoint inhibitors), radiation therapy, chemotherapy, stem cell transplantation, cell therapy, or other non-drug based therapy presently used to treat, prevent or manage multiple myeloma. The combined use of the compound provided herein and conventional therapy may provide a unique treatment regimen that is unexpectedly effective in certain patients. Without being limited by theory, it is believed that Compound 1, Compound 2 or Compound 3 may provide additive or synergistic effects when given concurrently with conventional therapy.

As discussed elsewhere herein, encompassed herein is a method of reducing, treating and/or preventing adverse or undesired effects associated with conventional therapy including, but not limited to, surgery, chemotherapy, radiation therapy, biological therapy and immunotherapy. A compound provided herein, e.g., Compound 1, Compound 2 or Compound 3, or an enantiomer, mixture of enantiomers, tautomer, isotopolog, or pharmaceutically acceptable salt thereof, and other active ingredient can be administered to a patient prior to, during, or after the occurrence of the adverse effect associated with conventional therapy.

Compound 1, Compound 2 or Compound 3 provided herein, or an enantiomer, mixture of enantiomers, tautomer, isotopolog, or pharmaceutically acceptable salt thereof, can also be combined or used in combination with other therapeutic agents useful in the treatment and/or prevention of multiple myeloma described herein.

In one embodiment, provided herein is a method of treating, preventing, or managing multiple myeloma, comprising administering to a patient Compound 1, Compound 2 or Compound 3, or an enantiomer, mixture of enantiomers, tautomer, isotopolog, or pharmaceutically acceptable salt thereof, in combination with one or more second active agents, and optionally in combination with radiation therapy, blood transfusions, or surgery.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. A first therapy (e.g., a prophylactic or therapeutic agent such as a compound provided herein, e.g., Compound 1, Compound 2 or Compound 3, or an enantiomer, mixture of enantiomers, tautomer, isotopolog, or pharmaceutically acceptable salt thereof) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein, as is quadruple therapy. In one embodiment, the second therapy is dexamethasone.

Administration of Compound 1, Compound 2 or Compound 3, or an enantiomer, mixture of enantiomers, tautomer, isotopolog, or pharmaceutically acceptable salt thereof, and one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream).

The route of administration of Compound 1, Compound 2 or Compound 3, or an enantiomer, mixture of enantiomers, tautomer, isotopolog, or pharmaceutically acceptable salt thereof, is independent of the route of administration of a second therapy. In one embodiment, Compound 1, Compound 2 or Compound 3, or an enantiomer, mixture of enantiomers, tautomer, isotopolog, or pharmaceutically acceptable salt thereof, is administered orally. In another embodiment, Compound 1, Compound 2 or Compound 3 is administered intravenously. Thus, in accordance with these embodiments, Compound 1, Compound 2 or Compound 3, or an enantiomer, mixture of enantiomers, tautomer, isotopolog, or pharmaceutically acceptable salt thereof, is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, Compound 1, Compound 2 or Compound 3, or an enantiomer, mixture of enantiomers, tautomer, isotopolog, or pharmaceutically acceptable salt thereof, and a second therapy are administered by the same mode of administration, orally or by IV. In another embodiment, Compound 1, Compound 2 or Compound 3, or an enantiomer, mixture of enantiomers, tautomer, isotopolog, or pharmaceutically acceptable salt thereof, is administered by one mode of administration, e.g., by IV, whereas the second agent (an anti-multiple myeloma agent) is administered by another mode of administration, e.g., orally.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of multiple myeloma being treated or managed, the severity and stage of disease, and the amount of Compound 1, Compound 2 or Compound 3, or an enantiomer, mixture of enantiomers, tautomer, isotopolog, or pharmaceutically acceptable salt thereof, provided herein and any optional additional active agents concurrently administered to the patient.

One or more second active ingredients or agents can be used together with Compound 1, Compound 2 or Compound 3 in the methods and compositions provided herein. Second active agents can be large molecules (e.g., proteins), small molecules (e.g., synthetic inorganic, organometallic, or organic molecules), or cell therapies (e.g., CAR cells).

Examples of second active agents that can be used in the methods and compositions described herein include one or more of melphalan, vincristine, cyclophosphamide, etoposide, doxorubicin, bendamustine, obinutuzmab, a proteasome inhibitor (for example, bortezomib, carfilzomib, ixazomib, oprozomib or marizomib), a histone deacetylase inhibitor (for example, panobinostat, ACY241), a BET inhibitor (for example, GSK525762A, OTX015, BMS-986158, TEN-010, CPI-0610, INCB54329, BAY1238097, FT-1101, ABBV-075, BI 894999, GS-5829, GSK1210151A (I-BET-151), CPI-203, RVX-208, XD46, MS436, PFI-1, RVX2135, ZEN3365, XD14, ARV-771, MZ-1, PLX5117, 4-[2-(cyclopropylmethoxy)-5-(methanesulfonyl)phenyl]-2-methylisoquinolin-1(2H)-one, EP11313 and EP11336), a BCL2 inhibitor (for example, venetoclax or navitoclax), an MCL-1 inhibitor (for example, AZD5991, AMG176, MIK665, S64315, or S63845), an LSD-1 inhibitor (for example, ORY-1001, ORY-2001, INCB-59872, IMG-7289, TAK-418, GSK-2879552, 4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile or a salt therof), a corticosteroid (for example, prednisone), dexamethasone; an antibody (for example, a CS1 antibody, such as elotuzumab; a CD38 antibody, such as daratumumab or isatuximab; or a BCMA antibody or antibody-conjugate, such as GSK2857916 or BI 836909), a checkpoint inhibitor (as described herein), or CAR cells (as described herein).

In one embodiment, the second active agent used together with Compound 1, Compound 2 or Compound 3, or an enantiomer, mixture of enantiomers, tautomer, isotopolog, or pharmaceutically acceptable salt thereof, in the methods and compositions described herein is dexamethasone.

In some embodiments, the dexamethasone is administered at a 4 mg dose on days 1 and 8 of a 21 day cycle. In some other embodiments, the dexamethasone is administered at a 4 mg dose on days 1, 4, 8 and 11 of a 21 day cycle. In some embodiments, the dexamethasone is administered at a 4 mg dose on days 1, 8, and 15 of a 28 day cycle. In some other embodiments, the dexamethasone is administered at a 4 mg dose on days 1, 4, 8, 11, 15 and 18 of a 28 day cycle. In some embodiments, the dexamethasone is administered at a 4 mg dose on days 1, 8, 15, and 22 of a 28 day cycle. In one such embodiment, the dexamethasone is administered at a 4 mg dose on days 1, 10, 15, and 22 of Cycle 1. In some embodiments, the dexamethasone is administered at a 4 mg dose on days 1, 3, 15, and 17 of a 28 day cycle. In one such embodiment, the dexamethasone is administered at a 4 mg dose on days 1, 3, 14, and 17 of Cycle 1.

In some other embodiments, the dexamethasone is administered at a 8 mg dose on days 1 and 8 of a 21 day cycle. In some other embodiments, the dexamethasone is administered at a 8 mg dose on days 1, 4, 8 and 11 of a 21 day cycle. In some embodiments, the dexamethasone is administered at a 8 mg dose on days 1, 8, and 15 of a 28 day cycle. In some other embodiments, the dexamethasone is administered at a 8 mg dose on days 1, 4, 8, 11, 15 and 18 of a 28 day cycle. In some embodiments, the dexamethasone is administered at a 8 mg dose on days 1, 8, 15, and 22 of a 28 day cycle. In one such embodiment, the dexamethasone is administered at a 8 mg dose on days 1, 10, 15, and 22 of Cycle 1. In some embodiments, the dexamethasone is administered at a 8 mg dose on days 1, 3, 15, and 17 of a 28 day cycle. In one such embodiment, the dexamethasone is administered at a 8 mg dose on days 1, 3, 14, and 17 of Cycle 1.

In some embodiments, the dexamethasone is administered at a 10 mg dose on days 1 and 8 of a 21 day cycle. In some other embodiments, the dexamethasone is administered at a 10 mg dose on days 1, 4, 8 and 11 of a 21 day cycle. In some embodiments, the dexamethasone is administered at a 10 mg dose on days 1, 8, and 15 of a 28 day cycle. In some other embodiments, the dexamethasone is administered at a 10 mg dose on days 1, 4, 8, 11, 15 and 18 of a 28 day cycle. In some embodiments, the dexamethasone is administered at a 10 mg dose on days 1, 8, 15, and 22 of a 28 day cycle. In one such embodiment, the dexamethasone is administered at a 10 mg dose on days 1, 10, 15, and 22 of Cycle 1. In some embodiments, the dexamethasone is administered at a 10 mg dose on days 1, 3, 15, and 17 of a 28 day cycle. In one such embodiment, the dexamethasone is administered at a 10 mg dose on days 1, 3, 14, and 17 of Cycle 1.

In some embodiments, the dexamethasone is administered at a 20 mg dose on days 1 and 8 of a 21 day cycle. In some other embodiments, the dexamethasone is administered at a 20 mg dose on days 1, 4, 8 and 11 of a 21 day cycle. In some embodiments, the dexamethasone is administered at a 20 mg dose on days 1, 8, and 15 of a 28 day cycle. In some other embodiments, the dexamethasone is administered at a 20 mg dose on days 1, 4, 8, 11, 15 and 18 of a 28 day cycle. In some embodiments, the dexamethasone is administered at a 20 mg dose on days 1, 8, 15, and 22 of a 28 day cycle. In one such embodiment, the dexamethasone is administered at a 20 mg dose on days 1, 10, 15, and 22 of Cycle 1. In some embodiments, the dexamethasone is administered at a 20 mg dose on days 1, 3, 15, and 17 of a 28 day cycle. In one such embodiment, the dexamethasone is administered at a 20 mg dose on days 1, 3, 14, and 17 of Cycle 1.

In some embodiments, the dexamethasone is administered at a 40 mg dose on days 1 and 8 of a 21 day cycle. In some other embodiments, the dexamethasone is administered at a 40 mg dose on days 1, 4, 8 and 11 of a 21 day cycle. In some embodiments, the dexamethasone is administered at a 40 mg dose on days 1, 8, and 15 of a 28 day cycle. In one such embodiment, the dexamethasone is administered at a 40 mg dose on days 1, 10, 15, and 22 of Cycle 1. In some other embodiments, the dexamethasone is administered at a 40 mg dose on days 1, 4, 8, 11, 15 and 18 of a 28 day cycle. In other such embodiments, the dexamethasone is administered at a 40 mg dose on days 1, 8, 15, and 22 of a 28 day cycle. In other such embodiments, the dexamethasone is administered at a 40 mg dose on days 1, 3, 15, and 17 of a 28 day cycle. In one such embodiment, the dexamethasone is administered at a 40 mg dose on days 1, 3, 14, and 17 of Cycle 1.

In another embodiment, the second active agent used together with Compound 1, Compound 2 or Compound 3, or an enantiomer, mixture of enantiomers, tautomer, isotopolog, or pharmaceutically acceptable salt thereof, in the methods and compositions described herein is bortezomib. In yet another embodiment, the second active agent used together with Compound 1, Compound 2 or Compound 3, or an enantiomer, mixture of enantiomers, tautomer, isotopolog, or pharmaceutically acceptable salt thereof, in the methods and compositions described herein is daratumumab. In some such embodiments, the methods additionally comprise administration of dexamethasone. In some embodiments, the methods comprise administration of Compound 1, Compound 2 or Compound 3, or an enantiomer, mixture of enantiomers, tautomer, isotopolog, or pharmaceutically acceptable salt thereof, with a proteasome inhibitor as described herein, a CD38 inhibitor as described herein and a corticosteroid as described herein.

In another embodiment, the second active agent used together with Compound 1, Compound 2 or Compound 3, or an enantiomer, mixture of enantiomers, tautomer, isotopolog, or pharmaceutically acceptable salt thereof, in the methods and compositions described herein is panobinostat. In some such embodiments, the methods additionally comprise administration of dexamethasone.

In another embodiment, the second active agent used together with Compound 1, Compound 2 or Compound 3, or an enantiomer, mixture of enantiomers, tautomer, isotopolog, or pharmaceutically acceptable salt thereof, in the methods and compositions described herein is ACY241. In some such embodiments, the methods additionally comprise administration of dexamethasone.

In another embodiment, the second active agent used together with Compound 1, Compound 2 or Compound 3, or an enantiomer, mixture of enantiomers, tautomer, isotopolog, or pharmaceutically acceptable salt thereof, in the methods and compositions described herein is vincristine. In some such embodiments, the methods additionally comprise administration of dexamethasone.

In another embodiment, the second active agent used together with Compound 1, Compound 2 or Compound 3, or an enantiomer, mixture of enantiomers, tautomer, isotopolog, or pharmaceutically acceptable salt thereof, in the methods and compositions described herein is cyclophosphamide. In some such embodiments, the methods additionally comprise administration of dexamethasone.

In another embodiment, the second active agent used together with Compound 1, Compound 2 or Compound 3, or an enantiomer, mixture of enantiomers, tautomer, isotopolog, or pharmaceutically acceptable salt thereof, in the methods and compositions described herein is etoposide. In some such embodiments, the methods additionally comprise administration of dexamethasone.

In another embodiment, the second active agent used together with Compound 1, Compound 2 or Compound 3, or an enantiomer, mixture of enantiomers, tautomer, isotopolog, or pharmaceutically acceptable salt thereof, in the methods and compositions described herein is doxorubicin. In some such embodiments, the methods additionally comprise administration of dexamethasone.

In another embodiment, the second active agent used together with Compound 1, Compound 2 or Compound 3, or an enantiomer, mixture of enantiomers, tautomer, isotopolog, or pharmaceutically acceptable salt thereof, in the methods and compositions described herein is venetoclax. In some such embodiments, the methods additionally comprise administration of dexamethasone.

In another embodiment, the second active agent used together with Compound 1, Compound 2 or Compound 3, or an enantiomer, mixture of enantiomers, tautomer, isotopolog, or pharmaceutically acceptable salt thereof, in the methods and compositions described herein is AMG176. In some such embodiments, the methods additionally comprise administration of dexamethasone.

In another embodiment, the second active agent used together with Compound 1, Compound 2 or Compound 3, or an enantiomer, mixture of enantiomers, tautomer, isotopolog, or pharmaceutically acceptable salt thereof, in the methods and compositions described herein is MIK665. In some such embodiments, the methods additionally comprise administration of dexamethasone.

In another embodiment, the second active agent used together with Compound 1, Compound 2 or Compound 3, or an enantiomer, mixture of enantiomers, tautomer, isotopolog, or pharmaceutically acceptable salt thereof, in the methods and compositions described herein is GSK525762A. In some such embodiments, the methods additionally comprise administration of dexamethasone.

In another embodiment, the second active agent used together with Compound 1, Compound 2 or Compound 3, or an enantiomer, mixture of enantiomers, tautomer, isotopolog, or pharmaceutically acceptable salt thereof, in the methods and compositions described herein is OTX015. In some such embodiments, the methods additionally comprise administration of dexamethasone.

In another embodiment, the second active agent used together with Compound 1, Compound 2 or Compound 3, or an enantiomer, mixture of enantiomers, tautomer, isotopolog, or pharmaceutically acceptable salt thereof, in the methods and compositions described herein is 4-[2-(cyclopropylmethoxy)-5-(methanesulfonyl)phenyl]-2-methylisoquinolin-1(2H)-one. In some such embodiments, the methods additionally comprise administration of dexamethasone.

In another embodiment, the second active agent used together with Compound 1, Compound 2 or Compound 3, or an enantiomer, mixture of enantiomers, tautomer, isotopolog, or pharmaceutically acceptable salt thereof, in the methods and compositions described herein is 4-[2-(4-amino-piperidin-1-yl)-5-(3-fluoro-4-methoxy-phenyl)-1-methyl-6-oxo-1,6-dihydropyrimidin-4-yl]-2-fluoro-benzonitrile, or a salt thereof (for example a besylate salt). In some such embodiments, the methods additionally comprise administration of dexamethasone.

In certain embodiments, Compound 1, Compound 2 or Compound 3, or an enantiomer, mixture of enantiomers, tautomer, isotopolog, or pharmaceutically acceptable salt thereof, is administered in combination with checkpoint inhibitors. In one embodiment, one checkpoint inhibitor is used in combination with Compound 1, or a tautomer, isotopolog, or pharmaceutically acceptable salt thereof, in connection with the methods provided herein. In another embodiment, two checkpoint inhibitors are used in combination with Compound 1, or a tautomer, isotopolog, or pharmaceutically acceptable salt thereof, in connection with the methods provided herein. In yet another embodiment, three or more checkpoint inhibitors are used in combination with Compound 1, Compound 2 or Compound 3, or an enantiomer, mixture of enantiomers, tautomer, isotopolog, or pharmaceutically acceptable salt thereof, in connection with the methods provided herein.

As used herein, the term "immune checkpoint inhibitor" or "checkpoint inhibitor" refers to molecules that totally or partially reduce, inhibit, interfere with or modulate one or more checkpoint proteins. Without being limited by a particular theory, checkpoint proteins regulate T-cell activation or function. Numerous checkpoint proteins are known, such as CTLA-4 and its ligands CD80 and CD86; and PD-1 with its ligands PD-L1 and PD-L2 (Pardoll, *Nature Reviews Cancer,* 2012, 12, 252-264). These proteins appear responsible for co-stimulatory or inhibitory interactions of T-cell responses. Immune checkpoint proteins appear to regulate and maintain self-tolerance and the duration and amplitude of physiological immune responses. Immune checkpoint inhibitors include antibodies or are derived from antibodies.

In one embodiment, the checkpoint inhibitor is a CTLA-4 inhibitor. In one embodiment, the CTLA-4 inhibitor is an anti-CTLA-4 antibody. Examples of anti-CTLA-4 antibodies include, but are not limited to, those described in U.S. Pat. Nos. 5,811,097; 5,811,097; 5,855,887; 6,051,227; 6,207,157; 6,682,736; 6,984,720; and 7,605,238, all of which are incorporated herein in their entireties. In one embodiment, the anti-CTLA-4 antibody is tremelimumab (also known as ticilimumab or CP-675,206). In another embodiment, the anti-CTLA-4 antibody is ipilimumab (also known as MDX-010 or MDX-101). Ipilimumab is a fully human monoclonal IgG antibody that binds to CTLA-4. Ipilimumab is marketed under the trade name Yervoy™.

In one embodiment, the checkpoint inhibitor is a PD-1/PD-L1 inhibitor. Examples of PD-1/PD-L1 inhibitors include, but are not limited to, those described in U.S. Pat. Nos. 7,488,802; 7,943,743; 8,008,449; 8,168,757; 8,217,149, and PCT Patent Application Publication Nos. WO2003042402, WO2008156712, WO2010089411, WO2010036959, WO2011066342, WO2011159877, WO2011082400, and WO2011161699, all of which are incorporated herein in their entireties.

In one embodiment, the checkpoint inhibitor is a PD-1 inhibitor. In one embodiment, the PD-1 inhibitor is an anti-PD-1 antibody. In one embodiment, the anti-PD-1 antibody is BGB-A317, nivolumab (also known as ONO-4538, BMS-936558, or MDX1106) or pembrolizumab (also known as MK-3475, SCH 900475, or lambrolizumab). In one embodiment, the anti-PD-1 antibody is nivolumab. Nivolumab is a human IgG4 anti-PD-1 monoclonal antibody, and is marketed under the trade name Opdivo™. In another embodiment, the anti-PD-1 antibody is pembrolizumab. Pembrolizumab is a humanized monoclonal IgG4 antibody and is marketed under the trade name Keytruda™. In yet another embodiment, the anti-PD-1 antibody is CT-011, a humanized antibody. CT-011 administered alone has failed to show response in treating acute myeloid leukemia (AML) at relapse. In yet another embodiment, the anti-PD-1 antibody is AMP-224, a fusion protein. In another embodiment, the PD-1 antibody is BGB-A317. BGB-A317 is a monoclonal antibody in which the ability to bind Fc gamma receptor I is specifically engineered out, and which has a unique binding signature to PD-1 with high affinity and superior target specificity.

In one embodiment, the checkpoint inhibitor is a PD-L1 inhibitor. In one embodiment, the PD-L1 inhibitor is an anti-PD-L1 antibody. In one embodiment, the anti-PD-L1 antibody is MED14736 (durvalumab). In another embodiment, the anti-PD-L1 antibody is BMS-936559 (also known as MDX-1105-01). In yet another embodiment, the PD-L1 inhibitor is atezolizumab (also known as MPDL3280A, and Tecentriq®).

In one embodiment, the checkpoint inhibitor is a PD-L2 inhibitor. In one embodiment, the PD-L2 inhibitor is an anti-PD-L2 antibody. In one embodiment, the anti-PD-L2 antibody is rHIgM12B7A.

In one embodiment, the checkpoint inhibitor is a lymphocyte activation gene-3 (LAG-3) inhibitor. In one embodiment, the LAG-3 inhibitor is IMP321, a soluble Ig fusion protein (Brignone et al., *J. Immunol.,* 2007, 179, 4202-4211). In another embodiment, the LAG-3 inhibitor is BMS-986016.

In one embodiment, the checkpoint inhibitors is a B7 inhibitor. In one embodiment, the B7 inhibitor is a B7-H3 inhibitor or a B7-H4 inhibitor. In one embodiment, the B7-H3 inhibitor is MGA271, an anti-B7-H3 antibody (Loo et al., *Clin. Cancer Res.,* 2012, 3834).

In one embodiment, the checkpoint inhibitors is a TIM3 (T-cell immunoglobulin domain and mucin domain 3) inhibitor (Fourcade et al., *J. Exp. Med.,* 2010, 207, 2175-86; Sakuishi et al., *J. Exp. Med.,* 2010, 207, 2187-94).

In one embodiment, the checkpoint inhibitor is an OX40 (CD134) agonist. In one embodiment, the checkpoint inhibitor is an anti-OX40 antibody. In one embodiment, the anti-OX40 antibody is anti-OX-40. In another embodiment, the anti-OX40 antibody is MEDI6469.

In one embodiment, the checkpoint inhibitor is a GITR agonist. In one embodiment, the checkpoint inhibitor is an anti-GITR antibody. In one embodiment, the anti-GITR antibody is TRX518.

In one embodiment, the checkpoint inhibitor is a CD137 agonist. In one embodiment, the checkpoint inhibitor is an anti-CD137 antibody. In one embodiment, the anti-CD137 antibody is urelumab. In another embodiment, the anti-CD137 antibody is PF-05082566.

In one embodiment, the checkpoint inhibitor is a CD40 agonist. In one embodiment, the checkpoint inhibitor is an anti-CD40 antibody. In one embodiment, the anti-CD40 antibody is CF-870,893.

In one embodiment, the checkpoint inhibitor is recombinant human interleukin-15 (rhIL-15).

In one embodiment, the checkpoint inhibitor is an IDO inhibitor. In one embodiment, the IDO inhibitor is INCB024360. In another embodiment, the IDO inhibitor is indoximod.

In certain embodiments, the combination therapies provided herein include two or more of the checkpoint inhibitors described herein (including checkpoint inhibitors of the same or different class). Moreover, the combination therapies described herein can be used in combination with one or more second active agents as described herein where appropriate for treating diseases described herein and understood in the art.

In certain embodiments, Compound 1, Compound 2 or Compound 3 can be used in combination with one or more immune cells expressing one or more chimeric antigen receptors (CARs) on their surface (e.g., a modified immune cell). Generally, CARs comprise an extracellular domain from a first protein (e.g., an antigen-binding protein), a transmembrane domain, and an intracellular signaling domain. In certain embodiments, once the extracellular domain binds to a target protein such as a tumor-associated antigen (TAA) or tumor-specific antigen (TSA), a signal is generated via the intracellular signaling domain that activates the immune cell, e.g., to target and kill a cell expressing the target protein.

Extracellular domains: The extracellular domains of the CARs bind to an antigen of interest. In certain embodiments, the extracellular domain of the CAR comprises a receptor, or a portion of a receptor, that binds to said antigen. In certain embodiments, the extracellular domain comprises, or is, an antibody or an antigen-binding portion thereof. In specific embodiments, the extracellular domain comprises, or is, a single chain Fv (scFv) domain. The single-chain Fv domain can comprise, for example, a $V_L$ linked to $V_H$ by a flexible linker, wherein said $V_L$ and $V_H$ are from an antibody that binds said antigen.

In certain embodiments, the antigen recognized by the extracellular domain of a polypeptide described herein is a tumor-associated antigen (TAA) or a tumor-specific antigen (TSA). In various specific embodiments, the tumor-associated antigen or tumor-specific antigen is, without limitation, Her2, prostate stem cell antigen (PSCA), alpha-fetoprotein (AFP), carcinoembryonic antigen (CEA), cancer antigen-125 (CA-125), CA19-9, calretinin, MUC-1, B cell maturation antigen (BCMA), epithelial membrane protein (EMA), epithelial tumor antigen (ETA), tyrosinase, melanoma-24 associated antigen (MAGE), CD19, CD22, CD27, CD30, CD34, CD45, CD70, CD99, CD117, EGFRvIII (epidermal growth factor variant III), mesothelin, PAP (prostatic acid phosphatase), prostein, TARP (T cell receptor gamma alternate reading frame protein), Trp-p8, STEAPI (six-transmembrane epithelial antigen of the prostate 1), chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-I), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, or an abnormal p53 protein. In certain other embodiments, the TAA or TSA recognized by the extracellular domain of a CAR is integrin αvβ3 (CD61), galactin, or Ral-B.

In certain embodiments, the TAA or TSA recognized by the extracellular domain of a CAR is a cancer/testis (CT) antigen, e.g., BAGE, CAGE, CTAGE, FATE, GAGE, HCA661, HOM-TES-85, MAGEA, MAGEB, MAGEC, NA88, NY-ESO-1, NY-SAR-35, OY-TES-1, SPANXBI, SPA17, SSX, SYCPI, or TPTE.

In certain other embodiments, the TAA or TSA recognized by the extracellular domain of a CAR is a carbohydrate or ganglioside, e.g., fuc-GMI, GM2 (oncofetal antigen-immunogenic-1; OFA-I-1); GD2 (OFA-I-2), GM3, GD3, and the like.

In certain other embodiments, the TAA or TSA recognized by the extracellular domain of a CAR is alpha-actinin-4, Bage-1, BCR-ABL, Bcr-Abl fusion protein, beta-catenin, CA 125, CA 15-3 (CA 27.29BCAA), CA 195, CA 242, CA-50, CAM43, Casp-8, cdc27, cdk4, cdkn2a, CEA, coa-1, dek-can fusion protein, EBNA, EF2, Epstein Barr virus antigens, ETV6-AML1 fusion protein, HLA-A2, HLA-All, hsp70-2, KIAA0205, Mart2, Mum-1, 2, and 3, neo-PAP, myosin class I, OS-9, pml-RARα fusion protein, PTPRK, K-ras, N-ras, triosephosphate isomerase, Gage 3,4,5,6,7, GnTV, Herv-K-mel, Lage-1, NA-88, NY-Eso-1/Lage-2, SP17, SSX-2, TRP2-Int2, gpi00 (Pmel17), tyrosinase, TRP-1, TRP-2, MAGE-1, MAGE-3, RAGE, GAGE-1, GAGE-2, p15(58), RAGE, SCP-1, Hom/Mel-40, PRAME, p53, HRas, HER-2/neu, E2A-PRL, H4-RET, IGH-IGK, MYL-RAR, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, 13-Catenin, Mum-1, p16, TAGE, PSMA, CT7, telomerase, 43-9F, 5T4, 791Tgp72, 13HCG, BCA225, BTAA, CD68KP1, C0-029, FGF-5, G250, Ga733 (EpCAM), HTgp-175, M344, MA-50, MG7-Ag, MOV18, NB\0K, NY-C0-1, RCAS1, SDCCAG16, TA-90, TAAL6, TAG72, TLP, or TPS.

In various specific embodiments, the tumor-associated antigen or tumor-specific antigen is an AML-related tumor antigens, as described in S. Anguille et al, *Leukemia* (2012), 26, 2186-2196.

Other tumor-associated and tumor-specific antigens are known to those in the art.

Receptors, antibodies, and scFvs that bind to TSAs and TAAs, useful in constructing chimeric antigen receptors, are known in the art, as are nucleotide sequences that encode them.

In certain specific embodiments, the antigen recognized by the extracellular domain of a chimeric antigen receptor is an antigen not generally considered to be a TSA or a TAA, but which is nevertheless associated with tumor cells, or damage caused by a tumor. In certain embodiments, for example, the antigen is, e.g., a growth factor, cytokine or interleukin, e.g., a growth factor, cytokine, or interleukin associated with angiogenesis or vasculogenesis. Such growth factors, cytokines, or interleukins can include, e.g., vascular endothelial growth factor (VEGF), basic fibroblast growth factor (bFGF), platelet-derived growth factor (PDGF), hepatocyte growth factor (HGF), insulin-like growth factor (IGF), or interleukin-8 (IL-8). Tumors can also create a hypoxic environment local to the tumor. As such, in other specific embodiments, the antigen is a hypoxia-associated factor, e.g., HIF-1α, HIF-1β, HIF-2α, HIF-2β, HIF-3α, or HIF-3β. Tumors can also cause localized damage to normal tissue, causing the release of molecules known as damage associated molecular pattern molecules (DAMPs; also known as alarmins). In certain other specific embodiments, therefore, the antigen is a DAMP, e.g., a heat shock protein, chromatin-associated protein high mobility group box 1 (HMGB 1), S100A8 (MRP8, calgranulin A), S100A9 (MRP14, calgranulin B), serum amyloid A (SAA), or can be a deoxyribonucleic acid, adenosine triphosphate, uric acid, or heparin sulfate.

Transmembrane domain: In certain embodiments, the extracellular domain of the CAR is joined to the transmembrane domain of the polypeptide by a linker, spacer or hinge polypeptide sequence, e.g., a sequence from CD28 or a sequence from CTLA4. The transmembrane domain can be obtained or derived from the transmembrane domain of any transmembrane protein, and can include all or a portion of such transmembrane domain. In specific embodiments, the transmembrane domain can be obtained or derived from, e.g., CD8, CD16, a cytokine receptor, and interleukin receptor, or a growth factor receptor, or the like.

Intracellular signaling domains: In certain embodiments, the intracellular domain of a CAR is or comprises an intracellular domain or motif of a protein that is expressed on the surface of T cells and triggers activation and/or proliferation of said T cells. Such a domain or motif is able to transmit a primary antigen-binding signal that is necessary for the activation of a T lymphocyte in response to the antigen's binding to the CAR's extracellular portion. Typically, this domain or motif comprises, or is, an ITAM (immunoreceptor tyrosine-based activation motif). ITAM-containing polypeptides suitable for CARs include, for example, the zeta CD3 chain (CD3ζ) or ITAM-containing portions thereof. In a specific embodiment, the intracellular domain is a CD3 ζ intracellular signaling domain. In other specific embodiments, the intracellular domain is from a lymphocyte receptor chain, a TCR/CD3 complex protein, an Fe receptor subunit or an IL-2 receptor subunit. In certain embodiments, the CAR additionally comprises one or more co-stimulatory domains or motifs, e.g., as part of the intracellular domain of the polypeptide. The one or more co-stimulatory domains or motifs can be, or can comprise, one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell costimulatory (ICOS) polypeptide sequence, or other costimulatory domain or motif, or any combination thereof.

The CAR may also comprise a T cell survival motif. The T cell survival motif can be any polypeptide sequence or motif that facilitates the survival of the T lymphocyte after stimulation by an antigen. In certain embodiments, the T cell survival motif is, or is derived from, CD3, CD28, an intracellular signaling domain of IL-7 receptor (IL-7R), an intracellular signaling domain of IL-12 receptor, an intracellular signaling domain of IL-15 receptor, an intracellular signaling domain of IL-21 receptor, or an intracellular signaling domain of transforming growth factor β (TGFβ) receptor.

The modified immune cells expressing the CARs can be, e.g., T lymphocytes (T cells, e.g., CD4+ T cells or CD8+ T cells), cytotoxic lymphocytes (CTLs) or natural killer (NK) cells. T lymphocytes used in the compositions and methods provided herein may be naive T lymphocytes or MHC-restricted T lymphocytes. In certain embodiments, the T lymphocytes are tumor infiltrating lymphocytes (TILs). In certain embodiments, the T lymphocytes have been isolated from a tumor biopsy, or have been expanded from T lymphocytes isolated from a tumor biopsy. In certain other embodiments, the T cells have been isolated from, or are expanded from T lymphocytes isolated from, peripheral blood, cord blood, or lymph. Immune cells to be used to generate modified immune cells expressing a CAR can be isolated using art-accepted, routine methods, e.g., blood collection followed by apheresis and optionally antibody-mediated cell isolation or sorting.

The modified immune cells are preferably autologous to an individual to whom the modified immune cells are to be administered. In certain other embodiments, the modified immune cells are allogeneic to an individual to whom the modified immune cells are to be administered. Where allogeneic T lymphocytes or NK cells are used to prepare modified T lymphocytes, it is preferable to select T lymphocytes or NK cells that will reduce the possibility of graft-versus-host disease (GVHD) in the individual. For example, in certain embodiments, virus-specific T lymphocytes are selected for preparation of modified T lymphocytes; such lymphocytes will be expected to have a greatly reduced native capacity to bind to, and thus become activated by, any recipient antigens. In certain embodiments, recipient-mediated rejection of allogeneic T lymphocytes can be reduced by co-administration to the host of one or more immunosuppressive agents, e.g., cyclosporine, tacrolimus, sirolimus, cyclophosphamide, or the like.

T lymphocytes, e.g., unmodified T lymphocytes, or T lymphocytes expressing CD3 and CD28, or comprising a polypeptide comprising a CD3t signaling domain and a CD28 co-stimulatory domain, can be expanded using antibodies to CD3 and CD28, e.g., antibodies attached to beads; see, e.g., U.S. Pat. Nos. 5,948,893; 6,534,055; 6,352,694; 6,692,964; 6,887,466; and 6,905,681.

The modified immune cells, e.g., modified T lymphocytes, can optionally comprise a "suicide gene" or "safety switch" that enables killing of substantially all of the modified immune cells when desired. For example, the modified T lymphocytes, in certain embodiments, can comprise an HSV thymidine kinase gene (HSV-TK), which causes death of the modified T lymphocytes upon contact with gancyclovir. In another embodiment, the modified T lymphocytes comprise an inducible caspase, e.g., an inducible caspase 9 (icaspase9), e.g., a fusion protein between caspase 9 and human FK506 binding protein allowing for dimerization using a specific small molecule pharmaceutical. See Straathof et al., *Blood* 1 05(11):4247-4254 (2005).

In certain embodiments, Compound 1, Compound 2 or Compound 3 as provided herein is administered to patients with various types or stages of multiple myeloma in combination with chimeric antigen receptor (CAR) T-cells. In certain embodiments the CAR T cell in the combination targets B cell maturation antigen (BCMA), and in more specific embodiments, the CAR T cell is bb2121 or bb21217. In some embodiments, the CAR T cell is JCARH125.

G. Pharmaceutical Compositions

The pharmaceutical compositions provided herein contain therapeutically effective amounts of one or more of compounds provided herein and optionally a pharmaceutically acceptable carrier, diluent or excipient.

The compounds can be formulated into suitable pharmaceutical preparations such as solutions, suspensions, tablets, dispersible tablets, pills, capsules, powders, sustained release formulations or elixirs, for oral administration or in sterile solutions or suspensions for ophthalmic or parenteral administration, as well as transdermal patch preparation and dry powder inhalers. Typically the compounds described above are formulated into pharmaceutical compositions using techniques and procedures well known in the art (see, e.g., Ansel Introduction to Pharmaceutical Dosage Forms, Seventh Edition 1999).

In the compositions, effective concentrations of one or more compounds or pharmaceutically acceptable salts is (are) mixed with a suitable pharmaceutical carrier or vehicle. In certain embodiments, the concentrations of the compounds in the compositions are effective for delivery of an amount, upon administration, that treats, prevents, or ameliorates one or more of the symptoms and/or progression of multiple myeloma.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, tissue distribution, inactivation, metabolism and excretion rates of the active compound, the physicochemical characteristics of the compound, the dosage schedule, and amount administered as well as other factors known to those of skill in the art. For example, the amount that is delivered is sufficient to ameliorate one or more of the symptoms of cancer, including solid tumors and blood borne tumors.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, pens, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of the compounds or pharmaceutically acceptable salts thereof. The pharmaceutically therapeutically active compounds and salts thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Dosage forms or compositions containing active ingredient in the range of 0.005% to 100% with the balance made up from non toxic carrier may be prepared. For oral administration, a pharmaceutically acceptable non toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art.

The active compounds or pharmaceutically acceptable salts may be prepared with carriers that protect the compound against rapid elimination from the body, such as time release formulations or coatings.

The compositions may include other active compounds to obtain desired combinations of properties. The compounds provided herein, or pharmaceutically acceptable salts thereof as described herein, may also be advantageously administered for therapeutic or prophylactic purposes together with another pharmacological agent known in the general art to be of value in treating one or more of the diseases or medical conditions referred to hereinabove, such as diseases related to oxidative stress. It is to be understood that such combination therapy constitutes a further aspect of the compositions and methods of treatment provided herein.

H. Evaluation of the Activity and Properties of the Compounds

Standard physiological, pharmacological and biochemical procedures are available for testing the compounds to identify those that possess the desired properties, including anti-multiple myeloma proliferative activity and adequate safety profile. Such assays include, for example, biochemical assays such as binding assays, radioactivity incorporation assays, as well as a variety of cell based assays.

Isoindolinone derivatives and their therapeutic uses have been described in for example, U.S. Pat. No. 8,518,972. Surprisingly, Compound 1, Compound 2 and Compound 3 exhibit unexpected and beneficial properties, as shown in the Examples section. These beneficial properties include significantly increased anti-multiple myeloma potency, increased levels of apoptosis, and the more potent and efficacious combination response with dexamethasone, and surprisingly an improved safety profile, as shown by reduced functional activity at the α1 adrenergic and D2 dopamine receptors (in vitro, as well as in vivo), improved cell killing selectivity (as shown by reduced killing of non-myeloma cells), and reduced CYP3A4 inhibition.

It is understood that the foregoing detailed description and accompanying examples are merely illustrative, and are not to be taken as limitations upon the scope of the subject matter. Various changes and modifications to the disclosed embodiments will be apparent to those skilled in the art. Such changes and modifications, including without limitation those relating to the chemical structures, substituents, derivatives, intermediates, syntheses, formulations and/or methods of use provided herein, may be made without departing from the spirit and scope thereof. U.S. patents and publications referenced herein are incorporated by reference.

6. EXAMPLES

Certain embodiments of the invention are illustrated by the following non-limiting examples.

Abbreviations

AcN/ACN Acetonitrile
AIBN Azobisisobutyronitrile
Boc tert-Butyloxycarbonyl
Boc$_2$O di-tert-Butyl dicarbonate
tBuOK Potassium tert-butoxide
DIEA Diisopropylethylamine
DMF N,N'-Dimethylformamide
DMSO Dimethylsulfoxide
EtOAc Ethyl acetate
IPA Isopropanol or 2-propanol
MeOH Methanol
MM Multiple Myeloma
NBS N-bromosuccinimide,
NMR Nuclear Magnetic Resonance
PBMC Human peripheral blood mononuclear cell
i-PrOAc Isopropyl acetate
TBS tert-Butyl dimethylsilyl
TBSCl tert-Butyl dimethylsilylchloride
THF Tetrahydrofuran
TLC Thin layer chromatography
TMSCl Trimethylsilyl chloride Example 1: Synthesis of 4-(4-(4-(((2-(2,6-dioxopiperidin-3-yl)-1-oxoisoindolin-4-yl)oxy)methyl)benzyl)piperazin-1-yl)-3-fluorobenzonitrile (Compound 1)

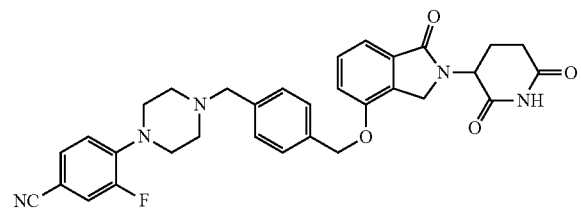 [SMILES: N#Cc1ccc(N2CCN(Cc3ccc(COc4cccc5c4CN(C4CCC(=O)NC4=O)C5=O)cc3)CC2)c(F)c1]

2-Amino-5-methoxy-5-oxopentanoic acid

To a suspension of 2-aminopentanedioic acid (250 g, 1.70 mol) in dry methanol (2.5 L) under nitrogen was added trimethylsilyl chloride (277 g, 2.55 mol) over 30 mins. The resulting clear solution was stirred at room temperature (20° C.) for 30 min. $^1$H NMR showed the starting material was consumed completely. The reaction mixture was used in the next step without further work-up. $^1$H NMR: 400 MHz CD$_3$OD δ: 4.17-4.15 (m, 1H), 3.71 (s, 3H), 2.70-2.60 (m, 2H), 2.33-2.25 (m, 2H).

2-((tert-Butoxycarbonyl)amino)-5-methoxy-5-oxopentanoic acid

To the above solution was added triethylamine (275 g, 2.72 mol) and di-tert-butyl dicarbonate (447.35 g, 2.05 mol). The reaction mixture was stirred at 25° C. for 2 h. The solution was concentrated to dryness, then water (2.5 L) was added to dissolve the residue. The resulting aqueous solution was washed with ethyl acetate (200 mL), then acidified to pH=3 by HCl (1 N) and extracted with ethyl acetate (1 L×3). The combined organic layers were washed with brine (800 mL), dried over sodium sulfate, filtered and concentrated to offer 2-(tert-butoxycarbonylamino)-5-methoxy-5-oxo-pentanoic acid (250 g 56% yield, two steps) as a white solid. $^1$H NMR: 400 MHz CD$_3$OD δ: 4.18-4.11 (m, 1H), 3.69 (s, 3H), 2.48-2.43 (m, 2H), 2.21-2.15 (m, 1H), 1.95-1.91 (m, 1H), 1.46 (s, 9H).

Methyl 5-amino-4-(tert-butoxycarbonyl amino)-5-oxo-pentanoate

To a solution of 2-(tert-butoxycarbonylamino)-5-methoxy-5-oxo-pentanoic acid (200 g, 765 mmol) in 1,4-dioxane (1.5 L) were added di-tert-butyl dicarbonate (267 g, 1.22 mol) and pyridine (121 g, 1.53 mol). After the reaction mixture was stirred at 25° C. for 30 min, ammonium carbonate (182 g, 2.30 mol) was added to the mixture and stirred for additional 16 h at 25° C. The organic solvent was removed by rotary evaporation, the residue was acidified by HCl (6 M) to pH=3 and then extracted with ethyl acetate (800 mL×3). The combined organic phase was washed with brine (800 mL), dried over sodium sulfate, and filtered. Volatile organics were removed under reduced pressure to offer methyl 5-amino-4-(tert-butoxycarbonyl amino)-5-oxopentanoate (180 g, 90% yield) as a white solid. $^1$H NMR: 400 MHz CDCl$_3$ δ: 6.51 (s, 1H), 5.94 (s, 1H), 5.43 (s, 1H), 4.21 (s, 1H), 3.63 (s, 3H), 2.59-2.40 (m, 2H), 2.15-2.11 (m, 1H), 1.94-1.90 (m, 1H), 1.42 (s, 9H).

Methyl 4,5-diamino-5-oxo-pentanoate hydrochloride

A mixture of methyl 5-amino-4-(tert-butoxycarbonylamino)-5-oxo-pentanoate (180 g, 692 mmol) and HCl/ethyl acetate (300 mL, 4 M) was stirred at 25° C. for 12 h. The precipitated solid was collected by vacuum filtration and washed with ethyl acetate (500 mL) to give methyl 4,5-diamino-5-oxo-pentanoate hydrochloride (130 g, 95% yield) as a white solid. $^1$H NMR: 400 MHz CD$_3$OD δ: 4.00-3.96 (m, 1H), 3.70 (s, 3H), 2.59-2.52 (m, 2H), 2.22-2.13 (m, 2H).

Methyl 3-hydroxy-2-methyl-benzoate

Four batches (200 g each) were run in parallel. To a solution of 3-hydroxy-2-methyl-benzoic acid (200 g, 1.31 mol) in methanol (4.0 L) was added concentrated sulfuric acid (47.7 g, 486 mmol). The reaction mixture was stirred at 60° C. for 17 h and was concentrated to 800 mL. The resulting mixture was cooled to 20° C. and slowly poured into water (400 mL) over 30 mins. Water (1200 mL) was added at 20° C. over 3 h and the resulting mixture was stirred at 20° C. for 1 h. The precipitated solid was collected by vacuum filtration (four batches combined) and was washed three times with water/methanol (1000 mL, 9:1) or until the filtrate has pH>3. The solid was dried under vacuum at 45° C. to give methyl 3-hydroxy-2-methyl-benzoate (700 g, 80.4% yield) as a gray solid. $^1$H NMR: 400 MHz DMSO-d$_6$ δ: 9.70 (s, 1H), 7.18 (t, J=6.8 Hz, 1H), 7.09 (t, J=7.6 Hz, 1H), 7.00 (t, J=6.8 Hz, 1H), 3.81 (s, 3H), 2.29 (s, 3H).

Methyl 3-[tert-butyl(dimethyl)silyl]oxy-2-methyl-benzoate

Two batches (240 g each) were run in parallel. To a solution of methyl 3-hydroxy-2-methyl-benzoate (240 g, 1.44 mol) in DMF (1.40 L) was added imidazole (246 g, 3.61 mol) and tert-butyl dimethylsilyl chloride (238 g, 1.58 mol) at 5° C. After addition, the mixture was warmed to 20° C. and stirred for 6 h. Isopropyl acetate (1700 mL) was added, and then water (2000 mL) was slowly added while the temperature was kept under 30° C. The resulting mixture was stirred and the organic phase was separated. The combined organic phase (two batches combined) was washed with water (1700 mL×3) and concentrated to ~1500 mL (KF<0.05%). The product was stored as an isopropyl acetate solution which was used in the next step without further purification.

Methyl 2-(bromomethyl)-3-[tert-butyl(dimethyl) silyl] oxy-benzoate

Two batches (~375 g each) were run in parallel. To the isopropyl acetate solution of methyl 3-[tert-butyl(dimethyl)silyl]oxy-2-methyl-benzoate (~375 g, 1.34 mol) was added N-bromosuccinimide (274 g, 1.54 mol) and azobisisobutyronitrile (4.40 g, 26.8 mmol). The reaction mixture was heated to 70° C. over at least 1 h and stirred at 70° C. for 4 h. The reaction mixture was cooled to 20° C. and held at 20° C. for at least 1 h. The two batches of solid (succinimide) was removed by filtration and washed with isopropyl acetate (700 mL). The filtrate was washed with solution of sodium sulfite (700 g) in water (6000 mL), followed by water (1500 mL). The organic layer was distilled under vacuum at 45° C. to dryness to give methyl 2-(bromomethyl)-3-[tert-butyl (dimethyl)silyl]oxy-benzoate (920 g, 95.5% yield) as dark orange oil. $^1$H NMR: 400 MHz DMSO-d$_6$ δ: 7.45 (d, J=6.8 Hz, 1H), 7.36 (t, J=8.0 Hz, 1H), 7.13 (t, J=7.2 Hz, 1H), 4.95 (s, 2H), 1.02 (s, 9H), 0.29 (s, 6H).

Methyl 5-amino-4-[4-[tert-butyl(dimethyl)silyl]oxy-1-oxo-isoindolin-2-yl]-5-oxo-pentanoate To a stirred solution of methyl 4,5-diamino-5-oxo-pentanoate hydrochloride (74.5 g, 379 mmol) in acetonitrile (2.50 L) was added methyl 2-(bromomethyl)-3-[tert-butyl (dimethyl)silyl] oxy-benzoate (125 g, 348 mmol). To the suspension was added diisopropylethylamine (89.9 g, 696 mmol) through an addition funnel over 10 min and then the mixture was stirred at 60° C. for 16 h. The reaction mixture was diluted with ethyl acetate (1.0 L), washed with HCl (1N, 1.0 L), sodium bicarbonate (sat. 1.0 L) and brine (1.0 L) successively. The organic layer was concentrated to give crude methyl 5-amino-4-[4-[tert-butyl(dimethyl)silyl]oxy-1-oxo-isoindolin-2-yl]-5-oxo-pentanoate (108 g, crude) as a light yellow solid. LCMS: m/z 407.3 [M+1]$^+$.

Methyl 5-amino-4-(4-hydroxy-1-oxo-isoindolin-2-yl)-5-oxo-pentanoate

To a stirred cold solution of methyl 5-amino-4-[4-[tert-butyl(dimethyl)silyl]oxy-1-oxo-isoindolin-2-yl]-5-oxo-pentanoate (108 g, 266 mmol) in N,N-dimethylformamide (350 mL) was added potassium carbonate (14.7 g, 106 mmol) in water (40 mL) in portions over 5 min. The resulting reaction mixture was stirred at 15° C. for 15 h. The reaction mixture was cooled in an ice bath and HCl (12 M, 15 mL) was added slowly at 0-5° C. Acetonitrile (200 mL) was added to the mixture and a precipitate formed. The suspension was stirred at room temperature for 10 min and filtered. The filter cake was washed with ethyl acetate (200 mL×5) to give product (55 g). The filtrate was concentrated under high vacuum to give a crude product (100 g) which was dissolved in dichloromethane (1.0 L) and allowed to stand at 15° C. for 16 hrs. White solid was formed which was filtered to give 5 g of product. The solids were combined to give methyl 5-amino-4-(4-hydroxy-1-oxo-isoindolin-2-yl)-5-oxo-pentanoate (60 g, 77% yield) as a white solid. $^1$H NMR: 400 MHz DMSO-d$_6$ δ: 7.58 (s, 1H), 7.31 (t, J=8.0 Hz, 1H), 7.19-7.14 (m, 2H), 7.01 (d, J=7.6 Hz, 1H), 4.75-4.71 (m, 1H), 4.50 (d, J=17.6 Hz, 1H), 4.32 (d, J=17.6 Hz, 1H), 3.51 (s, 3H), 2.29-2.18 (m, 3H), 2.09-1.99 (m, 1H).

Methyl 5-amino-4-[4-[[4-(bromomethyl)phenyl] methoxy]-1-oxo-isoindolin-2-yl]-5-oxo-pentanoate Two reactions (25 g, 85.5 mmol) were run in parallel. A mixture of 1,4-bis(bromomethyl)benzene (67.7 g, 257 mmol), potassium carbonate (11.8 g, 85.5 mmol) and methyl 5-amino-4-(4-hydroxy-1-oxo-isoindolin-2-yl)-5-oxo-pentanoate (25 g, 85.5 mmol) in acetonitrile (1 L) was stirred at 60° C. for 16 h. The two batches were combined and the mixture was cooled to 15° C. and filtered. The filtrate was concentrated and the residue was purified by silica gel column chromatography (eluted by 50% petroleum ether in ethyl acetate to 100% ethyl acetate) to afford methyl 5-amino-4-[4-[[4-(bromomethyl)phenyl]methoxy]-1-oxo-isoindolin-2-yl]-5-oxo-pentanoate (52 g, 63% yield) as a white solid. $^1$H NMR: 400 MHz DMSO-$d_6$ δ: 7.59 (s, 1H), 7.50-7.44 (m, 5H), 7.32-7.28 (m, 2H), 7.19 (s, 1H), 5.26 (s, 2H), 4.79-4.71 (m, 3H), 4.55 (d, J=17.6 Hz, 1H), 4.43 (d, J=17.6 Hz, 1H), 3.52 (s, 3H), 2.30-2.19 (m, 3H), 2.10-2.08 (m, 1H).

3-[4-[[4-(bromomethyl)phenyl]methoxy]-1-oxo-isoindolin-2-yl]piperidine-2,6-dione Two reactions (28.5 g, 60.0 mmol) were run in parallel. Methyl 5-amino-4-[4-[[4-(bromomethyl)phenyl]methoxy]-1-oxo-isoindolin-2-yl]-5-oxo-pentanoate (28.5 g, 60.0 mmol) was dissolved in tetrahydrofuran (720 mL) and the solution was cooled in dry ice/acetone bath to −70° C. While stirring, potassium tert-butoxide (7.4 g, 66.0 mmol) was added in one portion to the clear solution. The reaction mixture turned to pale yellow and stirring was continued for additional 2 h at −70° C. A cooled solution of HCl (1N, 260 mL) was rapidly transferred to the reaction mixture while maintaining temperature at −70° C. The mixture immediately turned milky white and the dry ice/acetone bath was removed. The mixture was concentrated to remove most of the tetrahydrofuran. Upon concentration of the reaction mixture, a white solid precipitated. The white slurry was diluted with water (500 mL) and then filtered. The filter cake was washed with water (500 mL) and dried in vacuum oven at 40° C. for 12 h, then washed with ethyl acetate (500 mL). The batches were combined to give 3-[4-[[4-(bromomethyl)phenyl]methoxy]-1-oxo-isoindolin-2-yl]piperidine-2,6-dione (49.85 g, 93%) as a light yellow solid. $^1$H NMR: 400 MHz DMSO-$d_6$ δ: 10.95 (s, 1H), 7.51-7.41 (m., 5H), 7.35-7.28 (m, 2H), 5.23 (s, 2H), 5.12-5.07 (m, 1H), 4.70 (s, 2H), 4.41 (d, J=17.6 Hz, 1H), 4.25 (d, J=17.6 Hz, 1H), 2.90-2.84 (m, 1H), 2.58-2.53 (m, 1H), 2.44-2.41 (m, 1H), 1.98-1.95 (m, 1H).

4-(4-(4-(((2-(2,6-dioxopiperidin-3-yl)-1-oxoisoindolin-4-yl)oxy)methyl)benzyl)piperazin-1-yl)-3-fluorobenzonitrile 3-(4-((4-(bromomethyl)benzyl)oxy)-1-oxoisoindolin-2-yl)piperidine-2,6-dione (5.0 g, 11.28 mmol) was placed in a flask with 3-fluoro-4-(piperazin-1-yl)benzonitrile (2.315 g, 11.28 mmol), diisopropylethylamine (5.91 ml, 33.8 mmol), and acetonitrile (100 ml). The reaction mixture was stirred at 40° C. for 18 h. Volatile organics were removed under reduced pressure and purification by standard methods provided 4-(4-(4-(((2-(2,6-dioxopiperidin-3-yl)-1-oxoisoindolin-4-yl)oxy)methyl)benzyl)piperazin-1-yl)-3-fluorobenzonitrile. $^1$HNMR (400 MHz, DMSO-$d_6$) δ 10.97 (s, 1H), 7.68 (dd, J=1.96, 13.45 Hz, 1H), 7.56 (dd, J=1.77, 8.38 Hz, 1H), 7.43-7.52 (m, 3H), 7.30-7.38 (m, 4H), 7.11 (t, J=8.80 Hz, 1H), 5.24 (s, 2H), 5.11 (dd, J=5.14, 13.33 Hz, 1H), 4.37-4.46 (m, 1H), 4.22-4.30 (m, 1H), 3.54 (s, 2H), 3.12-3.23 (m, 4H), 2.84-2.98 (m, 1H), 2.52-2.62 (m, 5H), 2.36-2.48 (m, 1H), 1.92-2.04 (m, 1H). MS (ESI) m/z 568.2 [M+1]$^+$. Anal. Calcd for $C_{32}H_{30}FN_5O_4$: C, 67.71; H, 5.33; N, 12.34. Found: C, 67.50; H, 5.44; N 12.34.

Example 2: Synthesis of (S)-4-(4-(4-(((2-(2,6-dioxopiperidin-3-yl)-1-oxoisoindolin-4-yl)oxy)methyl)benzyl)piperazin-1-yl)-3-fluorobenzonitrile (Compound 2)

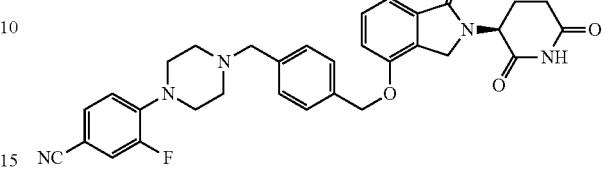

tert-Butyl (4S)-5-amino-4-(benzyloxycarbonylamino)-5-oxo-pentanoate

To a solution of (2S)-2-(benzyloxycarbonylamino)-5-tert-butoxy-5-oxo-pentanoic acid (150 g, 445 mmol) in 1,4-dioxane (1.50 L) was added di-tert-butyl dicarbonate (155 g, 711 mmol), pyridine (70.3 g, 889 mmol) and ammonium bicarbonate (105 g, 1.33 mol). The reaction mixture was stirred at 18° C. for 16 h and then concentrated. The residue was dissolved in ethyl acetate (5.0 L) and water (5.0 L), the organic layer was separated and washed with HCl (3.0 mL, 1 N), saturated sodium bicarbonate (3.0 L), brine (3.0 L), dried over anhydrous sodium sulfate, filtered and concentrated to give crude tert-butyl (4S)-5-amino-4-(benzyloxycarbonylamino)-5-oxo-pentanoate (450 g, crude) as a white solid, which was used in the next step without further purification. $^1$H NMR 400 MHz DMSO-$d_6$ δ: 7.35-7.30 (m, 5H), 7.02 (s, 1H), 5.01 (d, J=3.2 Hz, 1H), 3.93-3.90 (m, 1H), 2.20 (t, J=8.0 Hz, 2H), 1.88-1.84 (m, 1H), 1.72-1.69 (m, 1H), 1.35 (s, 9H).

tert-Butyl (4S)-4,5-diamino-5-oxo-pentanoate

To a solution of tert-butyl (4 S)-5-amino-4-(benzyloxycarbonylamino)-5-oxo-pentanoate (112 g, 333 mmol) in methanol (1.0 L) was added 10% palladium on carbon (15 g) under nitrogen. The suspension was degassed under vacuum and purged with hydrogen several times. The mixture was stirred under hydrogen gas (40 psi) at 30° C. for 16 h. The reaction mixture was filtered and the filtrate was concentrated to give crude tert-butyl (4S)-4,5-diamino-5-oxo-pentanoate as a colorless oil. $^1$H NMR 400 MHz DMSO-$d_6$ δ: 7.30 (s, 1H), 6.95 (s, 1H), 3.10-3.07 (m, 1H), 2.27-2.23 (m, 2H), 1.69-1.78 (m, 1H), 1.59-1.55 (m, 1H), 1.38 (s, 9H).

Methyl 3-hydroxy-2-methyl-benzoate

Four batches (200 g each) were run in parallel. To a solution of 3-hydroxy-2-methyl-benzoic acid (200 g, 1.31 mol) in methanol (4.0 L) was added concentrated sulfuric acid (47.7 g, 486 mmol). The reaction mixture was stirred at 60° C. for 17 h. The reaction mixture was concentrated to 800 mL. The resulting mixture was cooled to 20° C. and slowly poured into water (400 mL) over 30 mins. Water (1200 mL) was added at 20° C. over 3 h and the resulting mixture was stirred at 20° C. for 1 h. The precipitated solid was collected by vacuum filtration (four batches combined) and was washed three times with water/methanol (1000 mL, 9:1) or until the filtrate had pH>3. The solid was dried under vacuum at 45° C. to give methyl 3-hydroxy-2-methyl-benzoate (700 g, 80.4% yield) as a gray solid. $^1$H NMR: 400 MHz DMSO-d$_6$ δ: 9.70 (s, 1H), 7.18 (t, J=6.8 Hz, 1H), 7.09 (t, J=7.6 Hz, 1H), 7.00 (t, J=6.8 Hz, 1H), 3.81 (s, 3H), 2.29 (s, 3H).

Methyl 3-[tert-butyl(dimethyl)silyl]oxy-2-methyl-benzoate

Two batches (240 g each) were run in parallel. To a solution of methyl 3-hydroxy-2-methyl-benzoate (240 g, 1.44 mol) in N,N-dimethylformamide (1.40 L) were added imidazole (246 g, 3.61 mol) and tert-butyl dimethylsilyl chloride (238 g, 1.58 mol) at 5° C. After addition, the mixture was warmed up to 20° C. and stirred for 6 h. Isopropyl acetate (1700 mL) was added, and then water (2000 mL) was slowly added while the temperature was kept under 30° C. The resulting mixture was stirred followed by separation of the organic phase. The combined organics (two batches combined) were washed with water (1700 mL×3) and concentrated to ~1500 mL (KF<0.05%). The product was stored as an isopropyl acetate solution which was used in the next step without further purification.

Methyl 2-(bromomethyl)-3-[tert-butyl(dimethyl) silyl] oxy-benzoate

Two batches (~375 g each) were run in parallel. To the isopropyl acetate solution of methyl 3-[tert-butyl(dimethyl)silyl]oxy-2-methyl-benzoate (~375 g, 1.34 mol) was added N-bromosuccinimide (274 g, 1.54 mol) and azobisisobutyronitrile (4.40 g, 26.8 mmol). The reaction mixture was heated to 70° C. over at least 1 h and stirred at 70° C. for 4 h. The reaction mixture was cooled to 20° C. and held at 20° C. for at least 1 h. The two batches of solid (succinimide) were removed by filtration and washed with isopropyl acetate (700 mL). The filtrate was washed with solution of sodium sulfite (700 g) in water (6000 mL), followed by water (1500 mL). The organic layer was distilled under vacuum at 45° C. to dryness to give methyl 2-(bromomethyl)-3-[tert-butyl(dimethyl)silyl]oxy-benzoate (920 g, 95.5% yield) as dark orange oil. $^1$H NMR: 400 MHz DMSO-d$_6$ δ: 7.45 (d, J=6.8 Hz, 1H), 7.36 (t, J=8.0 Hz, 1H), 7.13 (t, J=7.2 Hz, 1H), 4.95 (s, 2H), 1.02 (s, 9H), 0.29 (s, 6H).

tert-Butyl (4S)-5-amino-4-[4-[tert-butyl(dimethyl) silyl]oxy-1-oxo-isoindolin-2-yl]-5-oxo-pentanoate To a solution of tert-butyl (4S)-4,5-diamino-5-oxo-pentanoate (130 g, 643 mmol) in acetonitrile (4.0 L) was added methyl 2-(bromomethyl)-3-[tert-butyl(dimethyl)silyl]oxy-benzoate (210 g, 584 mmol) and diisopropylethylamine (113 g, 877 mmol). The reaction mixture was stirred at 50° C. for 16 h. The reaction mixture was concentrated to remove most of the acetonitrile, the residue was dissolved in methyl tert-butyl ether (2.0 L) and water (1.5 L), the organic layer was washed with saturated monopotassium phosphate (1.0 L×2), brine (1.0 L), dried over anhydrous sodium sulfate, filtered and concentrated to give crude tert-butyl (4S)-5-amino-4-[4-[tert-butyl(dimethyl)silyl]oxy-1-oxo-isoindolin-2-yl]-5-oxo-pentanoate (524 g), which was used into next step without further purification.

tert-Butyl (4S)-5-amino-4-(4-hydroxy-1-oxo-isoindolin-2-yl)-5-oxo-pentanoate

To a solution of tert-butyl (4S)-5-amino-4-[4-[tert-butyl (dimethyl)silyl]oxy-1-oxo-isoindolin-2-yl]-5-oxo-pentanoate (275 g, 613 mmol) in methanol (2.0 L) was added tetrabutylammonium fluoride trihydrate (38.7 g, 123 mmol). The mixture was stirred at 18° C. for 16 h. The reaction mixture was concentrated to remove most of the methanol, the residue was dissolved in dichloromethane/water (3 L/2 L), the organic layer was separated and washed with brine (1.0 L), dried over anhydrous sodium sulfate, filtered, and concentrated to give crude product, which was purified by silica gel column to give product (260 g). Product was added into acetonitrile (750 mL) and the mixture was stirred at 60° C. for 2 h, cooled to 18° C., and stirred for another 2 h. The solid was filtered and the cake was dried to give tert-butyl (4S)-5-amino-4-(4-hydroxy-1-oxo-isoindolin-2-yl)-5-oxo-pentanoate (248 g, 60.5% yield) as a gray solid. $^1$H NMR 400 MHz DMSO-d$_6$ δ: 10.00 (s, 1H), 7.54 (s, 1H), 7.29 (t, J=7.6 Hz, 1H), 7.14 (d, J=4.8 Hz, 2H), 4.72-4.68 (m, 1H), 4.49-4.28 (m, 2H), 2.17-1.97 (m, 4H), 1.31 (s, 9H).

4-(4-(4-(chloromethyl)benzyl)piperazin-1-yl)-3-fluorobenzonitrile 1,4-bis(chloromethyl)benzene (51.2 g, 292 mmol) was placed in a flask with acetonitrile (195 mL) and N,N-dimethylformamide (195 mL). The reaction mixture was stirred at ambient temperature until all the solids dissolved. Diisopropylamine (51.1 mL, 292 mmol) was then added along with 3-fluoro-4-(piperazin-1-yl)benzonitrile (20 g, 97 mmol). The reaction was heated to 60° C. for 1 h. The acetonitrile was removed under reduced pressure. The remaining mixture was partitioned between ethyl acetate (1.0 L), water (700 mL), and brine (300 mL). The organic layer was separated and the aqueous layer was extracted with ethyl acetate twice. Volatile organics were combined and removed under reduced pressure. The solid was dissolved in minimal dichloromethane and purified on silica gel column (0-100% ethyl acetate in hexanes over 3 L). Fractions containing desired product were combined and volatile organics were removed under reduced pressure. The residue was dissolved in minimal dichloromethane and purified a second time on silica gel column (10% isocratic ethyl acetate in hexanes over 800 mL followed by 20-80% ethyl acetate in hexanes over 4 L). Fractions containing desired product were combined and volatile organics were removed under reduced pressure to afford 4-(4-(4-(chloromethyl) benzyl)piperazin-1-yl)-3-fluorobenzonitrile (22.7 g, 66.0 mmol, 67.7% yield) as an off-white solid. $^1$H NMR (400 MHz, CDCl$_3$) δ ppm 7.33-7.39 (m, 5H) 7.29 (d, J=1.96 Hz, 1H) 7.25 (d, J=1.96 Hz, 1H) 6.91 (t, J=8.56 Hz, 1H) 4.60 (s, 2H) 3.58 (s, 2H) 3.19-3.27 (m, 4H) 2.58-2.66 (m, 4H). MS (ESI) m/z 344.2 [M+1]$^+$.

(S)-tert-butyl 5-amino-4-(4-((4-((4-(4-cyano-2-fluorophenyl)piperazin-1-yl)methyl)benzyl)oxy)-1-oxoisoindolin-2-yl)-5-oxopentanoate (S)-tert-butyl 5-amino-4-(4-hydroxy-1-oxoisoindolin-2-yl)-5-oxopentanoate (22.05 g, 65.9 mmol) was placed in a flask with 4-(4-(4-(chloromethyl)benzyl)piperazin-1-yl)-3-fluorobenzonitrile (22.67 g, 65.9 mmol), potassium carbonate (18.23 g, 132 mmol), and N,N-dimethylformamide (330 mL). The reaction mixture was heated to 45° C. for 16 h. The reaction was diluted with ethyl acetate (50 mL) and filtered. The filtrate was partitioned with ethyl acetate (900 mL) and water (600 mL) and brine (200 mL). The organic layer was isolated and washed with water (600 mL). The organic layer was dried over sodium sulfate, and volatiles were removed under reduced pressure. The residue was treated with 20% ethyl acetate in hexanes and volatiles were removed under reduced pressure to afford (S)-tert-butyl 5-amino-4-(4-((4-((4-(4-cyano-2-fluorophenyl)piperazin-1-yl)methyl)benzyl)oxy)-1-oxoisoindolin-2-yl)-5-oxopentanoate (44.02 g, 68.6 mmol, 104% yield) as an off-white solid. Yield was slightly over quantitative as some DMF remained. $^1$H NMR (400 MHz, CDCl$_3$) δ ppm 7.43-7.49 (m, 2H) 7.40 (s, 4H) 7.36 (dd, J=8.38, 1.28 Hz, 1H) 7.29 (d, J=1.96 Hz, 1H) 7.26 (d, J=1.83 Hz, 1H) 7.11 (dd, J=7.64, 1.16 Hz, 1H) 6.92 (t, J=8.50 Hz, 1H) 6.23 (br s, 1H) 5.24-5.32 (m, 1H) 5.15 (s, 2H) 4.86-4.94 (m, 1H) 4.38-4.55 (m, 2H) 3.61 (s, 2H) 3.18-3.32 (m, 4H) 2.58-2.70 (m, 4H) 2.09-2.47 (m, 4H) 1.43 (s, 8H). MS (ESI) m/z 642.4 [M+1]$^+$.

(S)-4-(4-(4-(((2-(2,6-Dioxopiperidin-3-yl)-1-oxoisoindolin-4-yl)oxy)methyl)benzyl)piperazin-1-yl)-3-fluorobenzonitrile (S)-tert-butyl 5-amino-4-((4-((4-(4-cyano-2-fluorophenyl)piperazin-1-yl)methyl)benzyl)oxy)-1-oxoisoindolin-2-yl)-5-oxopentanoate (12.1 g, 18.86 mmol) was placed in a vial with acetonitrile (189 mL) and benzenesulfonic acid (3.96 g, 24.51 mmol). The reaction mixture was placed under vacuum and purged with nitrogen. This was repeated once more and the mixture was then heated to 85° C. overnight under a nitrogen atmosphere. The warm reaction mixture was poured directly into 2 separatory funnels containing dichloromethane (1000 mL) and ethyl acetate (300 mL). To this mixture a saturated solution of sodium bicarbonate (900 mL), water (100 mL), and brine (450 mL) was added. The organic layer was isolated and the aqueous layer was extracted with dichloromethane (800 mL) and ethyl acetate (200 mL). The combined organic layers were dried over anhydrous magnesium sulfate, and concentrated. Purification by standard methods provided the title compound. $^1$H NMR (400 MHz, DMSO-d$_6$) δ ppm 10.96 (s, 1H) 7.68 (dd, J=13.45, 1.83 Hz, 1H) 7.56 (dd, J=8.44, 1.83 Hz, 1H) 7.43-7.52 (m, 3H) 7.29-7.39 (m, 4H) 7.11 (t, J=8.80 Hz, 1H) 5.24 (s, 2H) 5.11 (dd, J=13.20, 5.14 Hz, 1H) 4.22-4.46 (m, 2H) 3.54 (s, 2H) 3.12-3.22 (m, 4H) 2.85-2.97 (m, 1H) 2.53-2.62 (m, 2H) 2.38-2.48 (m, 2H) 1.93-2.03 (m, 1H). MS (ESI) m/z 568.2 [M+1]$^+$.

Example 3: Synthesis of (S)-4-(4-(4-(((2-(2,6-dioxopiperidin-3-yl)-1-oxoisoindolin-4-yl)oxy)methyl)benzyl)piperazin-1-yl)-3-fluorobenzonitrile (Compound 2)

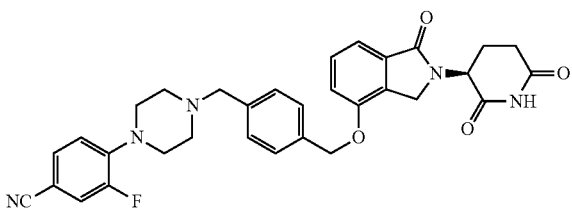 [SMILES: N#Cc1ccc(N2CCN(Cc3ccc(COc4cccc5c4CN([C@H]4CCC(=O)NC4=O)C5=O)cc3)CC2)c(F)c1]

4-(4-(4-(Chloromethyl)benzyl)piperazin-1-yl)-3-fluorobenzonitrile hydrochloride

To a solution of 3-fluoro-4-(piperazin-1-yl)benzonitrile (100 g) in toluene (1400 mL) was charged acetic acid (28 mL) at 25° C. and the reaction mixture was kept for 30 min. 4-(Chloromethyl)benzaldehyde (79 g) was charged at 25° C. and the mixture was kept for 2 h. Sodium triacetoxyborohydride (52 g each) was charged at 25° C. every 30 min three times. The mixture was agitated at 25° C. for about 10 h. Water (600 mL) was charged over 1 hour while maintaining the batch temperature below 30° C. Most of the lower layer was separated. The mixture was filtered and the lower layer was separated. The organic layer was washed with water (200 mL). To the organic layer was charged IPA (75 mL), 5-6 N HCl in IPA (8 ml), then a slurry of 4-(4-(4-(chloromethyl)benzyl)piperazin-1-yl)-3-fluorobenzonitrile hydrochloride seeds (2 g) in toluene (20 ml). To the mixture was charged 5-6 N HCl in IPA (115 ml) at 25° C. over 2 h. The mixture was kept for about 10 h, then filtered to give a crude solid. The solid was washed with toluene (400 ml), and dried in a vacuum oven to give 4-(4-(4-(chloromethyl)benzyl)piperazin-1-yl)-3-fluorobenzonitrile hydrochloride as a pale yellow solid (152 g, 82% yield). $^1$H NMR (300 MHz, DMSO-d$_6$) δ ppm 11.82 (s, 1H), 7.50-7.79 (m, 6H), 7.18-7.24 (m, 1H), 4.80 (s, 2H), 4.38-4.39 (m, 2H), 3.44-3.70 (m, 2H), 3.14-3.44 (m, 6H).

tert-Butyl (S)-5-amino-4-(4-((4-((4-(4-cyano-2-fluorophenyl)piperazin-1-yl)methyl)benzyl)oxy)-1-oxoisoindolin-2-yl)-5-oxopentanoate tartrate To a mixture of 4-(4-(4-(chloromethyl)benzyl)piperazin-1-yl)-3-fluorobenzonitrile hydrochloride (100 g) and tert-butyl (S)-5-amino-4-(4-hydroxy-1-oxoisoindolin-2-yl)-5-oxopentanoate (97 g) in DMF (600 ml) was charged potassium carbonate (K$_2$CO$_3$) (75 g) at 35° C. and the reaction mixture was kept for 24 h. To the mixture was charged triethylamine (11 ml) and the mixture was stirred at 45° C. for about 2 h. To the mixture was charged EtOAc (1 L) and aqueous potassium carbonate solution (5%, 500 mL). The organic layer was washed with aqueous sodium chloride solution (5%, 500 mL). To the mixture was charged Ecosorb C948 E-pak (30 g) and the mixture was kept for 2 h. The mixture was filtered. To the mixture was charged a solution of L-tartaric acid (47 g) in methanol (850 mL) at 45° C. and the mixture was kept for 2 h. The mixture was cooled to 25° C. The solids were filtered to give the tartrate salt of tert-butyl (S)-5-amino-4-(4-((4-((4-(4-cyano-2-fluorophenyl)piperazin-1-yl)methyl)benzyl)oxy)-1-oxoisoindolin-2-yl)-5-oxopentanoate. (145 g, 70% yield). $^1$H NMR (300 MHz, DMSO-d$_6$) δ ppm 1.31 (s, 9H), 1.87-2.27 (m, 4H), 2.55 (br s, 4H), 3.18 (br s, 4H), 4.29 (s, 2H), 4.36-4.62 (m, 2H), 4.71 (dd, J=4.2, 10.0 Hz, 1H), 5.22 (s, 2H), 7.10 (t, J=8.8 Hz, 1H), 7.18 (s, 1H), 7.29 (d, J=7.7 Hz, 2H), 7.33-7.40 (m, 2H), 7.40-7.51 (m, 3H), 7.51-7.63 (m, 2H).

(S)-4-(4-(4-(((2-(2,6-Dioxopiperidin-3-yl)-1-oxoisoindolin-4-yl)oxy)methyl)benzyl)piperazin-1-yl)-3-fluorobenzonitrile The solution of the tartrate salt of tert-butyl (S)-5-amino-4-(4-((4-((4-(4-cyano-2-fluorophenyl)piperazin-1-yl)methyl)benzyl)oxy)-1-oxoisoindolin-2-yl)-5-oxopentanoate (100 g) in 2-methyltetrahydrofuran (1 L) was washed with aqueous potassium carbonate solution (10%, 85 mL). The lower layer was separated. The solvent 2-methyltetrahydrofuran was swapped to acetonitrile to afford a solution. To the solution, benzenesulfonic acid (60 g) in acetonitrile (200 ml) was added at 70° C. over 2 h. Purification by standard methods provided the title compound. $^1$H NMR (400 MHz, DMSO-d$_6$) δ ppm 10.96 (s, 1H) 7.68 (dd, J=13.45, 1.83 Hz, 1H) 7.56 (dd, J=8.44, 1.83 Hz, 1H) 7.43-7.52 (m, 3H) 7.29-7.39 (m, 4H) 7.11 (t, J=8.80 Hz, 1H) 5.24 (s, 2H) 5.11

(dd, J=13.20, 5.14 Hz, 1H) 4.22-4.46 (m, 2H) 3.54 (s, 2H) 3.12-3.22 (m, 4H) 2.85-2.97 (m, 1H) 2.53-2.62 (m, 2H) 2.38-2.48 (m, 2H) 1.93-2.03 (m, 1H). MS (ESI) m/z 568.2 [M+1]+.

Example 4: Synthesis of (S)-4-(4-(4-(((2-(2,6-di-oxopiperidin-3-yl)-1-oxoisoindolin-4-yl)oxy)methyl) benzyl)piperazin-1-yl)-3-fluorobenzonitrile (Compound 2)

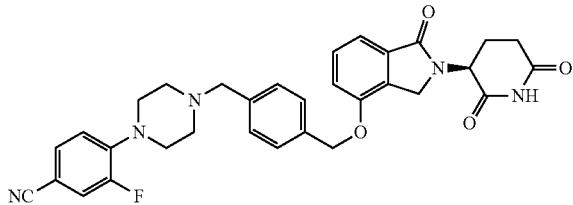 [SMILES: N#Cc1ccc(N2CCN(Cc3ccc(COc4cccc5c4CN([C@H]4CCC(=O)NC4=O)C5=O)cc3)CC2)c(F)c1]

4-(4-(4-(Chloromethyl)benzyl)piperazin-1-yl)-3-fluorobenzonitrile hydrochloride

To a solution of 3-fluoro-4-(piperazin-1-yl)benzonitrile (100 g) in toluene (1400 mL) was charged acetic acid (28 mL) at 25° C. and the mixture was kept for 30 min. 4-(Chloromethyl)benzaldehyde (79 g) was charged at 25° C. and the mixture was kept for 2 h. Sodium triacetoxyborohydride (52 g each) was charged at 25° C. every 30 min three times. The mixture was agitated at 25° C. for about 10 h. Water (600 mL) was charged over 1 hour while maintaining the batch temperature below 30° C. Most of the lower layer was separated. The mixture was filtered and the lower layer was separated. The organic layer was washed with water (200 mL). To the organic layer was charged IPA (75 mL), 5-6 N HCl in IPA (8 mL), then a slurry of 4-(4-(4-(chloromethyl)benzyl)piperazin-1-yl)-3-fluorobenzonitrile hydrochloride seeds (2 g) in toluene (20 mL). To the mixture was charged 5-6 N HCl in IPA (115 mL) at 25° C. over 2 h. The mixture was kept for about 10 h, then filtered to give a crude solid. The solid was washed with toluene (400 mL), and dried in a vacuum oven to give 4-(4-(4-(chloromethyl) benzyl)piperazin-1-yl)-3-fluorobenzonitrile hydrochloride as a white solid (152 g, 82% yield). $^1$H NMR (300 MHz, DMSO-$d_6$) δ ppm 11.82 (s, 1H), 7.50-7.79 (m, 6H), 7.18-7.24 (m, 1H), 4.80 (s, 2H), 4.38-4.39 (m, 2H), 3.44-3.70 (m, 2H), 3.14-3.44 (m, 6H).

tert-Butyl (S)-5-amino-4-(4-((4-((4-(4-cyano-2-fluorophenyl)piperazin-1-yl)methyl)benzyl)oxy)-1-oxoisoindolin-2-yl)-5-oxopentanoate To a mixture of 4-(4-(4-(chloromethyl)benzyl)piperazin-1-yl)-3-fluorobenzonitrile hydrochloride (100 g) and tert-butyl (S)-5-amino-4-(4-hydroxy-1-oxoisoindolin-2-yl)-5-oxopentanoate (88 g) in dimethylsulfoxide (DMSO) (700 mL) was charged potassium carbonate (K$_2$CO$_3$) (73 g) at 35° C. and the mixture was kept for 24 h. To the mixture was charged EtOAc (1.2 L) and water (1.1 L). The organic layer was washed with aqueous sodium chloride solution (5%, 1 L). To the mixture was charged n-heptane (200 mL). The mixture was washed with aqueous acetic acid (3%, 1 L), water (1 L), aqueous K$_3$PO$_4$ solution (20%, 10 L), and water (10 L). The solvent was distilled to about 1.2 L. The mixture was crystallized with n-heptane to give tert-butyl (S)-5-amino-4-(4-((4-((4-(4-cyano-2-fluorophenyl)piperazin-1-yl)methyl)benzyl)oxy)-1-oxoisoindolin-2-yl)-5-oxopentanoate (143 g, 85% yield). $^1$HNMR (400 MHz, CDCl$_3$) δ ppm 7.43-7.49 (m, 2H) 7.40 (s, 4H) 7.36 (dd, J=8.38, 1.28 Hz, 1H) 7.29 (d, J=1.96 Hz, 1H) 7.26 (d, J=1.83 Hz, 1H) 7.11 (dd, J=7.64, 1.16 Hz, 1H) 6.92 (t, J=8.50 Hz, 1H) 6.23 (br s, 1H) 5.24-5.32 (m, 1H) 5.15 (s, 2H) 4.86-4.94 (m, 1H) 4.38-4.55 (m, 2H) 3.61 (s, 2H) 3.18-3.32 (m, 4H) 2.58-2.70 (m, 4H) 2.09-2.47 (m, 4H) 1.43 (s, 8H).

(S)-4-(4-(4-(((2-(2,6-Dioxopiperidin-3-yl)-1-oxoisoindolin-4-yl)oxy)methyl)benzyl)piperazin-1-yl)-3-fluorobenzonitrile The solution of tert-butyl (S)-5-amino-4-(4-((4-((4-(4-cyano-2-fluorophenyl)piperazin-1-yl)methyl)benzyl)oxy)-1-oxoisoindolin-2-yl)-5-oxopentanoate (100 g) in acetonitrile (1 L) was kept at 70° C. To the solution, benzenesulfonic acid (74 g) in acetonitrile (200 mL) was added at 70° C. over 2 h. Purification by standard methods provided the title compound. $^1$H NMR (400 MHz, DMSO-$d_6$) δ ppm 10.96 (s, 1H) 7.68 (dd, J=13.45, 1.83 Hz, 1H) 7.56 (dd, J=8.44, 1.83 Hz, 1H) 7.43-7.52 (m, 3H) 7.29-7.39 (m, 4H) 7.11 (t, J=8.80 Hz, 1H) 5.24 (s, 2H) 5.11 (dd, J=13.20, 5.14 Hz, 1H) 4.22-4.46 (m, 2H) 3.54 (s, 2H) 3.12-3.22 (m, 4H) 2.85-2.97 (m, 1H) 2.53-2.62 (m, 2H) 2.38-2.48 (m, 2H) 1.93-2.03 (m, 1H). MS (ESI) m/z 568.2 [M+1]+.

Example 5: 4-(4-(4-(((2-(2,6-Dioxopiperidin-3-yl)-1-oxoisoindolin-4-yl)oxy)methyl)benzyl)piperazin-1-yl-2,2,3,3,5,5,6,6-d$^8$)-3-fluorobenzonitrile

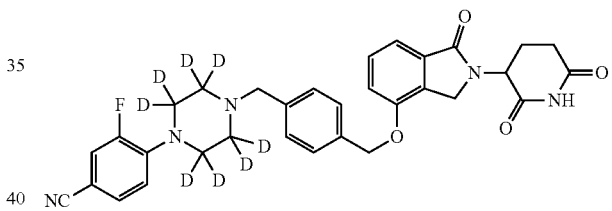

3-Fluoro-4-(piperazin-1-yl-2,2,3,3,5,5,6,6-d8)benzonitrile

A solution of 3,4-difluorobenzonitrile (278 mg, 2.00 mmol) and piperazine-2,2,3,3,5,5,6,6-d$^8$ (942 mg, 10.0 mmol) in dry DMA (6 mL) was stirred at 110° C. for 16 h. The mixture was cooled to ambient temperature and was slowly added to H$_2$O (60 mL) with mixing. The mixture was extracted with EtOAc (3×) and the organic portions were combined, washed with saturated NaCl (3×), dried over MgSO$_4$, filtered and concentrated. The residual colorless syrup was dried under vacuum to afford the crude product as a white solid (599 mg). The solid was dissolved in EtOAc and the solution was washed with H$_2$O (3×), saturated aqueous NaCl (3×) and dried over MgSO$_4$. The dried solution was filtered, concentrated and the residue dried in vacuum to afford the title compound (447 mg, 105%) as a white solid. LCMS (ESI) m/z 214.2 [M+H]+.

4-(4-(4-(((2-(2,6-Dioxopiperidin-3-yl)-1-oxoisoindolin-4-yl)oxy)methyl)benzyl)piperazin-1-yl-2,2,3,3,5,5,6,6-d$^8$)-3-fluorobenzonitrile To a solution of 3-[4-[[4-(bromomethyl)phenyl] methoxy]-1-oxo-isoindolin-2-yl]piperidine-2,6-dione (736 mg, 1.66 mmol) and 3-fluoro-4-(piperazin-1-yl-2,2,3,3,5,5,6,6-d$^8$)benzonitrile (425 mg, 1.99 mmol) in dry DMF (5.0 mL) was added DIEA (0.870 mL, 4.99 mmol) and the mixture was stirred at ambient temperature for 4 h. The mixture was filtered (0.45 μm nylon membrane) and the solution was purified by standard methods to give the title product (532 mg, 56%). LCMS (ESI) m/z 576.4 [M+H]$^+$.

Example 6: Antiproliferative and Proapoptotic Effects on Multiple Myeloma

Cell Culture Materials: Human multiple myeloma cell lines were purchased from the vendors and cultured at 37° C. with 5% $CO_2$ in the media as indicated in Table 1. Lenalidomide and pomalidomide resistant cell lines were obtained by methods as generally described previously (Lopez-Girona et al *Leukemia* 2012; 26(11): 2335). All cell lines were kept in log phase, and cell density and viability were monitored by trypan blue exclusion using the Vi-cell XR cell viability analyzer (Beckman Coulter, Brea, Calif.).

TABLE 1

Multiple Myeloma Cell Lines Tested

| MM Cell Line | Vendor/Source | Catalog Number | Culture Conditions |
|---|---|---|---|
| NCI-H929 | ATCC (Manassas, VA) | CRL-9068 | RPMI-1640, 10% FBS |
| NCI-H929-1051 | developed in-house, made resistant to lenalidomide | NA | RPMI-1640, 10% FBS |
| OPM2 | DSMZ (Braunschweig, Germany) | ACC-50 | RPMI-1640, 10% FBS |
| OPM2-P10 | developed in-house, made resistant to 10 μM pomalidomide | NA | RPMI-1640, 10% FBS |

Preparation of Solutions of Test Article:

Compounds were plated into black 384-well plates (Corning Inc.) to a final DMSO volume of 0.1% assuming a maximal volume of 50 μL. A 10-point dose response starting at 10 μM with a 1:3 dilution was printed in duplicate by acoustic dispense using the EDC ATS-100 platform. Alternatively, the 10-point dose response starting at 10 μM with a 1:10 dilution, or starting at 100 nM with a 1:3 dilutions were used.

Cell Proliferation Assays:

The effect of compounds on the proliferation/viability of the hematological cell lines (Table 1), was assessed after 120 h incubation using CTG (Promega), according to manufacturer's instructions. Hematological cell lines were dispensed into compound plates by a Multidrop Combi Reagent Dispenser (Thermo Scientific, Waltham, Mass.) at a concentration of 0.1×10$^6$ cells per mL in a 50 μL total volume. At 120 h, 25 μL per well of CTG was dispensed by a Multidrop Combi Reagent Dispenser and adenosine triphosphate (ATP) release by viable cells was measured as relative luminescence units after 30 minutes using the Envision platform.

Cell Apoptosis Assays:

The ability of the compounds to induce apoptosis was assessed in selected MM cell lines at the time points and compound concentrations indicated. As a marker of apoptosis, the level of Caspase-3 activity was measured in MM cells using live cell imaging. To image suspension cells, 96-well plates were coated with fibronectin so cells would adhere and lie flat on the bottom of the plate. Cells were added to 96-well plates using a Multidrop Combi Reagent Dispenser (Thermo Scientific, Waltham, Mass.) the night before compound addition. Compounds were spotted on top of cells into the appropriate well of 96-well plates using a Hewlett-Packard D300 Digital Dispenser (Tecan, Mannedorf, Switzerland). MM cell lines were treated with compound and at 6 h the media was changed to mimic compound turnover in vivo, resulting in about a 20-fold dilution of compound concentration. Cells were grown in the presence of NucView 488 Caspase-3 Enzyme Substrate (Biotium) and incubated in an IncuCyte ZOOM Live-Cell Analysis System (Essen Bioscience, Ann Arbor, Mich.) housed in a standard incubator. Cleavage of the Caspase-3 enzyme substrate and cellular confluence in each well was detected via imaging at 10× on the IncuCyte ZOOM System every 4-6 h for 5 days. Each well/condition was run in replicate on the same plate and each condition was the average of 4 10× images captured at each time point.

Results. Compound 1 and Compound 2 Demonstrate Antiproliferative Activity Against MM Cell Lines.

The MM cell lines selected for this study were lines sensitive and resistant to lenalidomide and/or pomalidomide (Table 1), two agents used in the clinic to treat myeloma patients. Proliferation was assessed using the CellTitre-Glo® assay. Results for cultures incubated with the compounds were normalized to results for control cultures for each cell line. The $IC_{50}$ for inhibition of cell growth by the compounds was determined for each cell line using ActivityBase software. Compound 1 and Compound 2 potently inhibited cell proliferation in the four cell lines, as determined by the quantitative assessment of ATP levels present in the media after 120 h. The antiproliferative $IC_{50}$ values of Compound 1 and Compound 2 ranged between 0.07 nM and 19 nM (Table 2). Compound 1 and Compound 2 showed very potent multiple myeloma anti-proliferative activity even on cell lines that were lenalidomide- and/or pomalidomide-resistant.

TABLE 2

Inhibition of Cell Growth by Compound 1 and Compound 2 in a MM Cell Lines in Liquid Culture

| Compd. No. | NCI-H929 120 h $IC_{50}$ | NCI-H929.1051 120 h $IC_{50}$ | OPM-2 120 h $IC_{50}$ | OPM-2.P10 120 h $IC_{50}$ |
|---|---|---|---|---|
| 1 | <0.5 nM | 2.5 nM | <0.5 nM | 19 nM |
| 2 | 0.07 nM | 1.0 nM | 0.07 nM | 4.3 nM |

Compound 1 Induced Apoptosis in Multiple Myeloma Cell Lines.

Figure 1B:
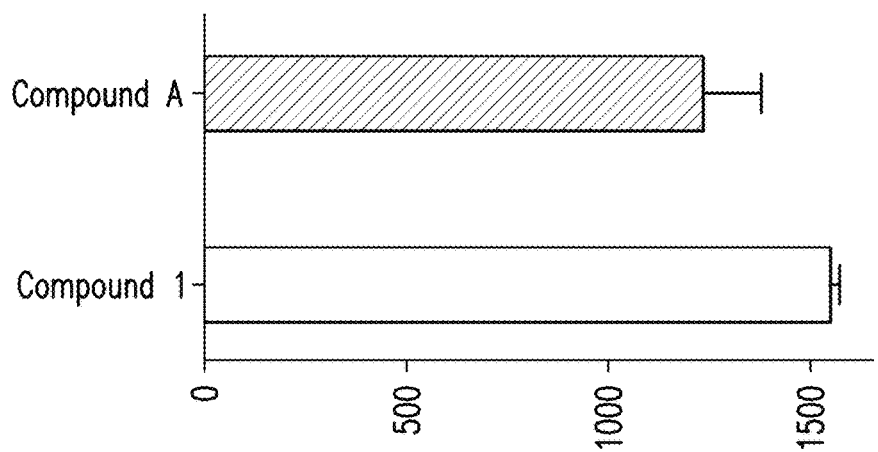

The effects of compounds on apoptosis in MM cell lines were investigated. To determine the ability of compounds to induce apoptosis and to characterize kinetically the onset of this process, Caspase-3 induction was measured over time in lenalidomide-resistant, H929-1051 cells (FIG. 1). H929-1051 cells were incubated with the compounds at concentrations of 1 nM, 10 nM, 100 nM and 1000 nM and apoptosis was assessed over time. Results showed that for H929-1051 cells, all concentrations of Compound 1 induced apoptosis beginning at around 48 h and reaching near maximal induction at ~72 h of incubation. Next, the area under the curve (AUC) was calculated for each concentration and used to generate the concentration-response curves for each compound. This provided quantitative evidence of the ability of Compound 1 to induce apoptosis in H929-1051. Surprisingly, the apoptosis induction by Compound 1 was significantly higher than the apoptosis induction observed for the previously reported compound 3-(4-((4-((4-(2,4-difluorophenyl)piperazin-1-yl)methyl)benzyl)oxy)-1-oxoisoindolin-2-yl)piperidine-2,6-dione (Example 5.285 in U.S. Pat. No. 8,518,972) (Compound A). As shown in FIG. 1B, the apoptotic induction (as measured by total AUC) by Compound 1 was increased by nearly 30% (126%) compared to the apoptotic induction by Compound A.

Combination with Dexamethasone.

The activity of pomalidomide with that of Compound 2 alone or in combination with dexamethasone was evaluated across a panel of MM cell lines. FIG. 2 is a representative set of dose-response curves in the lenalidomide-resistant H929-1051 cell line, demonstrating that single agent Compound 2 is 10-fold more potent than a pomalidomide-dexamethasone combination and nearly as efficacious (FIG. 2, panel A). Surprisingly, when Compound 2 is combined with dexamethasone, it not only creates a more potent response, but the efficacy is also dramatically improved (FIG. 2, panel B); nearly complete cell killing is achieved. Table 3 summarizes the potency ($IC_{50}$) of the single agent and dexamethasone combination studies performed in the H929-1051 cell line. The $IC_{50}$s of either single agent pomalidomide or Compound 2, and the combination of 1, 0.1, or 0.01 µM dexamethasone (Dex) in lenalidomide-resistant cells (H929-1051) are listed. Each $IC_{50}$ is the average from at least 3 independent experiments. Proliferation was monitored on Day 5 using Cell Titer-Glo. Consistently, Compound 2 in combination with dexamethasone was dramatically more active than pomalidomide in combination with dexamethasone, and this increased activity was achieved at 10-100 fold lower concentrations of dexamethasone. Together this data indicates the potential for increased safety of the combination treatment of Compound 2 and dexamethasone, by allowing for the use of lower doses of dexamethasone while maintaining efficacy and synergy.

on THLE-2 cells ($IC_{50}$>10 µM) or on unstimulated primary human PBMCs ($IC_{50}$>10 µM) compared with the MM cell lines shown above.

Antitumor Activity of Compound 2 in Lenalidomide-resistant Multiple Myeloma Xenograft Model.

The purpose of the study was to test the single agent antitumor activity of Compound 2 in an H929-1051 xenograft model with once daily dosing (QD) at 1, 3, 10, and 30 mg/kg. Significant (p<0.0001) antitumor activity was observed at all dose levels with a tumor volume reduction of 75%, 86%, 84%, and 85% at 1, 3, 10, and 30 mg/kg, respectively (FIG. 4).

Conclusion:

taken together this data shows that Compound 1 and Compound 2 show very potent anti-multiple myeloma activity and surprisingly show significantly increased levels of apoptosis compared to the previously reported compounds Compound A and pomalidomide. In addition, Compound 2 combined with dexamethasone not only creates a more potent response, but the efficacy is also dramatically improved. Additionally, selective cell killing of multiple myeloma compared to normal cells was shown.

Example 7: Off-target Effects of Compound 1/Compound 2 and Implications

α1 Adrenergic and Dopamine D2 Receptors. Methods:

Binding and functional assays for α1 adrenergic and dopamine D2 receptors were performed by Eurofins Cerep according to their methods.

α1 Adrenergic Receptor. Binding at 10 µM.

The binding assay evaluated the affinity of test article for the non-selective α1 adrenergic receptor in rat cerebral cortex. Membrane homogenates of cerebral cortex were incubated in duplicate for 60 minutes at room temperature with 0.25 nM [$^3$H]prazosin in the absence or presence of test articles at 10 µM. After the incubation period, samples were filtered through glass fiber filters, the filters dried and then counted for radioactivity using a scintillation counter. Results are expressed as mean percent inhibition of control radioligand binding.

Binding $IC_{50}$. To determine the binding $IC_{50}$ for the non-selective α1 adrenergic receptor, varying concentrations of test article were incubated in duplicate with 0.25 nM [$^3$H]prazosin. Compound A was tested at 0.01-30 µM. Compound B, the S-enantiomer of Compound A, was tested at 0.0003-10 µM. Compound 1 and Compound 2, the S-enan-

TABLE 3

Comparison of Anti-proliferative $IC_{50}$ Values for Compound 2 and Pomalidomide as Single Agents or in Combination with Dexamethasone in the Lenalidomide-resistant H929-1051 Cell Line

| | Single Agent $IC_{50}$ µM | 1 µM Dex Combo $IC_{50}$ | 0.1 µM Dex Combo $IC_{50}$ | 0.01 µM Dex Combo $IC_{50}$ |
|---|---|---|---|---|
| Pomalidomide | >10 µM | 0.01884 µM | 0.11824 µM | 3.837 µM |
| Compound 2 | 0.00098 µM | 0.000018 µM | 0.0000429 µM | 0.00041 µM |

In Vitro Safety Evaluation as Evaluated by Anti-proliferative Selectivity over Normal Cells.

To demonstrate that Compound 2 is not generally cytotoxic, a counter-screen against the immortalized (but non-tumorigenic) human hepatocyte-derived cell line THLE-2 (Pfeifer et al, *Proc Natl Acad Sci USA*. 1993; 90(11):5123-7) and against primary, healthy human PBMCs (FIG. 3) was performed. Compound 2 had little anti-proliferative effect tiomer of Compound 1, were assayed at 0.03-100 µM. Radioactivity was measured as described above. The $IC_{50}$ was defined as the concentration causing a half-maximum inhibition of control specific binding.

Antagonist Activity.

The antagonistic effects of test compounds on the $α_{1A}$ and $α_{1B}$ adrenergic receptors were measured using human receptor-transfected Chinese hamster ovary (CHO) cells. Antagonist activity was determined by measuring compound effect on agonist (epinephrine)-induced calcium mobilization in the $\alpha_{1A}$ receptor assay or cAMP levels in the $\alpha_{1B}$ receptor assay. In these experiments, CHO cells were incubated in duplicate at room temperature with test article and epinephrine at 3 nM in the $\alpha_{1A}$ receptor assays or at 3000 nM in the $\alpha_{1B}$ receptor assay. Compound A was tested in the $\alpha_{1A}$ receptor assay at 0.01-30 μM. Compound B was tested in the $\alpha_{1A}$ and $\alpha_{1B}$ receptor assays at 0.0003-30 μM. Compound 1 and Compound 2 were assayed at 0.03 to 30 μM in the $\alpha_{1A}$ receptor assay and 0.03 to 100 μM in the $\alpha_{1B}$ receptor assay. In the $\alpha_{1A}$ receptor assay, cytosolic calcium levels were measured fluorometrically using the fluorescent probe, Fluo4 Direct. Intracellular cAMP levels in the $\alpha_{1B}$ adrenergic receptor assay were measured by homogenous time-resolved fluorescence (HTRF). The antagonism $IC_{50}$ was defined as the concentration causing a half-maximum inhibition of control agonist response.

Dopamine D2 Receptor.

Binding at 10 μM. The binding assay evaluated the affinity of test articles for the dopamine D2 receptor in transfected human embryonic kidney (HEK)-293 cells. For determining the binding in the D2s receptor assay, test article was incubated with 0.3 nM [$^3$H] methylspiperone or 1 nM [$^3$H] 7-hydroxy-2-N,N-dipropylaminotetralin (7-OH-DPAT). [$^3$H] Methylspiperone at 0.3 nM also was used as control ligand in the $D_{2L}$ binding assay. Cell membrane homogenates were incubated in duplicate at room temperature for 60 minutes with ligand in the absence or presence of test articles at 10 μM. After the incubation period, samples were filtered through glass fiber filters, the filters dried and then counted for radioactivity using a scintillation counter. Results are expressed as mean percent inhibition of control radioligand binding.

Binding $IC_{50}$.

To determine the binding $IC_{50}$ in the D2 receptor assays, HEK-293 were tested as described above but with varying concentrations of test article. Compound A was tested at 0.01-30 μM in the $D_{2S}$ radioligand binding assay. Compound B was tested at 0.0003-10 μM in both the $D_{2S}$ and $D_{2L}$ binding assays. Compound 1 was assayed at 0.03-100 μM in both the $D_{2S}$ and $D_{2L}$ assays, while Compound 2 was tested at 0.03-100 μM in the $D_{2S}$ assay and 0.01-100 μM in the $D_{2L}$ assays. The $IC_{50}$ was defined as the concentration causing a half-maximum inhibition of control specific binding.

Agonist Activity.

The agonism of test compounds on the dopamine $D_{2S}$ receptor was assessed using human receptor-transfected HEK-293 cells. Agonist activity was determined by measuring compound effect on impedance modulation. In these experiments, HEK-293 cells were incubated in duplicate at 28° C. with test article. Compound A was tested at 0.01-30 μM. Compound B was tested at 0.0003-10 μM, while Compound 1 and Compound 2 were assayed at 0.01-10 μM. Dopamine (3 μM) was used as an agonist control. Impedance measurements were monitored for 10 minutes after ligand addition using cellular dielectric spectroscopy. The $EC_{50}$ was defined as the concentration causing a half-maximum response, compared to the control agonist (dopamine) response.

Results.

Binding at 10 μM at the α1 adrenergic and dopamine D2 receptors was evaluated for Compound 1, Compound 2, Compound A, Compound B and a number of compounds exemplified in U.S. Pat. No. 8,518,972 (Table 4). While the previously disclosed compounds fully inhibited binding of ligand at both receptors, surprisingly, Compound 1 and Compound 2 showed greatly diminished ability to inhibit ligand binding, showing only 67/62% (α1 adrenergic receptor) and 55/52% (dopamine $D_{2S}$) inhibition of ligand binding, respectively. The differentiated effect of Compound 1 and Compound 2, compared to Compound A and Compound B at the α1 adrenergic and dopamine D2 receptors was therefore further analyzed.

TABLE 4

Effects of Compound A, Compound B, Compound 1 and Compound 2 and previously reported compounds on α1 Adrenergic and Dopamine D2 Receptor

| Cmpd No. | $R^1$ | $R^2$ | X | Stereo | Adrenergic α1 % Inh. (@10 μM) | Dopamine $D_{2S}$ % Inh. (@10 μM) |
|---|---|---|---|---|---|---|
| 1 | CN | F | $CH_2$ | rac | 67 | 55 |
| 2 | CN | F | $CH_2$ | S | 62 | 52 |
| A | F | F | $CH_2$ | rac | 102 | 99 |
| B | F | F | $CH_2$ | S | 98 | 99 |
| Ex. 5.229 | H | H | $CH_2$ | rac | 98.3 | 98.7 |
| Ex. 5.273 | F | H | $CH_2$ | rac | 100.3 | 94.7 |
| Ex. 5.289 | F | H | CO | rac | 97.9 | 92.4 |

The detailed effects of Compound A, Compound B, Compound 1 and Compound 2 on the α1 adrenergic receptor are summarized in Table 5. Compound A inhibited binding of ligand to the α1 adrenergic receptor by 102%. The binding $IC_{50}$ for Compound A to the receptor was 0.064 μM. Compound A was shown to be a strong antagonist of the $\alpha_{1A}$ adrenergic receptor, with an $IC_{50}$ of 0.014 μM. Similarly, Compound B inhibited binding of ligand to the α1 adrenergic receptor by 98-100% at 10 μM and had a binding $IC_{50}$ of 0.024 μM. Strong antagonism of the α1 adrenergic receptor was observed with Compound B, with $IC_{50}$ values of 0.0064 and 0.078 μM on the $\alpha_{1A}$ and $\alpha_{1B}$ receptors, respectively. Surprisingly, in contrast, Compound 1 and Compound 2 both were shown to have weak activity on the α1 adrenergic receptor. The $IC_{50}$ values for receptor antagonism by Compound 1 were 0.98 μM and 6.9 μM for $\alpha_{1A}$ and $\alpha_{1B}$ receptors, respectively. Comparable results were observed for Compound 2.

TABLE 5

Effects of Compound A, Compound B, Compound 1 and Compound 2 on α1 Adrenergic Receptor

| Compound | α1 (non-selective) % Inhibition (10 μM) | α1 (non-selective) Binding $IC_{50}$ (μM) | Antagonism $IC_{50}$ (μM) $\alpha_{1A}$ | Antagonism $IC_{50}$ (μM) $\alpha_{1B}$ |
|---|---|---|---|---|
| Compound A | 102 | 0.064 | 0.014 | ND |
| Compound B | 98, 100$^a$ | 0.024 | 0.0064 | 0.078 |
| Compound 1 | 67 | 3.9 | 0.98 | 6.9 |
| Compound 2 | 62 | 1.3 (estimated) | 0.58 | 2.4 |

$^a$Independent experiments.
ND, not determined

Dopamine D2 Receptor.

The effects of Compound A, Compound B, Compound 1 and Compound 2 on dopamine D2 receptor are summarized in Table 6. Compound A inhibited binding of ligand to the dopamine D2s receptor by 99%. The binding $IC_{50}$ for Compound A to the D2s receptor was 0.15 µM. Compound A was shown to be a partial agonist of the dopamine D2s receptor, with an $EC_{50}$ of 0.016 µM. Similarly, Compound B inhibited the D2s receptor by 99% at 10 µM and had a binding $IC_{50}$ of 0.084 and 0.016-0.047 µM on the $D_{2L}$ and D2s receptors, respectively. Surprisingly, in contrast, Compound 1 and Compound 2 both were shown to have weak activity on the dopamine D2 receptor, with inhibition at 10 µM of ≤55% and binding $IC_{50}$ values≥2 µM. Functional agonism ($EC_{50}$) of Compound B at the dopamine D2s receptor in three independent studies was >10, 2.7 and 1.9 µM. Although the extent of agonism by Compound B on the D2s receptor was less than that observed for Compound A, there was a trend towards greater agonism by Compound B compared to Compound 1 and Compound 2. Taken together, the % inhibition of binding at 10 µM, binding $IC_{50}$ and agonism $IC_{50}$ data demonstrated stronger activity of Compound A and Compound B on the dopamine D2 receptor compared to Compound 1 and Compound 2. This observation is consistent with evidence of dopamine D2 agonism (i.e., decreased gastric motility/emptying) in rats with Compound A, but not with Compound 1 (as discussed below).

TABLE 6

Effects of Compound A, Compound B, Compound 1 and Compound 2 on Dopamine D2 Receptor

| Compound | % Inhibition (10 µM) | | Binding $IC_{50}$ (µM) | | $D_{2S}$ Agonism $EC_{50}$ (µM) |
|---|---|---|---|---|---|
| | $D_{2L}$ | $D_{2S}$ | $D_{2L}$ | $D_{2S}$ | |
| Compound A | ND | 99 | ND | 0.15 | 0.016 |
| Compound B | 103 | 99, 99[a] | 0.084 | 0.016, 0.021, 0.047[a] | >10, 2.7, 1.9[a] |
| Compound 1 | 55 | 55 | 2.3 | 7.4 | Negative |
| Compound 2 | ND | 52 | 3 (estimated) | 2 (estimated) | >10 |

[a]Independent experiments;
ND, not determined

7-Day Exploratory Toxicology Studies in Male Rats.
Methods.

Male CD-IGS rats (n=5/group for toxicologic assessment; n=4/group for toxicokinetic assessment) were dosed once daily by oral gavage (10 mL/kg) with vehicle (0.5% HPMC/0.25% Tween-80 in 50 mM citrate, pH 2.6-2.8) or test articles (Compound A or Compound 1) at 100, 300 or 1000 mg/kg/day for 7 consecutive days. Blood samples for toxicokinetics were collected on Days 1 and 7. All rats were observed for clinical signs of toxicity at pre-dose, approximately 1 hour post-dose on Days 1-7 and prior to necropsy on Day 8. Body weight was recorded at randomization, prior to dosing on Days 1-7 and prior to necropsy. Samples for hematology and serum chemistry analyses were collected on Day 8, approximately 24 h after the last dose. Rats were euthanized on Day 8 for necropsy. Anatomic pathology evaluation consisted of gross observation, organ weight and histopathologic examination of select tissues.

Results.

Following daily oral administration of Compound A for 7 consecutive days, systemic exposure ($AUC_{0-t}$) increased in a dose-dependent manner from 100 to 1000 mg/kg. Exposure on Day 7 was approximately 3 to 7-fold greater than Day 1. AUCs on Day 7 were 441, 1230 and 1760 µM·hr at 100, 300, and 1000 mg/kg, respectively. Clinical signs of toxicity (hunched posture, piloerection and decreased activity) and decreased body weight were observed at ≥300 mg/kg. No body weight gain was seen at 100 mg/kg. Abnormal stomach content (dry, feed material) was observed grossly at ≥100 mg/kg, with no microscopic correlate. This finding suggests decreased gastric motility/emptying and is consistent with agonistic activity on the dopamine D2 receptor. Test article-related microscopic findings were limited to minimal multifocal myocardial necrosis and mixed cell infiltration in hearts of rats at all dose levels. Although the exact cause of this heart lesion remains to be determined, the finding is consistent with agonism of the dopamine D2 receptor and/or antagonism of the α1-adrenergic receptor. Alterations of these receptors can lead to vasodilation, resulting in decreased blood flow, hypotension and reflex tachycardia. The location of the heart lesions (apex, endocardial surface of ventricles) further supports an ischemia mechanism. For Compound 1, exposure ($AUC_{0-t}$) also increased in a dose-dependent manner from 100 to 1000 mg/kg and exposures on Day 7 was approximately 2- to 6-fold greater than Day 1. On Day 7, AUCs at 100, 300, and 1000 mg/kg were 143, 514, and 1220 µM·hr, respectively. There were no test article-related clinical observations. Minimal decreases in body weight gain were observed at ≥300 mg/kg. Surprisingly, in contrast to Compound A, no effects on stomach or heart were observed in rats dosed with Compound 1, consistent with reduced activities on α1 adrenergic and dopamine D2 receptors observed by Eurofins Cerep, described above.

In vitro Evaluation of Compound 2 and Compound B as an Inhibitor of Human Cytochrome p450 Enzymes.

The objective was to evaluate the potential of Compound B and Compound 2 to act as a direct or time-dependent inhibitor of cytochrome P450 (CYP) activities in pooled human liver microsomes. In this study, inhibition of nine human cytochrome P450 enzymes, namely CYP1A2, CYP2A6, CYP2B6, CYP2C8, CYP2C9, CYP2C19, CYP2D6, CYP2E1 and CYP3A4/5 (using two substrates) was investigated.

Methods.

To examine the potential of the compounds to act as a direct inhibitor of CYP enzymes, pooled human liver microsomes were incubated with probe substrates, at concentrations approximately equal to their apparent Km, in the absence or presence of Compound B (0.03 to 30 µM) or Compound 2 (0.03 to 30 µM) and NADPH (1 mM). In addition, the compounds were evaluated for their potential to act as a time-dependent inhibitors at the same concentrations mentioned above. When evaluating time-dependent inhibition, the compounds were preincubated with human liver microsomes and NADPH (1 mM) for 30 minutes prior to the addition of a probe substrate. In addition to appropriate vehicle controls, known direct inhibitors and time-dependent inhibitors of CYP isoforms were included as positive controls. Following the incubation, concentrations of probe substrate metabolites were quantified using established LC/MS/MS methods. The extent of inhibition was expressed as the percentage of control activity.

Results. Compound B.

Under the experimental conditions used to examine direct inhibition, Compound B (up to 30 µM) had little (≤30%) to no inhibitory effect on CYP1A2, CYP2A6, CYP2C8, CYP2D6, CYP2E1 and CYP3A4/5 (midazolam). At 30 µM, Compound B inhibited CYP2B6, CYP2C9 and CYP2C19 activity by 59, 38 and 45%, respectively. Compound B inhibited CYP3A4/5 (testosterone) with an $IC_{50}$ value of 2.92 µM. Under the conditions used to test time-dependent inhibition, Compound B (up to 30 µM) showed little to no time-dependent inhibition of CYP1A2, CYP2A6, CYP2B6, CYP2C8, CYP2C9, CYP2C19, CYP2D6 and CYP2E1 following a 30 minute preincubation with or without NADPH. Compound B inhibited CYP3A4/5 in a time-dependent manner. The shifted $IC_{50}$ value (with NADPH) was 2.23 and 1.93 µM for midazolam and testosterone as substrates, respectively.

Compound 2.

Under the experimental conditions used to examine direct inhibition, Compound 2 (up to 30 µM) had little (≤30%) to no inhibitory effect on CYP1A2, CYP2A6, CYP2B6, CYP2C8, CYP2C9, CYP2D6, CYP2E1 and CYP3A4/5 (midazolam). At 30 µM, Compound 2 inhibited CYP2C19 and CYP3A4/5 (testosterone) activity by 41 and 46%, respectively. Under the conditions used to test time-dependent inhibition, Compound 2 (up to 30 µM) showed little to no time-dependent inhibition of CYP1A2, CYP2A6, CYP2B6, CYP2C8, CYP2C9, CYP2C19, CYP2D6, CYP2E1 and CYP3A4/5 (midazolam) following a 30 minute preincubation with or without NADPH. Compound 2 (at 30 µM) inhibited CYP3A4/5 (testosterone) activity by 59% (with NADPH) and 23% (without NADPH), which indicated that Compound 2 was a weak time-dependent inhibitor of CYP3A4/5.

Conclusion.

In summary, Compound B (up to 30 µM) had little (≤30%) to no direct inhibitory effect on CYP1A2, CYP2A6, CYP2C8, CYP2D6, CYP2E1 and CYP3A4/5 (midazolam). Compound B inhibited CYP3A4/5 (testosterone) with an $IC_{50}$ value of 2.92 µM. Compound B inhibited CYP2B6, CYP2C9 and CYP2C19 activity by 59, 38 and 45% respectively at 30 µM. Compound B (up to 30 µM) is not a time-dependent inhibitor of CYP1A2, CYP2A6, CYP2B6, CYP2C8, CYP2C9, CYP2C19, CYP2D6 and CYP2E1 but is a time-dependent inhibitor of CYP3A4/5.

Surprisingly, in contrast Compound 2 (up to 30 µM) had little (≤30%) to no inhibitory effect on any of the CYP enzymes tested, and at 30 µM, Compound 2 inhibited CYP2C19 and CYP3A4/5 (testosterone) activity only by 41, and 46% (i.e. $IC_{50}$>30 µM), respectively. Compound 2 (up to 30 µM) is also only a weak time-dependent inhibitor of CYP3A4/5. The reduced inhibitory activity for CYP2C19 and CYP3A4/5 results in a reduced effect on metabolism including of other drugs, and therefor a reduced potential for adverse drug interactions.

Summary:

The combination of the potent anti-multiple myeloma activity while sparing normal cells, the significantly increased levels of apoptosis, and the more potent and efficacious combination response with dexamethasone, indicates Compound 1 and Compound 2 will be useful in the treatment of multiple myeloma. In addition, the surprisingly improved in vitro and in vivo off-target and CYP profile findings, in combination with the potential to use lower doses of dexamethasone, indicate that Compound 1 and Compound 2 should have improved safety profiles relative to previously reported compounds.

Example 8: Compound 2-Induced Apoptosis in Multiple Myeloma Cell Lines, Characterized by Oncogenic Drivers, Chromosomal Translocations, and p53 Mutations Methods.

The effect of compounds on the proliferation and induction of apoptosis of representative MM cell lines possessing common oncogenic mutations and chromosomal translocations, including those considered to be high risk translocations or mutations found in MM patients, was assessed utilizing a 96-well plate flow cytometry assay after 120 h of incubation with the compounds. Twenty MM cell lines (Table 7 and 8) (including the plasma cell leukemia (PCL) cell lines L363, JJN-3, ARH-77, and SKMM-2) were treated in duplicate with escalating concentrations of Compound 2 or pomalidomide, ranging from 0.015 to 100 nM. Using 5 mM stocks, compounds were pre-spotted into the appropriate wells of 96-well plates using a Hewlett-Packard D300 Digital Dispenser. Cells were added to 96-well plates using a Multidrop Combi Reagent Dispenser. After 5 days of treatment, flow cytometric analysis was used to determine the number of cells that were alive, dead, or apoptotic. After 5 days of treatment, cells were incubated with annexin V to stain exposed phosphatidylserine, an apoptotic cell-surface marker, and the vital dye 7-AAD, which is excluded from cells with intact cell membranes, and analyzed by flow cytometry (Attune®, Thermo Fisher). Analysis was then performed to determine the number of live cells (annexin V and 7-AAD double negative staining cells) and the percentage of apoptotic cells (annexin V positive cells) for each condition, relative to the DMSO control treated, was calculated. All described values were normalized to DMSO-only treated cells. All proliferation and apoptosis induction curves were processed and graphed as percent of control using XLFit (IDBS, Alameda, Calif.) and GraphPad Prism 7.03 (GraphPad Software, La Jolla, Calif.). The live cell count for every concentration was normalized to the DMSO control (considered as 100%) in Microsoft Excel to generate the proliferation curves. The $IC_{50}$ (compound concentration that achieves 50% inhibition) values were then calculated by performing log(inhibitor) vs. normalized response—Variable slope analysis, and area under the curve (AUC) values were calculated by performing area under curve analysis on GraphPad Prism 7.03. Similarly, for apoptosis analysis, the percentage of drug-induced apoptosis was calculated for all doses by combining both "early" (annexin V positive and 7-AAD negative) and "late" apoptosis (annexin V and 7-AAD positive) values and subtracting background values (cell treated with vehicle control DMSO). The AUC values for apoptosis curves were calculated by performing area under curve analysis on GraphPad Prism 7.03. The area under the dose-response curve (AUC) was calculated since it integrates potency and efficacy of the drugs to represent apoptosis into a single parameter. The $IC_{50}$ values for Compound 2 and pomalidomide in the flow cytometry assays are presented Table 9. Table 10 shows the area under the dose-response curves (AUC) comparing the activity of Compound 2 and pomalidomide using the flow cytometric assay in the panel of MM cell lines.

TABLE 7

Multiple Myeloma Cell Lines

| MM Cell Line | Vendor/Source | Catalog Number | Culture Conditions |
|---|---|---|---|
| ANBL-6 | Jelinek, Ahmann et at. Cancer Res (1993) 53(21): 5320-5327 | NA | RPMI-1640, 10% FBS, IL-6 |
| ARH-77 | ATCC (Manassas, VA) | CRL-1621 | RPMI-1640, 10% FBS |
| CAG | Borset, et al. Blood (2000) 96(7): 2528-2536 | NA | RPMI-1640, 10% FBS |
| DF15 | Shaughnessy, et al. US20070027175 | NA | RPMI-1640, 10% FBS |
| EJM | DSMZ (Braunschweig, Germany) | ACC-560 | RPMI-1640, 10% FBS |
| NCI-H929 | ATCC (Manassas, VA) | CRL-9068 | RPMI-1640, 10% FBS |
| H929-1051 | Developed in-house, made resistant to 10 µM lenalidomide | | RPMI-1640, 10% FBS |
| IM-9 | ATCC (Manassas, VA) | CCL-159 | RPMI-1640, 10% FBS, IL-6 |
| JJN-3 | DSMZ (Braunschweig, Germany) | ACC-541 | RPMI-1640, 10% FBS |
| KMS-11 | Japanese Collection of Research Bioresources Cell Bank (Osaka, Japan) | JRCB-1179 | RPMI-1640, 10% FBS |
| KMS-12-PE | DSMZ (Braunschweig, Germany) | ACC-606 | RPMI-1640, 10% FBS |
| KMS-34 | Japanese Collection of Research Bioresources Cell Bank (Osaka, Japan) | JRCB-1195 | RPMI-1640, 10% FBS |
| L363 | DSMZ (Braunschweig, Germany) | ACC-49 | RPMI-1640, 10% FBS |
| LP-1 | DSMZ (Braunschweig, Germany) | ACC-41 | RPMI-1640, 10% FBS |
| MM.1S | ATCC (Manassas, VA) | CRL-2174 | RPMI-1640, 10% FBS |
| OPM2 | DSMZ (Braunschweig, Germany) | ACC-50 | RPMI-1640, 10% FBS |
| OPM2-P10 | Developed in-house, made resistant to 10 µM pomalidomide | | RPMI-1640, 10% FBS |
| RPMI-8226 | ATCC (Manassas, VA) | CCL-155 | RPMI-1640, 10% FBS |
| SKMM-2 | DSMZ (Braunschweig, Germany) | ACC-430 | RPMI-1640, 10% FBS |
| U266 | ATCC (Manassas, VA) | TIB-196 | RPMI-1640, 10% FBS |

ATCC = American Type Tissue Collection;
DSMZ = German Collection of Microorganisms and Cell Cultures;
FBS = fetal bovine serum;
IL-6 = interleukin 6;
JCRB = Japanese Collection of Research Bioresources Cell Bank;
MM = multiple myeloma;
N/A = not applicable.

TABLE 8

Oncogenic Drivers, Chromosomal Translocations, and p53 Mutations Found in a Panel of Multiple Myeloma Cell Lines

| MM Cell Line | p53 status | Oncogenic Drivers | Translocations |
|---|---|---|---|
| ANBL-6 | mut (Q331)[a] | C-MAF | t(14;16) |
| ARH-77 | mut (R273H) | — | — |
| CAG | wt HD | C-MAF | t(14;16) |
| DF15 | wt | — | — |
| EJM | mut (K132N) | MAFB | t(14;20) |
| NCI-H929 | wt | FGFR3 and MMset | t(4;14) |
| H929-1051 | wt | FGFR3 and MMset | t(4;14) |
| IM-9 | wt | — | — |
| JJN-3 | wt | C-MAF | t(14;16) |
| KMS-11 | wt, HD | FGFR3/MMSET, C-MAF | t(4;14),t(14;16) |
| KMS-12-PE | wt HD/mut (R337L)[b] | Cyclin D1 | t(11;14) |
| KMS-34 | mut (W146[a]) | FGFR3 & MMset | t(4;14) |
| L363 | mut (S261T) | MAFB | t(6;20), t(20;22) |
| LP-1 | mut (E286K) | FGFR3 and MMset | t(4;14) |
| MM.1S | wt | C-MAF | t(14;16) |
| OPM2 | mut (R175H) | FGFR3 and MMset | t(4;14) |
| OPM2-P10 | mut (R175H) | FGFR3 and MMset | t(4;14) |
| RPMI-8226 | mut (E258K) | C-MAF | t(14;16), t(16;22) |
| SKMM-2 | wt | MAFB, Cyclin D1 | t(14;20), t(11;14) |
| U266 | mut (A161T) | Cyclin D | t(11;14) |

HD = homozygous deletion;
mut = mutation;
wt = wild type;
— = not available.
[a] = nonsense mutation.
[b] = conflicting reports in the literature whether wt p53 with only 1 copy or a mutation.

Sources: Bergsagel, et al. *Oncogene* (2001); 20:5611-5622; Berglind, et al. *Cancer Biology Therapeutics* (2008); 5:699-708; Keats, J. Common Genetics of Myeloma Cell Lines [Internet]. Jonathan Keats Laboratory. Translational Genomics Research Institute (TGen)—Integrated Cancer Genomics Division. 2012—[cited 5 Jan. 2017].

Results.

The antiproliferative activity of Compound 2 was assessed across a panel of representative MM cell lines possessing common oncogenic mutations and chromosomal translocations (Table 8), including those considered to be high risk translocations or mutations found in MM patients (Johnson, et al. *Int J Hematol.* (2011); 94:321-333; Zhou, et al. *Leukemia* (2009); 23:1941-1956; Terpos, et al. *Leuk*

Lymphoma (2006); 47:803-814; Tonon, *Hematol Oncol Clin North Am.* (2007); 21:985-1006). Concentration-response curves were obtained using flow cytometry to measure live cell numbers to demonstrate the antiproliferative activity of Compound 2 compared with pomalidomide. The $IC_{50}$ values for Compound 2 and pomalidomide are presented in Table 9.

TABLE 9

Compound 2 antiproliferative activity in multiple myeloma cell lines

| Cell Line | Antiproliferative Activity (Flow Cytometry) $IC_{50}$ (nM) | |
|---|---|---|
| | Compound 2 | Pomalidomide |
| MM1-S | 0.04 | 33.74 |
| DF15 | 0.05 | 40.98 |
| OPM2 | 0.05 | 69.68 |
| ANBL-6 | 0.06 | 60.61 |
| NCI-H929 | 0.05 | 63.10 |
| KMS-12-PE | 0.09 | 83.79 |
| LP-1 | 0.14 | 175.77 |
| JJN-3 | 0.10 | 365.84 |
| CAG | 0.12 | 1084.88 |
| U266 | 0.19 | 380.67 |
| EJM | 0.43 | 2843.08 |
| NCI-H929-1051 | 0.45 | 1949.67 |
| KMS34 | 0.45 | >10000 |
| KMS-11 | 1.41 | 5290.11 |
| RPMI-8226 | 0.75 | >10000 |
| OPM2-P10 | 1.81 | >10000 |
| SK-MM-2 | 0.82 | >10000 |
| L363 | 0.16 | >10000 |
| ARH-77 | >10000 | >10000 |
| IM-9 | 5569.43 | >10000 |

The apoptosis induction effect of Compound 2 was assessed using flow cytometry after 120 h of treatment and compared with pomalidomide treatment. The percentage of control was calculated by normalizing to the DMSO control (100% of control) to generate the dose response curves and to calculate the area under those curves (AUC). The AUC value reported corresponds to the area under the dose response curve in which values of 10000 correspond to complete induction of apoptosis at all doses and values of 0 correspond to no induction of apoptosis. Each data point represents 2 independent experiments with at least two samples in each experiment. (Table 10).

TABLE 10

Compound 2-induced apoptosis in Multiple Myeloma Cell Lines

| Cell lines | AUC | |
|---|---|---|
| | Compound 2 | Pomalidomide |
| CAG | 5804 | 1561 |
| DF15 | 6002 | 3707 |
| NCI-H929 | 6089 | 2115 |
| SKMM-2 | 3204 | 1033 |
| OPM2 | 5620 | 3298 |
| MM1.S | 5701 | 3525 |
| RPMI-8226 | 3245 | 1369 |
| ANBL-6 | 4751 | 2580 |
| H929-1051 | 3968 | 423 |
| EJM | 2591 | 900 |
| KMS-12-PE | 2017 | 1069 |
| KMS-11 | 1270 | 234.4 |
| JJN-3 (DSMZ) | 1125 | 199.1 |
| KMS-34 | 1614 | 429.7 |

TABLE 10-continued

Compound 2-induced apoptosis in Multiple Myeloma Cell Lines

| Cell lines | AUC | |
|---|---|---|
| | Compound 2 | Pomalidomide |
| IM-9 | 323.9 | 25.4 |
| U266 | 927.8 | 373 |
| OPM2-P10 | 1768 | 108.7 |
| ARH-77 | 709 | 28.16 |
| LP-1 | 630.7 | 174 |
| L363 | 347 | 293 |

Conclusion.

Compound 2 was broadly active across most MM cell lines, and was differentiated from pomalidomide by showing strong activity in cell lines that have intermediate pomalidomide sensitivity and in cell lines that are resistant to pomalidomide. Compound 2 was broadly active across this range of MM cell lines with varying p53 status, oncogenic drivers, or chromosomal translocations. For example, OPM2, LP-1, EJM, U266, and RPMI-8226 cells have mutant p53 and were sensitive to Compound 2. In addition, NCI-H929, KMS-11, KMS 34, OPM2, and LP-1 cell lines all contain the t(4; 14) "high risk" MM chromosomal translocation and were sensitive to Compound 2. The SK-MM-2 and EJM cells were also sensitive to Compound 2 and contain another "high risk" MM chromosomal translocation, t(14;20). (FIG. 5) The ability of Compound 2 to induce apoptosis after short, defined exposures may allow disease control to be achieved using intensive, intermittent schedules. Such schedules may also improve the therapeutic index by reducing the potential of Compound 2 to induce the cytopenias that are observed on more continuous dosing of current MM compounds.

Example 9: Compound 2 Has Activity in Multiple Myeloma Cell Lines that Have Acquired Resistance to Lenalidomide or Pomalidomide Compound 2 activity was tested in cells that have acquired resistance to lenalidomide or pomalidomide due to continued exposure to the either compound and, in the process, have acquired downregulated cereblon levels (Table 11). Cells were treated for 5 days and then assessed using an ATP determination assay (CellTiter-Glo). The percentage of control was calculated by subtracting the background and normalizing to the DMSO control (100% of control). The relative percentage of cereblon in cell lines with acquired resistance to lenalidomide or pomalidomide was determined by Western Blot and is presented, with the amount in parental cell lines designated as 100%.

Results.

FIG. 6 shows $IC_{50}$s of the concentration response curves comparing the activity of Compound 2 and pomalidomide, to measure proliferation in parental lines (DF 15, NCI-H929 and OPM2), a lenalidomide-resistant cell line (NCI-H929-1051), or five pomalidomide-resistant cell lines (NCI-H929-P01, OPM2-P01, OPM2-P1, OPM2-P10 and DF15R).

TABLE 11

Compound and Concentration of Compound Used to Develop
Drug Resistance in Multiple Myeloma Cell Lines and
Acquiring Changes in Cereblon Protein Expression

| Cell Line | Resistance | Cereblon (%) (Normalized to Parental Line) |
| --- | --- | --- |
| DF15 | N/A | 100 |
| DF15R | 100 μM Pom | 14* |
| NCI-H929 | N/A | 100 |
| NCI-H929-1051 | 10 μM Len | 50 |
| NCI-H929-P01 | 100 nM Pom | 35 |
| OPM2 | N/A | 100 |
| OPM2-P01 | 100 nM Pom | 61 |
| OPM2-P1 | 1 μM Pom | 33 |
| OPM2-P10 | 10 μM Pom | 31 |

N/A = not applicable;
Pom = pomalidomide;
*background level, not actual CRBN, which is absent in this cell line Conclusion:

The most striking effect of Compound 2 was the broad and potent antiproliferative activity across MM cell lines, but not on non-tumorigenic cells. Compound 2 has potent antiproliferative activity in MM cell lines containing high risk translocations, such as t(4; 14), t(14; 16) and others. Compared with lenalidomide and pomalidomide, Compound 2 is significantly more potent at killing most MM cell lines. Furthermore, Compound 2 induced apoptosis, as measured by induction of caspase-3 activity, in MM cell lines that have acquired resistance to lenalidomide and pomalidomide.

Example 10: Ex Vivo Effect of Compound 2 on Maturation of Myeloid Progenitors to Adult Neutrophils Methods: Ex vivo cultures of bone marrow (BM) CD34+ cells from healthy donors (HD) were used to investigate neutrophil-specific ex vivo maturation. In vitro differentiation of neutrophil progenitors was induced by adding stem cell factor (SCF), fms-related tyrosine kinase 3 ligand (Flt3-L), and granulocyte colony stimulating factor (G-CSF) to culture media. Cell differentiation was evaluated by flow cytometry as the percentage of cells in 5 subpopulations: hematopoietic stem cells (HSC, CD34+/CD33−/CD11b−) and Stage I (CD34+/CD33+/CD11b−), Stage II (CD34−/CD33+/CD11b−), Stage III (CD34−/CD33+/CD11b+), and Stage IV (CD34−/CD33−/CD11b+) (from immature to mature), as shown in FIG. 7. The effects of Compound 2 on maturation of neutrophil progenitors were assessed and different dosing schedules were evaluated to gain insight into the schedule dependence of these events.

Results. Short Daily Exposures of Compound 2.

The effects of different exposure periods (2, 4, and 6 h) at 1, 10, and 100 nM of Compound 2 for up to 3 consecutive days on maturation of neutrophil progenitors were evaluated at pre specified time points using flow cytometry. Results showed that late-stage maturation of neutrophil progenitors was blocked by Compound 2, with mature cells significantly reduced in number at the higher concentrations after one or more days of exposure. Maturational arrest appears to occur primarily at Stage III neutrophil progenitor development, as evidenced by an accumulation of cells with Stage III cell surface immunophenotype and a reduction in the population of cells with Stage IV cell surface immunophenotype (mature neutrophils). As shown in FIG. 8, in an example for the 6-hour incubation, this maturation effect was concentration-dependent and increased with the number of days of exposure, but was not altered by the duration (2, 4, or 6 h) of the individual exposures. Importantly, the viability of neutrophil progenitors and mature neutrophils exposed to Compound 2 was not affected, as evidenced by the absence of any detectable increase in the proportion of cells positive for Annexin V or 7-aminoactinomycin D, which accumulates in dead cells.

Recovery of mature neutrophils after Compound 2 exposure was also evaluated in the system. Recovery of mature neutrophil levels to at least 50% of the untreated control level in the assay system utilized in the present study correlates with the absence of induction of, or recovery from, clinically significant neutropenia. Indeed, after a period of one week without Compound 2, the proportion of Stage IV cells recovered by at least 50% from its nadir (FIG. 8, lower panels), with a trend towards more rapid and complete recovery at lower concentrations.

Conclusion:

The results indicate that successful management of neutropenia in MM patients treated with Compound 2 may be possible with use of appropriate dosing schedules.

Longer Daily Compound 2 Exposures.

To further characterize the potential impacts of different schedules on arrest of neutrophil progenitor maturation and subsequent recovery, changes in the relative proportions of each of the aforementioned stages of myeloid progenitor maturation to adult neutrophils were evaluated by flow cytometry after 3 or 5 consecutive days of exposure to 1, 10, or 100 nM Compound 2 for 6 or 24 h each day. CD34+ BM cells derived from healthy donors were exposed to Compound 2 on 3 or 5 consecutive days starting on Day 10 for 6 h (Donors No. 1 and 2) or for 24 h (Donors No. 3 and 4) each day. Following completion of the final exposure, cells were washed and reincubated in the absence of Compound 2 until Day 22. Both 6- and 24-hour exposures to Compound 2 for 3 or 5 consecutive days resulted in a buildup of the Stage III population of neutrophils with a corresponding decrease in the Stage IV population, consistent with a block in maturation from Stage III to Stage IV. As shown in FIG. 9 and FIG. 10, in examples for the 6-hour exposures for 3 and 5 days, respectively, the pace of recovery from maturational arrest was concentration-dependent and influenced by the number of daily exposures, being more protracted at higher concentrations of Compound 2 and following 5 vs 3 days of exposure, but a change in the duration (6 vs 24 h) of the daily exposures had little impact on the apparent pace of recovery.

After exposure to Compound 2 for 3 consecutive days, 50% or greater recovery of normal maturation was observed following a drug holiday of 8 to 10 days, in all conditions tested (FIG. 10, right panel). In contrast, following exposure to Compound 2 for 5 consecutive days, 50% or greater recovery of normal maturation was observed following a drug holiday of 8 to 10 days for the 1- and 10-nM concentrations only. With the highest concentration of Compound 2 (100 nM), a longer drug-free period may be required for recovery of maturation of neutrophil progenitors. However, despite this incomplete recovery of maturation, no loss of viability was observed under any of the conditions tested, including continuous (24-hour) exposures up to 5 days. This observation stands in contrast to the induction of apoptosis in myeloma cells, which was optimized by continuous exposure to Compound 2 for longer than 6 h.

During the 6 to 8 days following the last exposure in the 5-day schedule, initial stages of Stage IV (mature neutrophils) recovery were observed following exposure to Compound 2 at the 10-nM concentration only, whereas no recovery was observed within this time frame in cultures exposed to 100 nM Compound 2 over 5 days. These data suggest that exposures to higher concentrations of Compound 2 over an increasing number of consecutive days portend more protracted maturational arrest of neutrophil precursors (and neutropenia) and that the pace of recovery is independent of the duration (6 vs 24 h) of daily exposures.

Conclusion:

Taken together, the data suggest that induction of and recovery from neutropenia in patients may not be adversely affected by more intensive dosing of Compound 2 (multiple doses per day) as compared with once-daily dosing.

Example 11: Effect of Dexamethasone on In Vitro Maturation of Neutrophil Progenitors as a Single Agent and in Combination with Compound 2

Methods.

To understand the effects of dexamethasone on neutropenia, in vitro cultures of BM CD34$^+$ cells from healthy donors were used to evaluate the neutropenic events mediated by dexamethasone as a single agent and in combination with Compound 2. To define the effects of dexamethasone monotherapy in this model, 1, 10, or 100 nM dexamethasone exposure was maintained for 30 h comparing 7 different dosing schedules (FIG. 11). For combination studies, single exposure Compound 2 (1, 10, or 100 nM) and dexamethasone were maintained for 6 and 30 h, respectively, starting at Day 13 of culture.

Results.

Results showed that maturation of neutrophil progenitors was not affected by exposure to single agent dexamethasone under any tested schedule whereas maturation of late-stage neutrophil precursors was blocked by Compound 2 (FIG. 12), with the number of mature cells reduced at all tested concentrations after one exposure. This maturation arrest was also observed when Compound 2 was combined with dexamethasone. The maturation block was dependent on the concentration of Compound 2 but was not altered by varying the concentration of dexamethasone. The viability of immature and mature neutrophils was not affected by dexamethasone or Compound 2, alone or in combination. Following drug washout, full recovery of normal maturation was observed in all tested conditions following a one-week drug holiday.

Conclusion.

These data indicate that neutropenia caused by Compound 2 may be amenable to management by modifying dosing schedules, but is predicted to be neither alleviated nor exacerbated by concurrent dexamethasone treatment.

Example 12: Effect of Compound 2 Alone and In Combination with Dexamethasone on Lenalidomide-resistant Multiple Myeloma Methods:

Dexamethasone was assessed for its ability to induce apoptosis as a single agent or in combination with Compound 2, pomalidomide, or lenalidomide. Induction of apoptosis was measured using Caspase-Glo in lenalidomide-resistant multiple myeloma cells (H929-1051). Dexamethasone was dispensed at 20 concentrations, using an acoustic dispenser. The test articles were added as single concentrations onto the dexamethasone wells with a Hewlett-Packard D300 Digital Dispenser. The final concentrations of compounds for the assay were: dexamethasone (0.8 µM to 0.00002 µM), lenalidomide (1 µM), pomalidomide (0.1 µM), and Compound 2 (0.001, 0.01, or 0.1 µM). Cells were dispensed into the assay plates with a Multidrop dispenser and duplicate plates were made for the assay. The apoptosis read was taken at 72 h post-compound treatment using a Caspase-Glo 3/7 and CellTiter-Glo Assays. The Caspase-Glo 3/7 luminescence was normalized to the CellTiter-Glo luminescence to account for differences in cell number. The fold change of the treated sample was calculated as follows: normalized caspase of treated sample/average of normalized DMSO control.

Results:

The apoptosis activity of dexamethasone alone or in combination with lenalidomide, pomalidomide, or Compound 2 was measured by caspase-3 induction. Compound 2 synergized with dexamethasone to reduce cell viability and potentiated the apoptotic ability of dexamethasone in a concentration-dependent manner. The onset of dexamethasone activity was shifted by 1 log in the presence of Compound 2.

Conclusion:

Compound 2 potentiates the apoptotic activity of dexamethasone indicating the potential for reducing the dose of dexamethasone when used in combination with Compound 2 in the clinic.

As shown in FIG. 13, dramatic bidirectional synergy is observed following treatment with Compound 2 in combination with dexamethasone. As little as 10 nM dexamethasone enhances the cell killing ability of Compound 2 and low to sub-nanomolar concentrations of Compound 2 potentiate the apoptotic effects of dexamethasone.

Example 13: Compound 2 Enhances the Antitumor Activity of Immune Cells from Healthy Human Donors Coculture Experiments with Peripheral Blood Mononuclear Cells and K562 Cells. Methods:

Human Peripheral Blood Mononuclear Cell (PBMC) Preparation: PBMCs isolated from healthy donors were cultured in RPMI 1640 medium with 10% FBS at a density of 1×10$^6$ cells/mL.

Cell Culture: K562 cells were kept in log phase, and cell density and viability were monitored by trypan blue exclusion using the Vi-CELL® XR cell viability analyzer (Beckman Coulter, Brea, Calif.).

Assay Procedures: Freshly isolated human PBMCs were cultured with recombinant IL-2 at concentration of 20 units/mL for 72 h. Peripheral blood mononuclear cells were then spun down and re-suspended in fresh RPMI complete medium to 2×10$^6$ cells/mL. Cells were then treated with DMSO or compounds at the indicated concentrations and incubated for an additional 72 h. The PBMCs were then washed twice in fresh RPMI complete medium prior to coculture. K562 cells were re-suspended to a cell density of 1×10$^6$/mL and stained with 1 µM CellTrace CFSE according to manufacturer's instructions. The labeled K562 cells were then seeded into a 96-well round bottom plate at 1×10$^5$ cells/well. Peripheral blood mononuclear cells were then transferred into the same 96-well plate at a 1:15 ratio, in triplicate and incubated at 37° C. for 4 h. Specific target cell lysis by PBMC cells was measured using Annexin V-fluorescein isothiocyanate (FITC) and propidium iodide (PI) according to manufacturer's instructions and samples were run on the FACS Array scan. Non-labeled K562 cells, CellTrace CFSE-labeled K562 cells, and Annexin V-FITC- and PI labeled untreated K562 cells were included in each assay as controls.

Coculture Assays with Compound-treated Human Peripheral Blood Mononuclear Cells and Untreated Myeloma Cell Lines. Methods:

Cell Culture. All myeloma cell lines were kept in log phase, and cell density and viability were monitored bytrypan blue exclusion using the Vi-CELL XR cell viability analyzer.

PBMC Treatment Assay Procedure. Ninety-six-well dishes were pre-coated with anti-CD3 antibody (OKT3, 3 µg/mL) and incubated at 4° C. overnight before the start of the experiment. Frozen PBMC donors, were thawed at 37° C. for 2 minutes in RPMI medium with 10% FBS and cell counts and viability were measured on the Vi-CELL® (Beckman Coulter). Peripheral blood mononuclear cells were washed and diluted to $1\times10^6$ cells/mL and dispensed to the compound-treated plates in a total volume of 200 µL. Cells were incubated with compounds for 2 h before being transferred onto anti-CD3-coated plates and incubated for an additional 72 h at 37° C. After 72 h, the PBMCs were centrifuged, and cells were washed twice in RPMI medium+ 10% FBS. Untreated MM cell lines (H929 and H929-1051) were labeled with CellTrace CFSE according to manufacturer's instructions and re-suspended at a total concentration of $0.1\times10^6$ cells/mL into a U bottom 96-well plate in a total volume of 100 µL. Peripheral blood mononuclear cells were counted and added to the MM cells at a target:effector (T:E) ratio of 1:5. After 24 h co-culture, specific target cell lysis by PBMCs was measured using Annexin V-AF647 and 7-AAD according to manufacturer's instructions and samples were run on the Attune NxT Cytometer (Thermo Fisher).

PBMC and MM Cell Treatment Assay Procedure. Ninety-six-well dishes were pre-coated with anti-CD3 antibody (OKT3, 3 µg/mL) and incubated at 4° C. overnight before the start of the experiment. Frozen PBMC donor cells were thawed at 37° C. for 2 minutes in RPMI medium with 10% FBS and cell counts and viability were measured on the Vi-CELL analyzer. Peripheral blood mononuclear cells were washed and diluted to $1\times10^6$ cells/mL and dispensed into the compound-treated plates in a total volume of 200 µL. Cells were incubated with compounds for 2 h before being transferred onto anti-CD3-coated plates and incubated for an additional 72 h. At the same time, MM cell lines (NCI-H929, H929-1051, OPM2, OPM2-P10) were diluted to a final concentration of $0.1\times10^6$ cells/mL and labeled with CellTrace CFSE according to manufacturer's instructions. Multiple myeloma cell lines were then dispensed into compound-treated plates at a total volume of 200 µL and incubated for 72 h. After 72 h, the PBMCs and MM cells were counted and transferred into a U-bottom 96-well plate at a final T:E ratio of 1:5. After 24 h coculture, specific target cell lysis by PBMC cells was measured using Annexin V-AF647 and 7-AAD according to manufacturer's instructions and samples were run on the Attune NxT Cytometer.

Results.

The coculture model was used to determine the direct effects of Compound 2 on the anti-tumor activity of PBMCs taken from healthy donors. Compound 2 treatment of IL-2-activated PBMCs induced the killing of untreated K562 cells in a concentration-dependent manner (FIG. 14, right panel). Compound 2-treated PBMCs ($IC_{50}$=5.9 µM) were ~600-fold more potent than pomalidomide-treated (POM; $IC_{50}$=0.004 µM) and ~2600-fold more potent than lenalidomide-treated (LEN; $IC_{50}$=0.02 µM) PBMCs in achieving 50% direct K562 cell killing. Although Compound 2 was more potent than lenalidomide and pomalidomide, the magnitude of the response was similar among the compounds (FIG. 14, right panel).

The effects of Compound 2 on the anti-MM cell activity of PBMCs incubated with Compound 2 were examined further in cell lines displaying the resistance phenotype in order to compare with the response in sensitive cells. In a different co-culture model, PBMC donor cells were pretreated with Compound 2, lenalidomide, or pomalidomide for 2 h before being cultured on anti-CD3 antibody-coated plates for 72 h. The anti-CD3 antibody-activated PBMCs treated with Compound 2 demonstrated a concentration-dependent increase in the tumor cell lysis of untreated lenalidomide-sensitive (NCI-H929; $IC_{50}$=0.005 µM) and lenalidomide-resistant (H929-1051; $IC_{50}$=0.0002 µM) MM cell lines to a similar degree (FIG. 15). Compound 2 was more potent than lenalidomide and pomalidomide with respect to reducing the percentage of viable MM cells. A similar level of tumor cell killing by PBMCs was seen against the lenalidomide-sensitive and lenalidomide-resistant co-cultured tumor cells, showing that the PBMCs were primed to kill tumor cells independent of their resistance phenotype.

Because preincubation of immune cells with Compound 2 enhanced the targeting and lysing of MM cells, the effect of preincubation of MM cells with Compound 2 on their susceptibility to immune-mediated killing was also explored (FIG. 16, Table 12). Four MM cell lines and anti-CD3 antibody-activated PBMCs were separately preincubated with Compound 2, lenalidomide, or pomalidomide for 72 h. When anti-CD3 antibody-activated PBMCs and MM lines were both pretreated with Compound 2, lenalidomide, or pomalidomide, followed by co-culture, the effects on the PBMC-induced MM cell lysis were enhanced both in the potency and magnitude of the killing response. Comparing the $IC_{50}$ values from single MM cell cultures versus the immune and tumor cell co-cultures, Compound 2 enhanced the killing of the NCI-H929 cells by ~7000-fold, and it enhanced the killing of the H929-1051 cells by ~6000-fold. For the pomalidomide-resistant OPM2-P10 cell line, Compound 2 treatment of the MM cells enhanced the immune-mediated killing by ~3000-fold (Table 12).

TABLE 12

Immune-mediated Cell Killing in Multiple Myeloma Cell Lines in Single Cultures versus Co-cultures

| Multiple Myeloma Cell Line | Culture Conditions | Immune-mediated Cell Killing $IC_{50}$ (µM) | | |
|---|---|---|---|---|
| | | Lenalidomide | Pomalidomide | Compound 2 |
| NCI-H929 | Single | >10 | >10 | 0.5810 |
| | Co-culture | 0.3173 | 0.0444 | 8.702e−005 |
| H929-1051 | Single | >10 | >10 | 0.5753 |
| | Co-culture | 0.8782 | 0.0713 | 0.0001 |
| OPM2 | Single | >10 | 0.6273 | 0.0003 |
| | Co-culture | 1.722 | 0.1685 | 9.361e−005 |
| OPM2-P10 | Single | >10 | >10 | >10 |
| | Co-culture | 8.094 | 1.181 | 0.0031 |
| RPMI-8226 | Single | >10 | >10 | 0.0134 |
| | Co-culture | 0.1245 | 0.0676 | 8.387e−005 |

$IC_{50}$ = concentration resulting in 50% cell killing.

Conclusion:

Compound 2-treated PBMCs induced the tumor lysis of untreated K562 and MM cell lines to the same extent as seen with lenalidomide and pomalidomide, although with much greater potency. Moreover, tumor cell killing was greatly enhanced if both PBMCs and MM cell lines were pretreated with Compound 2, indicating that in addition to its potent cell autonomous effects, Compound 2 may also enhance the immunogenicity of MM cell lines. The combination of the potent cell-autonomous and immunogenic effects on MM cells, in addition to its immunomodulatory properties, make Compound 2 a potential candidate for the clinic.

Example 14: Effect of Compound 2 In Combination with Daratumumab on Multiple Myeloma Daratumumab, an anti-CD38 antibody approved for the treatment of multiple myeloma, exerts its anti-myeloma activity through antibody-dependent cellular cytotoxicity (ADCC), antibody-dependent cellular phagocytosis (ADCP), and complement-dependent cytotoxicity (CDC). The effect of Compound 2 or pomalidomide in combination with daratumumab was evaluated in MM cell lines.

ADCC Assay: The effect of Compound 2 or pomalidomide on daratumumab-mediated ADCC was evaluated in vitro by flow cytometry in a panel of MM cell lines. The NK cells were cultured overnight in NK culture medium containing 10 U/mL of recombinant human IL-2 before the start of the assay. The NK cells were washed and resuspended back in NK cell culture medium at $3.75 \times 10^6$ cells/mL. The MM cells were pretreated with sub-lethal concentrations of Compound 2 or pomalidomide for 72 h before using in the ADCC assay. The MM cells were washed and labelled with Tag-it Violet™ Proliferation and Cell Tracking Dye according to the manufacturer's instructions, followed by resuspension in NK culture medium at a concentration of $0.75 \times 10^6$ cells/mL. The ADCC assay was performed in triplicate with an effector to tumor ratio of 10:1 in a 96 well plate. MM cells (10 μL) were mixed with 10 μL of 2× concentration of daratumumab in the wells before the addition of 20 μL of NK cells. The co-cultures were incubated at 37° C. for 3 h followed by the addition of 50 μL of 7-AAD solution at room temperature for 15 minutes. The analysis was performed on a BD Celesta flow cytometer.

ADCP assay: The effect of Compound 2 or pomalidomide on daratumumab-mediated ADCP was determined in a panel of MM cell lines. Monocytes were plated in a 96 well plate at 40,000 cells per well in 100 μL volume of complete AIM-V media containing 50 ng/mL of M-CSF. The cells were allowed to settle onto the plate for 15 minutes at room temperature before placing into 37° C., 5% $CO_2$ incubator for 9 days to allow for differentiation into macrophages. The culture media was replenished with fresh complete media every 3-4 days. On the morning of the ADCP assay, the macrophages were serum starved for 2-4 hours at 37° C., 5% $CO_2$ before co-culturing with the MM cells. The MM cells were pretreated with sub-lethal concentrations of Compound 2 or pomalidomide for 72 h. On the day of the assay, the MM cells were washed with PBS and labeled with CSFE for 15 minutes. The reaction was stopped with an equal volume of 20% FBS. The cells were washed twice with PBS and resuspended in AIM-V media at $1.6 \times 10^6$ cells/mL. Then 50 μL of MM cells was mixed with 50 μL of 2 μg/mL daratumumab for 10 minutes at room temperature before adding to the serum starved macrophages. Each condition was assayed in triplicate. The final volume of the assay was 200 μL containing 10% human serum with an effector to target ratio of 2:1. The plate was spun at 500 rpm for 1 minute followed by incubation at 37° C., 5% $CO_2$ for 3 h. At the end of the incubation, the plate was washed with 100 μL of PBS and the remaining cells were stained with anti-CD14 and anti-CD138 to identify the macrophages and MM cells, respectively. The plate was washed and the wells were filled with 100 μL of PBS. The macrophages were detached from the bottom of the wells with the addition of 50 μL of 0.25% trypsin. The samples were neutralized with the addition of 50 μL of complete AIM-V media. The samples were analyzed on flow cytometer. The percent phagocytosis was determined by the CSFE/CD14 double positive cells divided by the total number of CD14+ cells times 100.

Results:

Treatment of MM cells with Compound 2 and pomalidomide resulted in a dose-dependent increase of CD38 expression (FIG. 17). The extent of CD38 expression was greater with Compound 2 and occurred at lower concentrations compared to pomalidomide. MM cells+/−Compound 2 or pomalidomide pretreatment were evaluated in ADCC assays with daratumumab. Compound 2 treated MM cells demonstrated a higher degree of tumor lysis with daratumumab compared to untreated cells (FIG. 18). Compound 2 treated cells were also more sensitive to daratumumab-mediated ADCC compared to pomalidomide treated cells. The ability of Compound 2 and pomalidomide to modulate daratumumab-mediated ADCP was also tested. Compound 2 treated MM cells were more sensitive to daratumumab-mediated ADCP compared to untreated and pomalidomide treated cells (FIG. 19). Only one cell line tested, ARH-77, showed no enhanced ADCP with either Compound 2 or pomalidomide but demonstrated enhanced ADCC with Compound 2.

Conclusion:

Compound 2 upregulates CD38 expression in MM cells resulting in increased daratumumab-mediated ADCC and ADCP compared to pomalidomide or untreated cells. This data suggests that combining daratumumab with Compound 2 may be more effective in the treatment of MM compared to combination with pomalidomide or daratumumab alone.

Example 15: Effect of Compound 2 in Combination with Proteasome Inhibitors on Multiple Myeloma Twenty four hours prior to treatment with a proteasome inhibitor and test compound, an appropriate number of cells were split to a concentration of $0.2 \times 10^6$/mL in fresh media to allow for exponential growth. On the day of treatment, compounds were freshly solvated in DMSO. Proteasome inhibitors bortezomib or carfilzomib were diluted and added to pre-warmed culture media at the final working concentrations of 150 nM or 300 nM for bortezomib and 300 nM or 550 nM for carfilzomib. Proteasome inhibitor concentrations were determined based upon clinical Cmax concentrations as well as previous studies in each cell line which determined the duration and concentration of PI required to inhibit a specific amount of β5 proteasome activity. Cells were counted and an appropriate number were placed into media containing proteasome inhibitor and thoroughly mixed. After incubation for 1 h at 37° C., 5% $CO_2$, cells were washed two times with 40 mL of complete media to remove the proteasome inhibitor. Aliquots of each proteasome treatment were assayed to confirm the extent of β5, β2, and β1 subunit inhibition. Cells were resuspended to $0.1 \times 10^6$/mL and plated at 100 μL/well into fresh culture-ware containing triplicate titrations of either Compound 2 or pomalidomide. Plated cells were cultured at 37° C., 5% $CO_2$, for the remainder of the experiment, up to 72 h. Every 24 h, proteasome inhibition was monitored by the Cell-Based Proteasome-Glo Assay. Proliferation and apoptosis were measured at 72 h by flow cytometry. Cells were stained with APC Annexin-V and 7-AAD to enumerate the number of viable cells remaining in culture.

Results.

An in vitro cell assay was established in order to mimic the clinical pharmacokinetics (PK) and pharmacodynamics (PD) of exposure to proteasome inhibitors bortezomib and carfilzomib. The model employs short exposures of proteasome inhibitor followed by thorough washout of compound in order to dose cells with clinically relevant concentrations of proteasome inhibitor, while achieving the rapid clearance observed in vivo. Moreover, a comparable level of 35 proteasome inhibition can be achieved across all cell lines. This model was used to evaluate the combination effects of Compound 2 in combination with either bortezomib or carfilzomib in a panel of multiple myeloma and plasma cell leukemia cell lines (Pomalidomide resistant OPM2.P10, RPMI.8226, and plasma cell leukemia lines L363 and JJN-3).

Figure 21A:
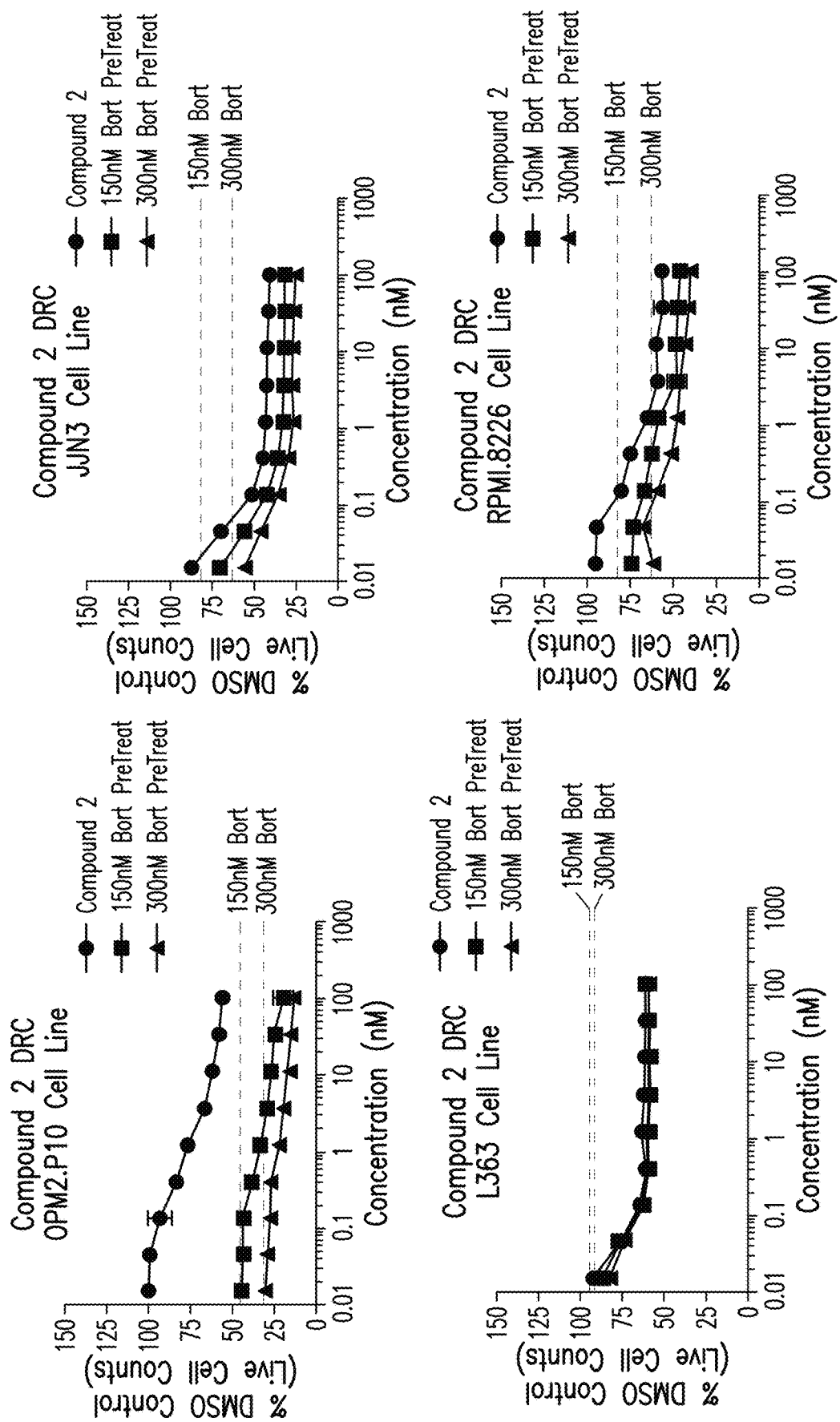

Bortezomib and Compound 2 demonstrated a combination effect in both MM lines tested, OPM2.P10 and RPMI.8226, as well as in one of the plasma cell leukemia cell lines, JJN-3. Combination effects in the L363 cell line could not be evaluated, as bortezomib had no single agent activity on cell viability under the conditions of this in vitro assay (FIG. 20 and FIG. 21A).

Figure 21B:
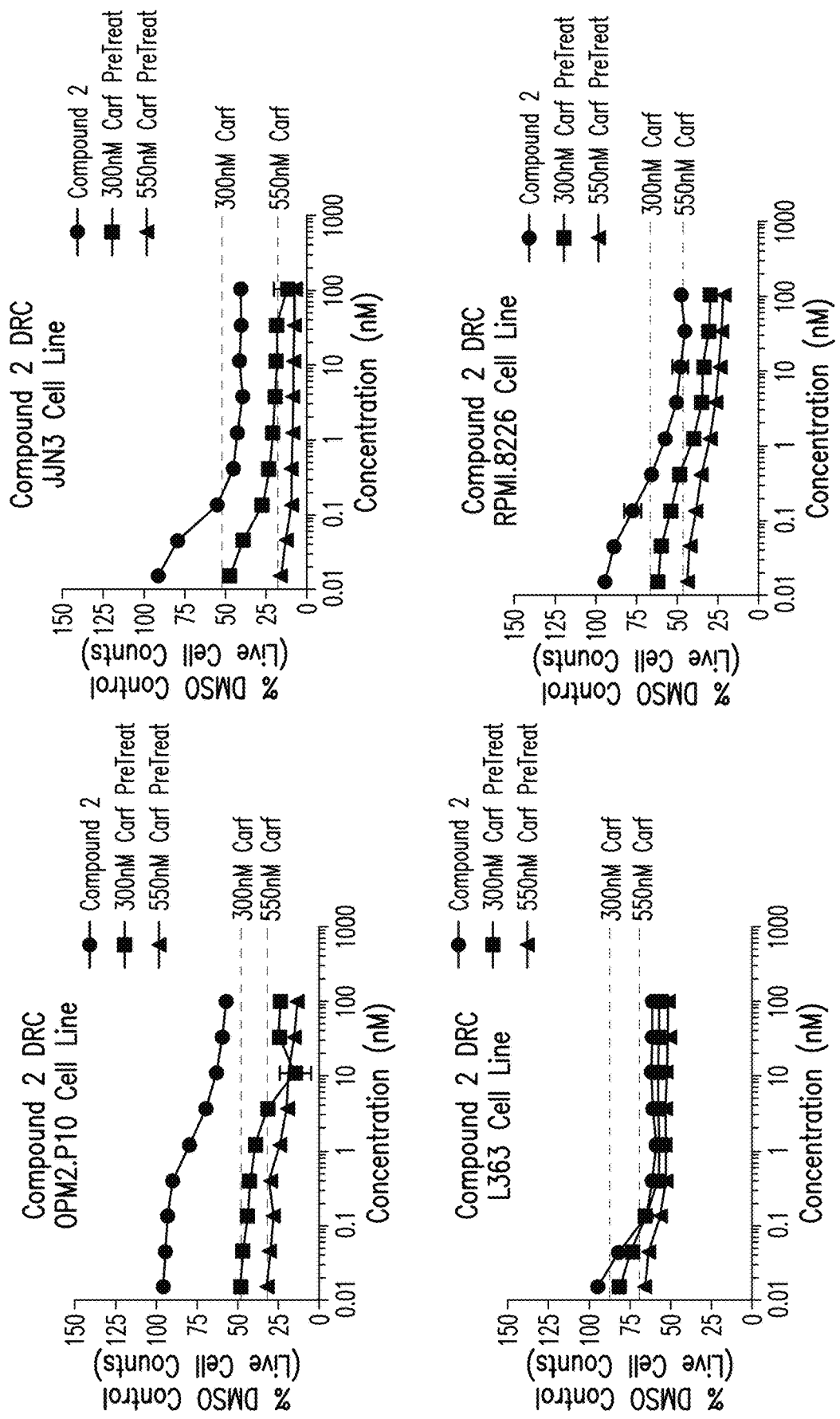

Although carfilzomib treatments between experiments were variable in the percent of cell kill they achieved over the course of the 1 h treatments, combination effects with Compound 2 were demonstrated in all 4 cell lines (FIG. 21B).

Conclusion:

Surprisingly, Compound 2 maintains its ability for cell killing at clinically relevant levels of proteasome inhibition. The combination of Compound 2 with either bortezomib or carfilzomib demonstrated an increase in apoptosis and antiproliferative activity against of MM cells.

Example 16: Effect of Compound 2 In Combination with Histone Deacetylase Inhibitors, Chemotherapy Agents, Bcl-2 Inhibitors, Mcl-1 Inhibitors, BET Inhibitors, or LSD-1 Inhibitors The effect of combining treatment with Compound 2 and small molecule inhibitors with various mechanisms was evaluated in a panel of MM cell lines. Thirteen small molecule inhibitors were selected for combination studies with Compound 2 based on their preclinical and/or activity against MM. The cell lines H929-1051, KMS 11, KMS-12PE, L363, OPM-P10, and RPMI8226 were selected for this study to represent the different genetic clustering groups across MM cell lines. Compound concentrations for the combination treatments were selected in the range of 1 log above and 2 logs below the $IC_{50}$ of the single agent. Combination agents were dosed in a 6 point dose-response curve (DRC) at a 1:3 dilution, Compound 2 was dosed in a 10 point DRC, also at a 1:3 dilution. The combination experiments were run twice, each time with replicate data on separate plates. Compounds were pre-spotted into the appropriate wells of 384-well plates using an acoustic dispenser. All MM cell lines were cultured in an incubator at 37° C. with 5% $CO_2$ using the indicated cell culture media containing 1× Penicillin-Streptomycin. Cells were added to the compound containing 384-well plates using a Multidrop Combi Reagent Dispenser and allowed to incubate for 3 days at 37° C. with 5% $CO_2$. After 3 days, cells were assessed for their level of ATP content via Cell Titer-Glo measured on a luminescence detector (PerkinElmer Envision).

The Highest Single Agent (HAS) method was used to detect synergy in the dose response curve data. Combinations were analyzed from a response surface perspective. A statistical framework (Van Der Borght, K., et al., BIGL: Biochemically Intuitive Generalized Loewe null model for prediction of the expected combined effect compatible with partial agonism and antagonism; Scientific Reports, 7 (1), 17935-1-17935-9 (2017)) was incorporated into the analysis on top of the HAS null model with two statistical tests: 1) Complete response surface differs from null model, 2) Single well differs from null model.

Figure 22:
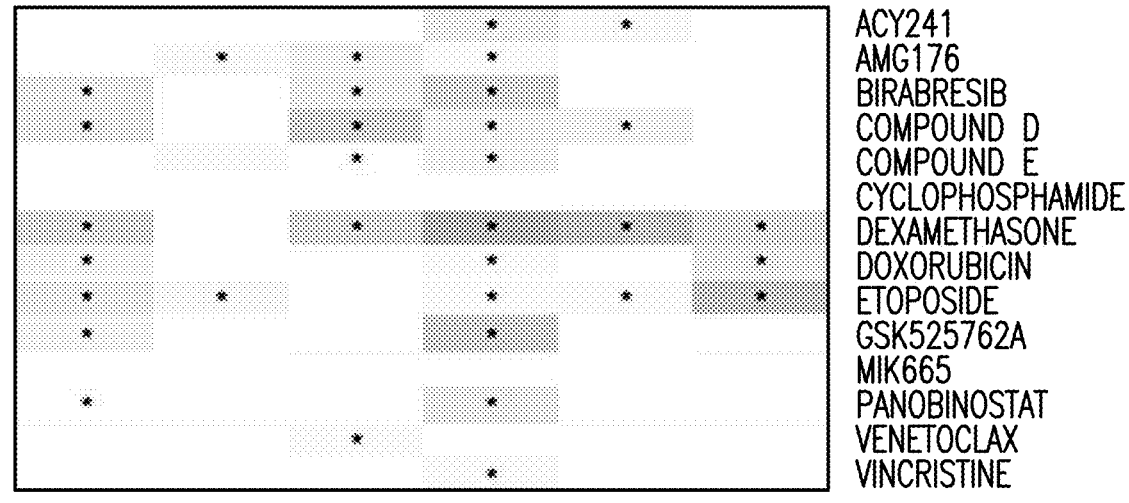
Figure 22:
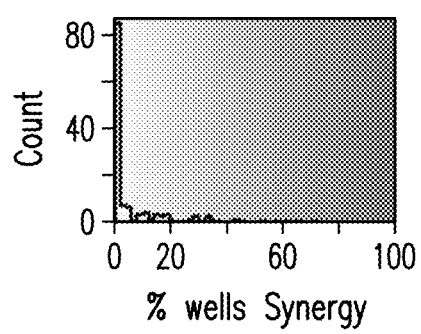

Results:

The effect of treatment with Compound 2 in combination with small molecule inhibitors was evaluated in a panel of multiple myeloma cell lines. Compound 2 was screened in combination with 14 compounds and the synergy was calculated across all wells for 6 cell lines. Dexamethasone and etoposide showed significant synergy in combination with Compound 2 in five out of the six cell lines tested (FIG. 22). Combination of Compound 2 with BET inhibitors (4-[2-(cyclopropylmethoxy)-5-(methanesulfonyl)phenyl]-2-methylisoquinolin-1(2H)-one (Compound D), birabresib, and GSK525762A) also demonstrated synergistic activity in the MM cells, with differing degrees of synergy among the three inhibitors. The combination of Compound 2 with AMG176 (MCL-1 inhibitor) showed synergistic activity in three cell lines (KMS11, KMS12-PE, L363) while combination of Compound 2 with ACY241 and panobinostat (histone deacetylase inhibitors) was synergistic in L363/OPM2-P10 and L363/H929-1051, respectively. Compound 2 in combination with 4-[2-(4-amino-piperidin-1-yl)-5-(3-fluoro-4-methoxy-phenyl)-1-methyl-6-oxo-1,6-dihydropyrimidin-4-yl]-2-fluoro-benzonitrile (Compound E) was synergistic in L363 and KMS12-PE cells. MIK665, a MCL-1 inhibitor, was the only compound that did not show significant synergy in the 6 MM cell lines tested.

Conclusions:

Treatment with Compound 2 in combination with 12 of the 14 small molecules demonstrated synergistic activity in at least one or more of the MM cell lines tested. Combination with six of the compounds showed synergy in at least 3 MM cell lines tested (FIG. 22). This data suggests that combination treatment with Compound 2 with the small molecule inhibitors tested represents a potential treatment paradigm for MM, including some with synergistic activity.

Example 17: In Vivo Anti-Tumor Activity of Compound 2 Alone and in Combination with Dexamethasone Methods:

The xenograft study was conducted with female SCID mice bearing lenalidomide-resistant NCI-H929 (H929-1051) multiple myeloma/plasmacytoma tumors. Female SCID mice were inoculated subcutaneously with H929-1051 cells in the flank region above the right hind leg. Following inoculation of animals, the tumors were allowed to grow to approximately 100 mm$^3$ prior to randomization. On day 13 following tumor cell inoculation, the mice bearing H929-1051 tumors ranging between 79 and 157 mm$^3$ were pooled together and randomized into various treatment groups. Compound 2 was formulated in 2% HPMC in water (as a suspension). Dexamethasone was formulated in 0.5% CMC/0.25% Tween 80 in deionized water. Compound 2 (0.1 mg/kg) and dexamethasone (0.5 mg/kg) were orally administered once daily for the duration of the study starting from day 13 after tumor cell inoculation. In the combination group the animals received Compound 2 (0.1 mg/kg/day) and dexamethasone (0.5 mg/kg/day) simultaneously for the duration of the study starting from day 13 after tumor cell inoculation. Tumors were measured twice a week using calipers and tumor volumes were calculated using the formula $W^2 \times L/2$. Statistical analysis was performed using a one-way or 2-way analysis of variance (ANOVA). Synergy calculations were performed using fractional product method.

Results:

Treatment with single agent Compound 2 significantly (p<0.01) inhibited (−34%) H929-1051 multiple myeloma tumor growth. Treatment with dexamethasone as single agent marginally inhibited (−20%) H929-1051 xenograft tumor growth. Treatment with Compound 2 at 0.1 mg/kg administered in combination with dexamethasone at 0.5 mg/kg yielded a significant (p<0.0001) decrease in tumor volume when compared with vehicle control, displaying a tumor volume reduction of 84%. In a 2-way ANOVA with Bonferroni's post-test, this combination antitumor activity was significantly better than Compound 2 alone (84% versus 34% TVR; p<0.0001) or dexamethasone alone (84% versus 20% TVR; p<0.0001). Using the fractional product method, the combination antitumor activity of Compound 2 at 0.1 mg/kg and dexamethasone at 0.5 mg/kg was determined to be synergistic in decreasing tumor volume. (FIG. 23)

Conclusion:

Compound 2 in combination with dexamethasone exhibited synergism in reducing tumor volume in the NCI-H929 multiple myeloma/plasmacytoma tumor model, indicating that combination treatment of Compound 2 and dexamethasone showed synergistic antitumor activity in a lenalidomide-resistant MM model. Compound 2 potentiates the apoptotic activity of dexamethasone indicating the potential for reducing the dose of dexamethasone when used in combination with Compound 2 in the clinic.

Example 18: In Vivo Anti-Tumor Activity of Compound 2 Alone and In Combination with Bortezomib Methods:

The xenograft study was conducted with female SCID mice bearing lenalidomide-resistant NCI-H929 (H929-1051) multiple myeloma/plasmacytoma tumors. Female SCID mice were inoculated subcutaneously with H929-1051 cells in the flank region above the right hind leg. Following inoculation of animals, the tumors were allowed to grow to approximately 500 mm³ prior to randomization. On Day 31 following tumor cell inoculation, the mice bearing H929-1051 tumors ranging between 366 and 535 mm³ were pooled together and randomized into various treatment groups. Compound 2 was formulated in 2% HPMC in water (as a suspension). Bortezomib was formulated in 1% DMSO in saline (as a solution). Compound 2 (1 mg/kg) was orally administered once daily for 3 consecutive days starting from day 31 after tumor cell inoculation. Bortezomib (1 mg/kg) was administered as single dose intravenously on day 31 after tumor cell inoculation. In the combination group the animals received Compound 2 (1 mg/kg/day) orally on days 31-33 and bortezomib was administered intravenously as single dose on day 31. On day 31 bortezomib was administered 1 h prior to the first dose of Compound 2. Tumors were measured twice a week using calipers and tumor volumes were calculated using the formula $W^2 \times L/2$. The animals were euthanized when the tumor volumes reached to predetermined endpoint of approximately 2000 mm³. Statistical analysis was performed up to day 50 using a one-way or 2-way analysis of variance (ANOVA). Synergy calculations were performed using fractional product method.

Results: Treatment with single agent Compound 2 when administered once a day for 3 consecutive days (qd×3) on days 31-33 after tumor cell inoculation, significantly (p<0.0001) inhibited (−44%) H929-1051 multiple myeloma tumor growth on day 50. Over the time Compound 2 (1 mg/kg)-treated animal tumors grew and reached to approximately 2000 mm³ by day 58. Treatment with bortezomib as single agent when administered at a single dose on day 31, significantly (p<0.0001) inhibited (−60%) H929-1051 xenograft tumor growth on day 50. Over the time bortezomib (1 mg/kg)-treated animal tumors grew and reached approximately 2000 mm³ by day 66. Treatment with Compound 2 at 1 mg/kg (qd×3) when administered in combination with bortezomib at 1 mg/kg (single dose) yielded a significant (p<0.0001) decrease in tumor volume when compared with vehicle control, displaying a tumor volume reduction of 98% by day 50. In a 2-way ANOVA with Bonferroni's post-test, this combination antitumor activity was significantly better than Compound 2 alone (98% versus 44% TVR; p<0.0001) or bortezomib alone (98% versus 60% TVR; p<0.0001). Using the fractional product method, the combination antitumor activity of Compound 2 at 1 mg/kg and dexamethasone at 1 mg/kg was determined to be synergistic in decreasing tumor volume. Surprisingly, by day 53 of tumor cell inoculation, 7 out of 9 animals treated with the combination of Compound 2 and bortezomib became tumor free and remained tumor free. (FIG. 24)

Conclusion:

Compound 2 in combination with bortezomib exhibited synergism in reducing tumor volume in the lenalidomide-resistant NCI-H929 plasmacytoma tumor model and surprisingly produced tumor free animals.

Example 19: Phase 1 Clinical Study—Relapsed and Refractory Multiple Myeloma

A phase 1 multicenter, open-label study is conducted to assess the safety, pharmacokinetics and preliminary efficacy of Compound 2 in combination with dexamethasone in subjects with relapsed and refractory multiple myeloma (RRMM).

Objectives:

The primary objective of the study is to assess the pharmacokinetics (PK), safety/tolerability and define the maximally tolerated dose (MTD)/recommended Part 2 dose (RP2D) of Compound 2 in combination with dexamethasone in conjunction with a minimum of two Compound 2 dosing schedules. The secondary objective is to assess the preliminary efficacy of Compound 2 in combination with dexamethasone.

Study Design: This is an open-label, multi-center, international, Phase 1 study to assess the safety, PK/PD and preliminary efficacy of Compound 2 in combination with dexamethasone in subjects with RRMM. All eligible subjects must have failed, be intolerant to or are not otherwise candidates for available therapies known to confer clinical benefit in RRMM.

The study is conducted in two parts: Part 1 assesses the PK/PD and safety of escalating doses of Compound 2 with concurrent, standard dose dexamethasone and determine the MTD/RP2D for the combination when administered according to a minimum of two different dosing schedules. Part 2 consists of a single-arm expansion cohort(s) of Compound 2 at the RP2D plus dexamethasone for both dosing schedules. In addition to safety, PK and PD assessments, all subjects undergo monthly response assessments per International Myeloma Working Group (IMWG) Uniform Response Criteria (Rajkumar et al., Consensus recommendations for the uniform reporting of clinical trials: report of the International Myeloma Workshop Consensus Panel 1. *Blood,* 2011, 117(18):4691-5; Kumar et al., International Myeloma Working Group consensus criteria for response and minimal residual disease assessment in multiple myeloma, *Lancet Oncology,* 2016, 17:e328-46) and may continue study treatment until disease progression, intolerable toxicity or physician or subject decision to discontinue study treatment.

The study is conducted in compliance with the International Council on Harmonisation (ICH) Technical Requirements for Registration of Pharmaceuticals for Human Use/Good Clinical Practice (GCP) and applicable regulatory requirements.

Part 1 (Dose Escalation): Cohorts of subjects with RRMM receive escalating doses of Compound 2 plus a fixed dose of dexamethasone (40 mg/dose; 20 mg/dose in subjects≥75 years) in order to assess its safety, the MTD/RP2D and PK/PD profiles. A minimum of two different dosing schedules are assessed in Part 1, the first consisting of 10 consecutive days of once daily (QD) dosing followed by 4 days of no treatment×2 each 28 day cycle (referred to as the 20/28 schedule). The second schedule consists of twice daily (BID) dosing for 3 consecutive days followed by 11 days of no study treatment×2 each cycle (referred to as the 6/28 schedule). The initial dose cohorts receive 0.1 mg/day Compound 2 QD on the 20/28 schedule and 0.2 mg BID on the 6/28 schedule. Subject allocation is assigned by the Sponsor contingent upon the availability of subject slots for one or both schedules. Switching between dosing schedules is not allowed. Additional dosing schedules (e.g., 5 days of Compound 2 dosing followed by 9 days of no treatment×2 OR 7 days of dosing following by 7 days of no treatment×2 per 28 day cycle) may be explored under the terms of a protocol amendment pending the outcome of initial safety and PK/PD results in association with the 20/28 and 6/28 schedules.

For all dosing schedules, Cycle 1, Days 1-28 constitute the dose-limiting toxicity (DLT) assessment period for purposes of MTD determination. Subjects are evaluable for DLT if they receive the prescribed dose of Compound 2 on at least 16 of the 20 dose days on the 20/28 schedule and at least 5 of the 6 dose days (10 doses) on the 6/28 schedule in Cycle 1 or experience a DLT. Non-DLT evaluable subjects are replaced.

In each schedule, cohorts of three or more subjects receive Compound 2 at doses that increase in 100% increments in successive cohorts until the occurrence of two, Grade 2 treatment-emergent adverse events that cannot be clearly and incontrovertibly attributed to extraneous causes. Thereafter, dose increments not to exceed 50% ensue until the occurrence of a first DLT. A Bayesian dose escalation methodology using logistic regression is utilized after the occurrence of a first DLT in either dosing schedule, with the assigned dose of Compound 2, number of doses per day (QD vs BID) and number of consecutive dose days for each schedule (3 vs 10) as covariates. The target toxicity rate for the combination of Compound 2 plus dexamethasone is 20% for all schedules.

Intra-subject dose escalation is not allowed during the DLT assessment period, however, in Cycle 2 and beyond, subjects without evidence of disease progression who are tolerating their assigned dose of Compound 2 may (at the investigator's discretion and in consultation with the study's medical monitor) escalate to the highest dose level shown to be adequately tolerated by at least one cohort of subjects within the assigned dosing schedule.

Part 2 (Cohort Expansion):

Upon completion of Part 1, a single-arm expansion study of Compound 2 plus dexamethasone is conducted in 20 subjects per dosing schedule to further assess its safety, PD and efficacy at the RP2D and schedule.

Upon determination of the RP2D for Compound 2 plus dexamethasone, an evaluation of the safety/tolerability, PK and preliminary efficacy of Compound 2/dexamethasone in combination with other anti-myeloma agents of interest, e.g., anti-CD38 in one or more subject cohorts with different prior treatment histories and/or prognostic features, may also be initiated in parallel as part of this protocol.

Study Population:

Subjects≥18 years of age with MM who are refractory to their last line of treatment, have failed or are intolerant to or not otherwise candidates for available therapies that are known to confer clinical benefit to subjects with relapsed and refractory disease, have an Eastern Cooperative Oncology Group Performance Status (ECOG PS) 0-2, measurable disease, and adequate bone marrow, renal and cardiac function may enroll. Subjects with a history of allogeneic transplantation, non- or oligosecretory MM, plasma cell leukemia or primary refractory MM (i.e., no history of at least a minor response to a prior treatment regimen) are excluded.

Inclusion Criteria:

Subjects must satisfy the following criteria to be enrolled in the study:

1. Subject is ≥18 years of age at the time of signing the informed consent form (ICF).
2. Subject must understand and voluntarily sign an ICF prior to any study-related assessments/procedures being conducted.
3. Subject is willing and able to adhere to the study visit schedule and other protocol requirements.
4. Eastern Cooperative Oncology Group (ECOG) performance status score of 0, 1 or 2.
5. Subjects must have a documented diagnosis of MM and measurable disease at enrollment. Measurable disease is defined as:
    a. M-protein quantities≥0.5 g/dL by sPEP or
    b. ≥200 mg/24 h urine collection by uPEP or
    c. Serum FLC levels>100 mg/L (milligrams/liter) involved light chain and an abnormal kappa/lambda (κ/λ) ratio in subjects without detectable serum or urine M-protein or
    d. for subjects with immunoglobulin class A (IgA), myeloma whose disease can only be reliably measured by quantitative immunoglobulin measurement, a serum IgA level≥0.50 g/dL.
6. All subjects must:
    a. have documented disease progression on or within 60 days from the last dose of their last myeloma therapy and,
    b. have failed treatment with, are intolerant to or are not otherwise candidates for available therapies that are known to confer clinical benefit to subjects with RRMM.

Note: Prior lines of therapy must include (at a minimum) a proteasome inhibitor and a cereblon modulating-agent administered individually (in any order) or together.

7. Subjects must have the following laboratory values:
   Absolute neutrophil count (ANC)≥1.25×10$^9$/L without growth factor support for ≥7 days (≥14 days for pegfilgrastim).
   Hemoglobin (Hgb)≥8 g/dL.
   Platelets (plt)≥75×10$^9$/L without transfusion for ≥7 days (≥50×10$^9$/L for subjects with >50% plasma cells in bone marrow).
   Corrected serum calcium≤13.5 mg/dL (≤3.4 mmol/L).
   24-hr creatinine clearance (CrCl)≥45 mL/min.
   AST/SGOT and ALT/SGPT≤3.0×upper limit of normal (ULN).
   Serum bilirubin≤1.5×ULN.
   Uric acid≤7.5 mg/dL (446 μmol/L).
   PT/INR<1.5×ULN and partial thromboplastin time (PTT)<1.5×ULN, (for subjects not receiving therapeutic anticoagulation).
   Note: Subjects receiving therapy for a thromboembolic event that occurred >3 months prior to enrollment are eligible as long as they are on a stable regimen of anticoagulation with warfarin, low-molecular weight heparin or other approved therapeutic anticoagulation regimen.

8. Females of childbearing potential (FCBP) must:
   a. Have two negative pregnancy tests as verified by the Investigator prior to starting study therapy. She must agree to ongoing pregnancy testing during the course of the study, and after discontinuation of Compound 2. This applies even if the subject practices true abstinence* from heterosexual contact.
   * True abstinence is acceptable when this is in line with the preferred and usual lifestyle of the subject. Periodic abstinence (e.g., calendar, ovulation, symptothermal, post-ovulation methods) and coitus interruptus (withdrawal) are not acceptable methods of contraception.
   b. Either commit to true abstinence* from heterosexual contact (which must be reviewed on a monthly basis and source documented) or agree to use, and be able to comply with, two reliable forms of contraception without interruption, 28 days prior to starting Compound 2, during the study therapy (including during dose interruptions), and for 28 days after discontinuation of study therapy.
   Note: A female of childbearing potential (FCBP) is a female who: 1) has achieved menarche at some point and, 2) has not undergone a hysterectomy or bilateral oophorectomy, or 3) has not been naturally post-menopausal (amenorrhea following cancer therapy does not rule out childbearing potential) for at least 24 consecutive months (ie, has had menses at any time in the preceding 24 consecutive months).

9. Male subjects must:
   a. Practice true abstinence* (which must be reviewed on a monthly basis) or agree to use of a condom during sexual contact with a pregnant female or a female of childbearing potential while participating in the study (even during dose interruptions) and for at least 3 months following Compound 2 discontinuation, even if he has undergone a successful vasectomy.

10. Males must agree to refrain from donating sperm while on Compound 2 and for 90 days after its discontinuation.

11. All subjects must agree to refrain from donating blood while on Compound 2 and for 28 days after its discontinuation.

Exclusion Criteria:
The presence of any of the following excludes a subject from enrollment:

1. Subject has a significant medical condition, laboratory abnormality, or psychiatric illness that would prevent the subject from participating in the study.
2. Subject has any condition including the presence of laboratory abnormalities, which places the subject at unacceptable risk if he/she were to participate in the study.
3. Subject has any condition that confounds the ability to interpret data from the study.
4. Subject has non- or oligosecretory multiple myeloma.
5. Subject has plasma cell leukemia or active leptomeningeal myelomatosis.
6. Subject has documented, systemic light chain amyloidosis or Polyneuropathy, Organomegaly, Endocrinopathy, Monoclonal gammopathy, and Skin changes (POEMS) Syndrome.
7. Subject has immunoglobulin class M (IgM) myeloma.
8. Subject has a history of allogeneic bone marrow transplantation.
9. Subject is undergoing dialysis.
10. Subjects with peripheral neuropathy≥Grade 2.
11. Subjects with gastrointestinal disease that may significantly alter the absorption of Compound 2.
12. Subject has impaired cardiac function or clinically significant cardiac disease, including any of the following:
    LVEF<45% as determined by ECHO or MUGA scan at Screening.
    Complete left bundle branch, bifascicular block or other clinically significant abnormal electrocardiographic (ECG) finding at Screening.
    A prolongation of QT interval on Screening ECG as defined by repeated demonstration of a QTc interval>480 milliseconds (ms) using Fredericia's QT correction formula; a history of or current risk factors for Torsades de Pointe (e.g., heart failure, hypokalemia, or a family history of Long QT Syndrome); and concurrent administration of medications that prolong the QT/QTc interval.
    Congestive heart failure (New York Heart Association Class III or IV).
    Myocardial infarction≤6 months prior to starting Compound 2.
    Unstable or poorly controlled angina pectoris, including the Prinzmetal variant of angina pectoris.
13. Concurrent administration of strong CYP3A modulators.
14. Subject had prior systemic myeloma treatment (approved or investigational) ≤5 half-lives or 4 weeks prior to starting Compound 2, whichever is shorter.
15. Subject had major surgery≤2 weeks prior to starting Compound 2. Note: Subjects must have recovered from any clinically significant effects of recent surgery.
16. Subject is a pregnant or nursing female or intends to become pregnant during participation in the study.
17. Subject has known human immunodeficiency virus (HIV) infection.
18. Subject has known active chronic hepatitis B or C virus (HBV/HCV) infection.
19. Subject has a history of concurrent second cancer requiring ongoing systemic treatment.

20. Subjects has a history of prior malignancy other than MM, unless the subject has been free of disease for ≥3 years except for the following noninvasive malignancies treated with curative intent:
   Basal or squamous cell carcinoma of the skin.
   Carcinoma in situ of the cervix or breast.
   Stage 1 bladder cancer.
   Incidental histological findings of localized prostate cancer such as tumor stage 1a or 1b (T1a or T1b) using the Tumor/Node/Metastasis (TNM) classification of malignant tumors OR prostate cancer that has been treated with curative intent.
21. Subject has a history of anaphylaxis to thalidomide, lenalidomide, pomalidomide or dexamethasone.
22. Subject has known or suspected hypersensitivity to the excipients contained in the formulation of Compound 2 or dexamethasone.
23. Subject has undergone either of the following within 14 days of initiating Compound 2:
   Plasmapheresis.
   Radiation therapy other than local therapy for symptomatic relief of MM associated bone lesions.
24. Subject has received immunosuppressive medication within 14 days prior to the first dose of Compound 2. The following are exceptions to this criterion:
   Intranasal, inhaled, topical or local corticosteroid injections (e.g., intra-articular injection).
   Systemic corticosteroids at doses that do not exceed 10 mg/day of prednisone or the equivalent.
   Steroids as premedication for hypersensitivity reactions (e.g., computed tomography (CT) scan premedication).
25. Subject is unable or unwilling to undergo protocol required venous thromboembolism (VTE) prophylaxis.

Length of Study:

The average per subject duration of study participation is expected to be approximately 6 months. Full enrollment is expected to take approximately 21 months to complete (18 months for Part 1 and 3 months for Part 2). Completion of active treatment and post-treatment follow-up is expected to take an additional 6 to 12 months. The entire study is expected to continue for approximately 33 months.

The End of Trial is defined as either the date of the last visit of the last subject to complete the post-treatment follow-up, or the date of receipt of the last data point from the last subject that is required for primary, secondary and/or exploratory analysis, as pre-specified in the protocol, whichever is the later date.

Study Treatments:

Compound 2 is administered orally either once daily for subjects enrolled to the 20/28 schedule or twice daily for subjects enrolled to the 6/28 schedule. For subjects enrolled to the 20/28 dosing schedule, Compound 2 is administered in the morning with at least 240 mL of water after an overnight fast lasting at least 6 h. Subjects must refrain from food or other medication intake for at least 2 h after each morning dose. Subjects enrolled to the 6/28 schedule follow the aforementioned instructions as outlined for the 20/28 schedule for the first dose of each dose day. The second dose is administered 12±2 h after the morning dose, at least 4 h after and 2 h before food intake. By way of example, subjects enrolled to the 6/28 dosing schedule could conceivably receive their initial dose of Compound 2 at 7:00 am, followed by breakfast at 9:00 am, lunch at noon, their second dose of Compound 2 as early as 5:00 pm with the evening meal taken 2 h later (i.e., no earlier than 7:00 pm). Note that in Cycle 1 only, Compound 2 is administered on Days 1 through 3 (morning and evening), Day 14 (in the evening only), Days 15 and 16 (morning and evening) and Day 17 (in the morning only).

For both dosing schedules, dexamethasone is administered with Compound 2 in the fasted state or at least 2 h after Compound 2 with food (except on PK assessment days when both must be given at the same time). Dexamethasone given on Days 1, 8 (Day 10 in Cycle 1 only), 15 and 22 or Days 1, 3, 15 (Day 14 in Cycle 1 only) and 17 of each cycle on the 20/28 or 6/28 dosing schedules respectively, can be administered in the fasted state concurrently with Compound 2. Alternatively (in subjects with a history of dexamethasone induced gastric irritation), it can be administered with food at least 2 h after Compound 2, except on PK assessment days when both should be administered concurrently to all subjects. For all subjects, each dose of dexamethasone is 40 mg for subjects<75 years of age and 20 mg for those ≥75 years old.

Overview of Key Efficacy Assessments:

The primary efficacy variable is the best overall response rate (ORR) defined as the percent of subjects whose best response is ≥PR as determined by IMWG Uniform Response Criteria (Rajkumar et al *Blood* 2011; 117(18): 4691-5). Subjects undergo response assessments monthly. Myeloma response is determined by the study site investigator based on laboratory investigations (serum protein electrophoresis (sPEP), urine protein electrophoresis (uPEP), immunofixation electrophoresis (IFE), serum free light chain (sFLC) levels, quantitative immunoglobulin A (IgA), bone marrow for plasma cell quantitation, as appropriate) assessed in a central reference laboratory and/or locally, (i.e., corrected serum calcium, positron emission tomography/computerized scan (PET/CT) or magnetic resonance imaging (MRI) for plasmacytoma evaluation and/or CT or skeletal survey for bone lesion evaluation). Additional efficacy variables include time to response (time from 1st dose of Compound 2 to the first documentation of response≥PR), duration of response (time from the first documentation of response (≥PR) to the first documentation of PD or death) and progression-free survival (time from 1st dose of Compound 2 to the first occurrence of disease progression or death from any cause).

All safety subjects with a valid baseline and at least one post-baseline response assessment are included in the efficacy analyses. If treatment is discontinued for reasons other than disease progression, subjects are requested to continue response assessments according to the specified assessment schedule until progression, withdrawal of consent, death or initiation of new systemic anti-myeloma therapy, whichever is earliest.

Overview of Key Safety Assessments:

The safety variables for this study include treatment-emergent adverse events (TEAEs) and changes from baseline in physical findings/vital signs, selected laboratory analytes, and 12-lead electrocardiograms (ECGs). Additional safety metrics include the extent of exposure to study treatment (both Compound 2 and dexamethasone), assessments of concomitant medication use, and pregnancy testing for females of child bearing potential (FCBP).

Overview of Pharmacokinetic Assessments:

PK profiles (initial dose and steady state) are evaluated for Compound 2, its R-enantiomer (Compound 3) and dexamethasone. Exposure-response analyses may be conducted, as appropriate, to assist in identification of the Compound 2 RP2D.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method of treating multiple myeloma comprising administering a therapeutically effective amount of Compound 2 of the formula:

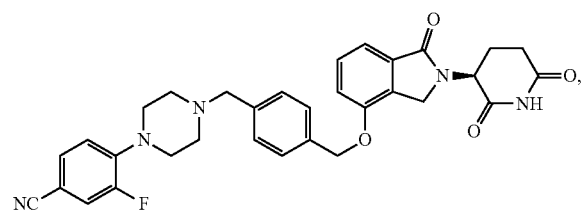

or a tautomer, isotopolog, or pharmaceutically acceptable salt thereof, to a patient in need thereof, wherein the method further comprises administering a second agent, and wherein the second agent is dexamethasone, daratumumab, a proteasome inhibitor, a histone deacetylase inhibitors, a chemotherapy agent, a Bcl-2 inhibitor, an Mcl-1 inhibitor, a BET inhibitor, or an LSD-1 inhibitor, or a combination thereof.

2. The method of claim 1, wherein the second agent is daratumumab.

3. The method of claim 1, wherein the second agent is a proteasome inhibitor.

4. The method of claim 3, wherein the proteasome inhibitor is bortezomib, carfilzomib, ixazomib, oprozomib, or marizomib.

5. The method of claim 3, wherein the proteasome inhibitor is carfilzomib.

6. The method of claim 1, wherein the second agent is a combination of daratumumab and dexamethasone.

7. The method of claim 1, wherein the second agent is a combination of bortezomib and dexamethasone.

8. The method of claim 1, wherein the second agent is a combination of carfilzomib and dexamethasone.

9. The method of claim 1, wherein the second agent is a histone deacetylase inhibitor.

10. The method of claim 9, wherein the histone deacetylase inhibitor is ACY241 or panobinostat.

11. The method of claim 1, wherein the second agent is a chemotherapy agent.

12. The method of claim 11, wherein the chemotherapy agent is vincristine, cyclophosphamide, etoposide, or doxorubicin.

13. The method of claim 1, wherein the second agent is a Bcl-2 inhibitor.

14. The method of claim 13, wherein the Bcl-2 inhibitor is venetoclax.

15. The method of claim 1, wherein the second agent is an Mcl-1 inhibitor.

16. The method of claim 15, wherein the Mcl-1 inhibitor is AMG176 or MIK665.

17. The method of claim 1, wherein the second agent is a BET inhibitor.

18. The method of claim 17, wherein the BET inhibitor is 4-[2-(cyclopropylmethoxy)-5-(methanesulfonyl)phenyl]-2-methylisoquinolin-1(2H)-one, birabresib, or GSK525762A.

19. The method of claim 1, wherein the second agent is an LSD-1 inhibitor.

20. The method of claim 19, wherein the LSD-1 inhibitor is 4-[2-(4-amino-piperidin-1-yl)-5-(3-fluoro-4-methoxyphenyl)-1-methyl-6-oxo-1,6-dihydropyrimidin-4-yl]-2-fluoro-benzonitrile.

* * * * *